(12) United States Patent
Song et al.

(10) Patent No.: US 11,690,292 B2
(45) Date of Patent: Jun. 27, 2023

(54) ORGANIC ELECTRONIC ELEMENT COMPRISING A COMPOUND FOR ORGANIC ELECTRONIC ELEMENT AND AN ELECTRONIC DEVICE THEREOF

(71) Applicant: DUK SAN NEOLUX CO., LTD., Cheonan-si (KR)

(72) Inventors: Hyun Ju Song, Cheonan-si (KR); Yun Suk Lee, Cheonan-si (KR); Hyo Min Jin, Cheonan-si (KR); Hyung Dong Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/058,957

(22) Filed: Nov. 28, 2022

(65) Prior Publication Data

US 2023/0129535 A1 Apr. 27, 2023

Related U.S. Application Data

(63) Continuation-in-part of application No. 17/212,886, filed on Mar. 25, 2021, which is a continuation of
(Continued)

(30) Foreign Application Priority Data

Oct. 26, 2020 (KR) ........................ 10-2020-0139441

(51) Int. Cl.
*C07D 251/24* (2006.01)
*C09K 11/06* (2006.01)
(Continued)

(52) U.S. Cl.
CPC ....... *H10K 85/6574* (2023.02); *C07D 251/24* (2013.01); *C09K 11/06* (2013.01);
(Continued)

(58) Field of Classification Search
CPC .. C07D 251/24; H10K 85/654; H10K 85/631; H10K 50/11
See application file for complete search history.

(56) References Cited

U.S. PATENT DOCUMENTS

2014/0367654 A1 12/2014 Kim et al.
2015/0303379 A1 10/2015 Lee et al.
(Continued)

FOREIGN PATENT DOCUMENTS

WO 2019124902 A1 6/2019
WO WO-2020171530 A1 * 8/2020 ........... C07D 405/04

OTHER PUBLICATIONS

SciFinder Search, 4 pages, Apr. 7, 2021.
STN Search, 351 pages, Apr. 7, 2021.

*Primary Examiner* — Vu A Nguyen
(74) *Attorney, Agent, or Firm* — Vorys, Sater, Seymour and Pease LLP; Mih Suhn Koh

(57) ABSTRACT

Provided are an organic electronic element including an anode, a cathode, and an organic material layer between the anode and the cathode, and an electronic device including the organic electronic element, wherein the organic material layer includes each of the compounds represented by Formulas 1 and 2 and the driving voltage of the organic electronic element is lowered, and the luminous efficiency and lifetime of the element are improved.

15 Claims, 3 Drawing Sheets

Related U.S. Application Data application No. 17/096,790, filed on Nov. 12, 2020, now Pat. No. 11,063,226.

(51) Int. Cl.
*H01L 51/00* (2006.01)
*H01L 51/50* (2006.01)
*H10K 85/60* (2023.01)
*H10K 50/11* (2023.01)
*H10K 50/15* (2023.01)
*H10K 50/16* (2023.01)
*H10K 50/18* (2023.01)
*H10K 101/10* (2023.01)
*H10K 101/00* (2023.01)

(52) U.S. Cl.
CPC ......... *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01); *C09K 2211/1018* (2013.01); *H10K 50/11* (2023.02); *H10K 50/15* (2023.02); *H10K 50/16* (2023.02); *H10K 50/18* (2023.02); *H10K 2101/10* (2023.02); *H10K 2101/90* (2023.02)

(56) References Cited

U.S. PATENT DOCUMENTS

| | | |
|---|---|---|
| 2016/0133674 A1 | 5/2016 | Lee et al. |
| 2018/0072695 A1 | 3/2018 | Byun et al. |
| 2018/0123048 A1 | 5/2018 | So et al. |
| 2018/0151806 A2 | 5/2018 | Park et al. |
| 2018/0261774 A1 | 9/2018 | Park et al. |

\* cited by examiner

ORGANIC ELECTRONIC ELEMENT COMPRISING A COMPOUND FOR ORGANIC ELECTRONIC ELEMENT AND AN ELECTRONIC DEVICE THEREOF

TECHNICAL FIELD

The present invention relates to compound for organic electronic element, organic electronic element using the same, and an electronic device thereof.

BACKGROUND ART

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

In the organic light emitting diode, the most problematic is the lifetime and the efficiency. As the display becomes large, the efficiency and the lifetime problem must be solved. Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in a hole transport layer, an emitting-auxiliary layer must be present between the hole transport layer and an emitting layer, and it is necessary to develop different emitting-auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic device are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against joule heating generated when the device is driven, while delaying penetration of the metal oxide from the anode electrode (ITO), which is one of the causes of shortening the lifetime of the organic electronic device, into the organic layer. The low glass transition temperature of the hole transport layer material has a characteristic that when the device is driven, the uniformity of the surface of the thin film is lowered, which has been reported to have a great influence on the lifetime of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, development of new materials is continuously required, and development of materials for the hole transport layer or the emitting-auxiliary layer is urgently required.

SUMMARY OF INVENTION

Problems to be Solved by the Invention

An object of the present invention is to provide an organic electronic element including a compound capable of lowering a driving voltage of an element and improving luminous efficiency, color purity, stability, and lifetime of the element, and an electronic element thereof.

The present invention provides a compound represented by Formula 1.

<Formula 1>

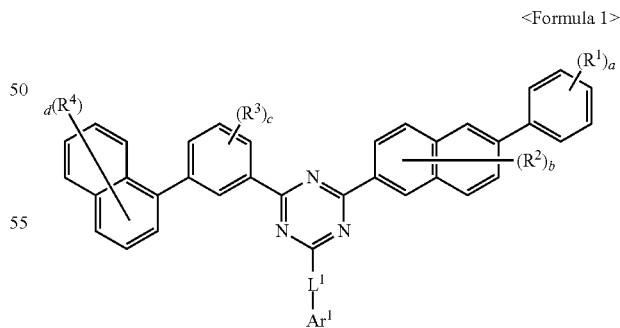

In another aspect, the present invention provides an electronic device including the organic electronic element.

Effects of the Invention

By using the compound according to the present invention, it is possible to achieve a high luminous efficiency, a low driving voltage, and a high heat resistance of the element, and can greatly improve the color purity and lifetime of the element.

Figure 1:
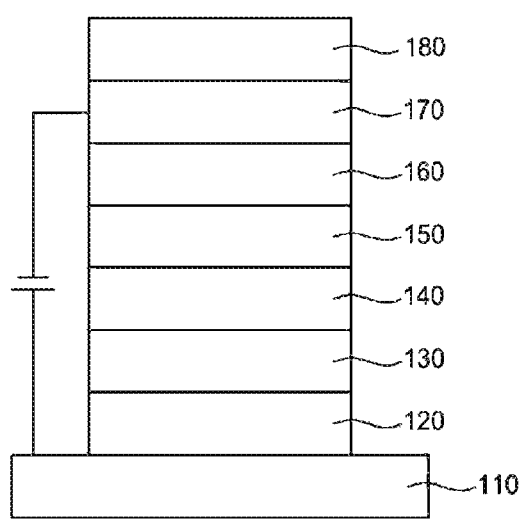
FIG. 1 to FIG. 3 are each an exemplary view of an organic electronic element according to one aspect of the present invention.

| | |
|---|---|
| 100, 200, 300: | organic electronic element |
| 110: | the first electrode |
| 120: | hole injection layer |
| 130: | hole transport layer |
| 140: | emitting layer |
| 150: | electron transport layer |
| 160: | electron injection layer |
| 170: | second electrode |
| 180: | light efficiency enhancing Layer |
| 210: | buffer layer |
| 220: | emitting-auxiliary layer |
| 320: | first hole injection layer |
| 330: | first hole transport layer |
| 340: | first emitting layer |
| 350: | first electron transport layer |
| 360: | first charge generation layer |
| 361: | second charge generation layer |
| 420: | second hole injection layer |
| 430: | second hole transport layer |
| 440: | second emitting layer |
| 450: | second electron transport layer |
| CGL: | charge generation layer |
| ST1: | first stack |
| ST1: | second stack |

DETAILED DESCRIPTION OF THE INVENTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected," coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

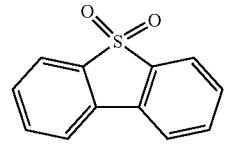 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R'' are all hydrogen in the following structures, and the term "substituted fluorenyl group" or "substituted fluorenylene group" means that at least one of the substituents R, R', R'' is a substituent other than hydrogen, and include those in which R and R' are bonded to each other to form a spiro compound together with the carbon to which they are bonded.

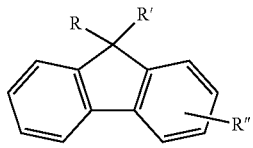

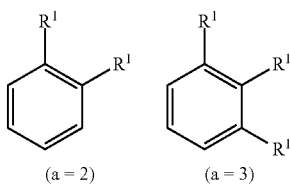

(a = 2)        (a = 3)

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro' and 'tri-spiro', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

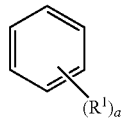

here, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$s may be the same and different, when a is an integer of 4 to 6, and is linked to the benzene ring in a similar manner, whereas the indication of hydrogen bound to the carbon forming the benzene ring is omitted.

Hereinafter, a laminated structure of an organic electronic device including the compound of the present invention will be described with reference to FIGS. 1 to 3.

In adding reference numerals to elements of each figure, it should be noted that the same elements have the same numerals as possible even if they are indicated on different figures.

In addition, in describing the present invention, when it is determined that a detailed description of a related known configuration or function may obscure the subject matter of the present invention, a detailed description thereof will be omitted.

Figure 2:
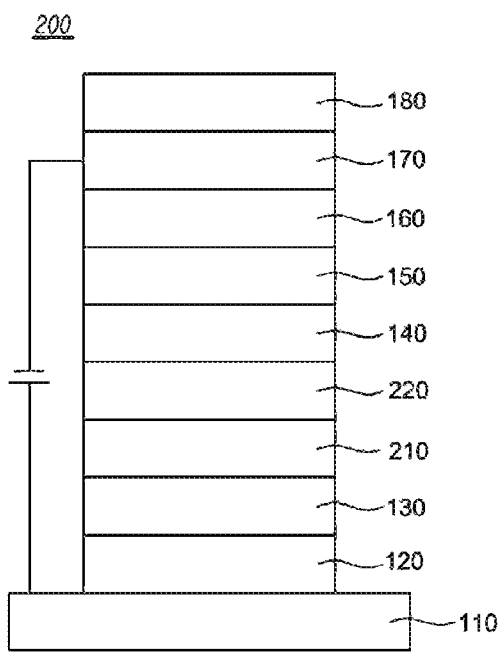
Figure 3:
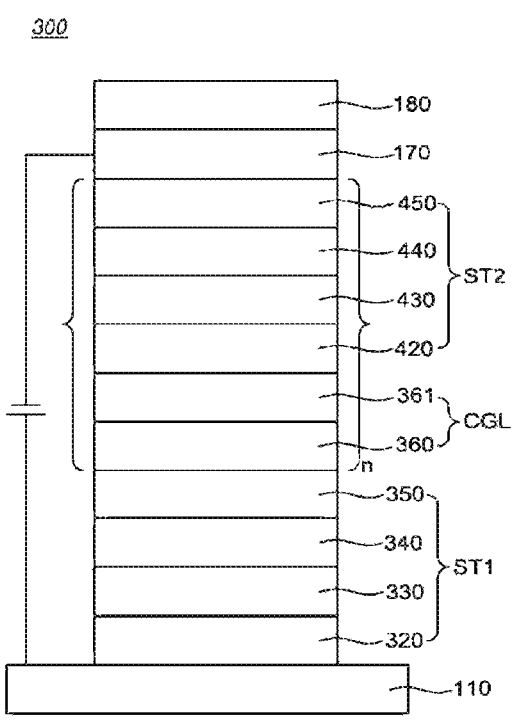

FIG. 1 to FIG. 3 illustrate an example of an organic electronic element according to an embodiment of the present invention.

Referring to FIG. 1, an organic electronic element (100) according to an embodiment of the present invention includes a first electrode (110), a second electrode (170) formed on a substrate (not shown) and an organic material layer formed between the first electrode (110) and the second electrode (170).

The first electrode (110) may be an anode, the second electrode (170) may be a cathode, and in the case of an inverted type, the first electrode may be a cathode and the second electrode may be an anode.

The organic material layer may include a hole injection layer (120), a hole transport layer (130), an emitting layer (140), an electron transport layer (150), and an electron injection layer (160). Specifically, a hole injection layer (120), a hole transport layer (130), an emitting layer (140), an electron transport layer (150), and an electron injection layer (160) may be sequentially formed on the first electrode (110).

The present invention may further include a light efficiency enhancing layer formed on one of not in contact with the organic material layer among one side of the first electrode (110) or of the second electrode (170), and when the light efficiency enhancing layer (180) is formed, the light efficiency of the organic electronic element may be improved.

For example, the light efficiency enhancing layer (180) may be formed on the second electrode (170), and in the case of a top emission organic light emitting device, the light efficiency enhancing layer (180) is formed, thereby reducing optical energy loss due to surface plasmon polaritons (SPPs) in the second electrode (170), and in the case of a bottom emission organic light emitting device, the light efficiency enhancing layer (180) may function as a buffer for the second electrode (170).

A buffer layer (210) or an emitting auxiliary layer (220) may be further formed between the hole transport layer (130) and the emitting layer (140), which will be described with reference to FIG. 2.

Referring to FIG. 2, an organic electric device (200) according to another embodiment of the present invention includes a hole injection layer (120), a hole transport layer (130), a buffer layer (210), an emitting auxiliary layer (220), an emitting layer (140), an electron transport layer (150), an electron injection layer (160), a second electrode (170), sequentially formed on the first electrode (110), and a light efficiency enhancing layer (180) formed on the second electrode.

Although not shown in FIG. 2, an electron transport auxiliary layer may be further formed between the emitting layer (140) and the electron transport layer (150).

Also, according to another embodiment of the present invention, the organic material layer may have a plurality of stacks including a hole transport layer, an emitting layer, and an electron transport layer. This will be described with reference to FIG. 3.

Referring to FIG. 3, in the organic electronic element (300) according to another embodiment of the present invention, 2 or more sets of stacks (ST1 and ST2) made of a multi-layered organic material layer may be formed between the first electrode (110) and the second electrode (170), and a charge generation layer (CGL) may be formed between the stacks of organic material layers.

Specifically, the organic electronic element according to an embodiment of the present invention includes a first electrode (110), a first stack (ST1), a charge generation layer (CGL), a second stack (ST2), and a second electrode. (170) and a light efficiency enhancing layer (180) may be included.

The first stack (ST1) is an organic material layer formed on the first electrode (110) and may include a first hole injection layer (320), a first hole transport layer (330), a first emitting layer (340), and a first electron transport layer (350), and the second stack (ST2) may include a second hole injection layer (420), a second hole transport layer (430), a second emitting layer (440), and a second electron transport layer (450). As described above, the first stack and the second stack may be organic material layers having the same laminated structure, but may be organic material layers having different laminated structures.

A charge generation layer (CGL) may be formed between the first stack (ST1) and the second stack (ST2). The charge generation layer (CGL) may include a first charge generation layer (360) and a second charge generation layer (361). The charge generation layer (CGL) is formed between the first emitting layer (340) and the second emitting layer (440) to increase the current efficiency generated in each emitting layer and smoothly distribute charge.

When a plurality of emitting layers are formed by the multilayer stack structure method as shown in FIG. 3, an organic electronic element that emits white light by a mixing effect of light emitted from each emitting layer can be manufactured, as well as an organic electronic element that emits light of various colors.

The compounds represented by Formulas 1 and 2 of the present invention may be used as a material fora hole injection layer (120, 320, 420), a hole transport layer (130, 330, 430), a buffer layer (210), an emitting auxiliary layer (220), and an electron transport layer (150, 350, 450), the electron injection layer (160), the emitting layer (140, 340, 440), or the light efficiency enhancing layer (180), but preferably, the compounds represented by Formulas 1 and 2 of the present invention may be used as a host of the emitting layers (140, 340, 440).

Otherwise, even if the same or similar core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electronic element according to an embodiment of the present invention may be manufactured using various deposition methods. It can be manufactured using a vapor deposition method such as PVD or CVD. For example, an anode (110) is formed by depositing a metal or a conductive metal oxide or an alloy thereof on a substrate, and after forming an organic material layer including the hole injection layer (120), the hole transport layer (130), the emitting layer (140), the electron transport layer (150) and the electron injection layer (160) thereon, the organic electroluminescent device according to an embodiment of the present invention can be manufactured by depositing a material that can be used as a cathode (170) thereon. Also, an emitting auxiliary layer (220) may be further formed between the hole transport layer (130) and the emitting layer (140), and an electron transport auxiliary layer (not shown) may be further formed between the emitting layer (140) and the electron transport layer (150), and as described above, may be formed in a stack structure.

Also, the organic material layer may be manufactured with a smaller number of layers by using various polymer materials and not by a deposition method, but by a solution process, a solvent process, such as a spin coating process, a nozzle printing process, an inkjet printing process, a slot coating process, a dip coating process or a roll-to-roll process, doctor blading process, screen printing process, or a thermal transfer method. Since the organic material layer according to the present invention can be formed by various methods, the scope of the present invention is not limited by the forming method.

In addition, the organic electric device according to an embodiment of the present invention may be selected from the group consisting of an organic electroluminescent device, an organic solar cell, an organic photoreceptor, an organic transistor, a monochromatic lighting device, and a quantum dot display device.

Another embodiment of the present invention may include an electronic device comprising a display device including the organic electronic element; and a control unit for driving the display device. At this time, the electronic device may be a current or future wired/wireless communication terminal, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electronic element according to an aspect of the present invention will be described.

The present invention provides a compound represented by Formula 1.

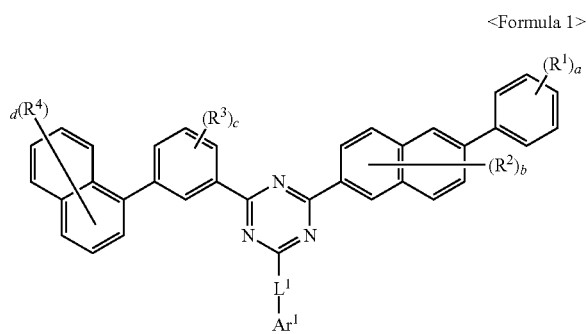

<Formula 1>

Wherein:

$R^1$, $R^2$ and $R^3$ are each the same or different, and each independently hydrogen; deuterium; halogen; or a $C_1$-$C_{60}$ alkyl group;

$R^4$ is hydrogen; deuterium; a $C_6$~$C_{60}$ aryl group; or $C_6$~$C_{60}$ aryl group substituted with deuterium;

$L^1$ is a single bond; or $C_6$-$C_{60}$ arylene group, wherein in case $R^4$ is a substituted or unsubstituted group, it is preferably an $C_6$-$C_{30}$ aryl group, more preferably an $C_6$-$C_{24}$ aryl group, for example, it may be phenylene, biphenyl, naphthalene, terphenyl, and the like.

$Ar^1$ is $C_6$~$C_{60}$ aryl group, preferably an $C_6$-$C_{30}$ aryl group, more preferably an $C_6$-$C_{24}$ aryl group, for example, it may be phenylene, biphenyl, naphthalene, terphenyl, and the like.

a is an integer from 0 to 5, b is an integer from 0 to 6, c is an integer from 0 to 4, d is an integer from 0 to 7, wherein, the alkyl group, aryl group or arylene group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, Formula 1 is represented by Formula 1-1 or Formula 1-2.

< Formula 1-1 >

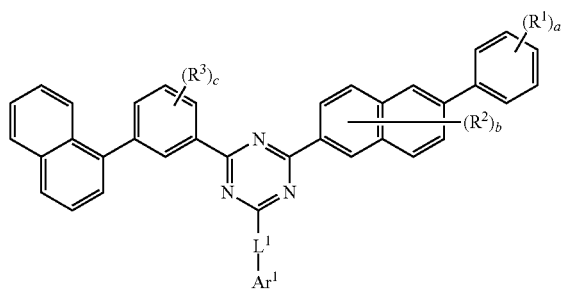

< Formula 1-2 >

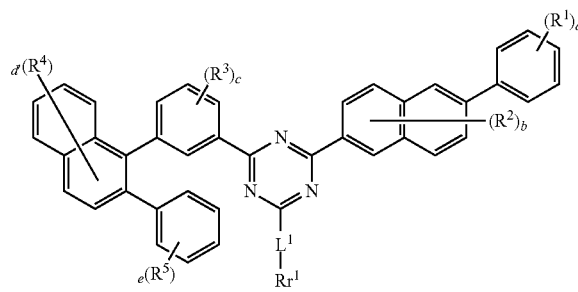

Wherein $R^1$, $R^2$, $R^3$, a, b, c, $L^1$ and $Ar^1$ are the same as defined in Formula 1.

Also, Formula 1 is represented by Formula 1-3 or Formula 1-4.

<Formula 1-3>

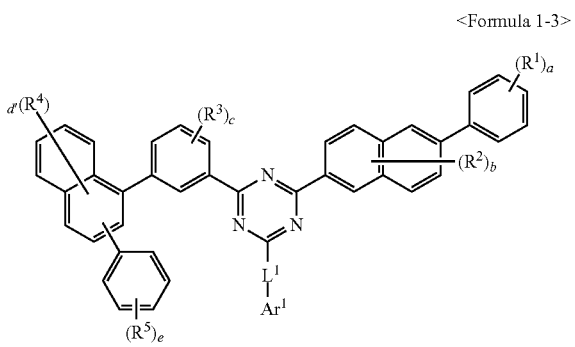

<Formula 1-4>

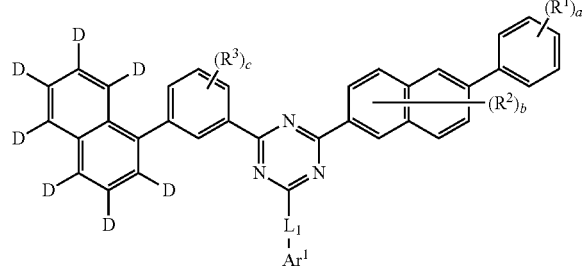

Wherein:

$R^1$, $R^2$, $R^3$, $R^4$, a, b, c, $L^1$ and $Ar^1$ are the same as defined in Formula 1.

d is an integer from 0 to 6, e is an integer from 0 to 5, $R^5$ is hydrogen; or deuterium.

Also, Formula 1 is represented by any one of Formulas 1-3-1 to 1-3-3.

< Formula 1-3-1 >

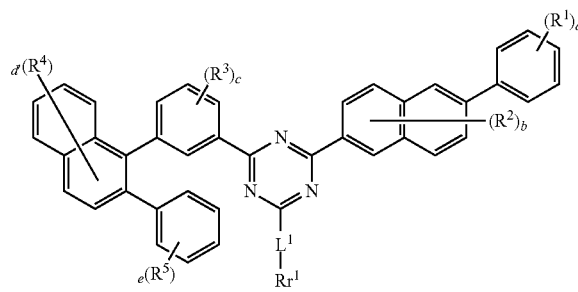

< Formula 1-3-2 >

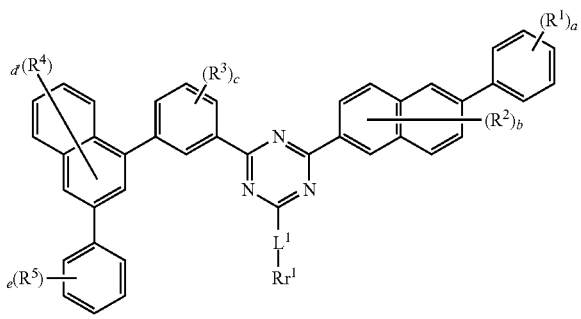

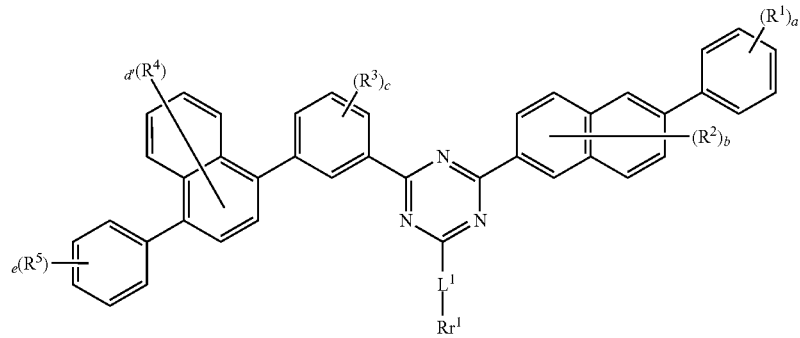
<Formula 1-3-3>
Wherein:
$R^1$, $R^2$, $R^3$, $R^4$, a, b, c, $L^1$ and $Ar^1$ are the same as defined in Formula 1,
d' is an integer from 0 to 6, e is an integer from 0 to 5,
$R^5$ is hydrogen; or deuterium.
Also, Formula 1 is represented by any one of Formulas 1-4-1 to 1-4-4.
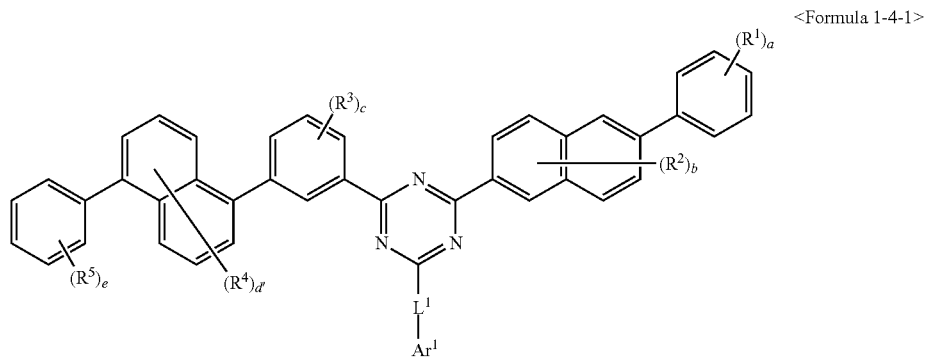
<Formula 1-4-1>
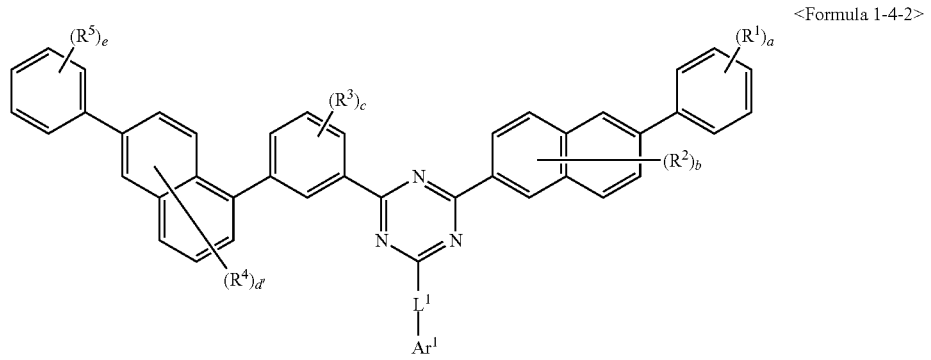
<Formula 1-4-2>
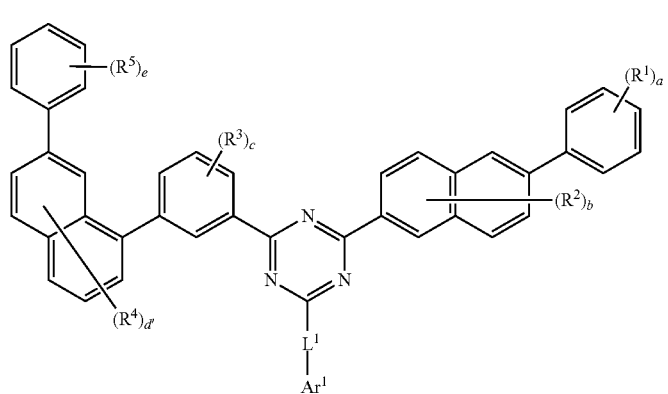
<Formula 1-4-3>

-continued

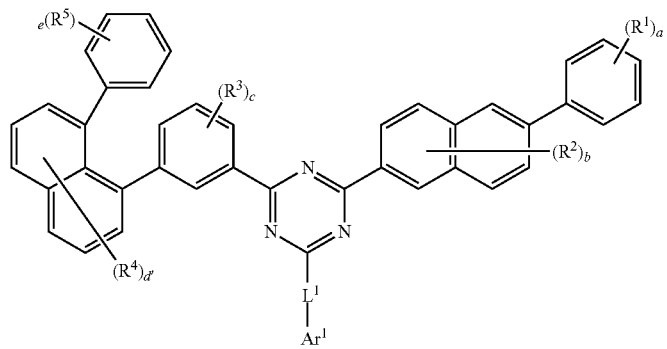

<Formula 1-4-4>

Wherein:
$R^1$, $R^2$, $R^3$, $R^4$, a, b, c, $L^1$ and $Ar^1$ are the same as defined in Formula 1,
d' is an integer from 0 to 6, e is an integer from 0 to 5,
$R^5$ is hydrogen; or deuterium.
Also, $L^1$ of Formula 1 is represented by Formula L1 or Formula L2

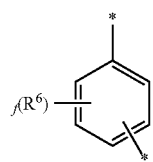

<Formula L1>

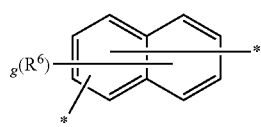

<Formula L2>

Wherein:
$R^6$ is hydrogen; or deuterium;
f is an integer from 0 to 4, g is an integer from 0 to 6,
* means the bonding position.
Also, $Ar^1$ of Formula 1 is represented by any one of Formulas Ar1 to Ar3

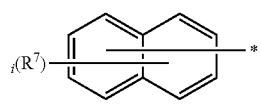

<Formula Ar1>

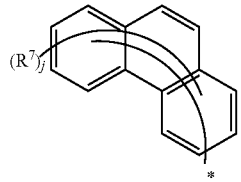

<Formula Ar2>

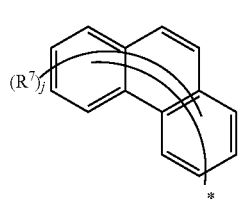

<Formula Ar3>

Wherein:
$R^7$ is hydrogen; or deuterium;
h is an integer from 0 to 5, i is an integer from 0 to 7, j is an integer from 0 to 9,
* means the bonding position.
Also, the compound represented by Formula 1 is represented by any one of the following compounds P-1 to P-104.

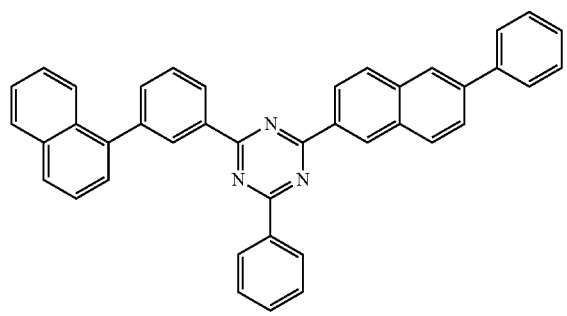

P-1

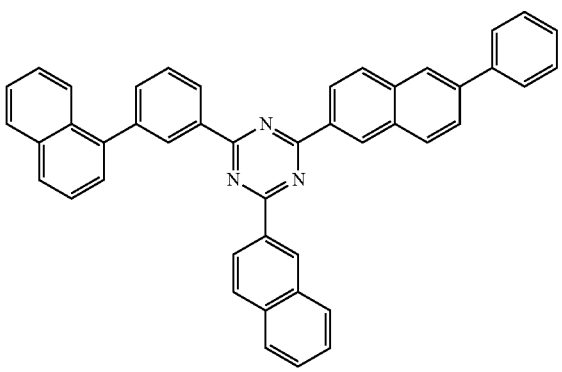

P-2

-continued
P-3
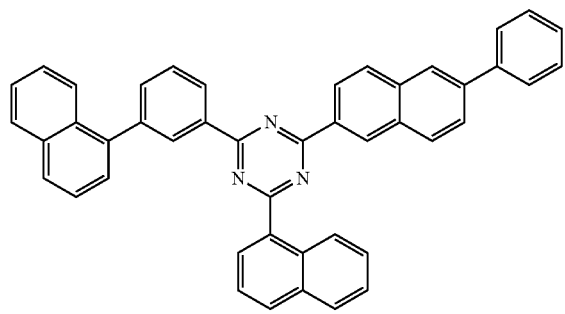
P-4
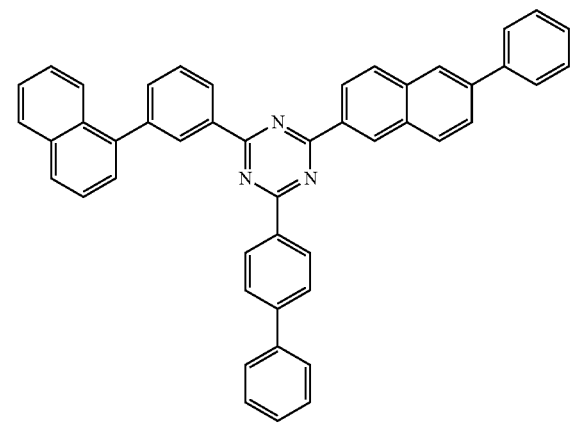
P-5
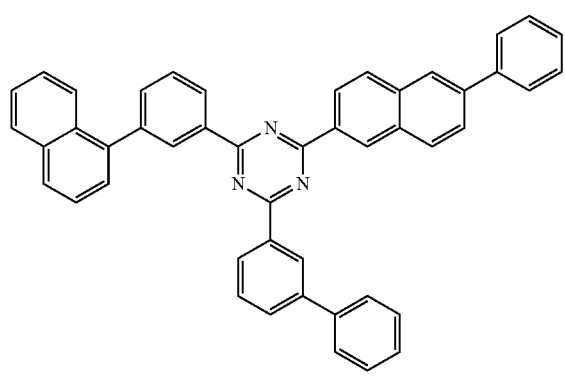
P-6
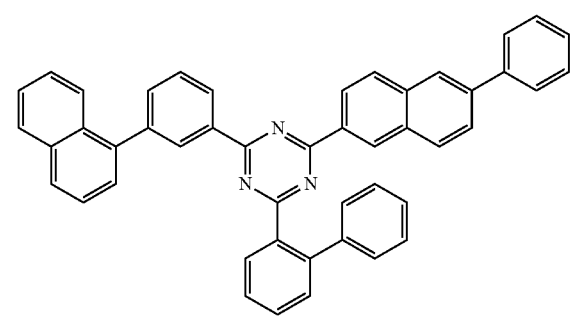
P-7
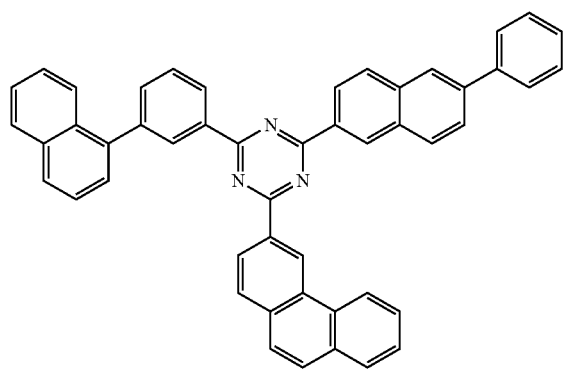
P-8
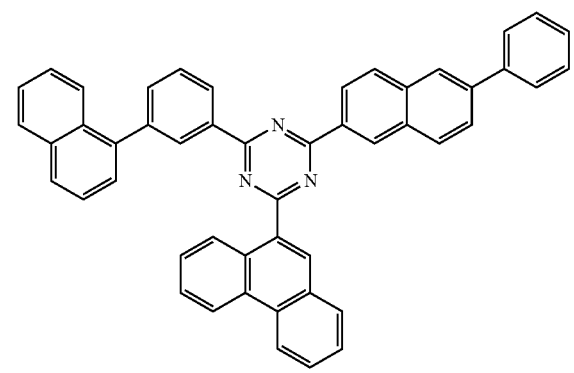
P-9
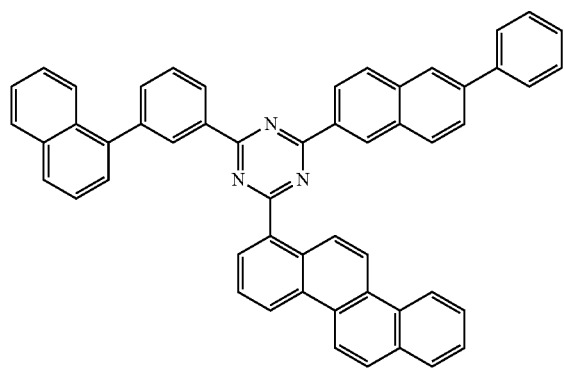
P-10
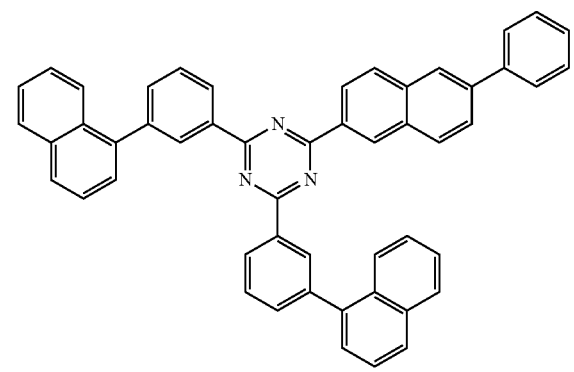

-continued
P-11
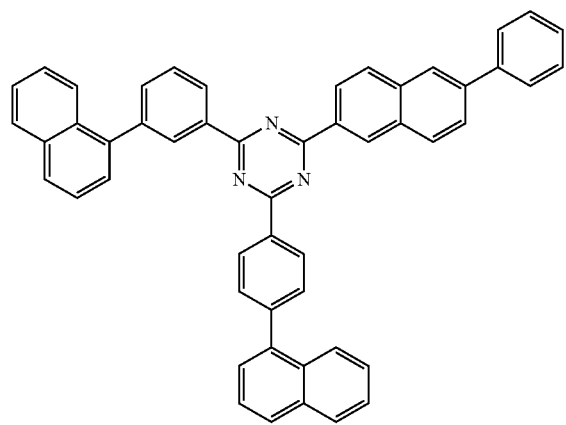
P-12
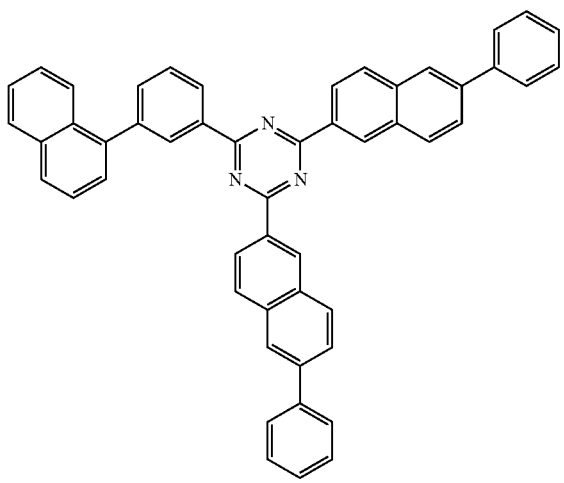
P-13
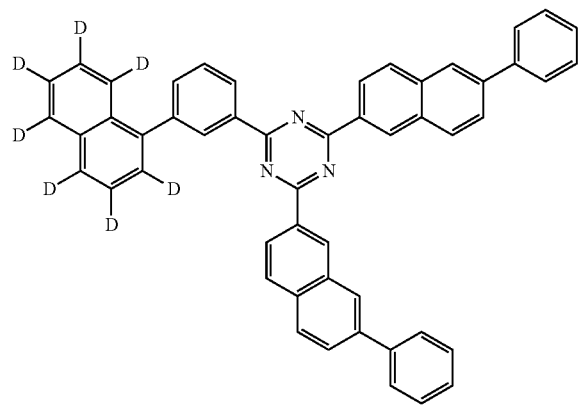
P-14
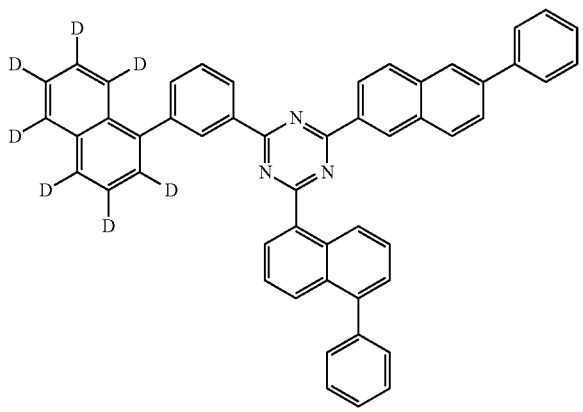
P-15
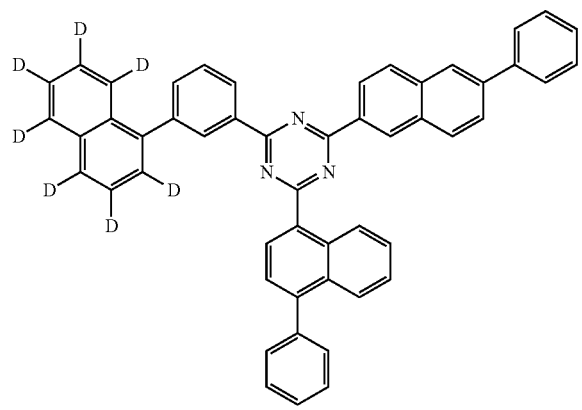
P-16
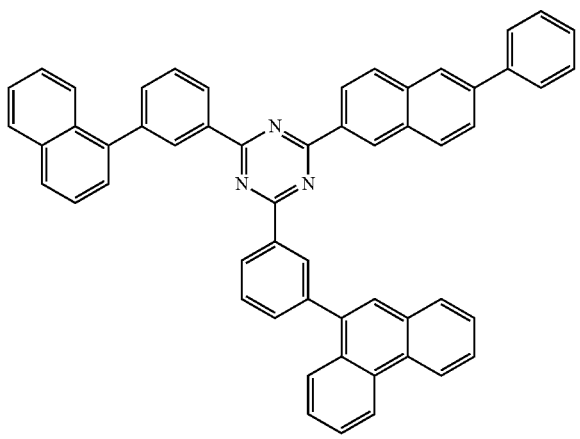

-continued
P-17
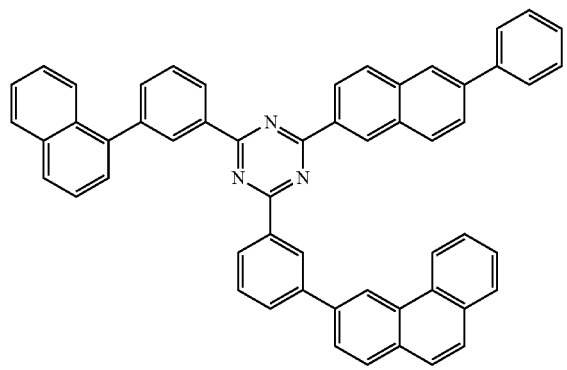
P-18
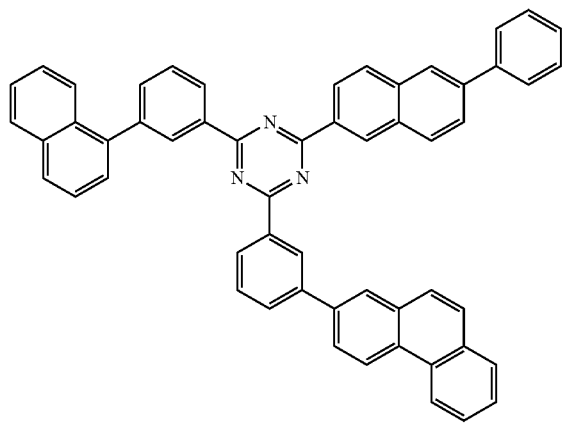
P-19
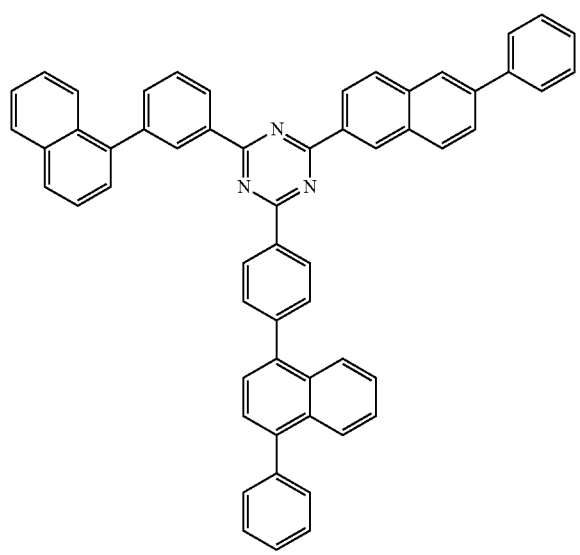
P-20
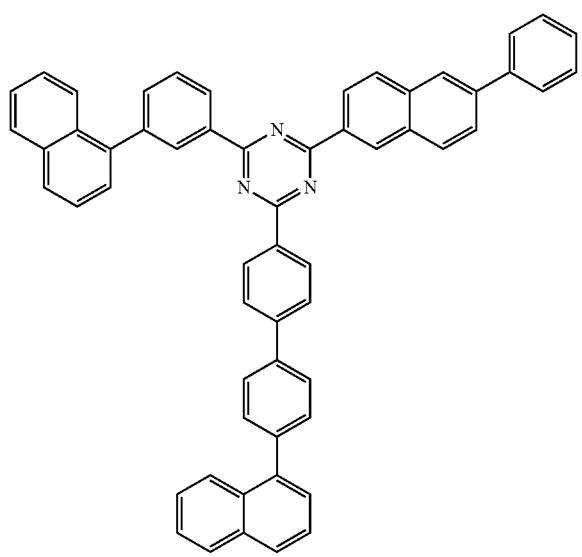
P-21
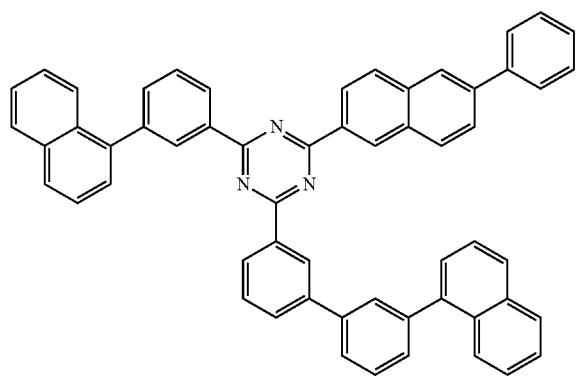
P-22
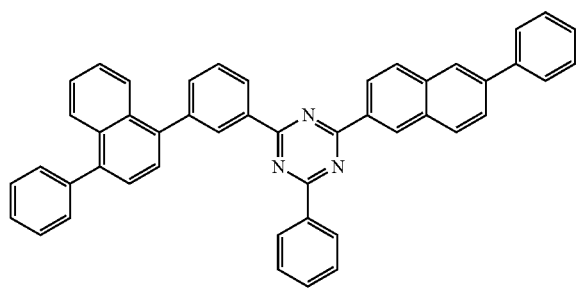

-continued
P-23 P-24
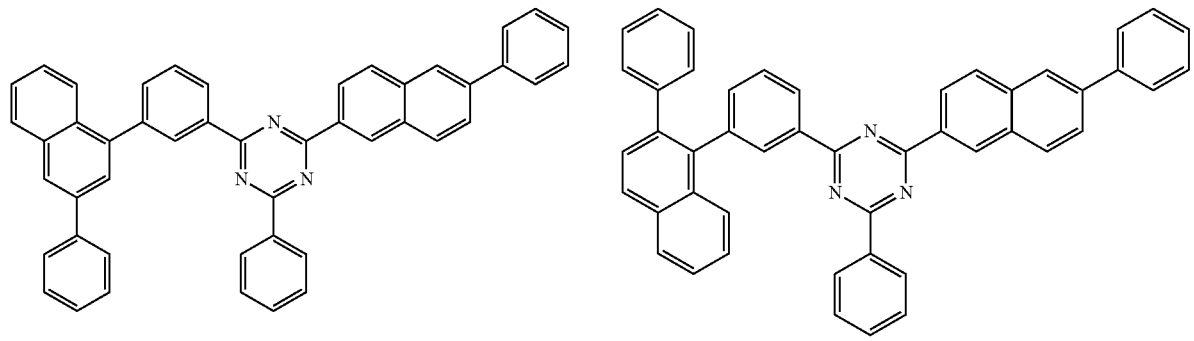
P-25 P-26
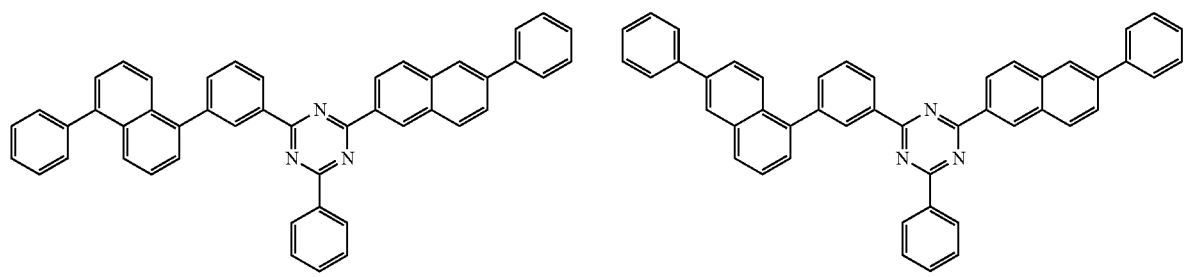
P-27 P-28
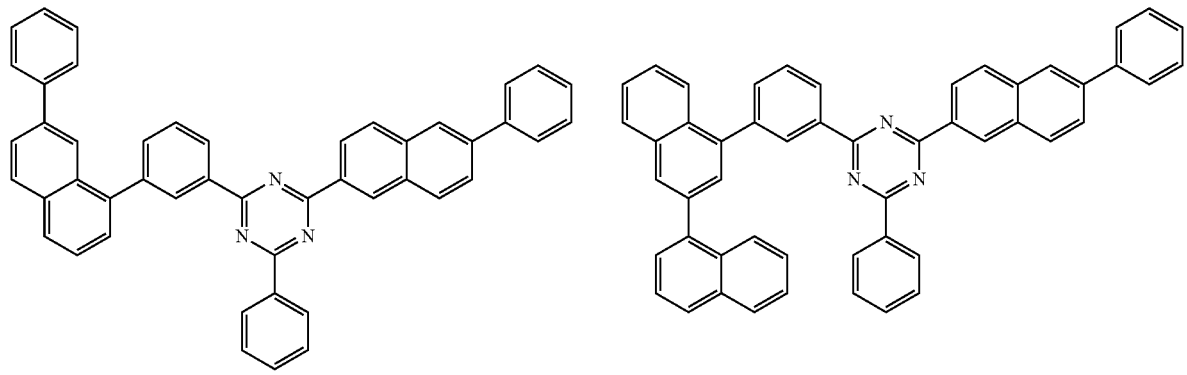
P-29 P-30
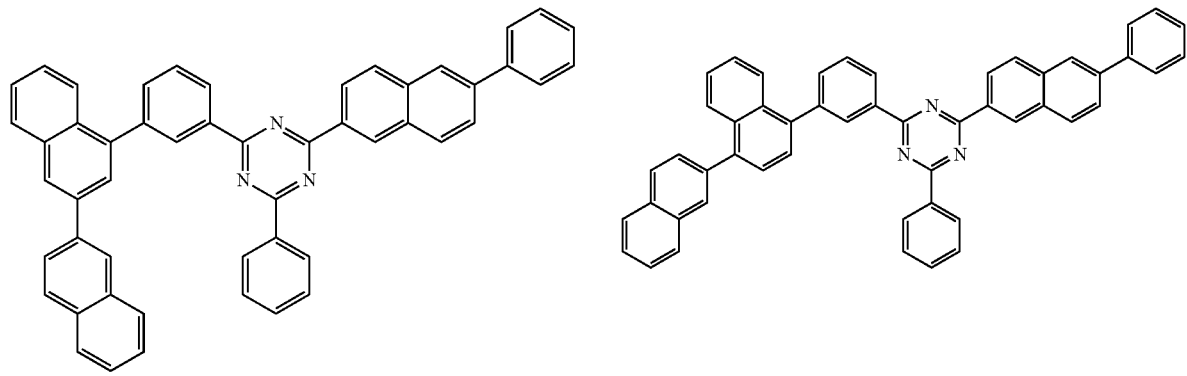

-continued
P-31
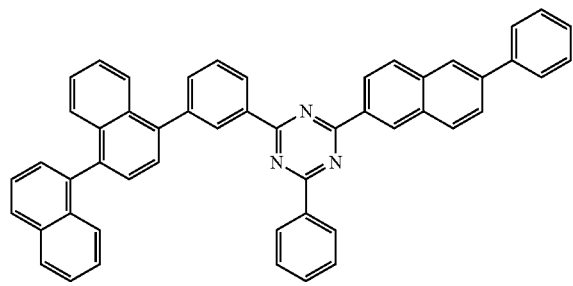
P-32
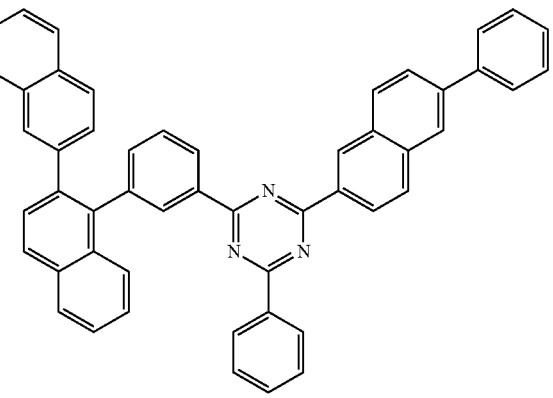
P-33
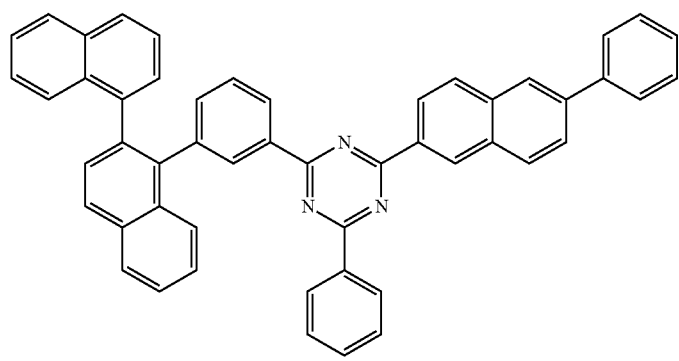
P-34
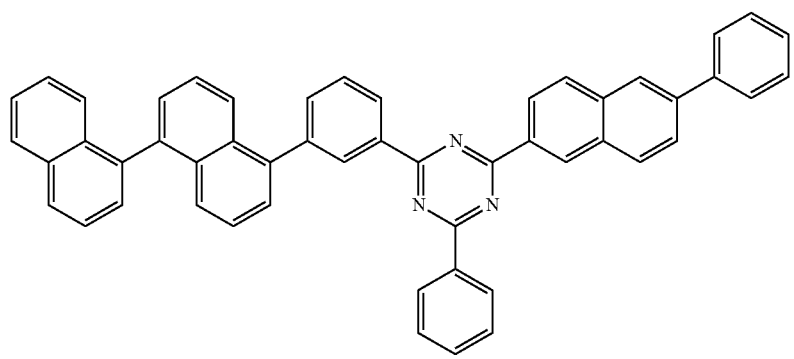
P-35
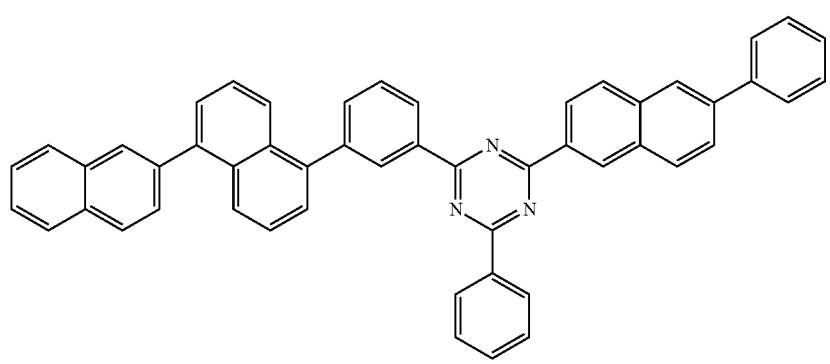

-continued
P-36
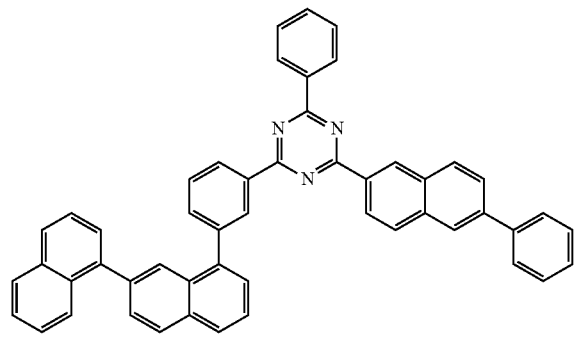
P-37
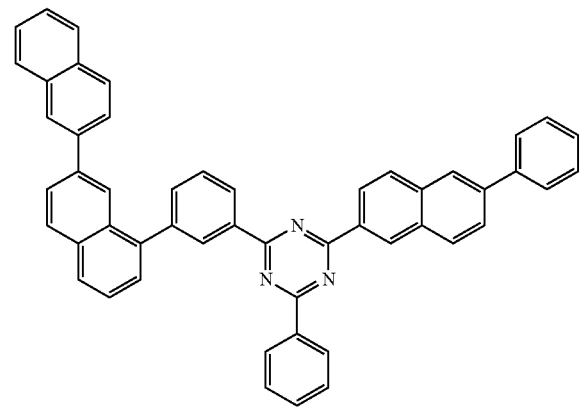
P-39
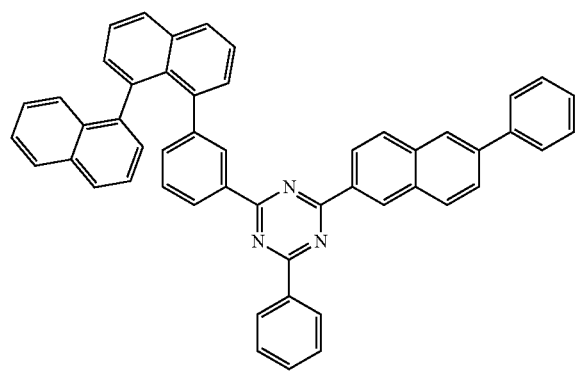
P-40
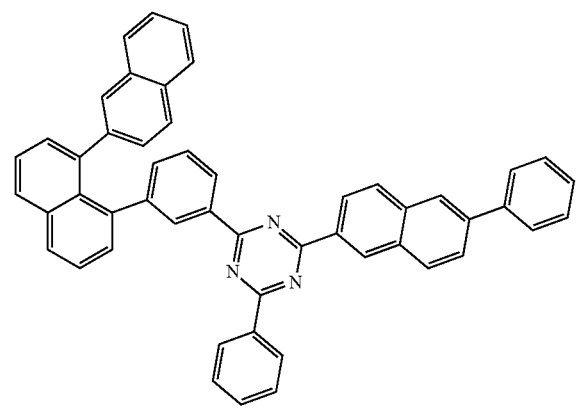
P-38
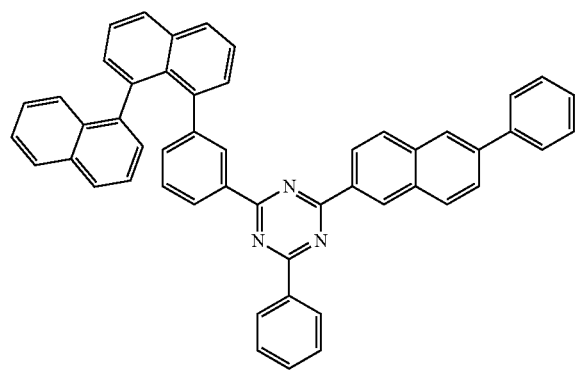
P-39
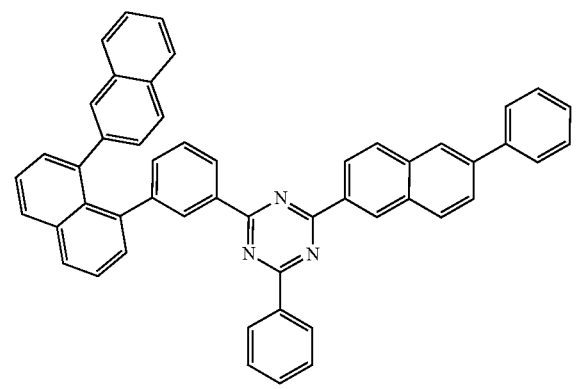

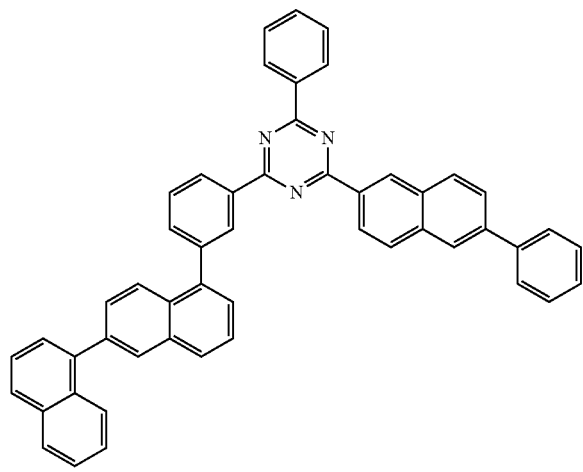
P-40
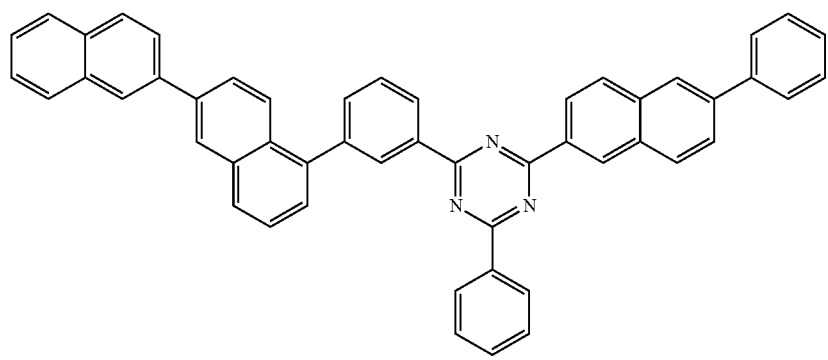
P-41
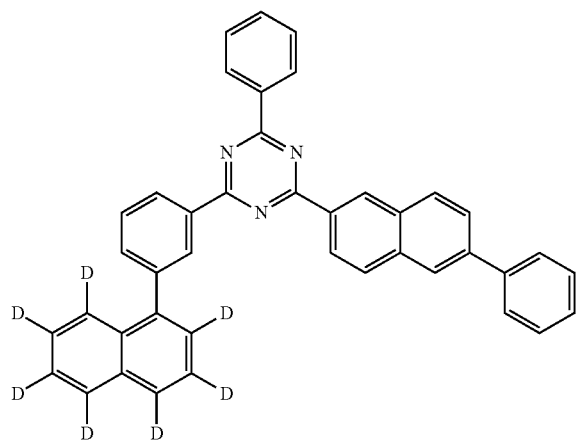
P-42
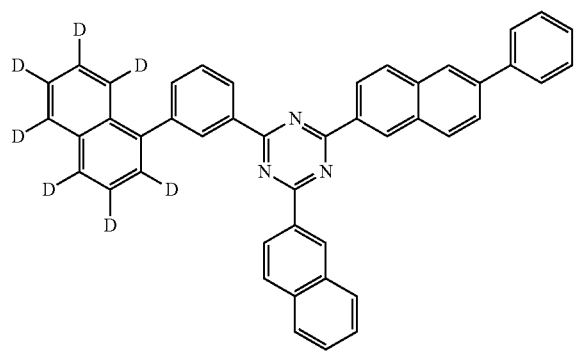
P-43

-continued
P-44
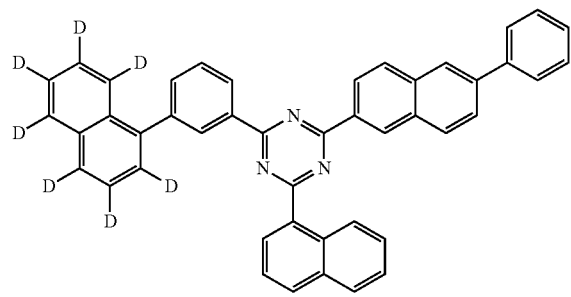
P-45
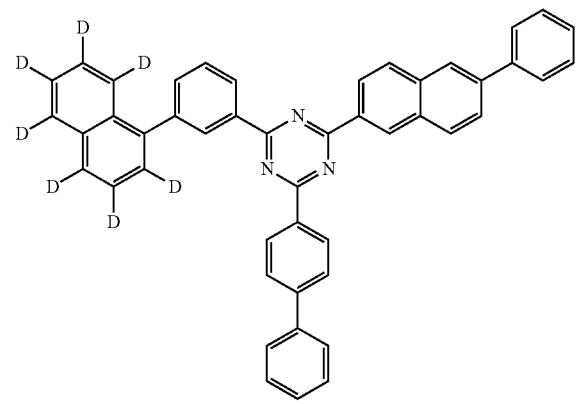
P-46
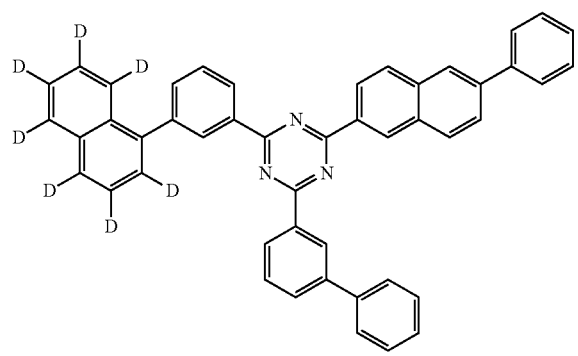
P-47
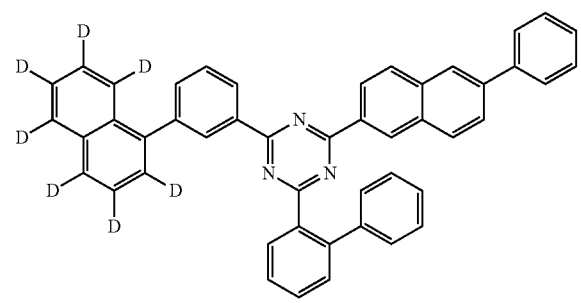
P-48
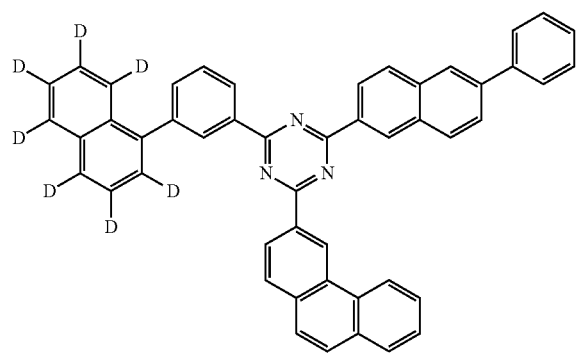
P-49
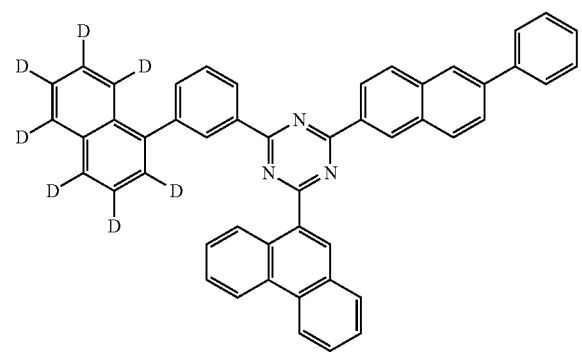
P-50
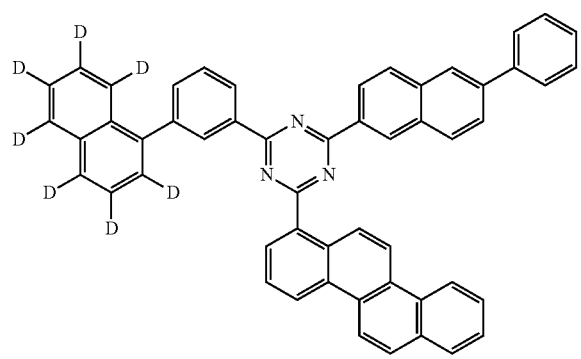
P-51
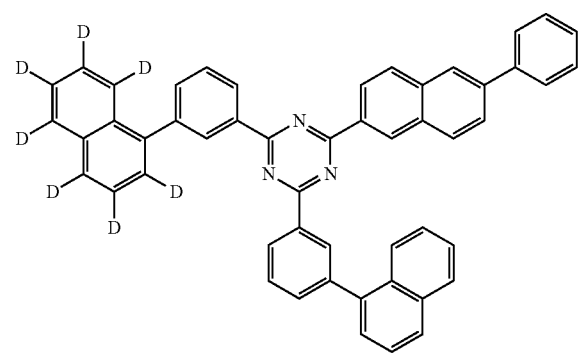

-continued
P-52
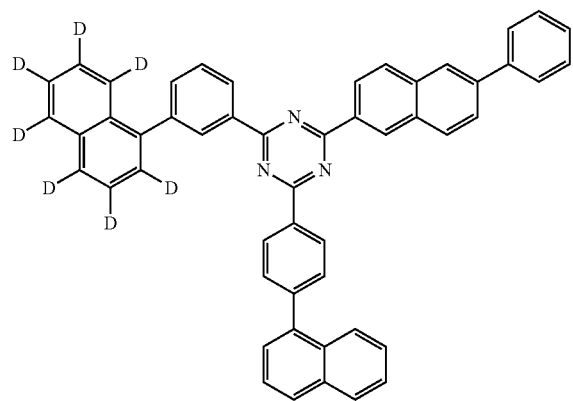
P-53
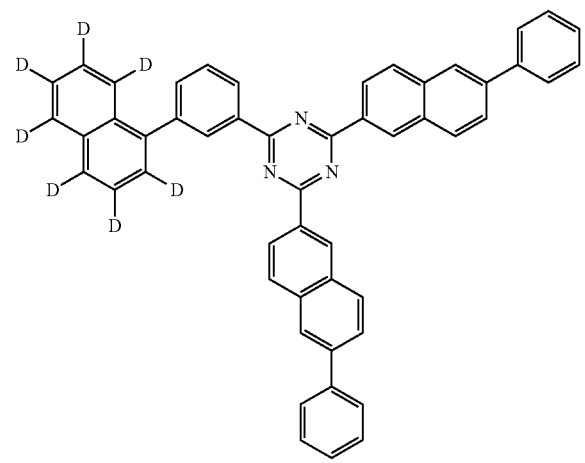
P-54
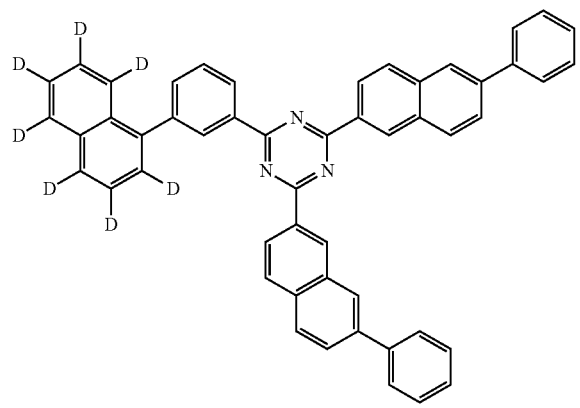
P-55
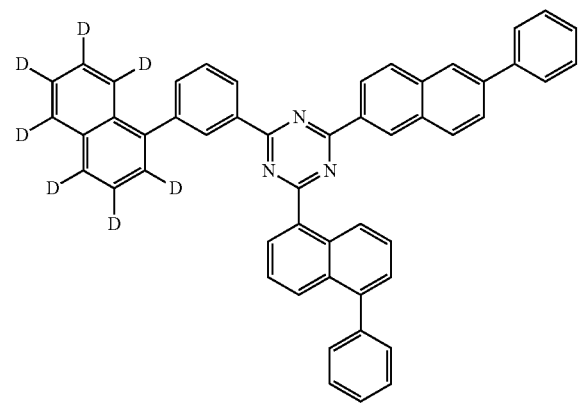
P-56
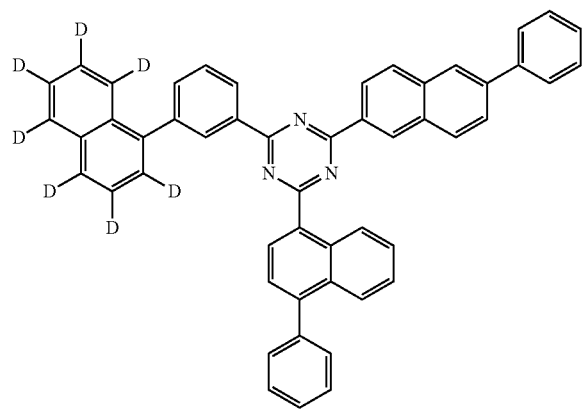
P-57
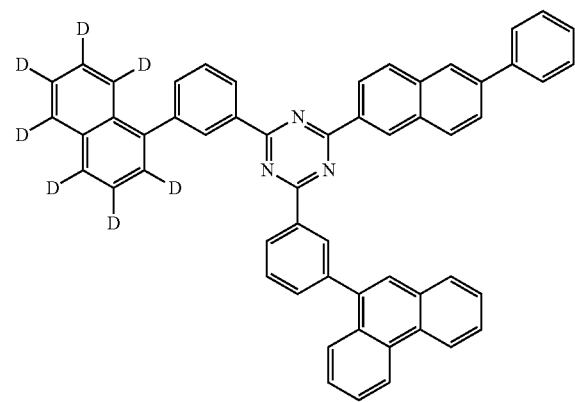

-continued
P-58
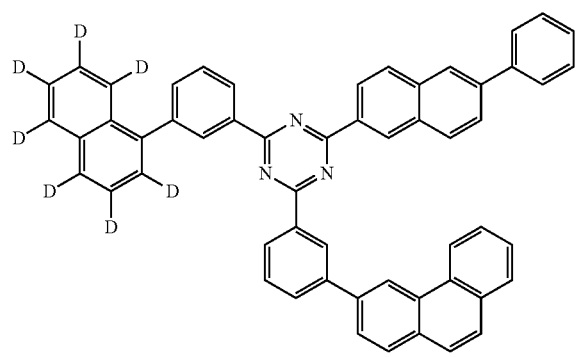
P-59
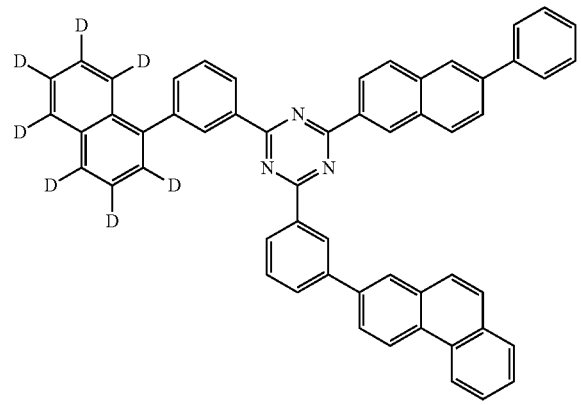
P-60
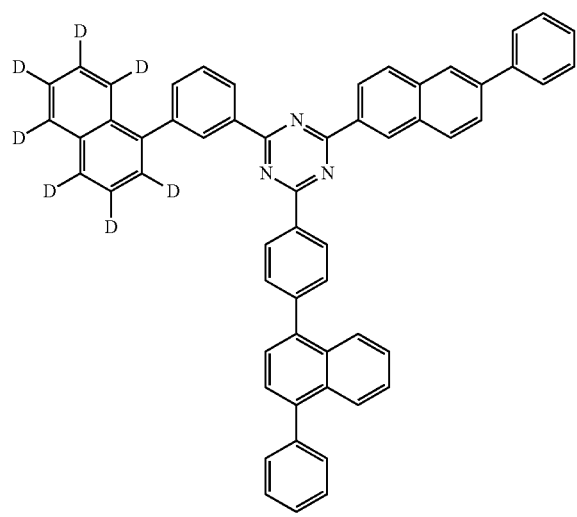
P-61
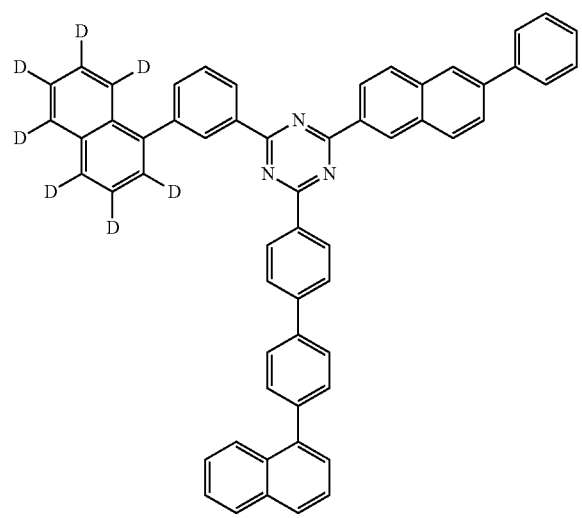
P-62
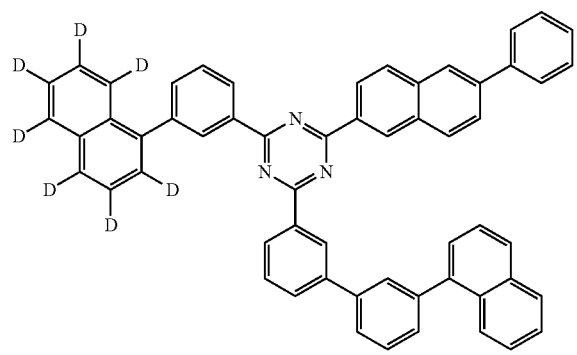
P-63
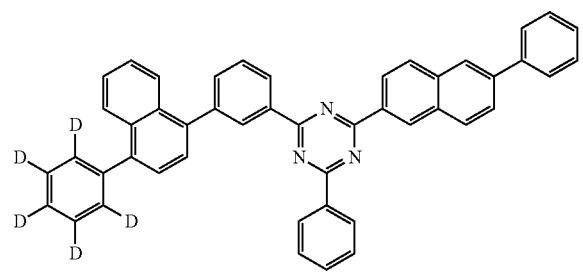

-continued
P-64
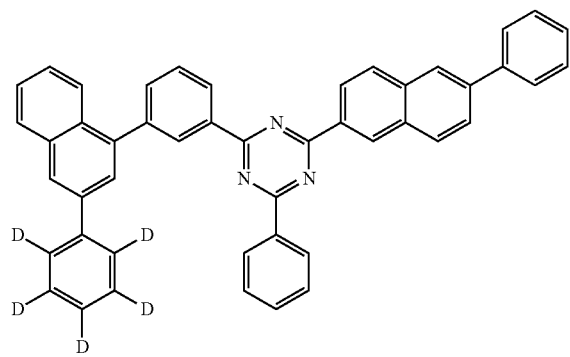
P-65
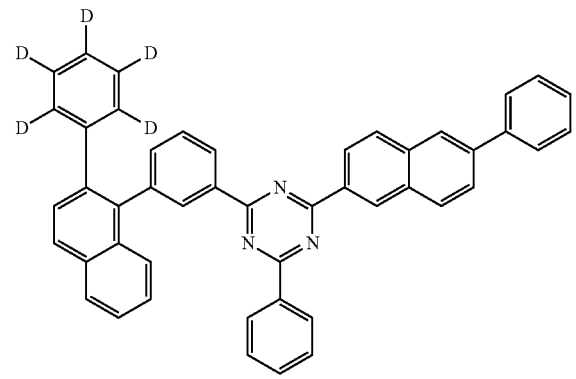
P-66
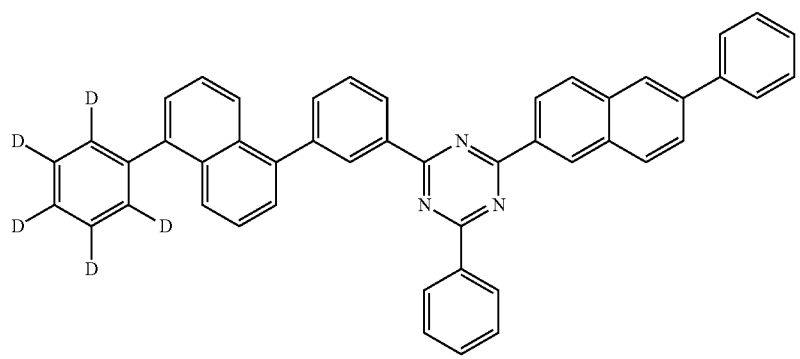
P-67
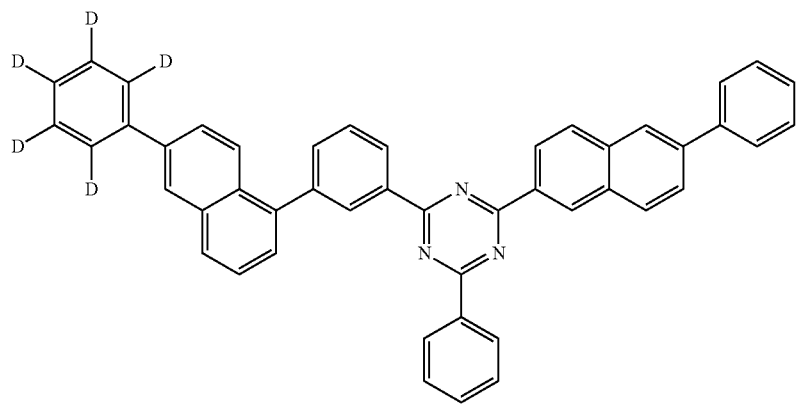
P-68
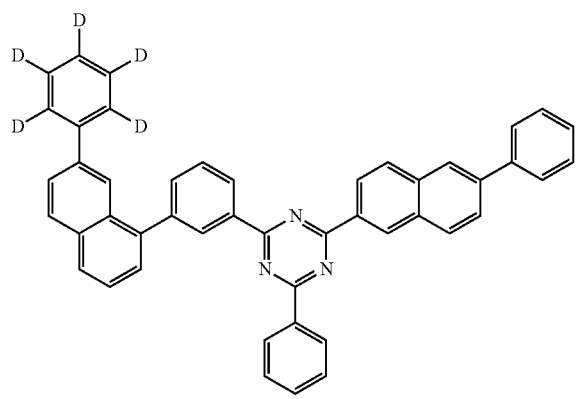
P-69
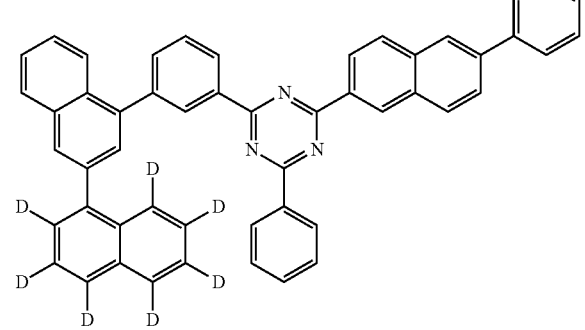

-continued
P-70
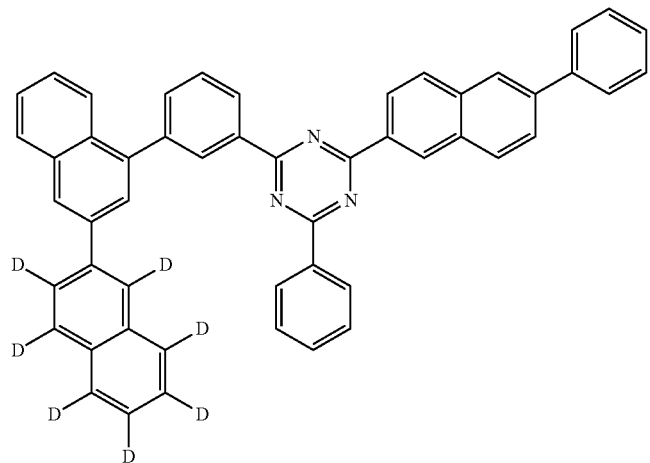
P-71
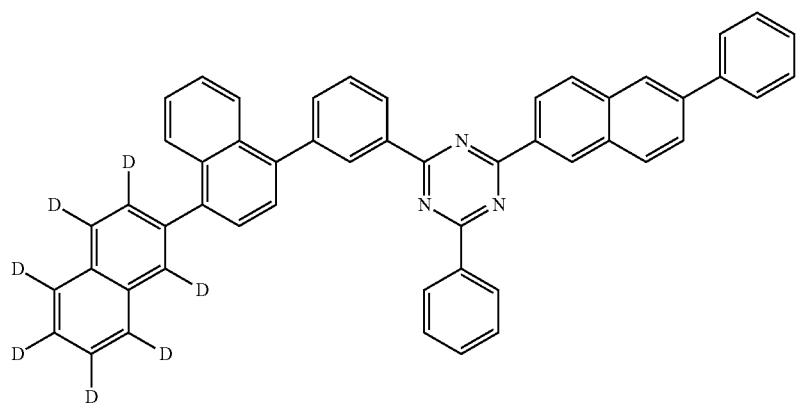
P-72
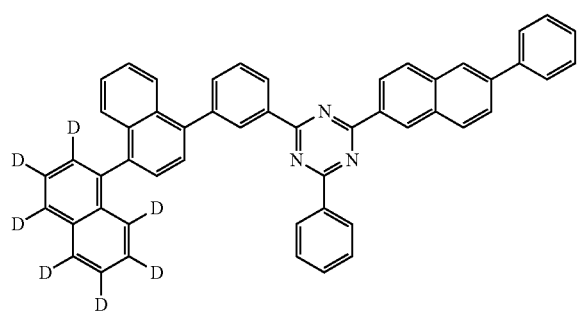
P-73
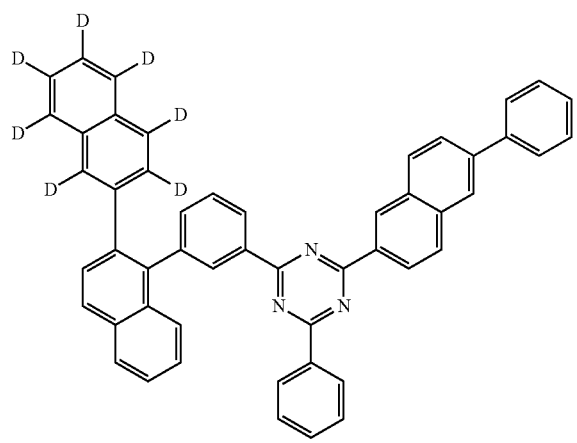

P-74
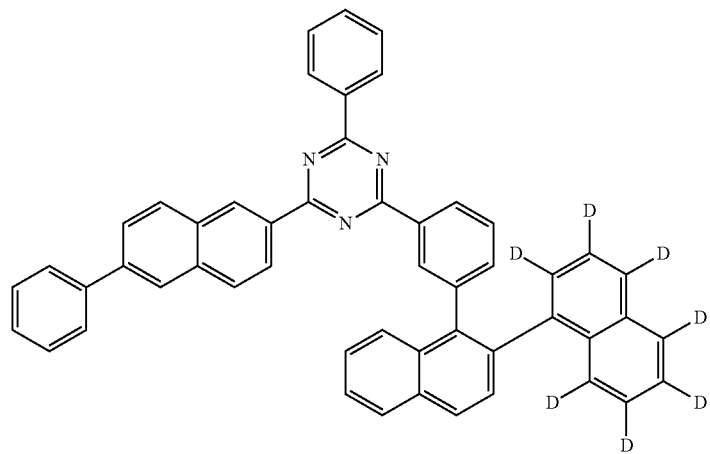
P-75
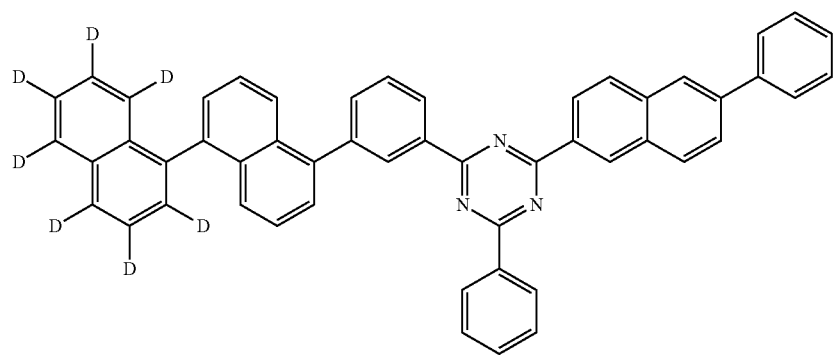
P-76
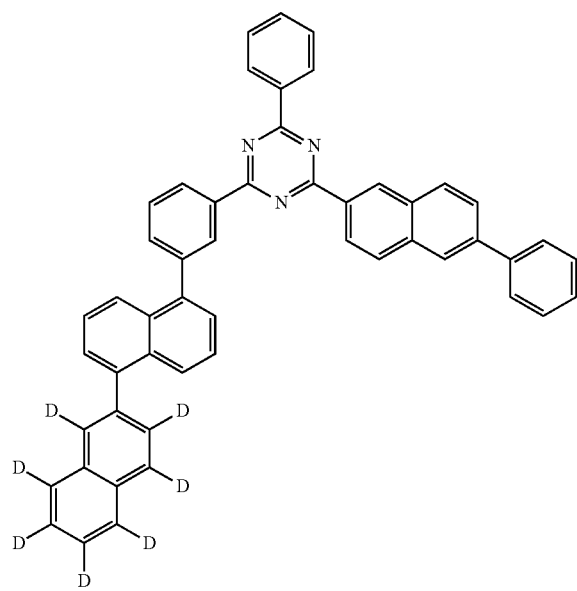
P-77
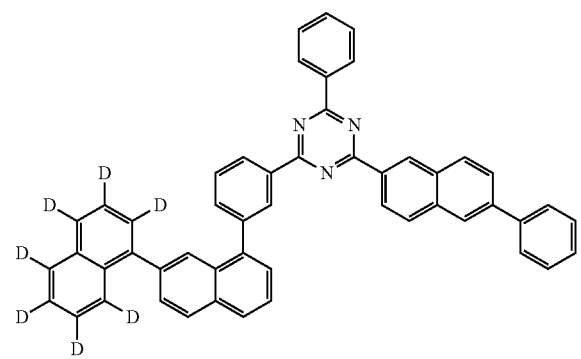

-continued
P-78
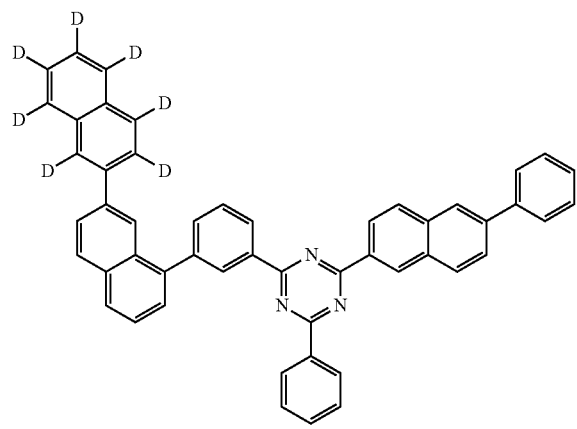
P-79
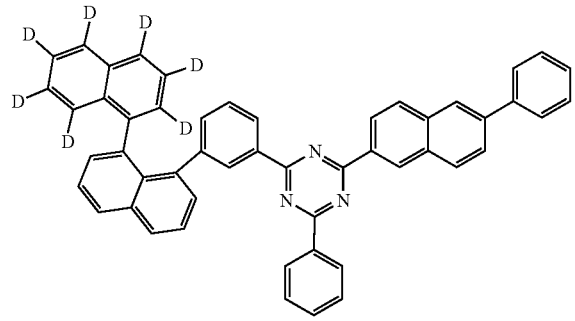
P-80
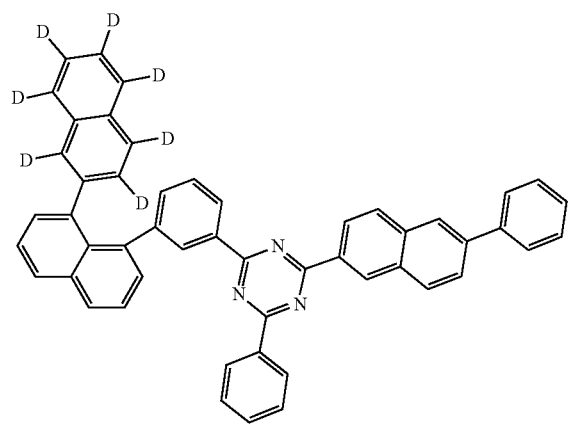
P-81
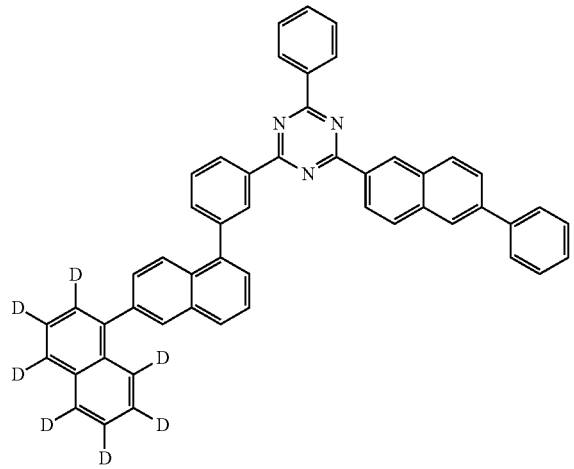
P-82
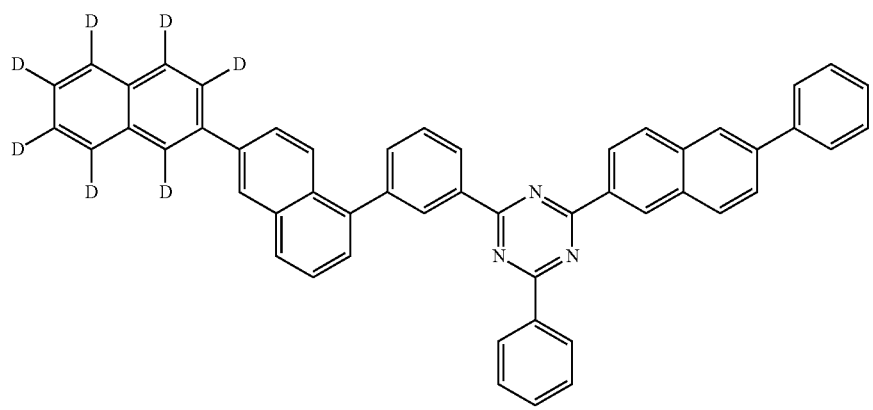

P-83
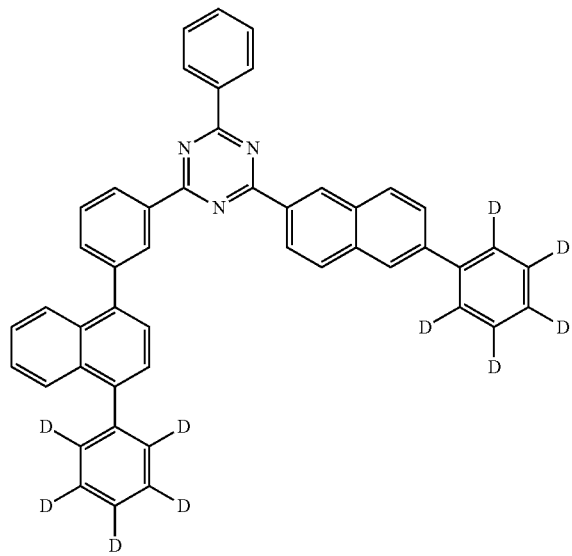
P-84
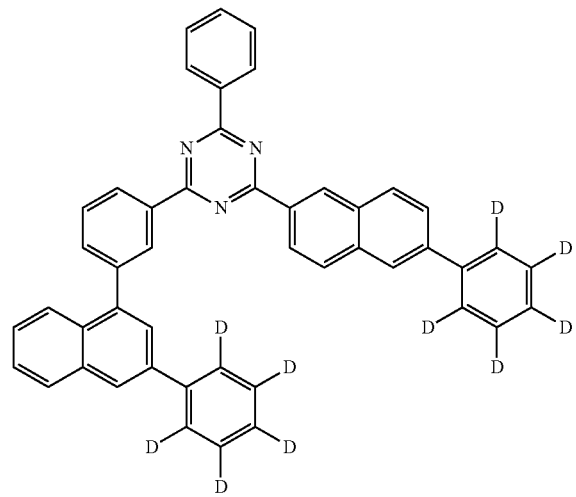
P-85
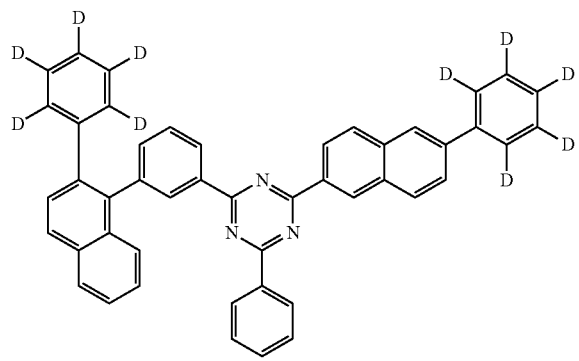
P-86
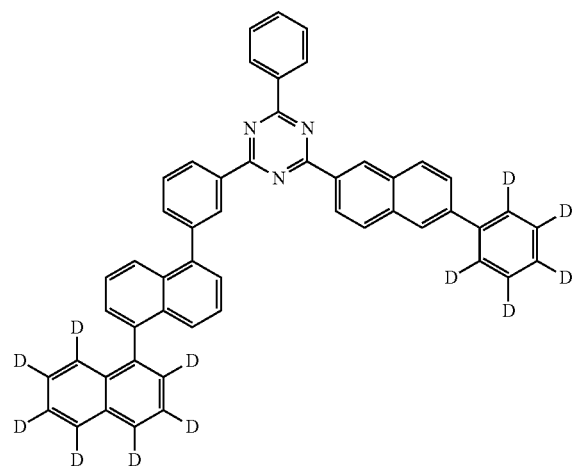
P-87
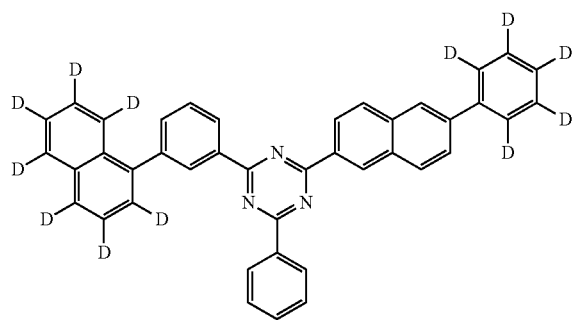
P-88
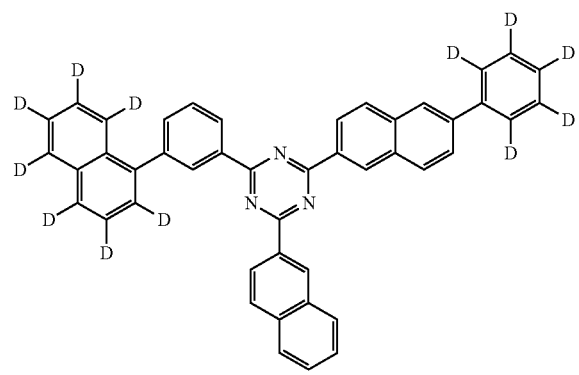

-continued
P-89
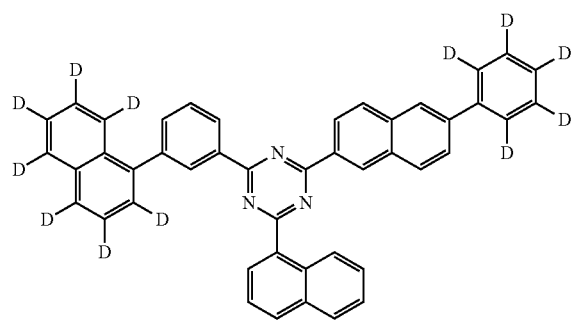
P-90
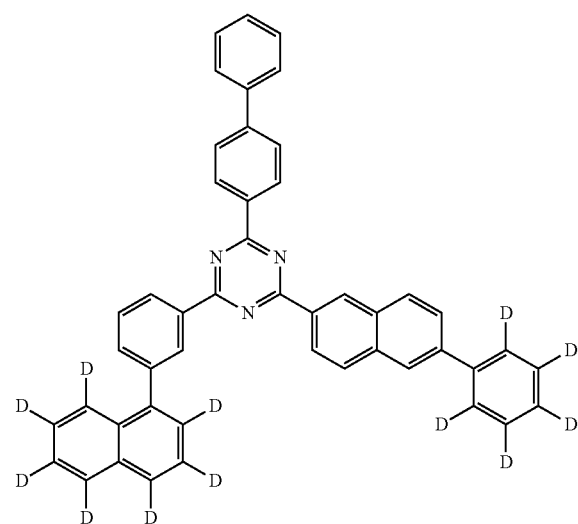
P-91
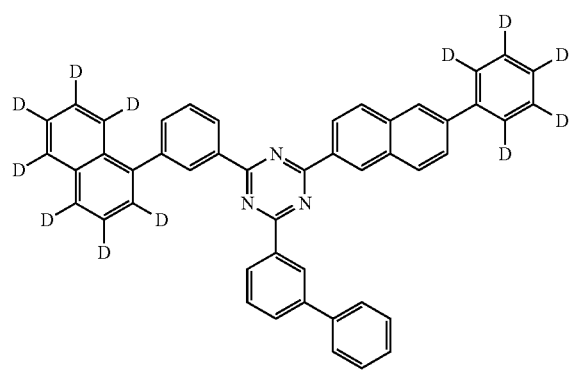
P-92
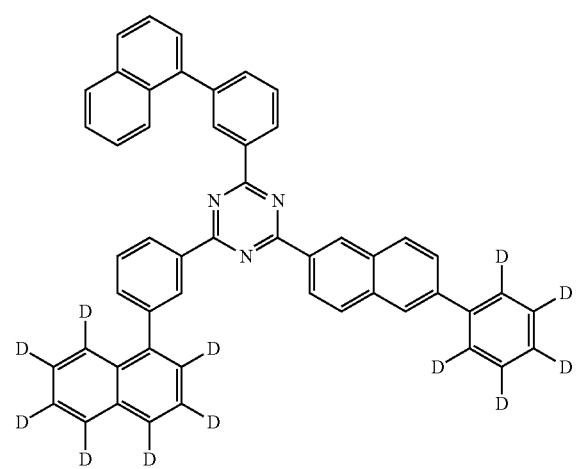

-continued
P-93
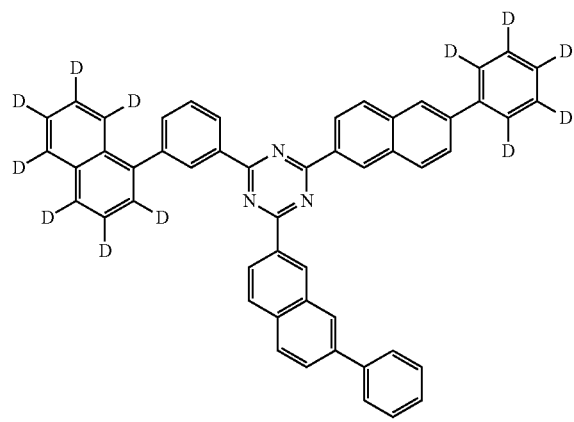
P-94
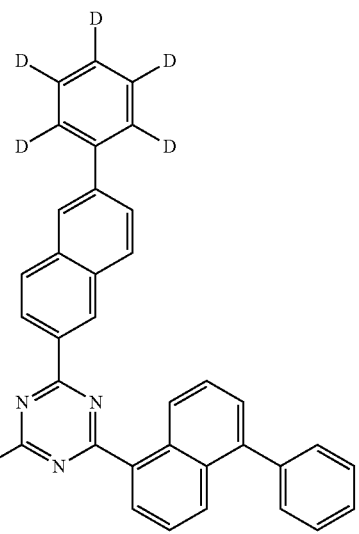
P-95
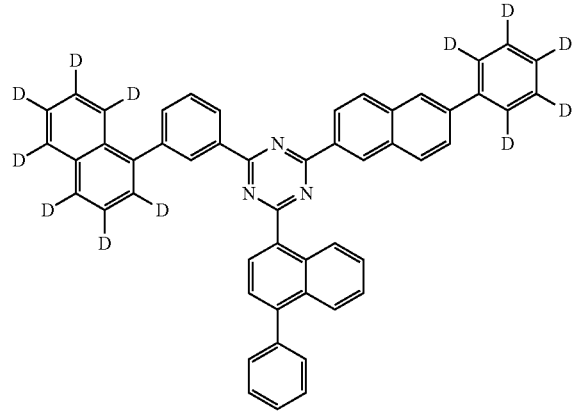
P-96
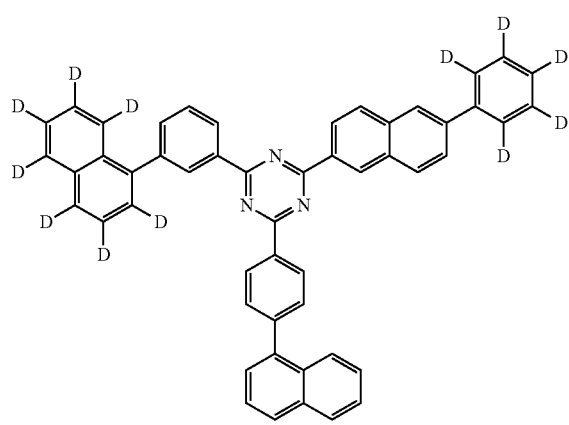
P-97
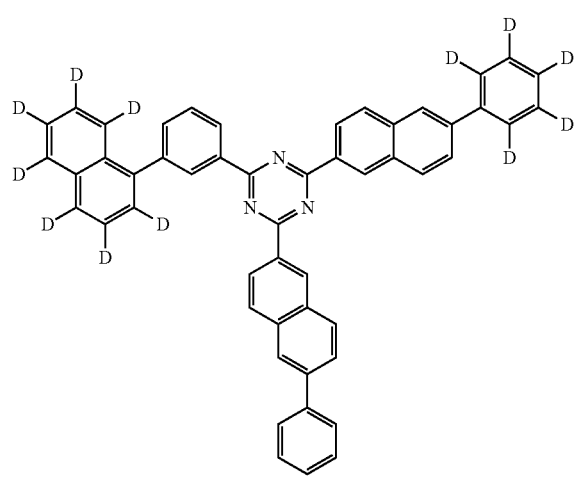
P-98
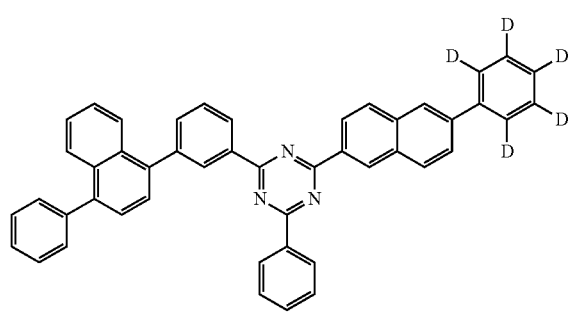

-continued
P-99
P-100
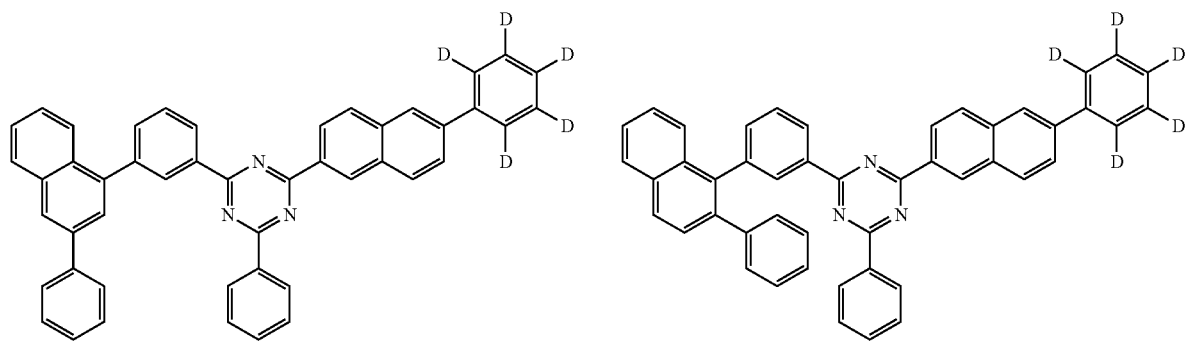
P-101
P-102
P-103
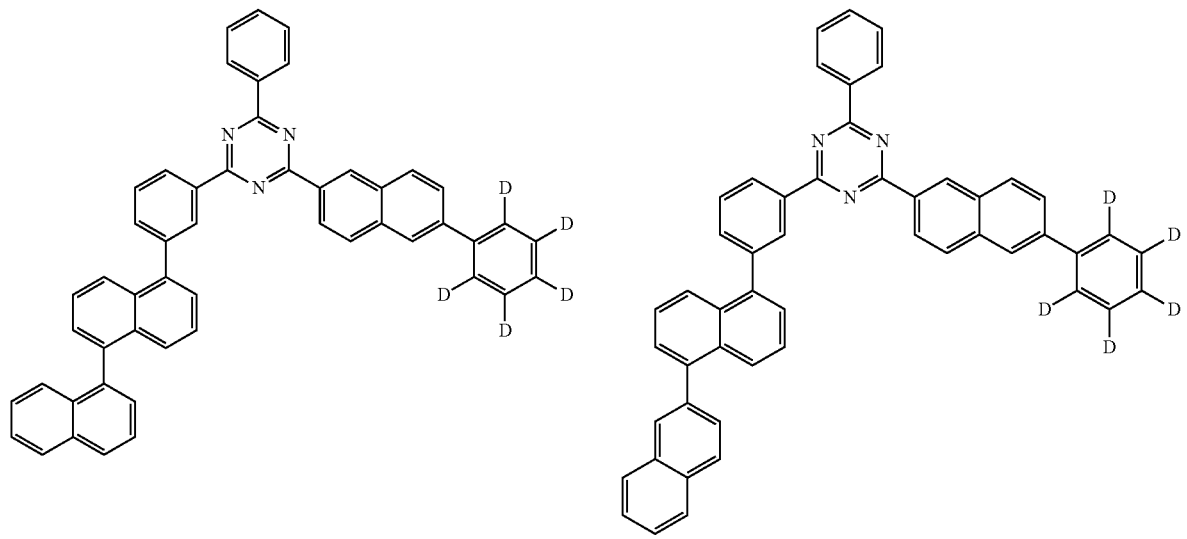
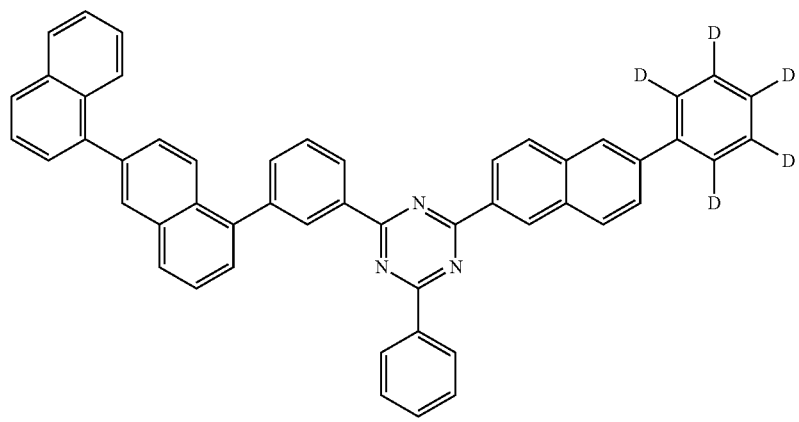

P-104

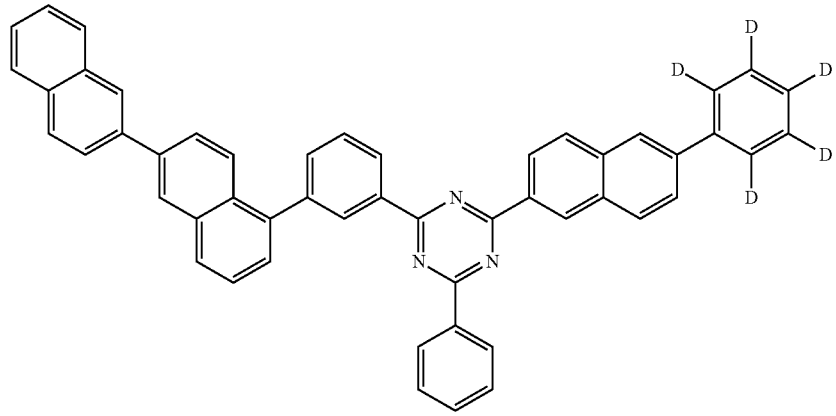

Also, the present invention relates to an organic electronic element comprising a first electrode, a second electrode, and an organic material layer formed between the first electrode and the second electrode, wherein the organic material layer includes an emitting layer, wherein the emitting layer is a phosphorescent emitting layer, and comprises a first host compound represented by Formula 1 of claim 1 and a second host compound represented by Formula 2 or Formula 3.

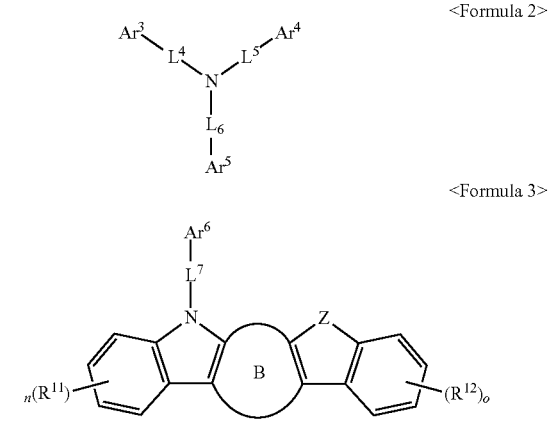

<Formula 2>

<Formula 3>

Wherein:

$L^4$, $L^5$, $L^6$ and $L^7$ are each independently selected from the group consisting of a single bond; a $C_6$-$C_{60}$ arylene group; fluorenylene group; a fused ring group of a $C_3$-$C_{60}$ aliphatic ring and a $C_6$-$C_{60}$ aromatic ring; a $C_2$-$C_{60}$ heterocyclic group;

wherein in case $L^4$, $L^5$, $L^6$ and $L^7$ are an arylene group, it is preferably an $C_6$-$C_{30}$ arylene group, more preferably an $C_6$-$C_{24}$ arylene group, for example, it may be phenylene, biphenyl, naphthalene, terphenyl, and the like.

when $L^4$, $L^5$, $L^6$ and $L^7$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

when $L^4$, $L^5$, $L^6$ and $L^7$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, $Ar^3$, $Ar^4$ and $Ar^5$ are each independently selected from the group consisting of a $C_6$-$C_{60}$ aryl group; fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

$Ar^6$ is each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-N($R^b$)($R^c$);

When $Ar^3$, $Ar^4$, $Ar^5$ and $Ar^6$ are an aryl group, it is preferably an $C_6$-$C_{30}$ aryl group, more preferably an $C_6$-$C_{24}$ aryl group, for example, it may be phenylene, biphenyl, naphthalene, terphenyl, and the like.

When $Ar^3$, $Ar^4$, $Ar^5$ and $Ar^6$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

when $Ar^3$, $Ar^4$, $Ar^5$ and $Ar^6$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, Wherein L' is selected from the group consisting of a single bond; a $C_6$-$C_{60}$ arylene group; a $C_2$-$C_{60}$ heterocyclic group including at least one heteroatom of O, N, S, Si or P;

Wherein $R^b$ and $R^c$ are each independently selected from the group consisting of a $C_6$-$C_{60}$ aryl group; fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P; $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group;

Z is O, S, CR'R" or NRa,

B is a $C_6$-$C_{20}$ aryl group,

R' and R" are each independently selected from a group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or may be bonded to each other to form a ring, $R^{11}$ and $R^{12}$ are each independently the same as or different from each other, and each independently selected from the group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_6$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or a plurality of adjacent $R^{11}$ or a plurality of $R^{12}$ may be bonded to each other to form a ring, When R', R", $R^{11}$ and $R^{12}$ are an aryl group, it is preferably an $C_6$-$C_{30}$ aryl group, more preferably an $C_6$-$C_{24}$ aryl group, for example, it may be phenylene, biphenyl, naphthalene, terphenyl, and the like.

When R', R", $R^{11}$ and $R^{12}$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

when R', R", $R^{11}$ and $R^{12}$ are a fused ring group, it is preferably a fused ring group of an $C_3$-$C_{30}$ aliphatic ring and an $C_6$-$C_{30}$ aromatic ring, and more preferably a fused ring group of an $C_3$-$C_{24}$ aliphatic ring and an $C_6$-$C_{24}$ aromatic ring, when R', R", $R^{11}$ and $R^{12}$ are an alkyl group, it is preferably a $C_1$-$C_{30}$ alkyl group, and more preferably a $C_1$-$C_{24}$ alkyl group.

when R', R", $R^{11}$ and $R^{12}$ are an alkoxyl group, it is preferably a $C_1$-$C_{24}$ alkoxyl group.

when R', R", $R^{11}$ and $R^{12}$ are an aryloxy group, it is preferably a $C_1$-$C_{24}$ aryloxy group.

n and o are each independently an integer from 0 to 4,

Ra is a $C_6$-$C_{60}$ aryl group; or a $C_2$-$C_{60}$ heterocyclic group including at least one heteroatom of O, N, S, Si and P;

When Ra is an aryl group, it is preferably an $C_6$-$C_{30}$ aryl group, more preferably an $C_6$-$C_{24}$ aryl group, for example, it may be phenylene, biphenyl, naphthalene, terphenyl, and the like.

When Ra is a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzofuran, Benzothienopyrimidine, benzofuropyrimidine, phenothiazine, phenylphenothiazine.

wherein the aryl group, arylene group, heterocyclic group, fluorenyl group, fluorenylene group, fused ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Formula 2 is represented by any one of Formulas 2-1 to 2-3.

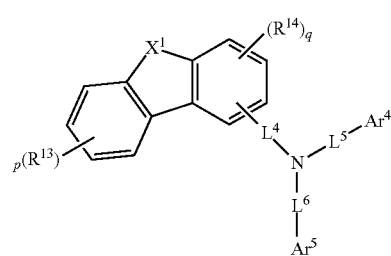

Formula 2-1

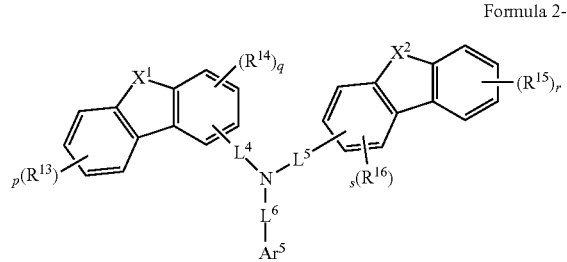

Formula 2-2

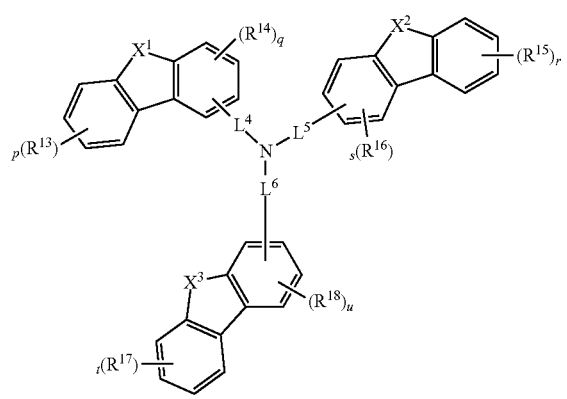

Formula 2-3

Wherein:

$Ar^4$, $Ar^5$, $L^4$, $L^5$ and $L^6$ are the same as defined in Formula 2, $X^1$, $X^2$ and $X^3$ are the same as defined for Z, $R^{13}$, $R^{14}$, $R^{15}$, $R^{16}$, $R^{17}$ and $R^{18}$ are the same as the definition of $R^{11}$, or a plurality of adjacent $R^{13}$s or a plurality of $R^{14}$s or a plurality of $R^{15}$s or a plurality of $R^{16}$s or a plurality of $R^{17}$s or a plurality of $R^1$s may be bonded to each other to form a ring, p, r and t are an integer of 0 to 4, q, s and u are each independently an integer from 0 to 3.

Formula 3 is represented by any one of Formulas 3-1 to 3-6.

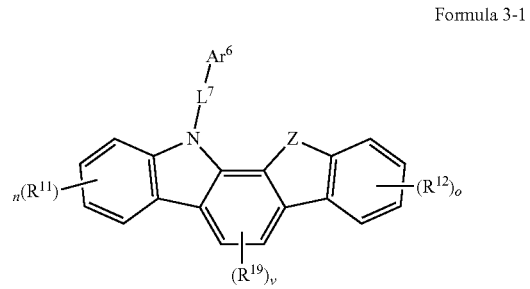

Formula 3-1

Formula 3-2

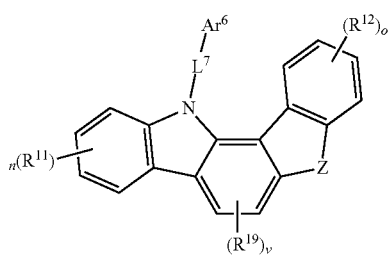

Formula 3-3

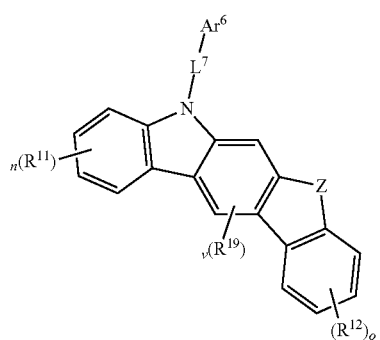

Formula 3-4

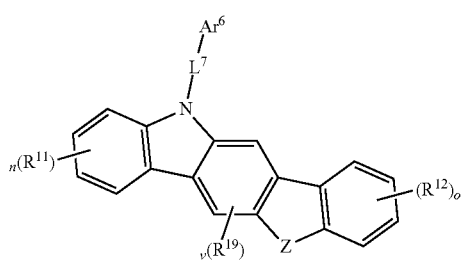

Formula 3-5

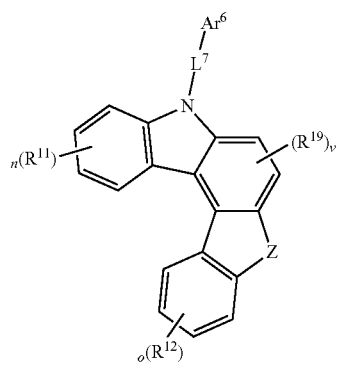

Formula 3-6

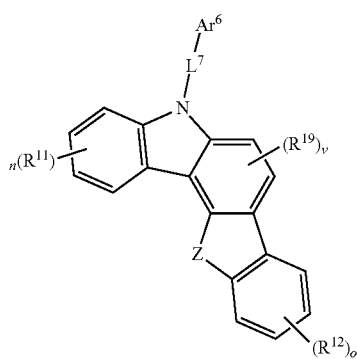

Wherein:

Z, $R^{11}$, $R^{12}$, $Ar^6$, $L^7$, n, o are the same as defined in Formula 3, $R^{19}$ is the same as the definition of $R^{11}$, v is an integer from 0 to 2.

Formula 3 is represented by any one of Formulas 3-7 to 3-9.

<Formula 3-7>

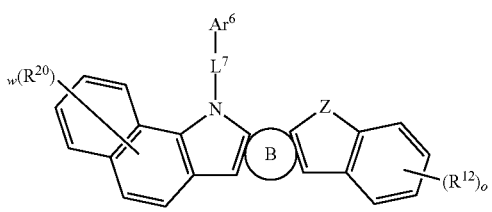

<Formula 3-8>

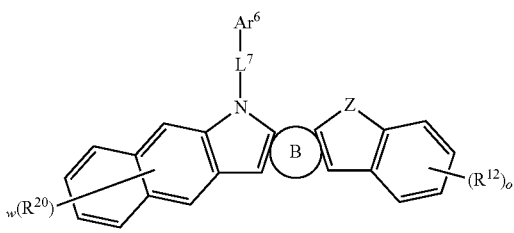

<Formula 3-9>

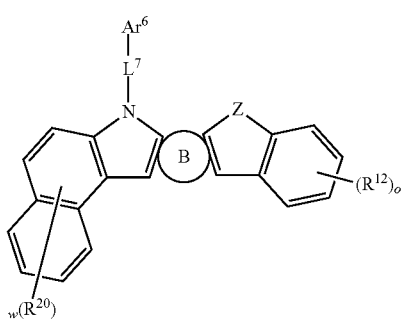

Wherein:

Z, B, $R^{12}$, o, $Ar^6$ and $L^7$ are the same as defined in Formula 3, $R^{20}$ is the same as the definition of $R^{11}$, w is an integer from 0 to 6

Formula 3 is represented by any one of Formulas 3-10 to 3-12.

Formula 3-10

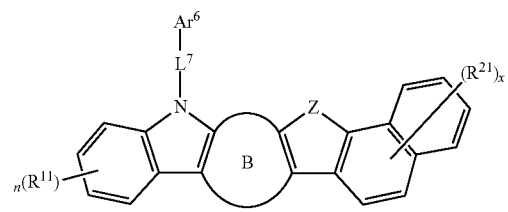

<Formula 3-11>

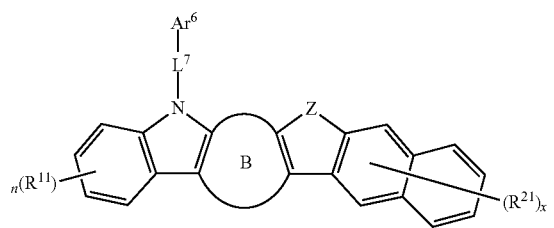

<Formula 3-12>

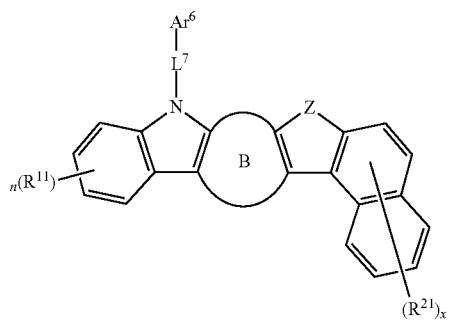

Wherein:

Z, B, Ar⁶, L⁷, R¹¹ and n are the same as defined in Formula 3,

R²¹ is the same as definition of R¹¹, x is an integer from 0 to 6.

Formula 3 is represented by Formulas 3-13 to 3-18.

<Formula 3-13>

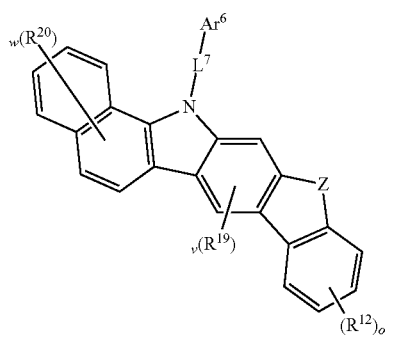

<Formula 3-14>

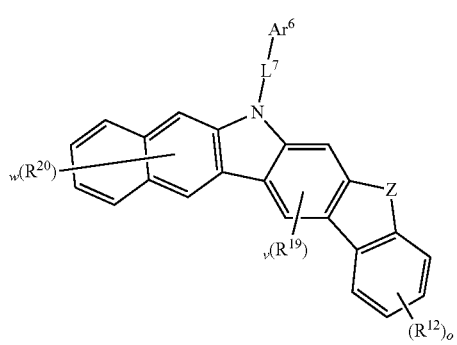

<Formula 3-15>

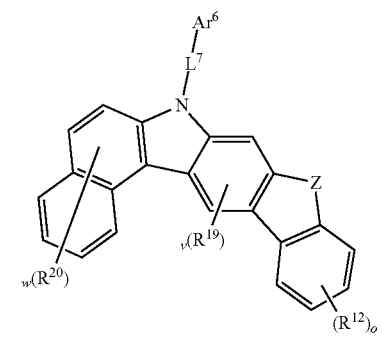

<Formula 3-16>

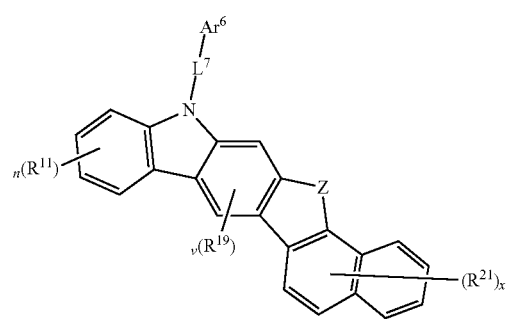

<Formula 3-17>

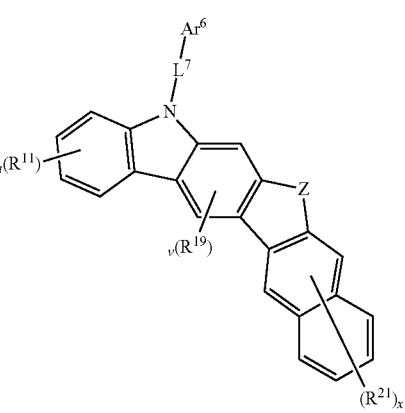

<Formula 3-18>

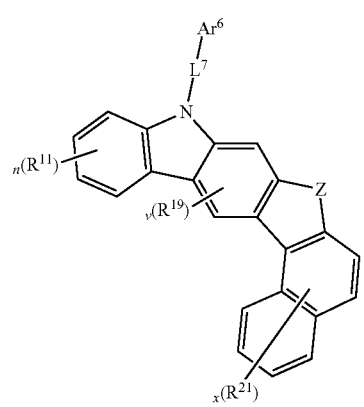

Wherein:

Z, L⁷, Ar⁶, R¹¹, R¹², n and o are the same as defined in Formula 3,

R¹⁹, R²⁰ and R²¹ are the same as the definition of R¹¹, v is an integer from 0 to 2, w and x are each independently an integer from 0 to 6.

Formula 3 is represented by Formula 3-19.

<Formula 3-19>

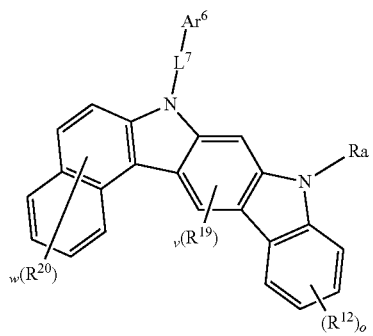

wherein:

$L^7$, $Ar^6$, Ra, $R^{12}$ and o are the same as defined in Formula 3, $R^{19}$ and $R^{20}$ are the same as the definition of $R^{11}$, v is an integer from 0 to 2, w is an integer from 0 to 6.

Also, the compound represented by Formula 2 is any one of the following compounds N-1 to N-96.

N-1

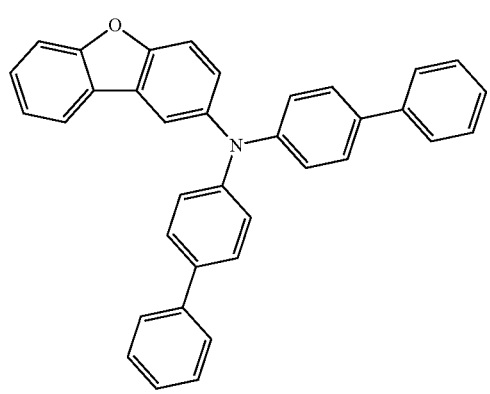

N-2

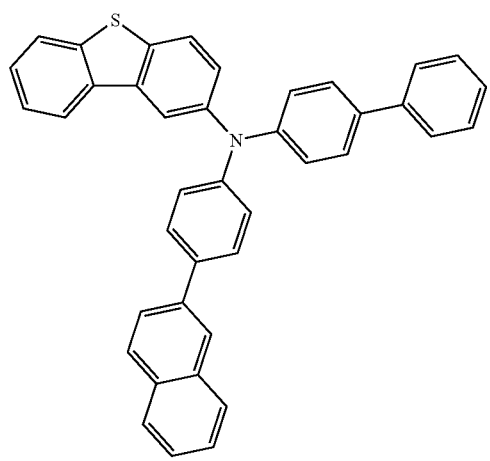

N-3

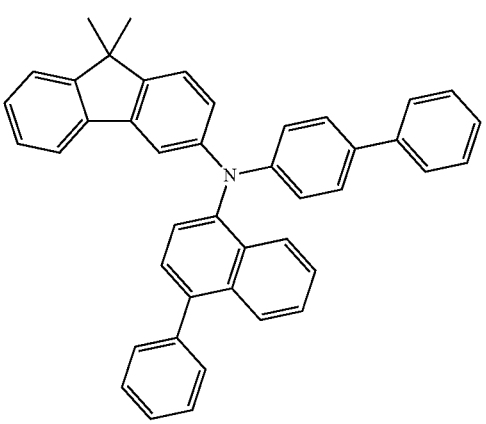

N-4

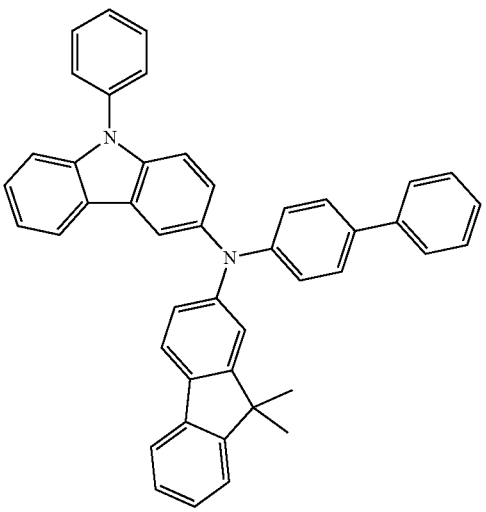

N-5

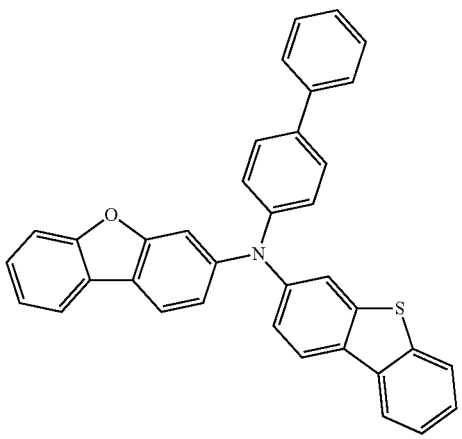

N-6
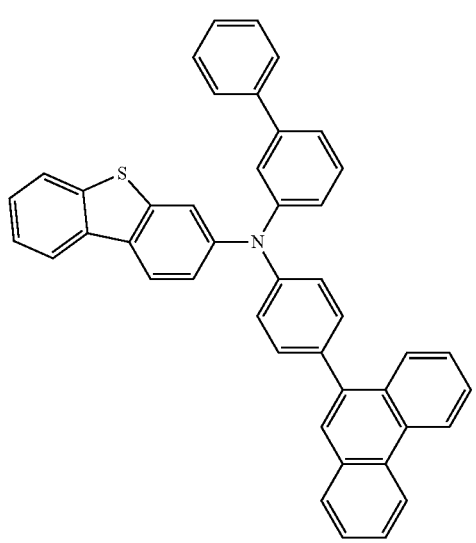
N-9
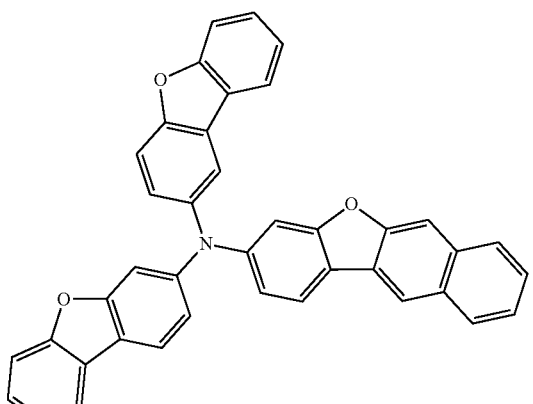
N-7
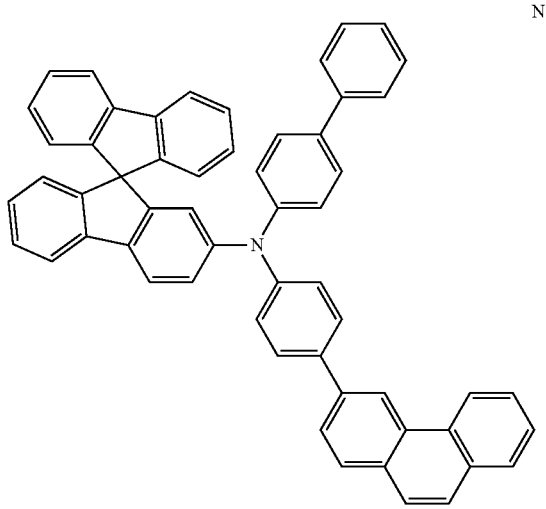
N-10
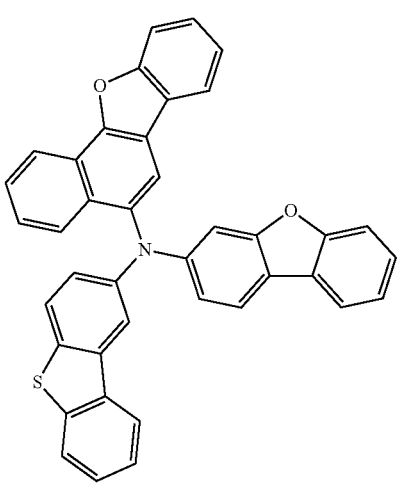
N-8
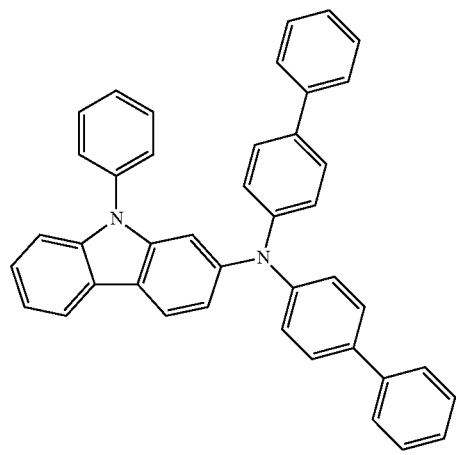
N-11
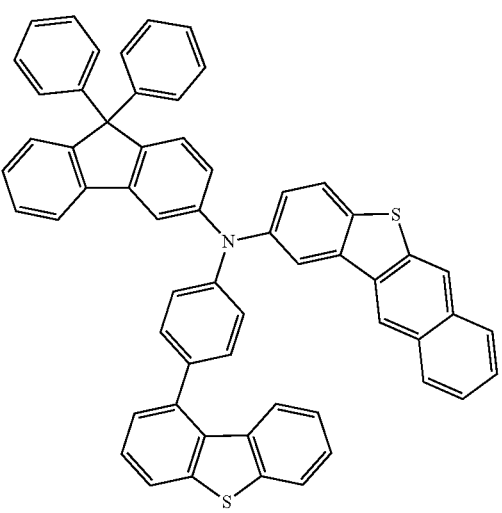

N-12
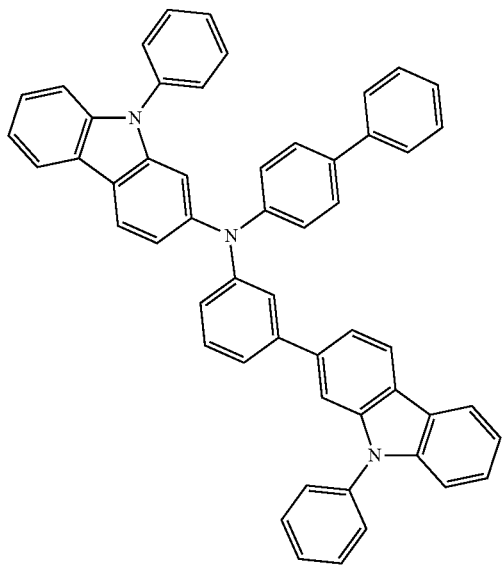
N-15
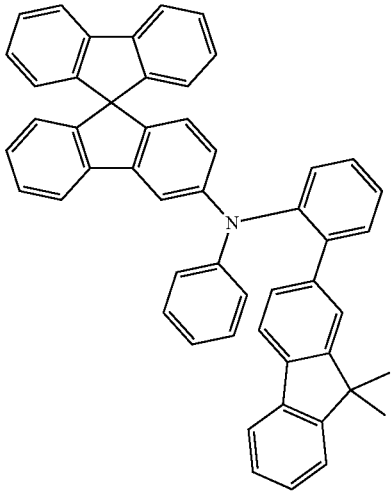
N-13
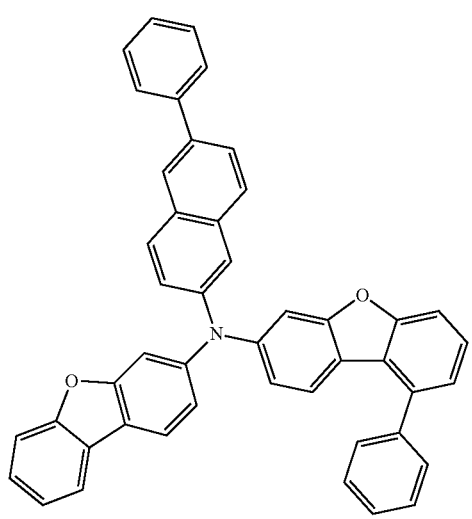
N-16
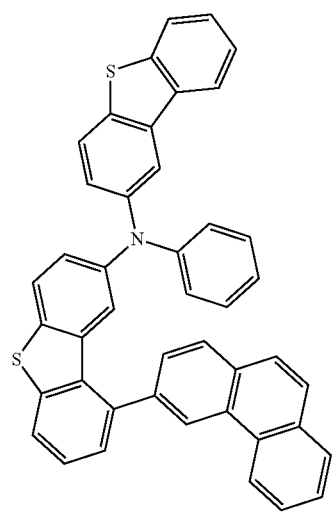
N-14
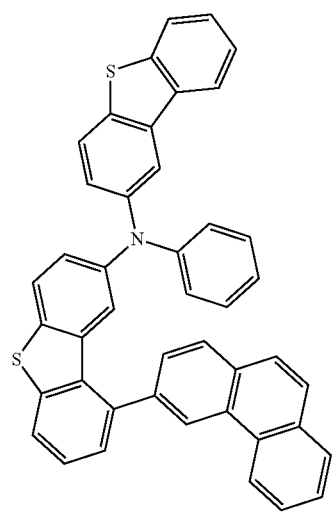
N-17
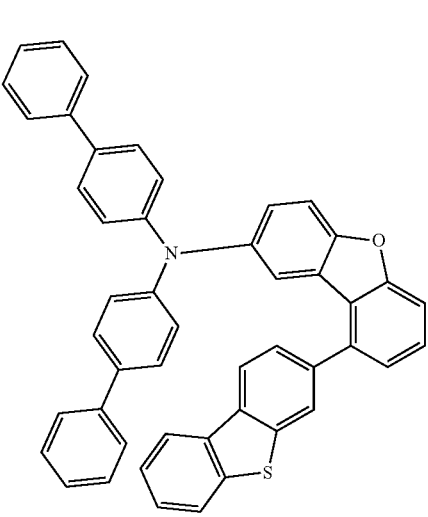

N-18
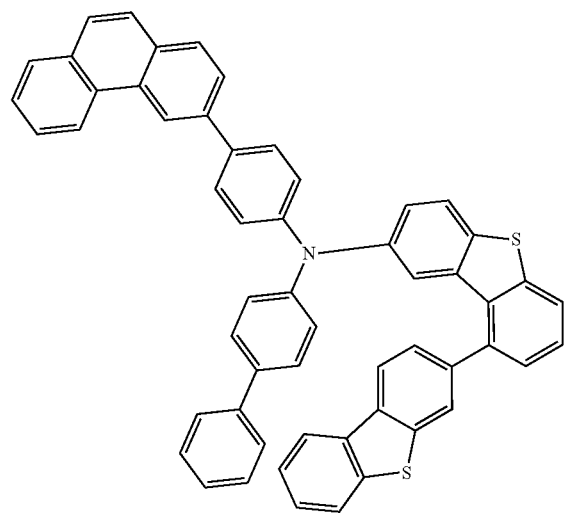
N-19
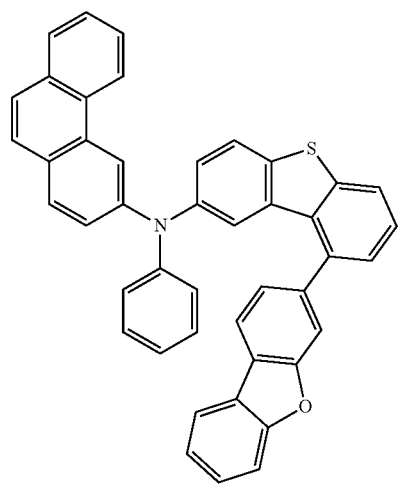
N-20
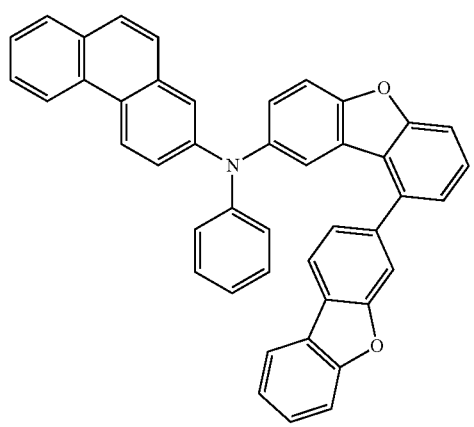
N-21
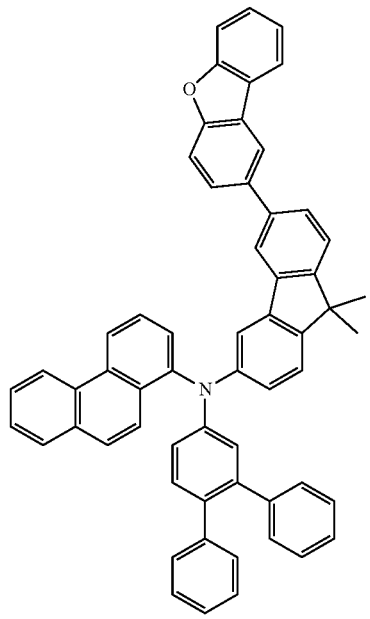
N-22
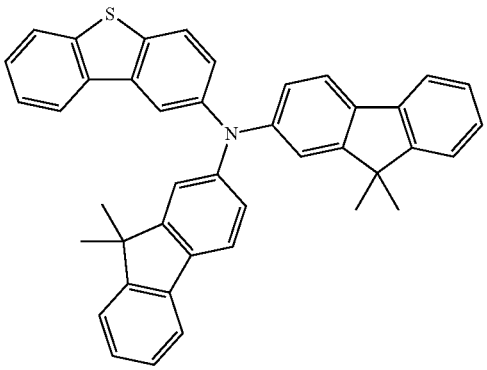
N-23
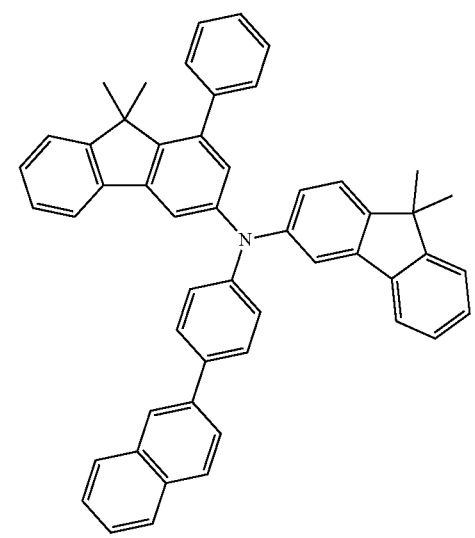

N-24
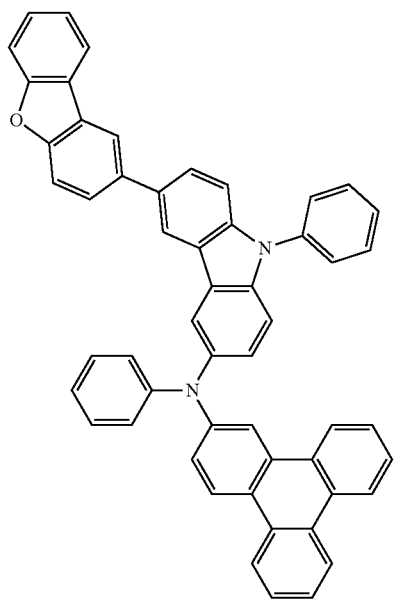
N-25
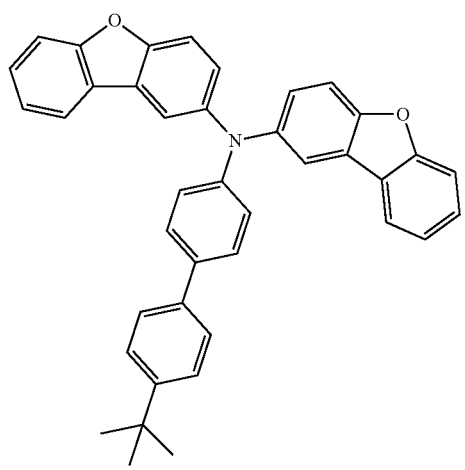
N-27
N-28
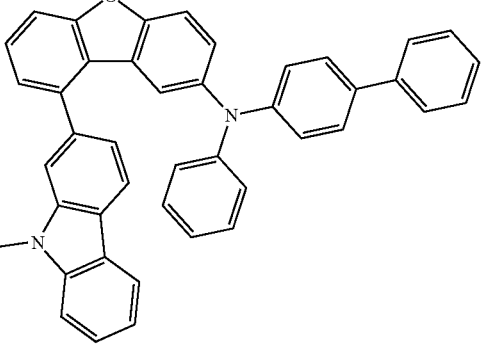
N-26
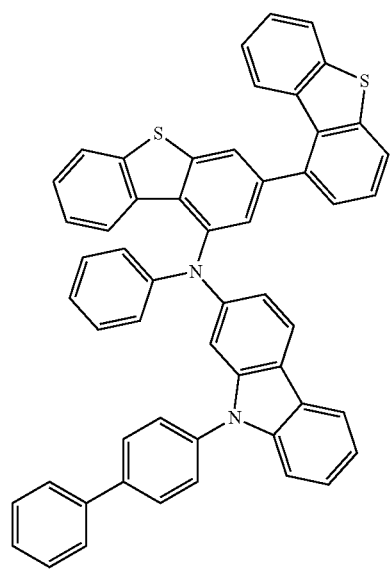
N-29
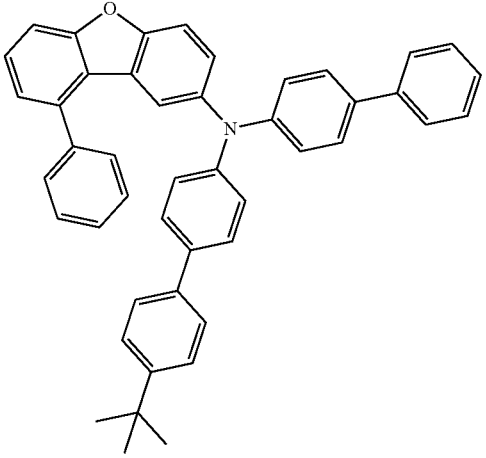

N-30
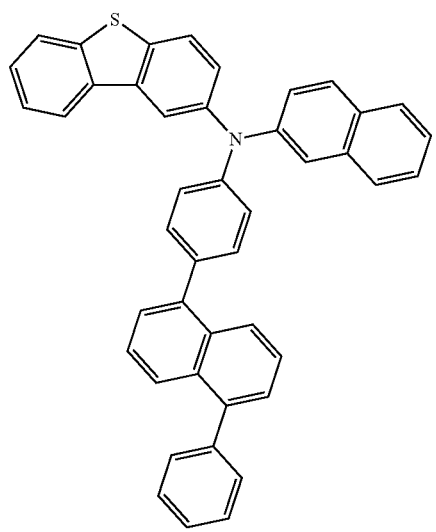
N-32
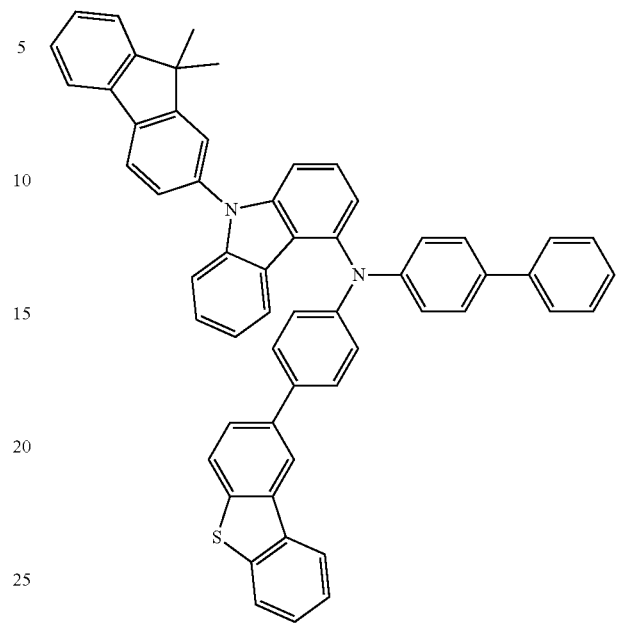
N-33
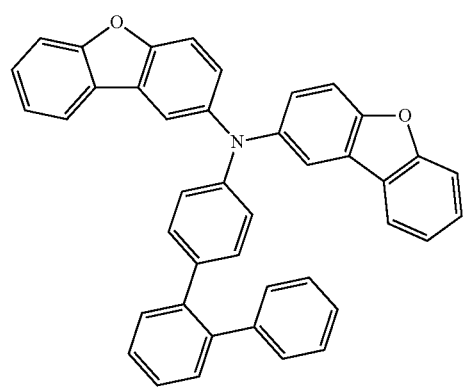
N-31
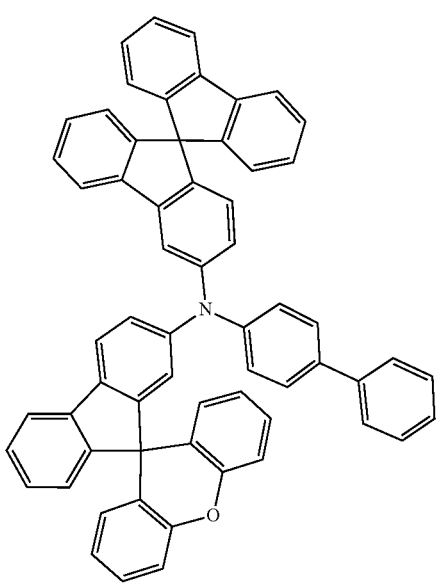
N-34
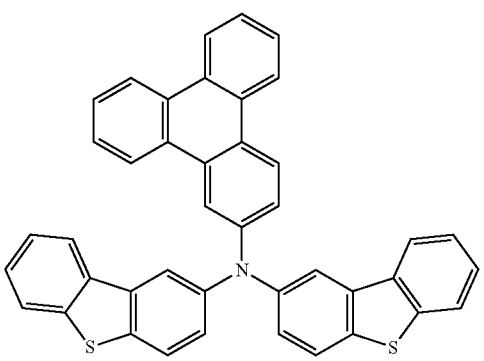

N-35
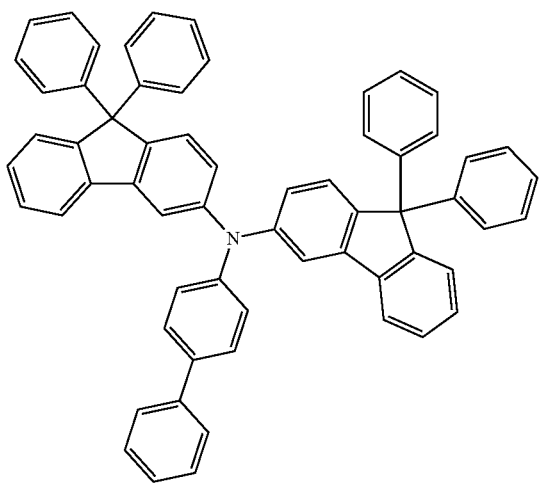
N-36
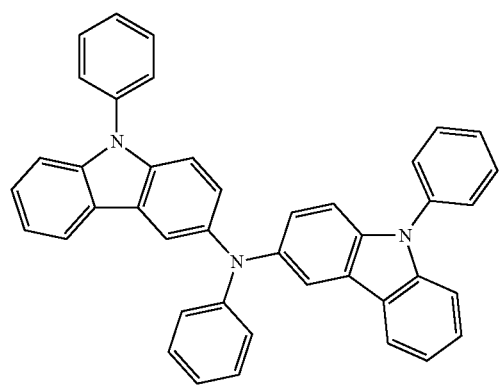
N-37
N-38
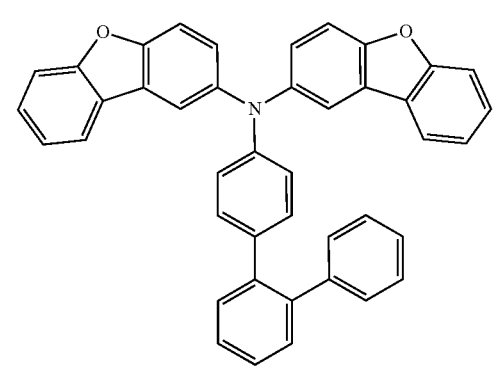
N-39
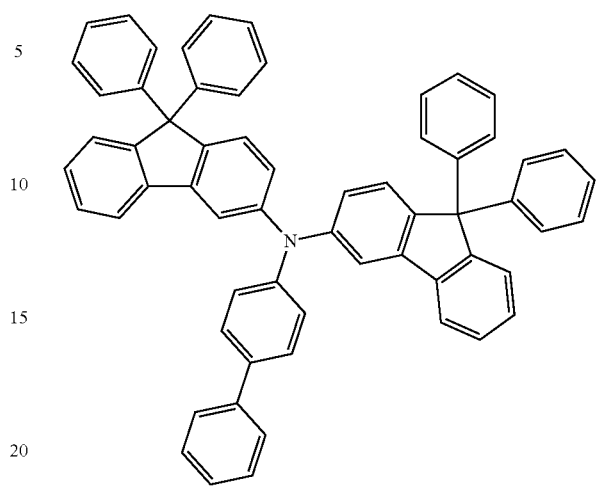
N-40
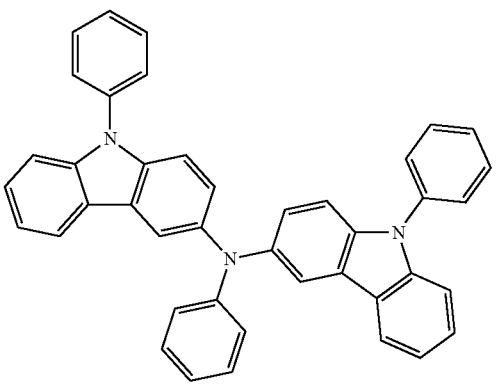
N-41
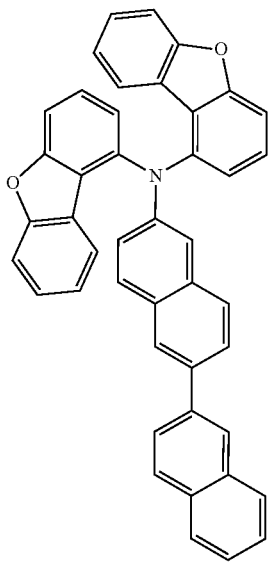

-continued
N-42
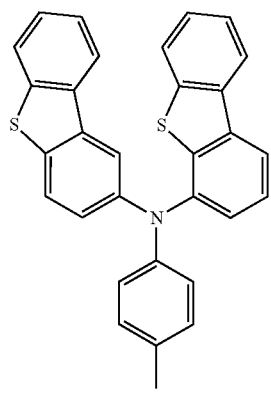
N-45
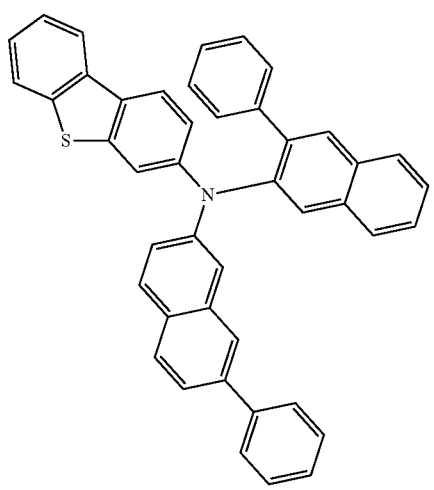
N-43
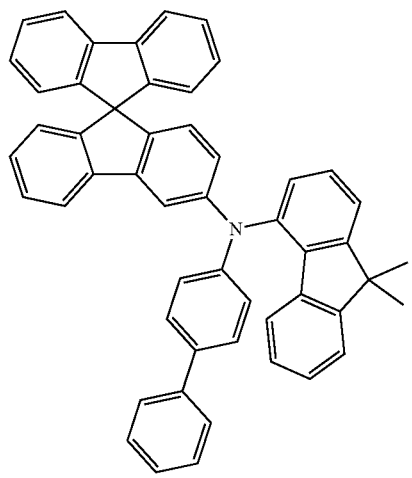
N-46
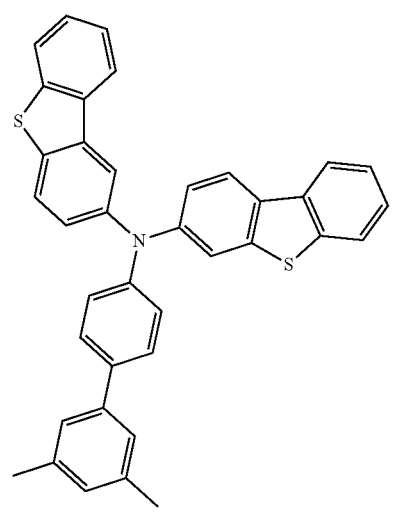
N-44
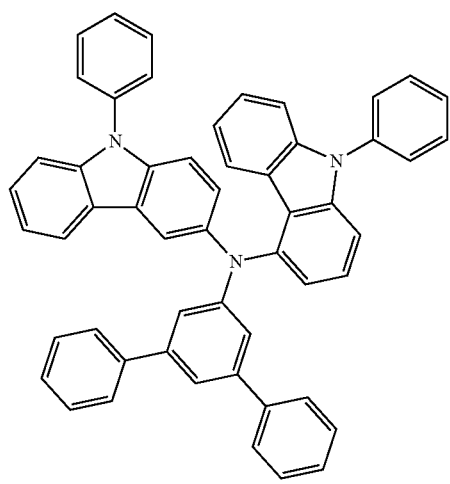
N-47
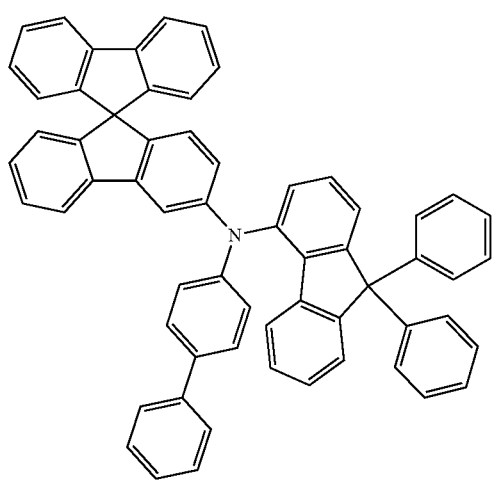

-continued
N-48
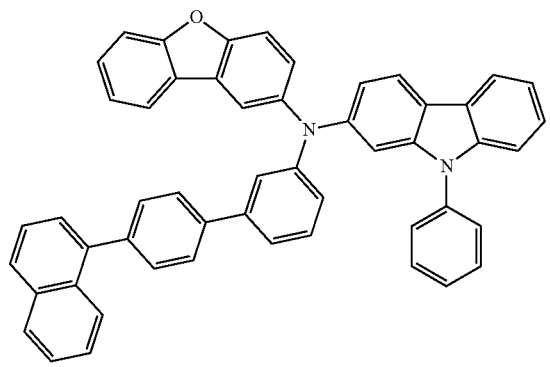
N-49
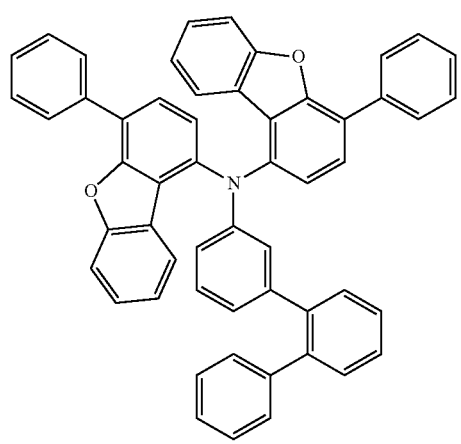
N-50
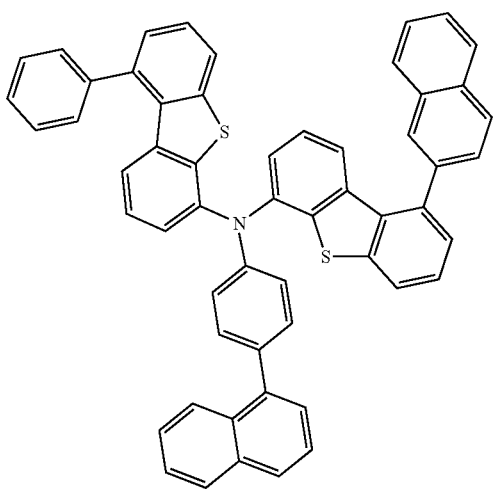
N-51
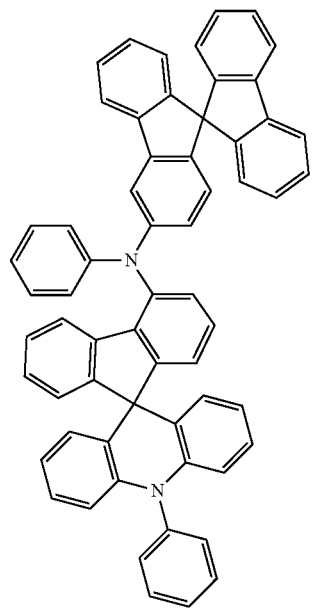
N-52
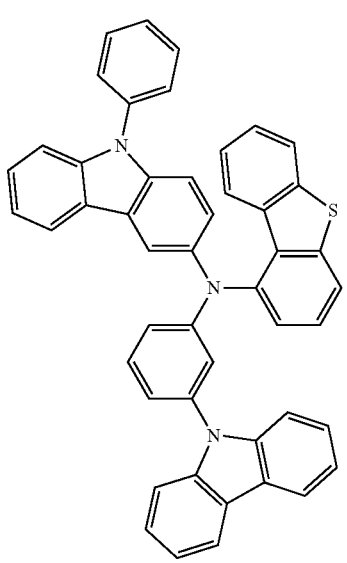
N-53
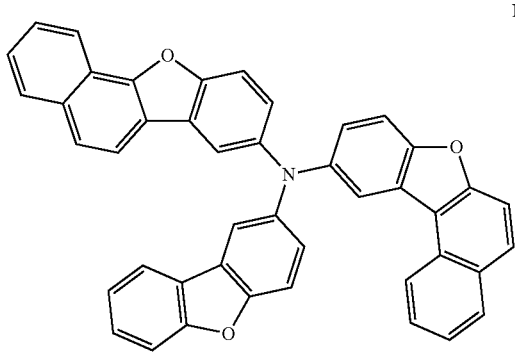

N-54
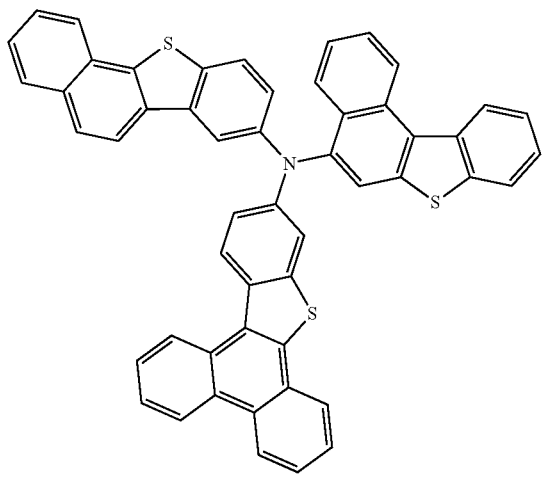
N-55
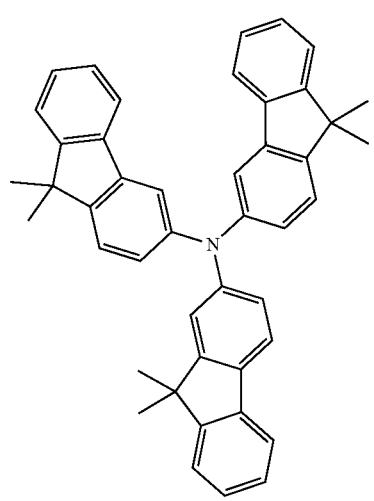
N-56
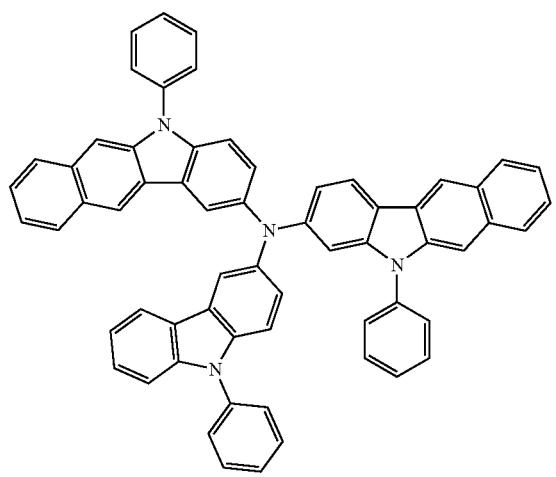
N-57
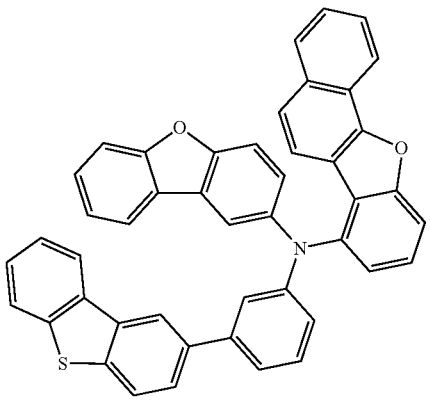
N-58
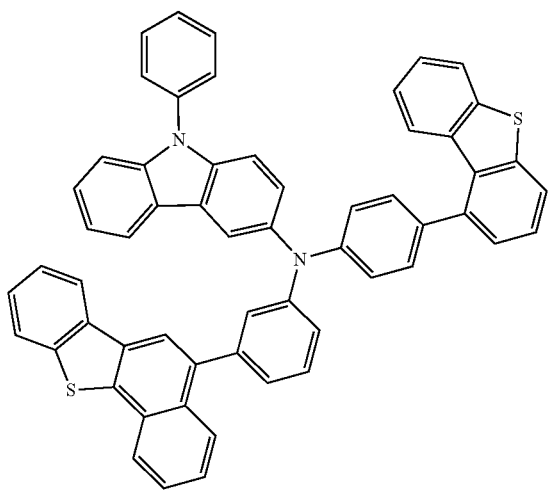
N-59
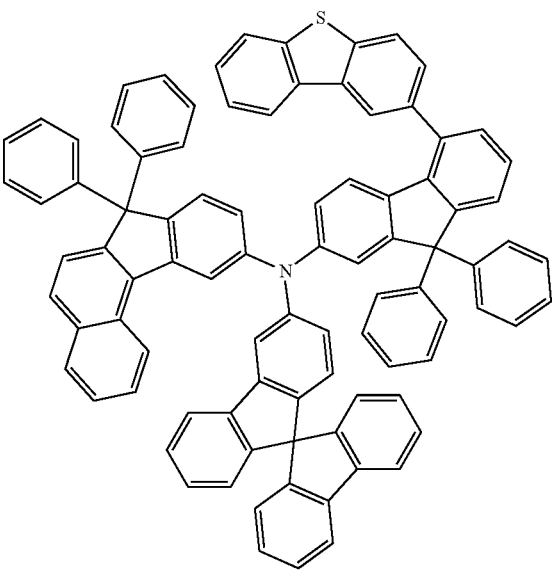

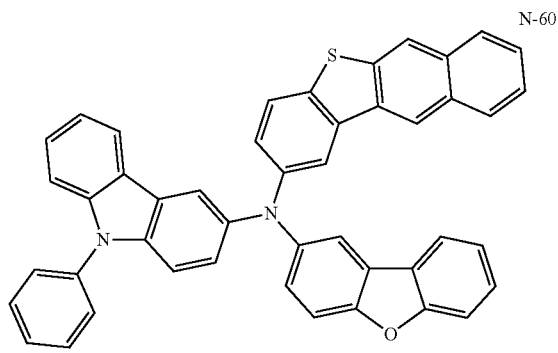
N-60
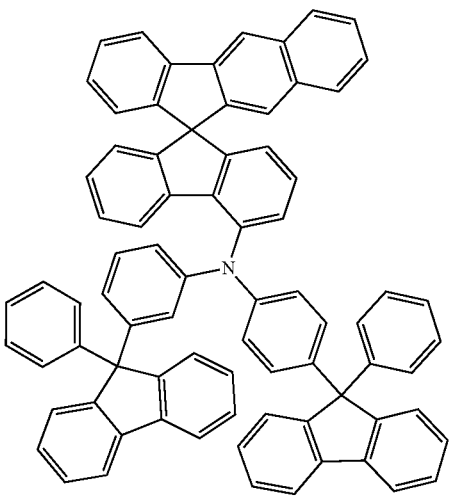
N-63
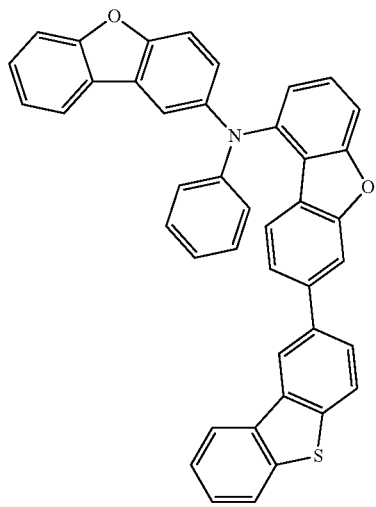
N-61
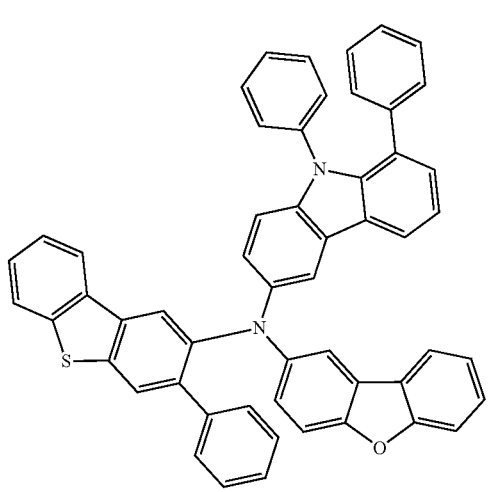
N-64
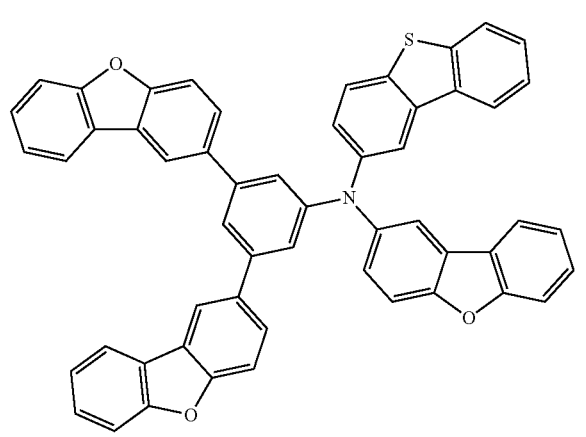
N-62
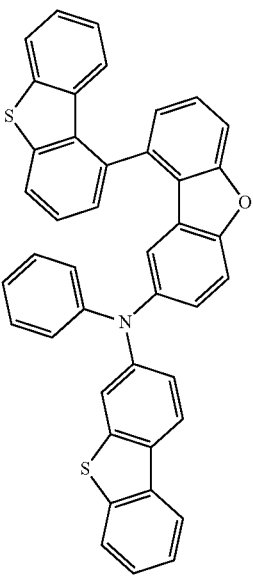
N-65

-continued
N-66
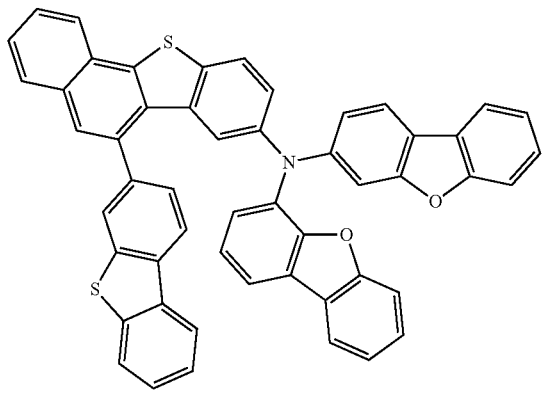
N-67
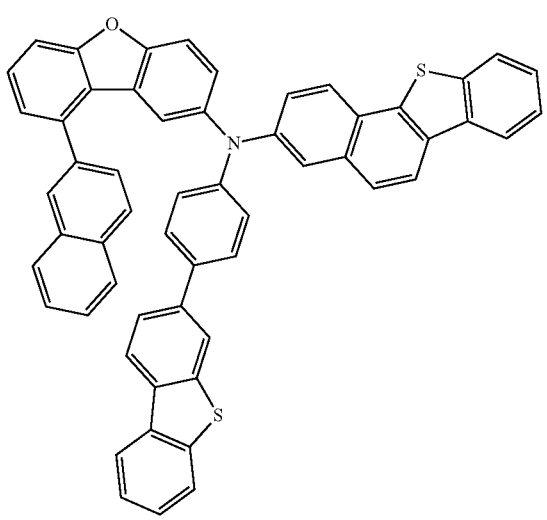
N-68
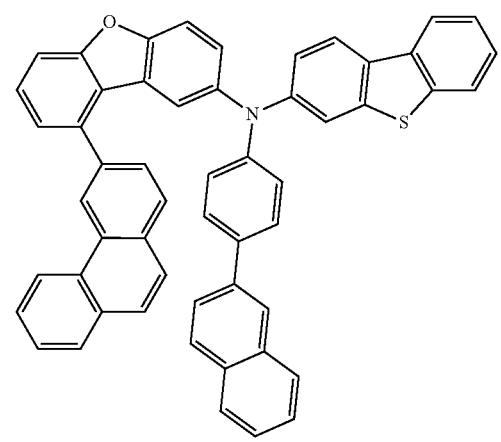
N-69
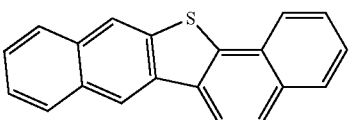
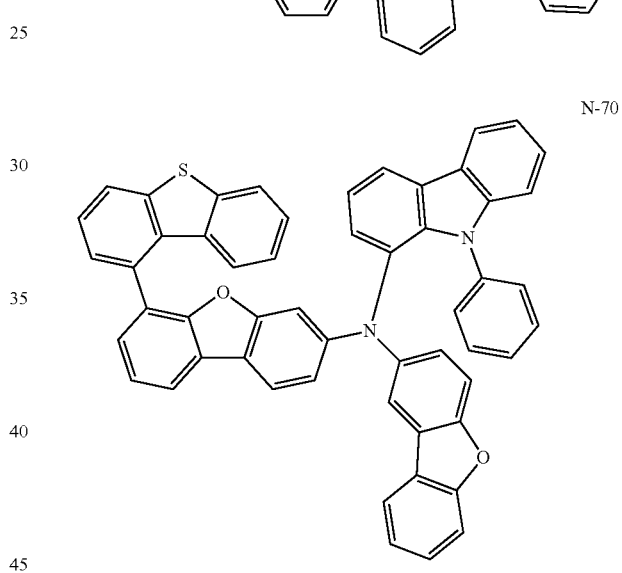
N-70
N-71
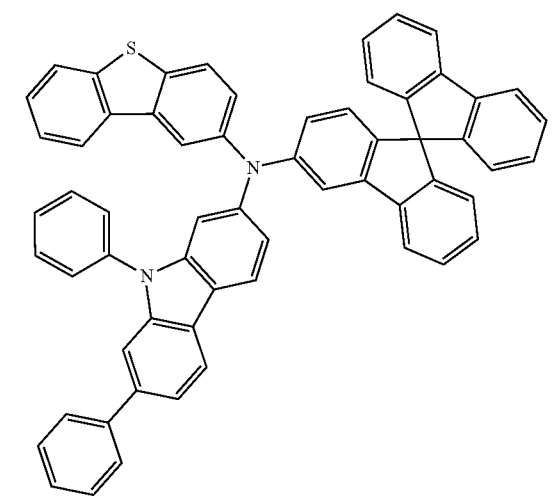

N-72
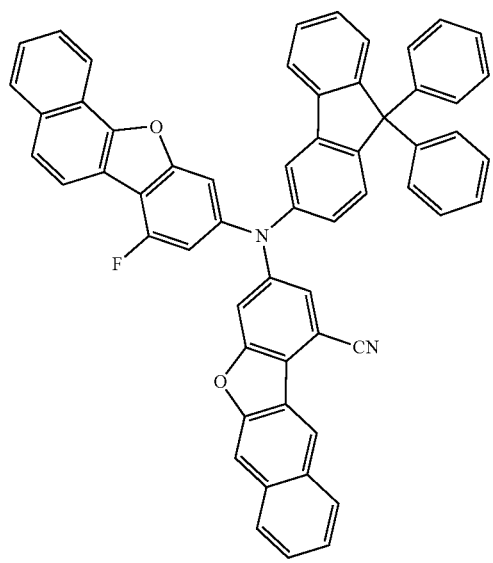
N-74
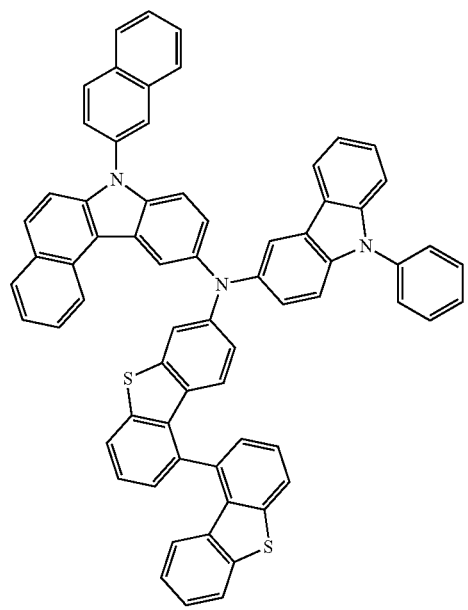
N-73
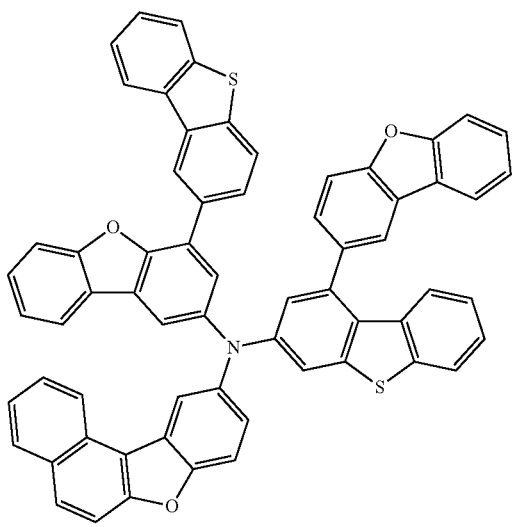
N-75
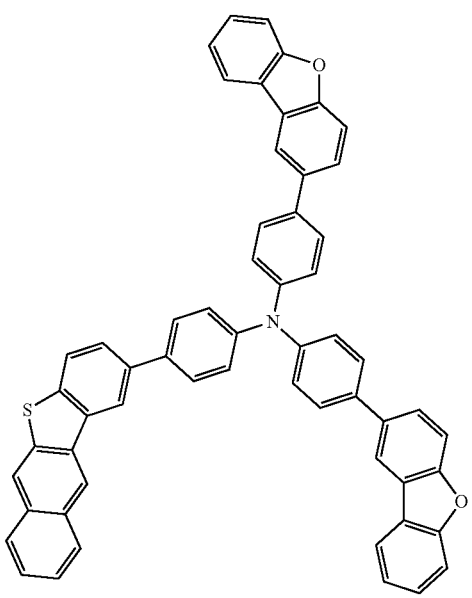

N-76
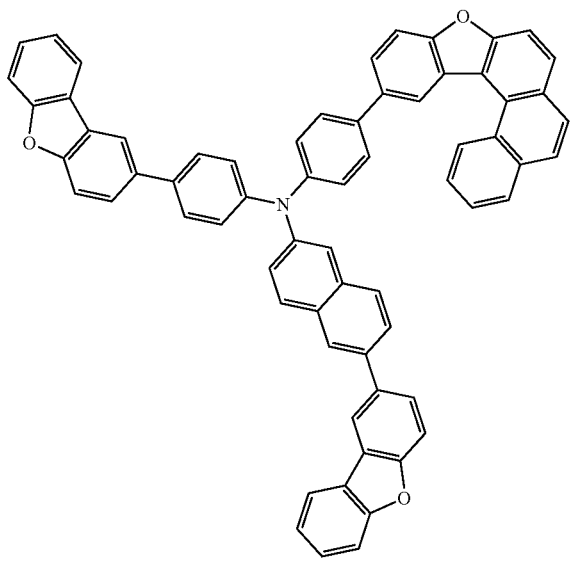
N-78
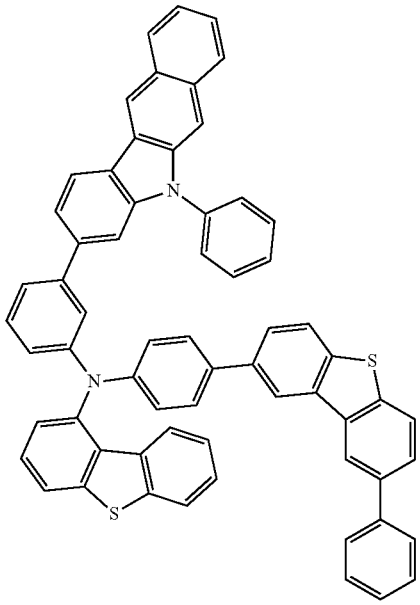
N-77
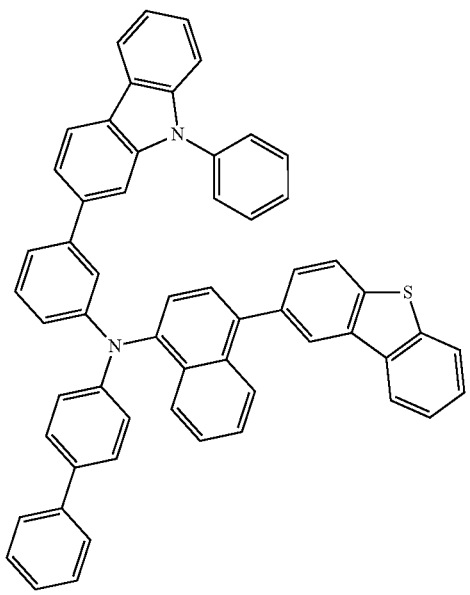
N-79
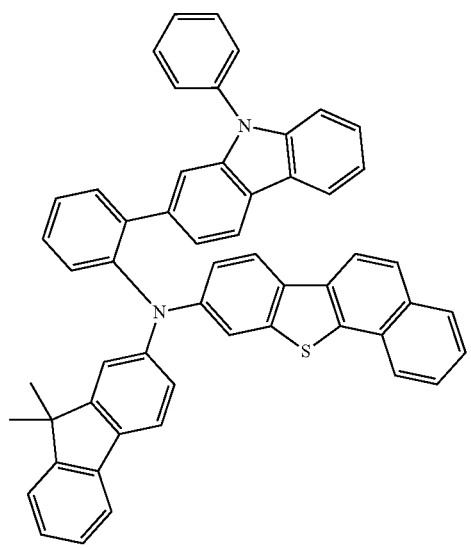

N-80
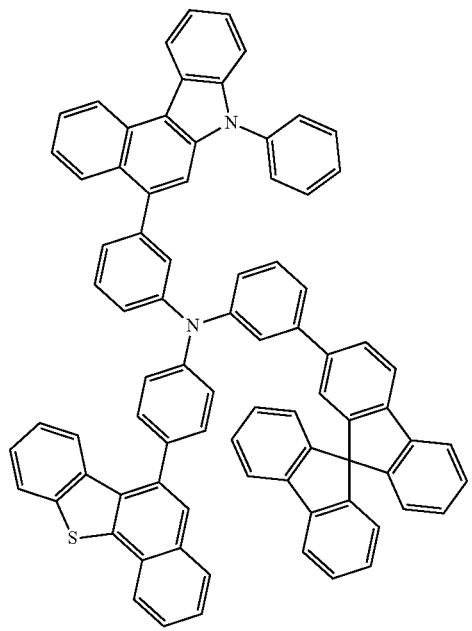
N-82
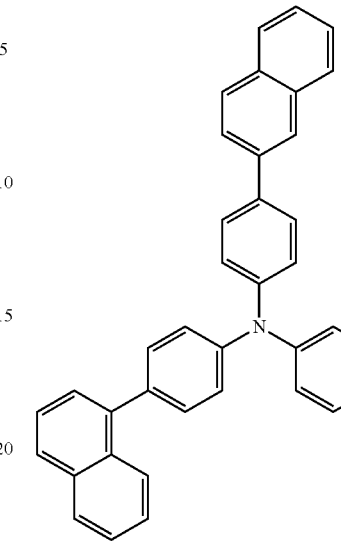
N-81
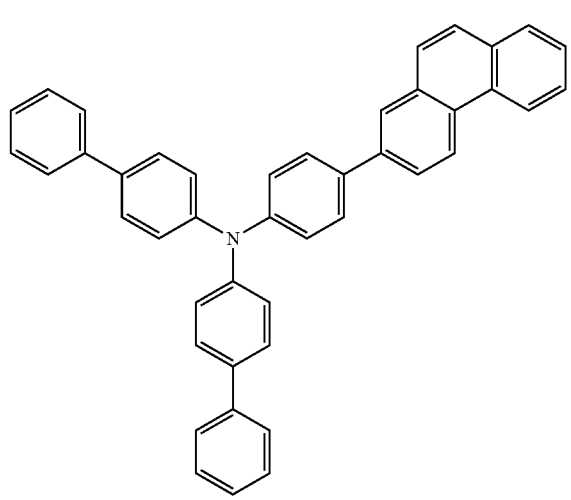
N-83
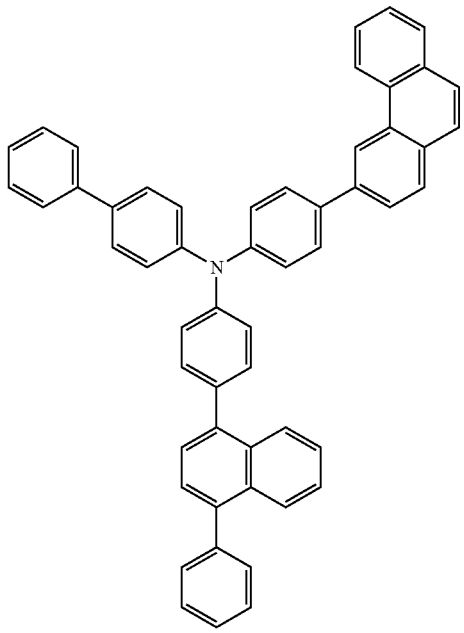

N-84
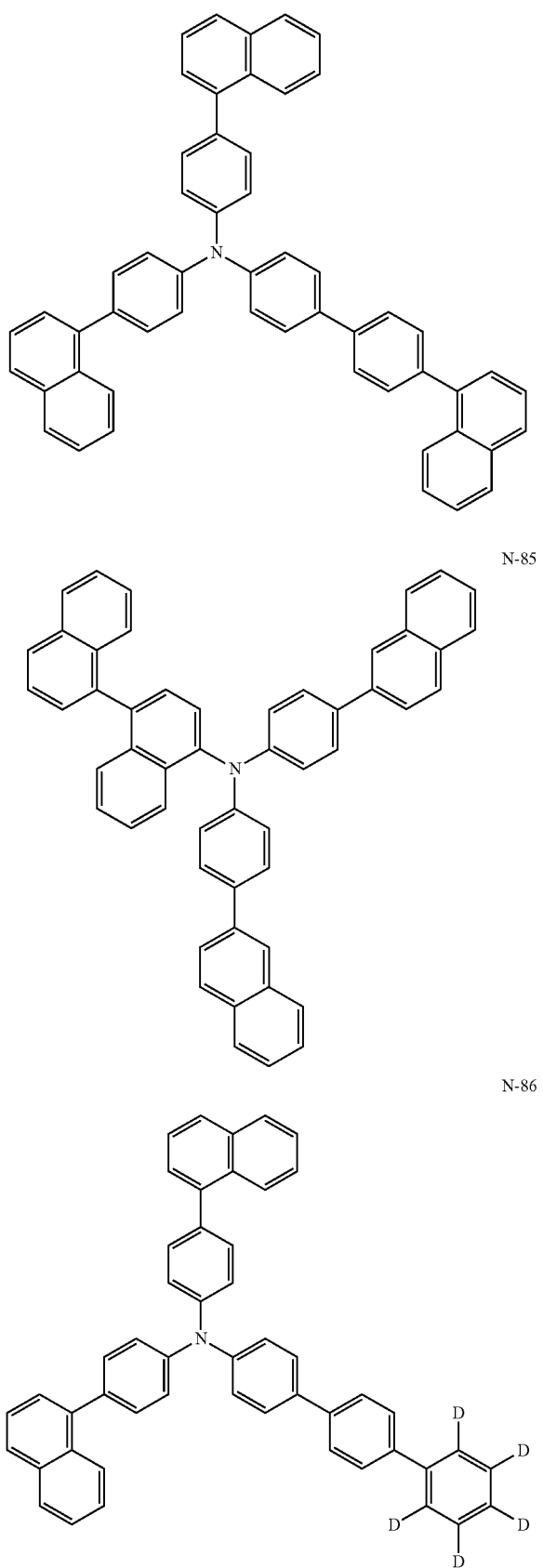
N-85
N-86
N-87
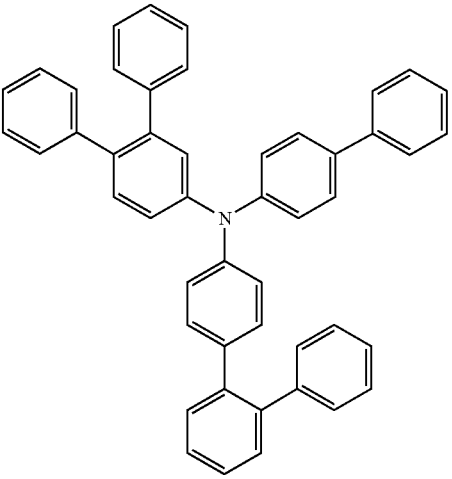
N-88
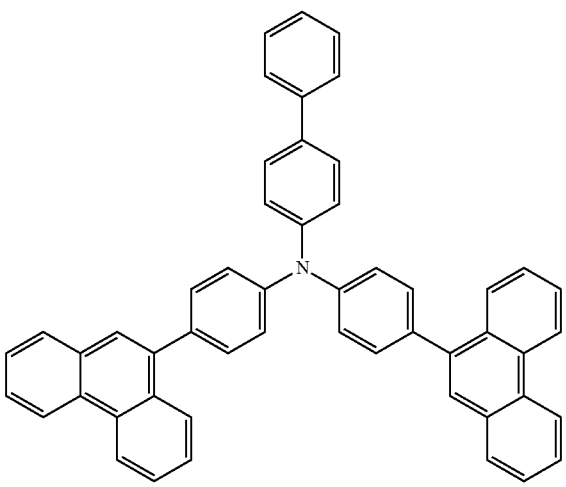
N-89
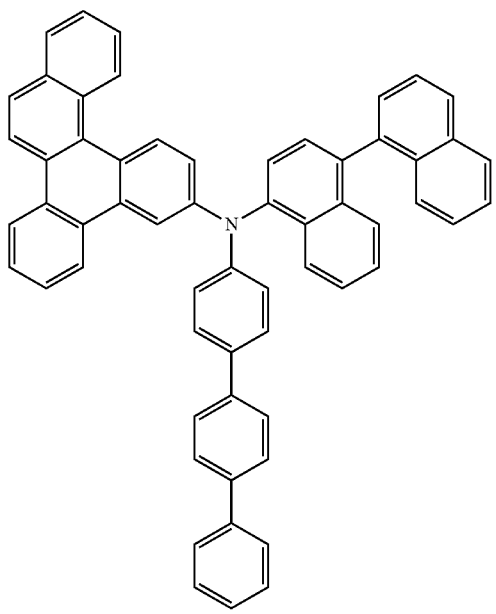
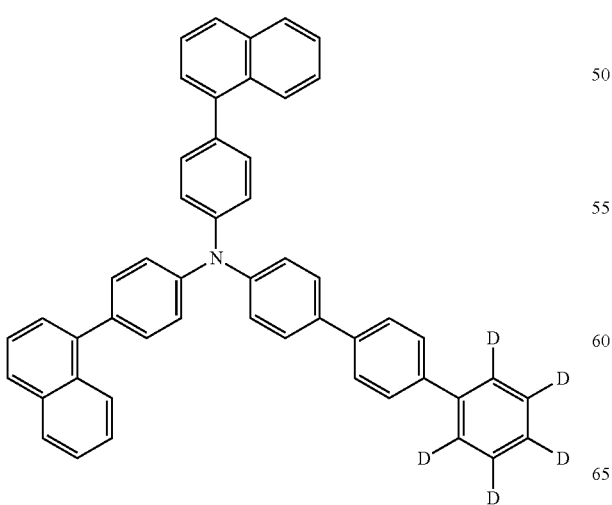

N-90
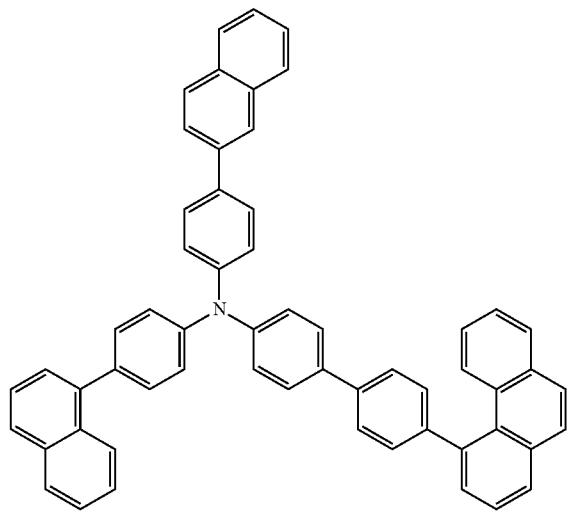
N-93
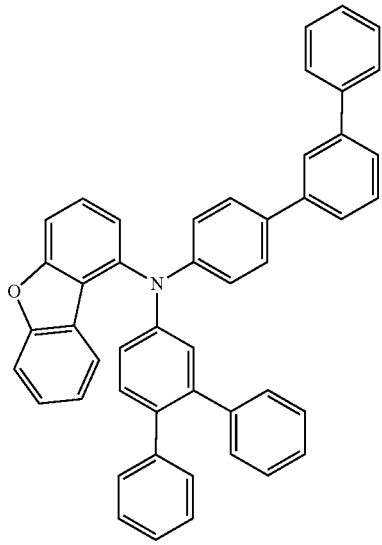
N-91
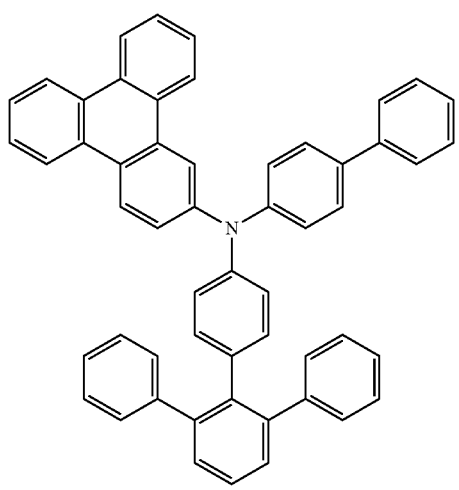
N-94
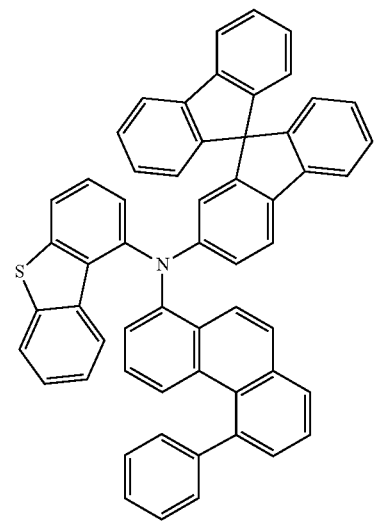
N-92
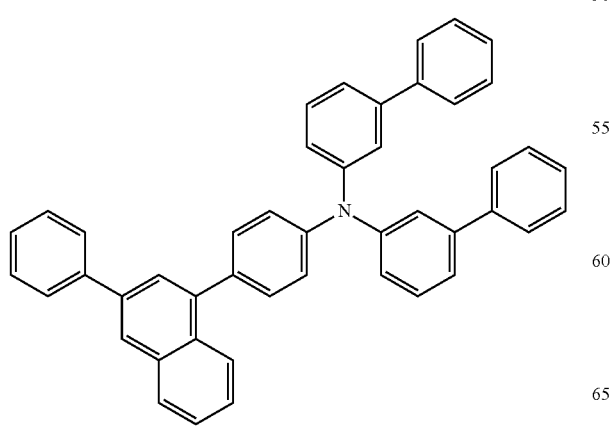
N-95
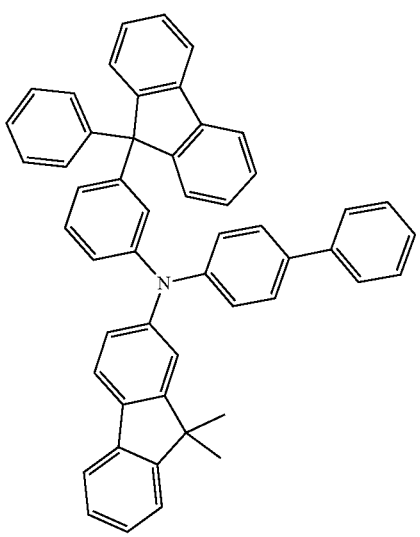

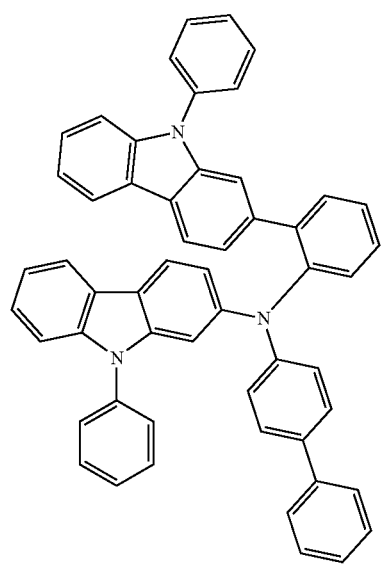
N-96
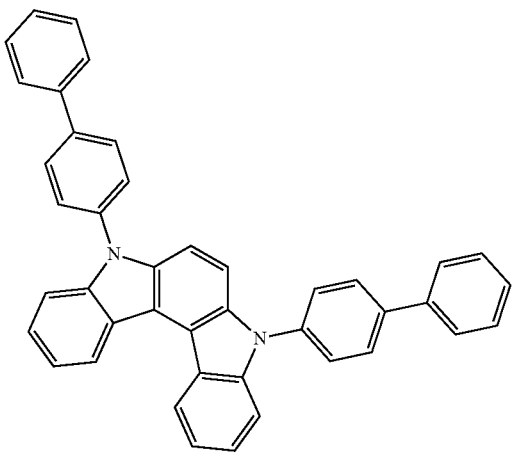
S-3
Also, the compound represented by Formula 3 is any one of the following compounds S-1 to S-108.
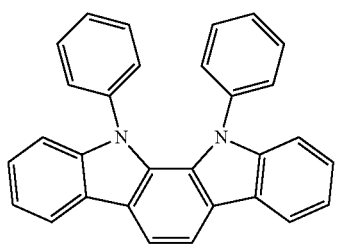
S-1
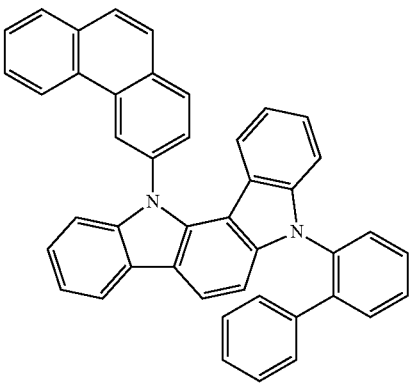
S-4
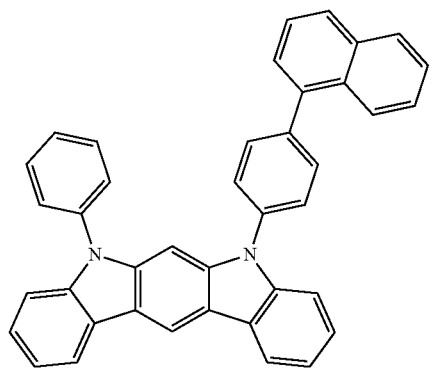
S-2
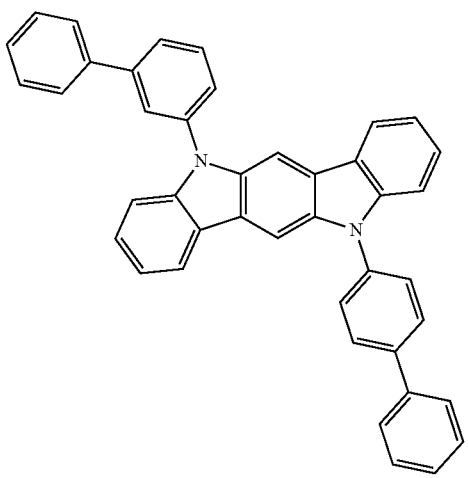
S-5

S-6
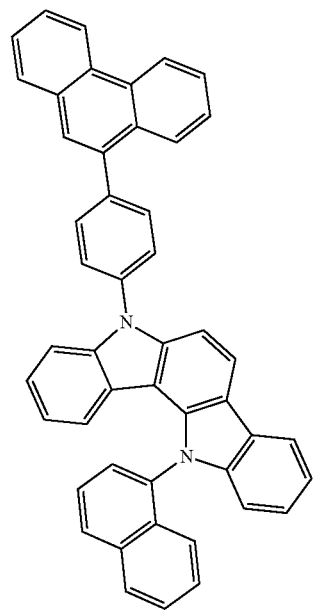
S-9
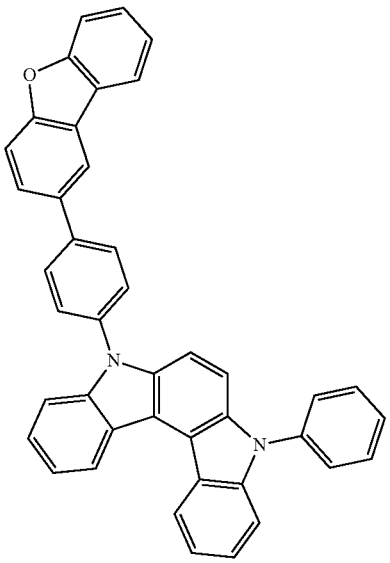
S-7
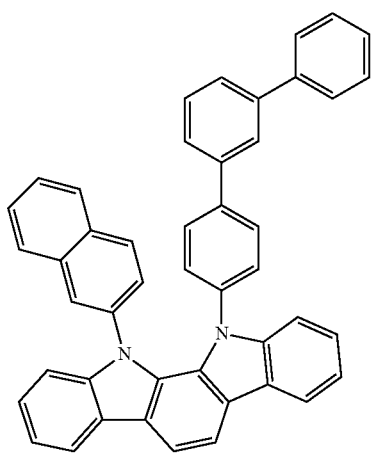
S-10
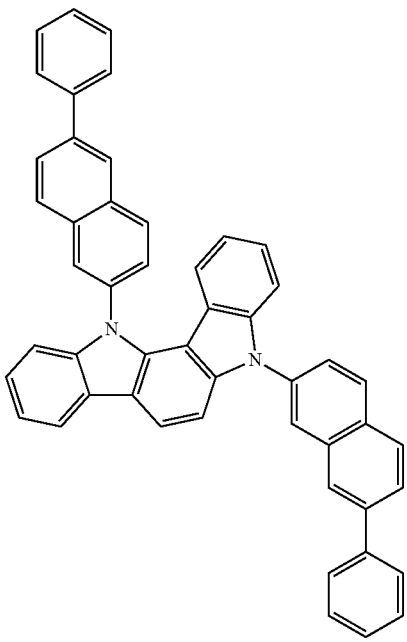
S-8
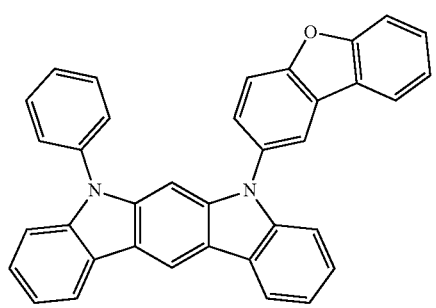

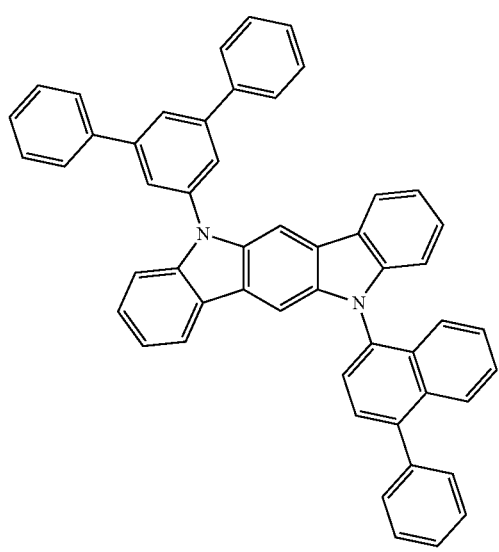
S-11
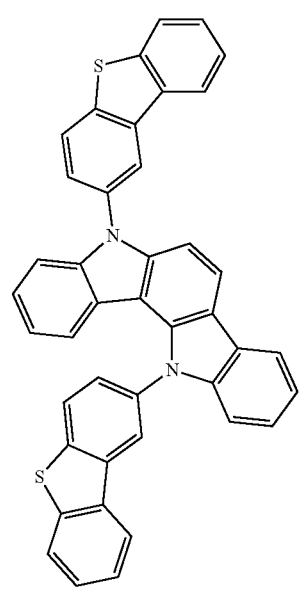
S-12
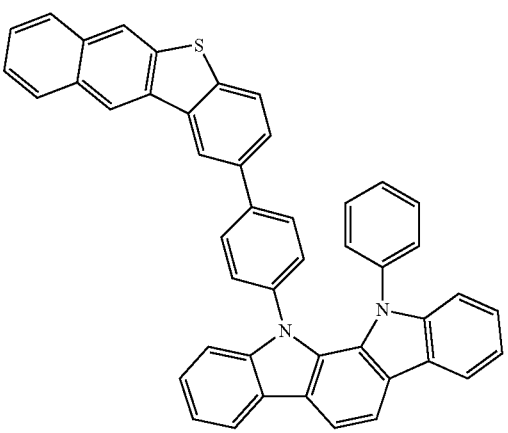
S-13
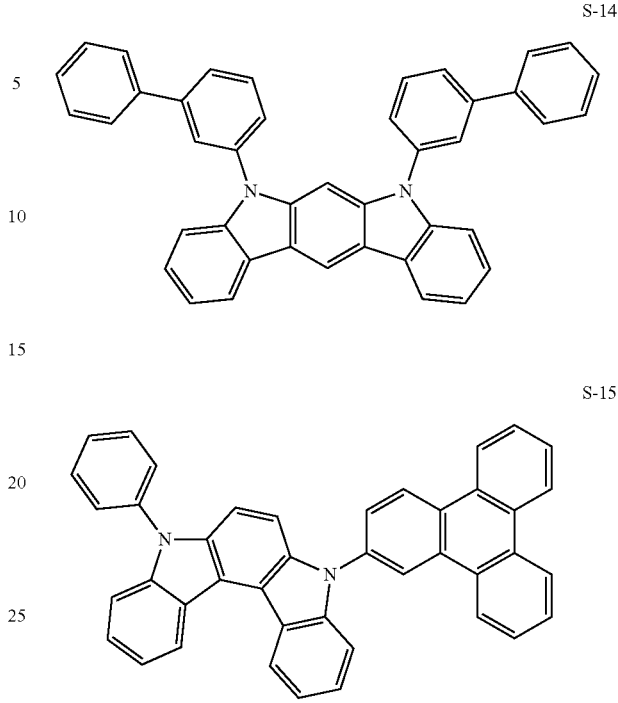
S-14
S-15
S-16
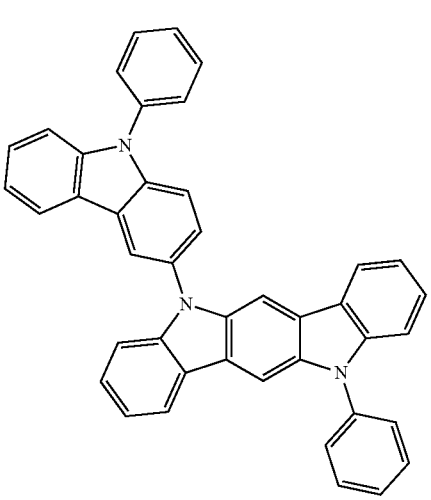
S-17

-continued
S-18
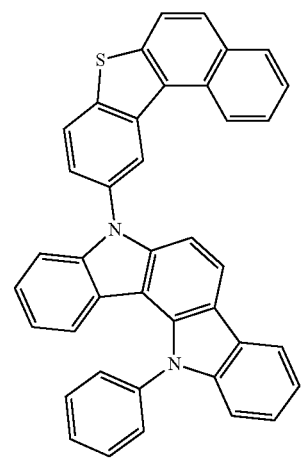
S-19
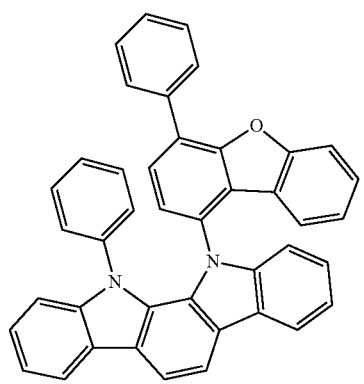
S-20
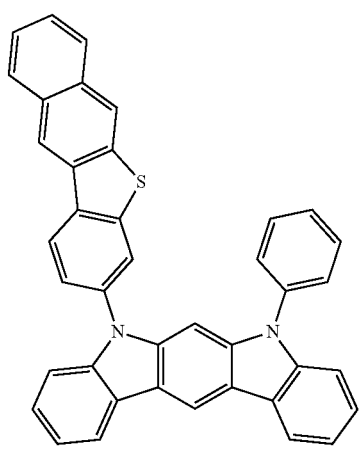
-continued
S-21
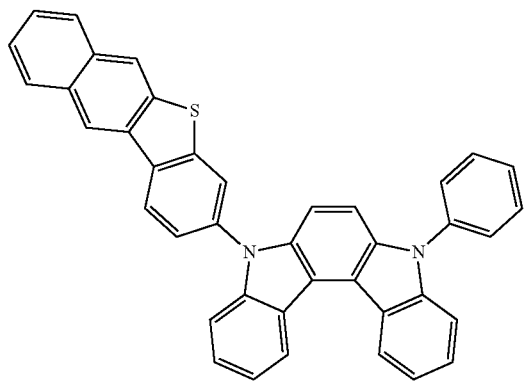
S-22
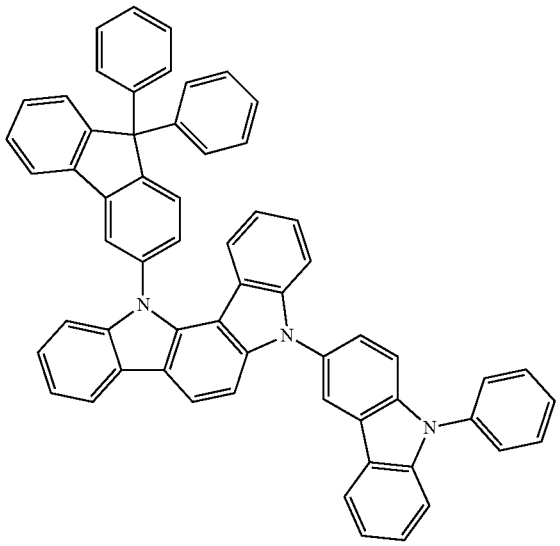
S-23
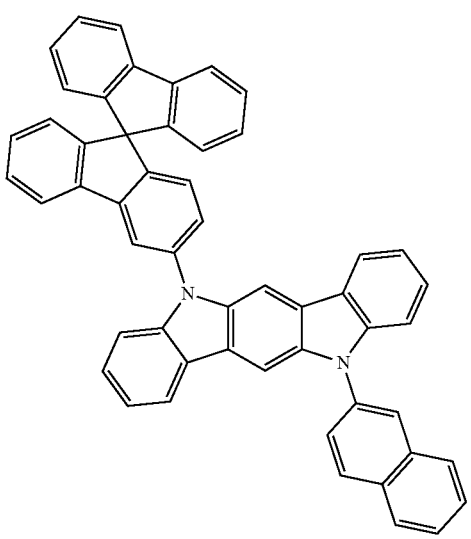

-continued
S-24
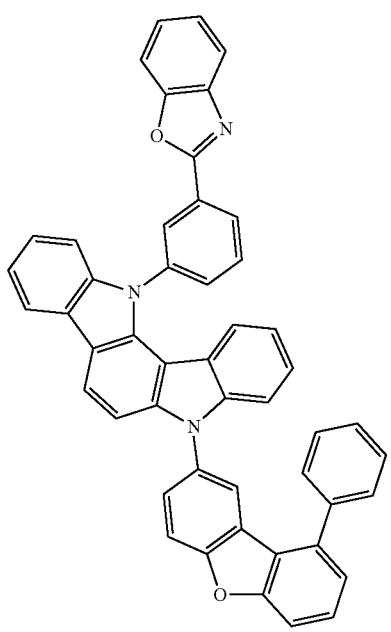
S-25
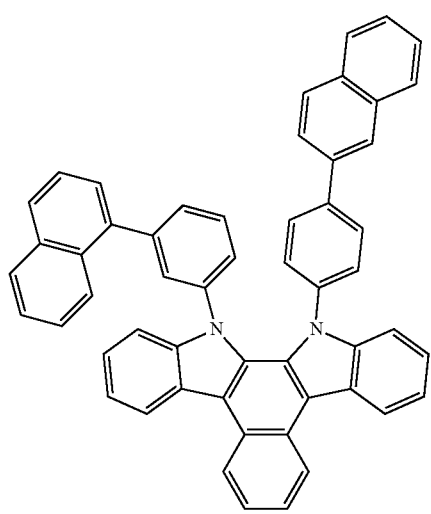
S-26
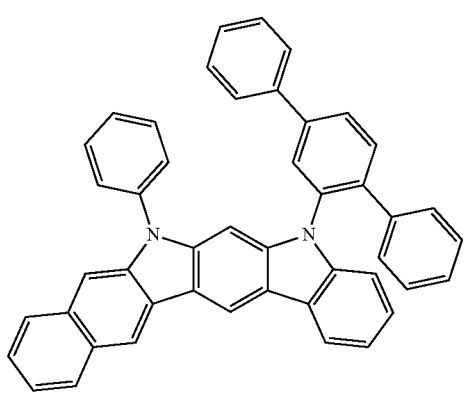
-continued
S-27
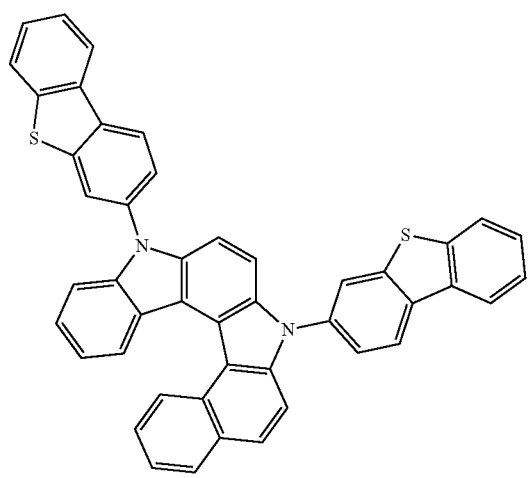
S-28
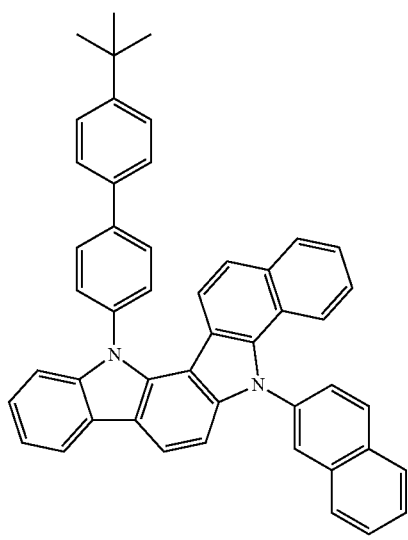
S-29
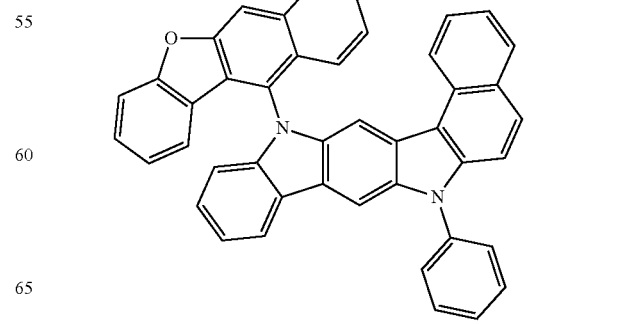

-continued
S-30
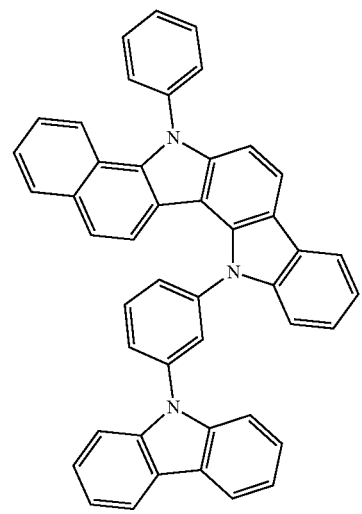
S-31
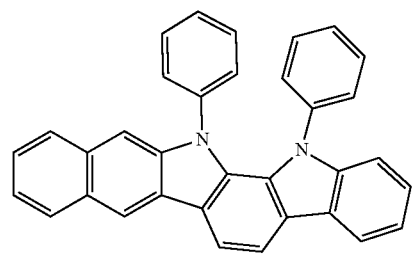
S-32
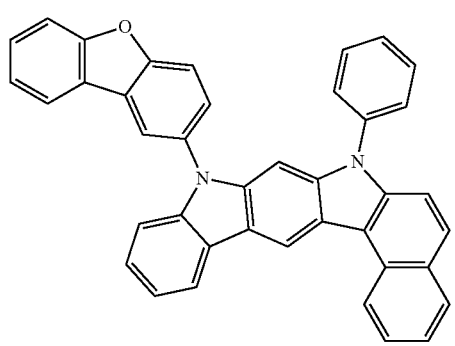
S-33
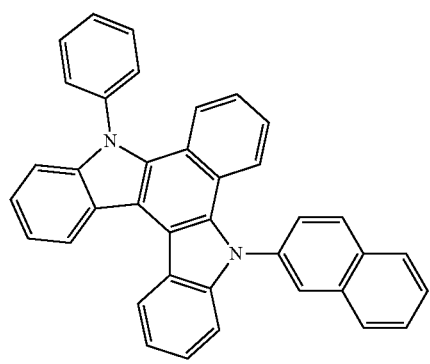
-continued
S-34
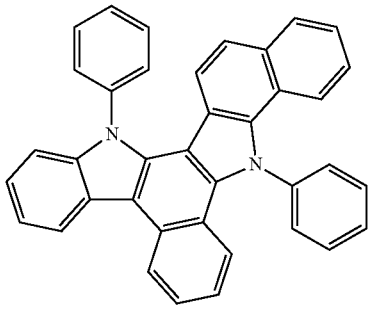
S-35
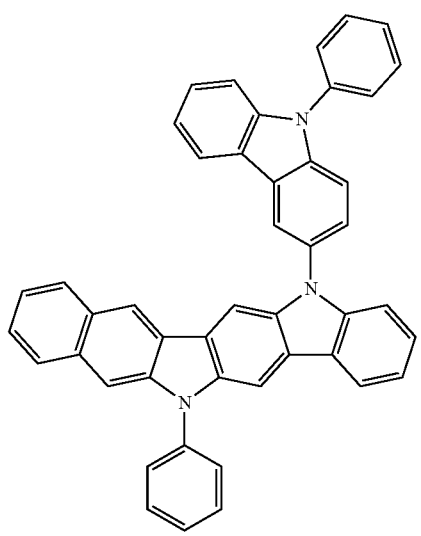
S-36
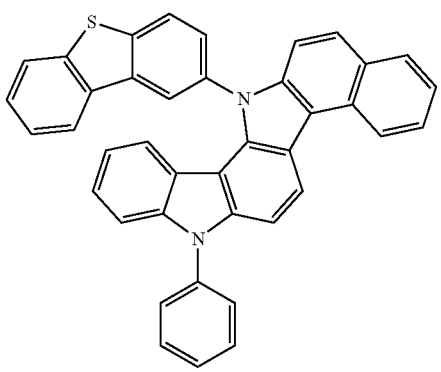
S-37
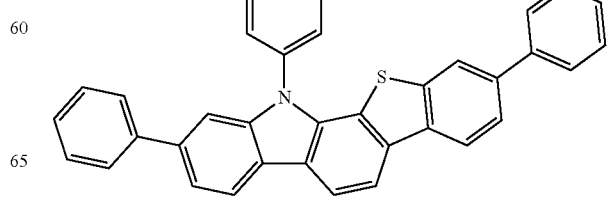

105
-continued
S-38
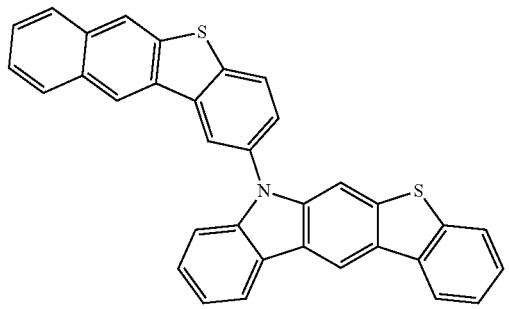
S-39
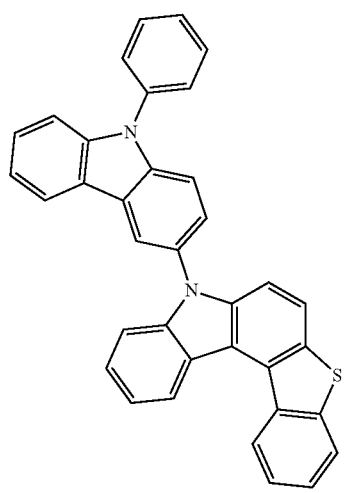
S-40
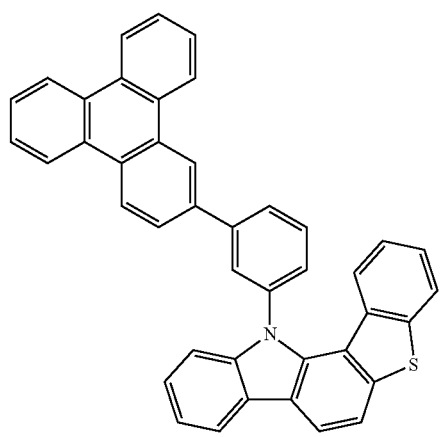
106
-continued
S-41
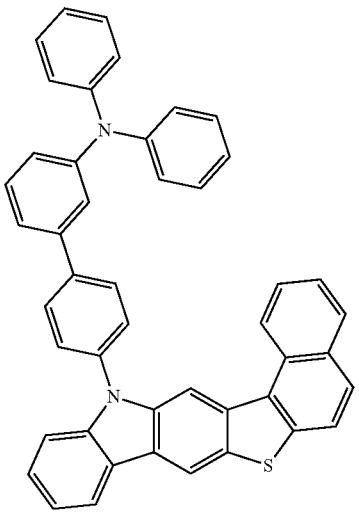
S-42
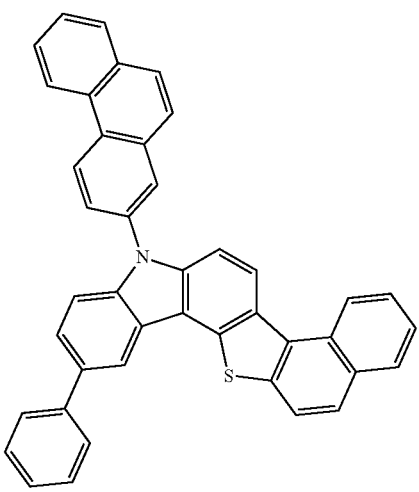
S-43
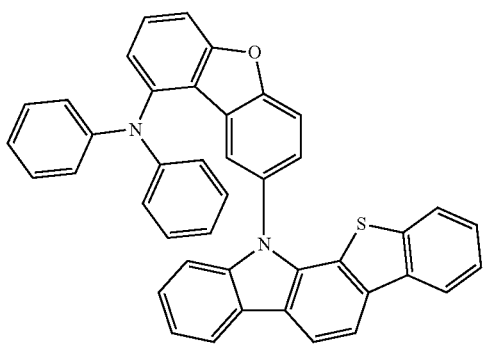

-continued
S-44
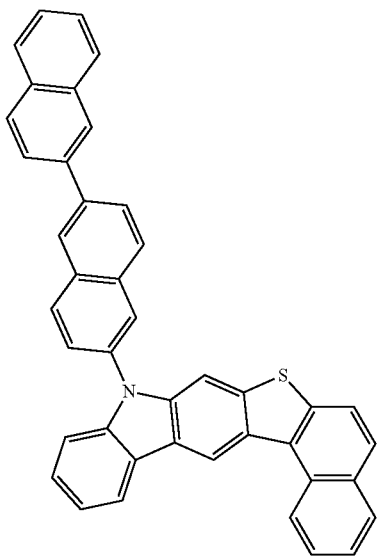
S-45
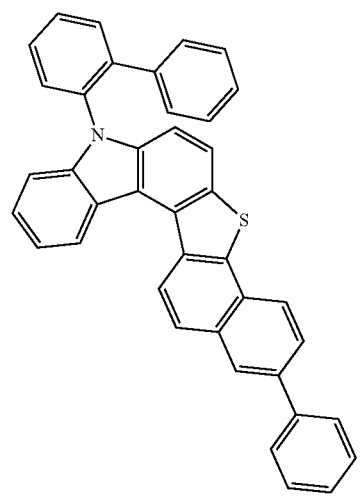
S-46
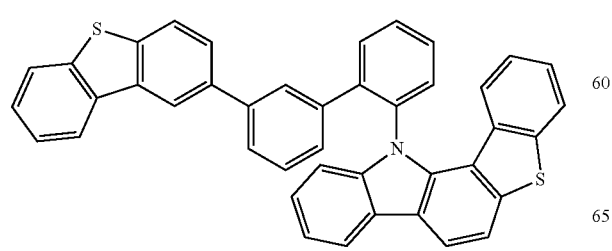
-continued
S-47
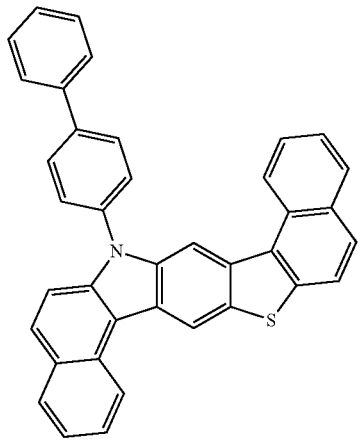
S-48
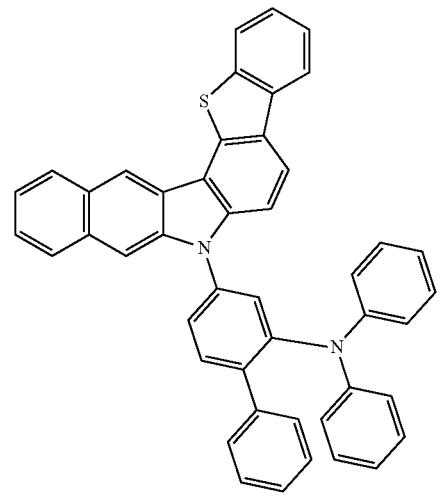
S-49
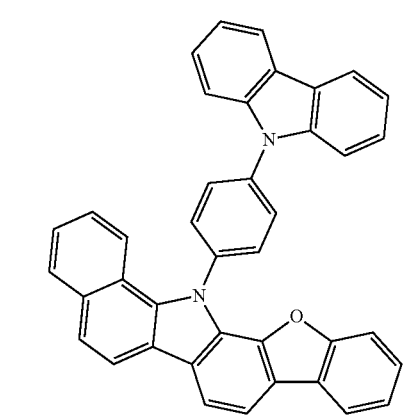

-continued
S-50
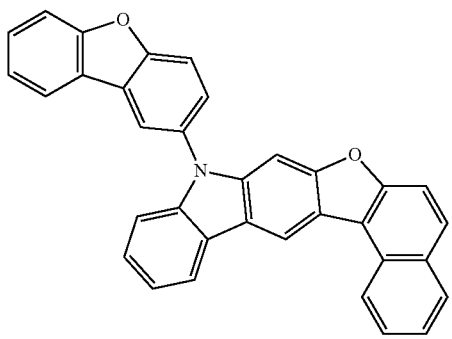
S-51
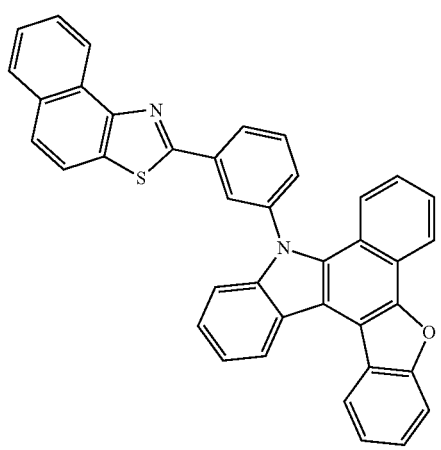
S-52
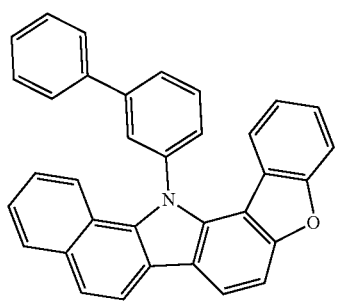
S-53
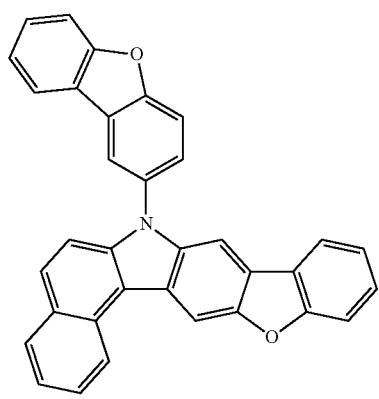
S-54
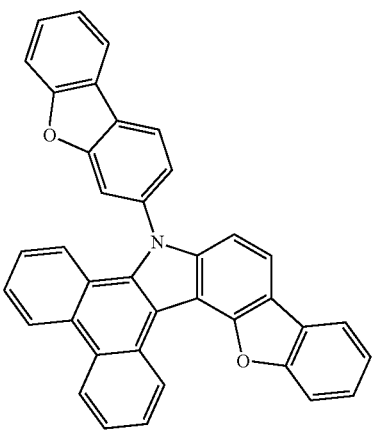
S-55
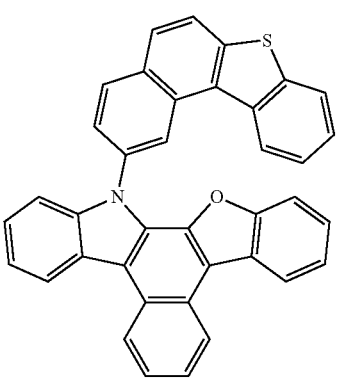
S-56
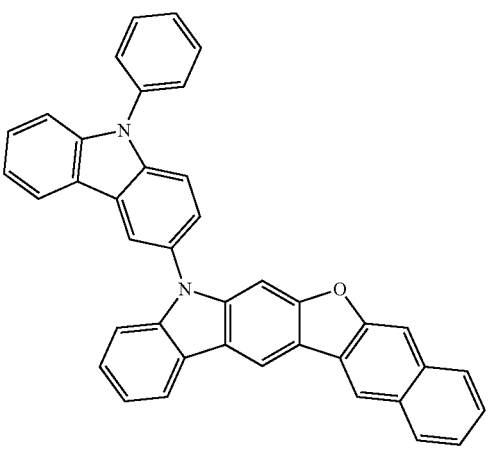
S-57
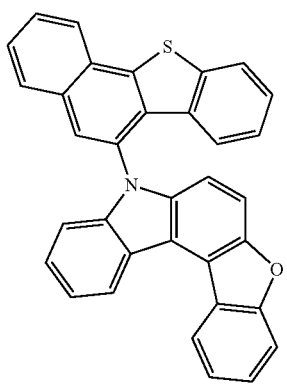

S-58
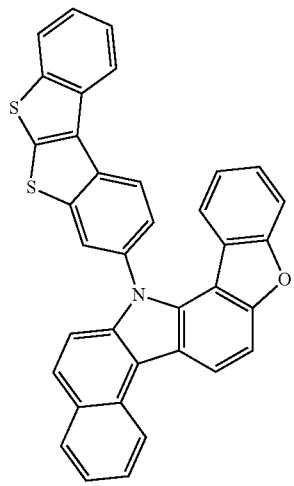
S-61
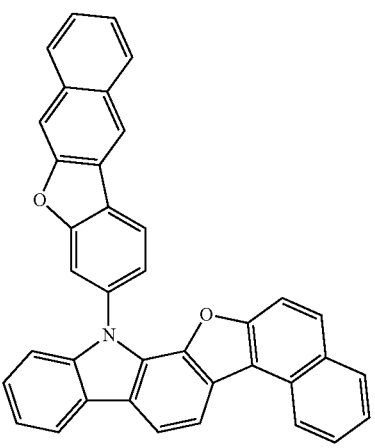
S-59
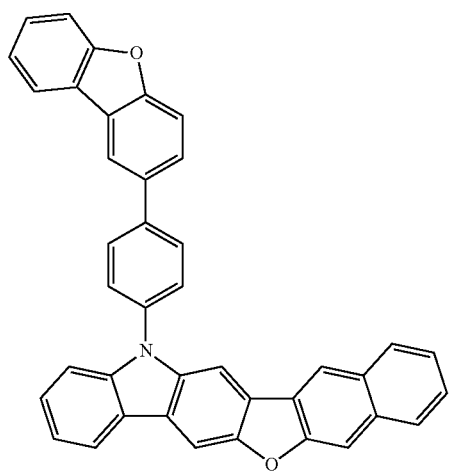
S-62
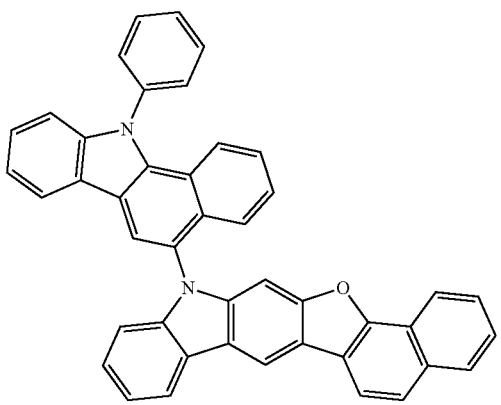
S-60
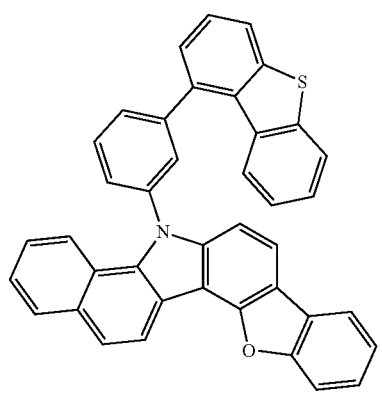
S-63
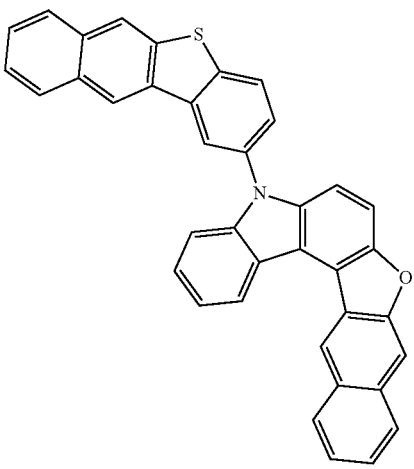

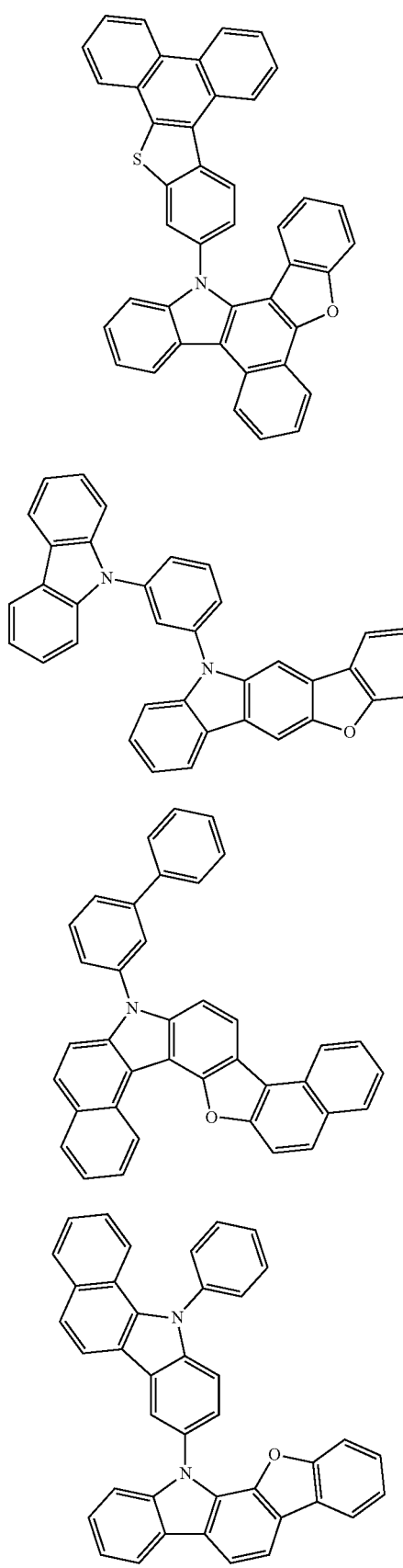
S-64
S-65
S-66
S-67
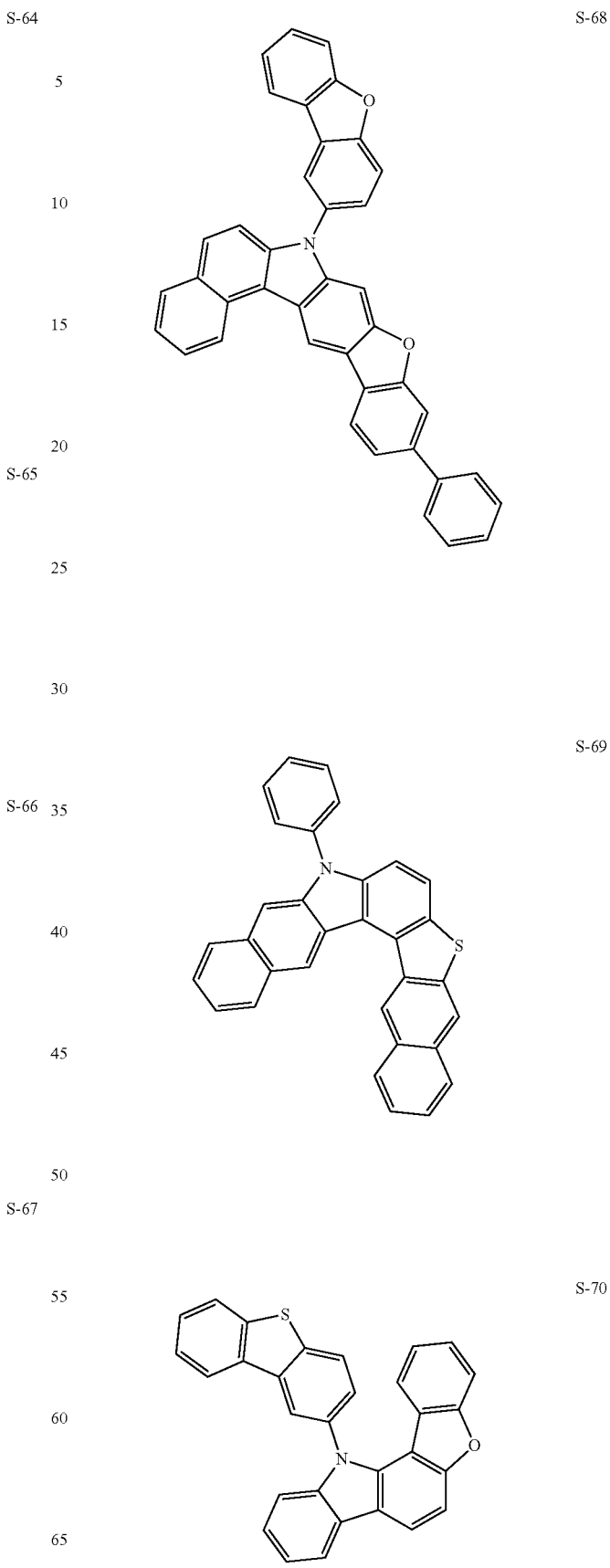
S-68
S-69
S-70

S-71
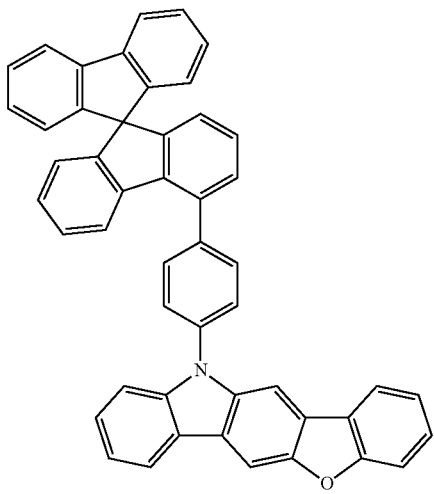
S-72
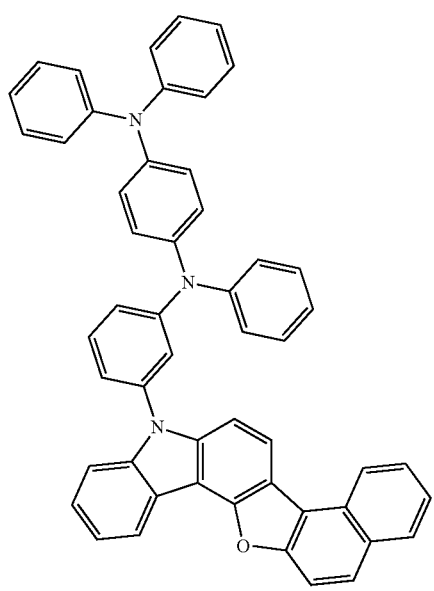
S-73
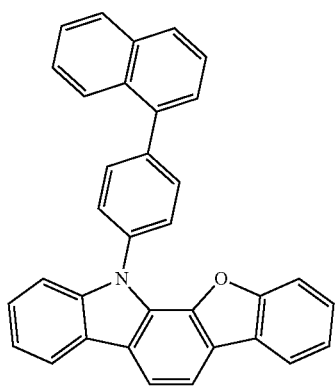
S-74
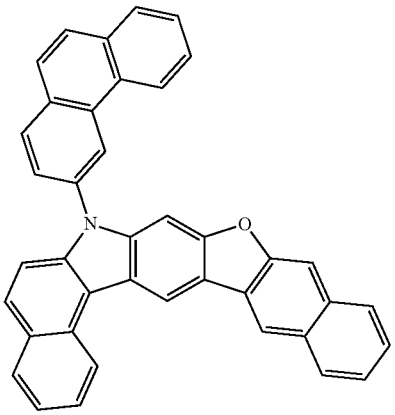
S-75
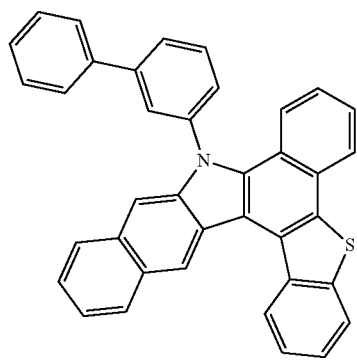
S-76
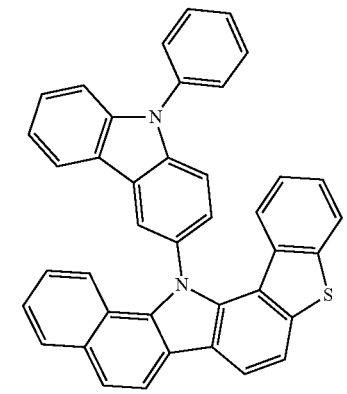
S-77
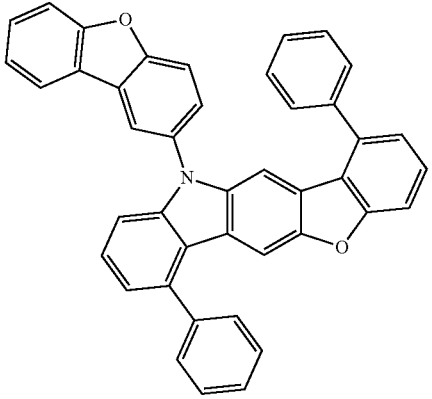

-continued
S-78
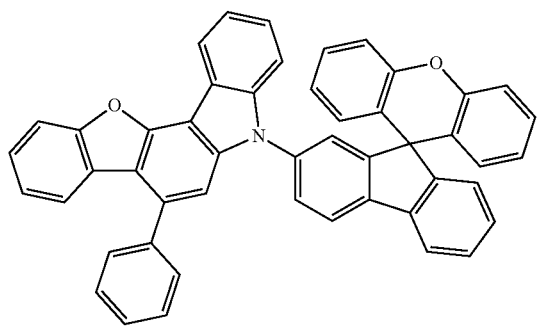
S-79
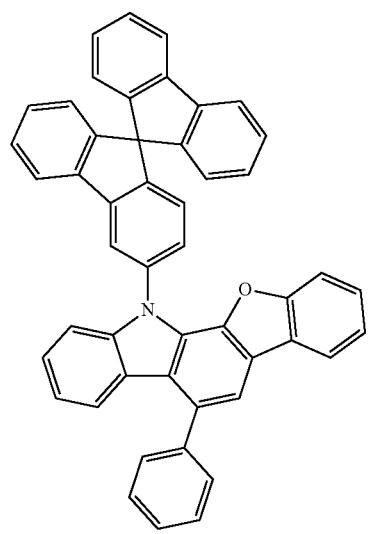
S-80
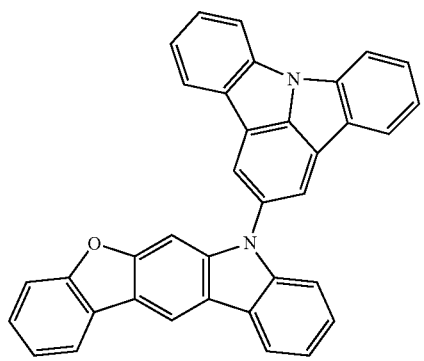
S-81
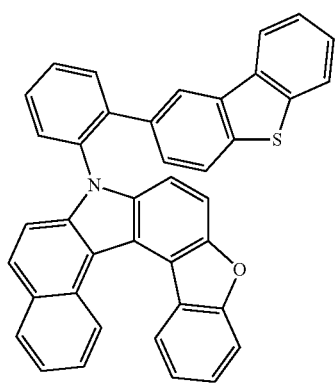
-continued
S-82
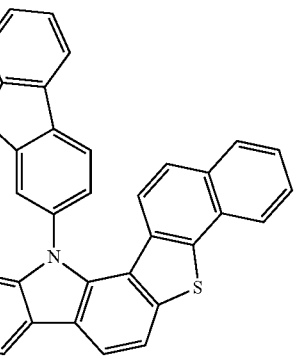
S-83
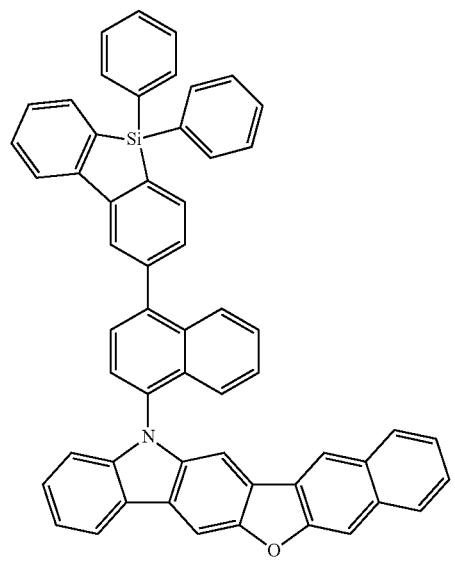
S-84
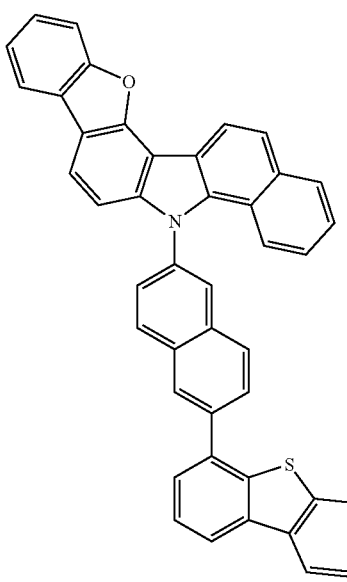

S-85
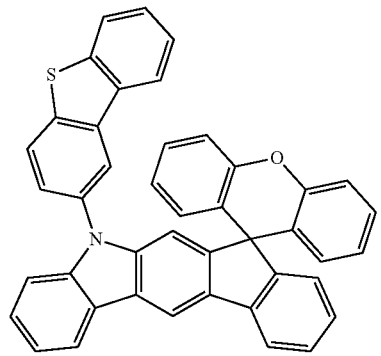
S-88
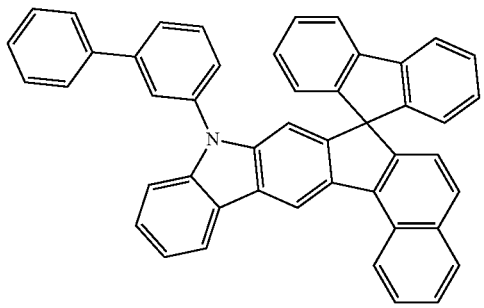
S-86
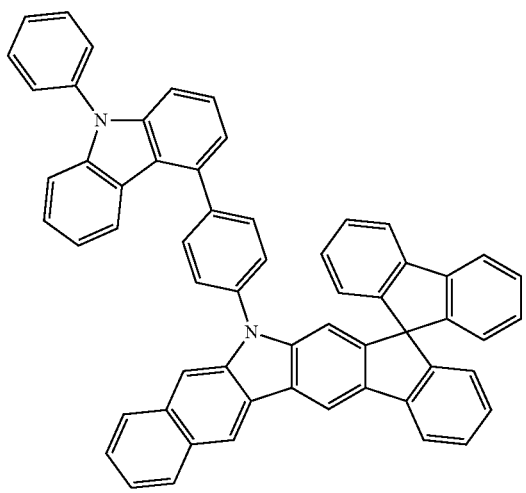
S-89
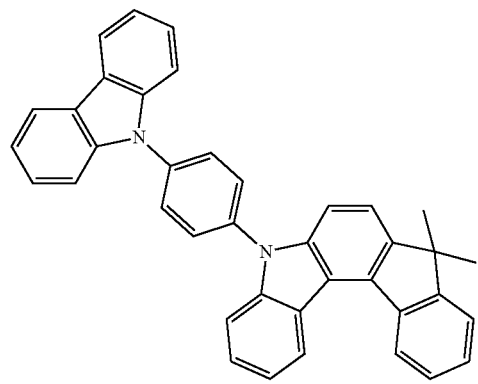
S-90
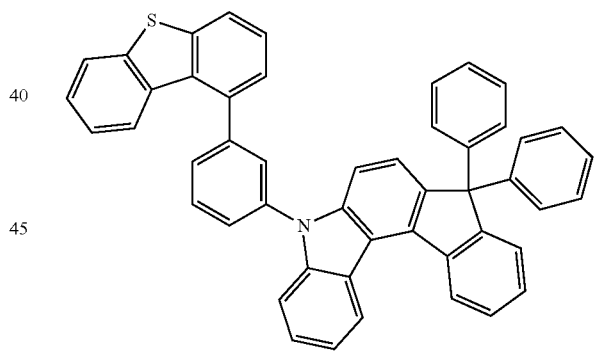
S-87
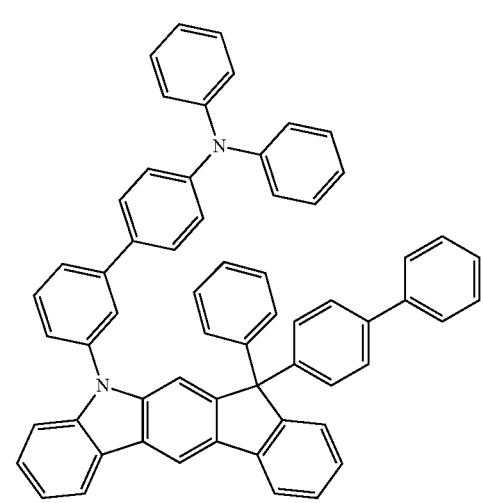
S-91
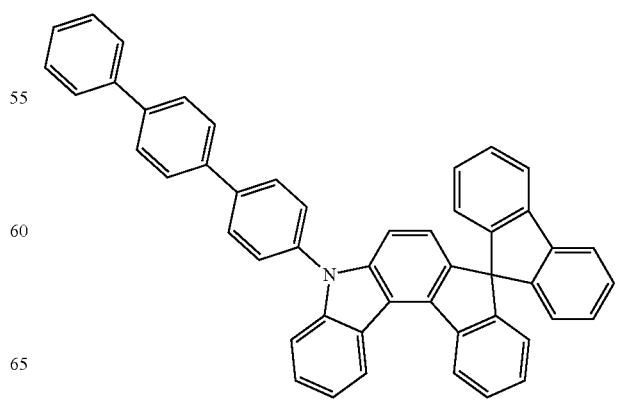

-continued
S-92
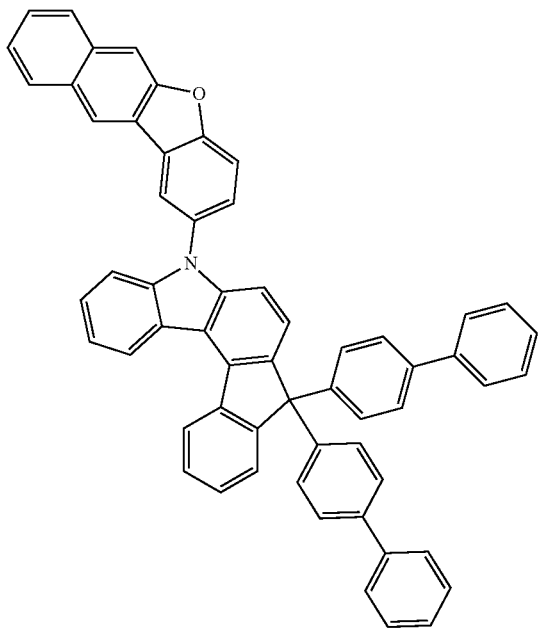
S-93
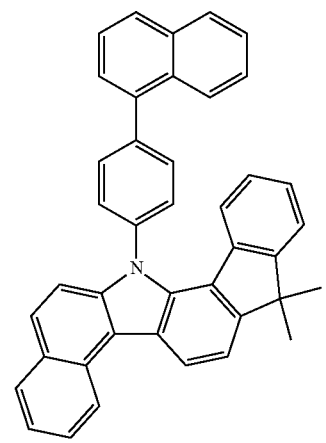
S-94
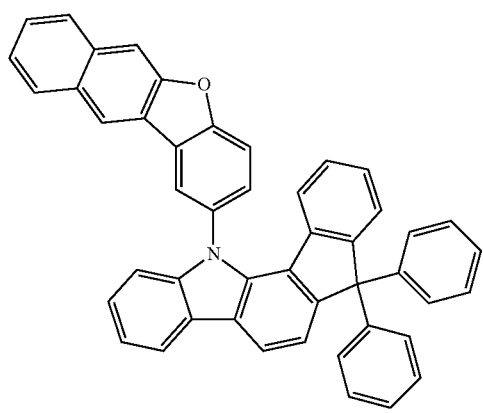
-continued
S-95
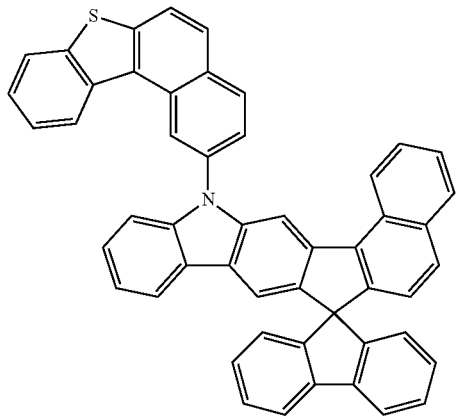
S-96
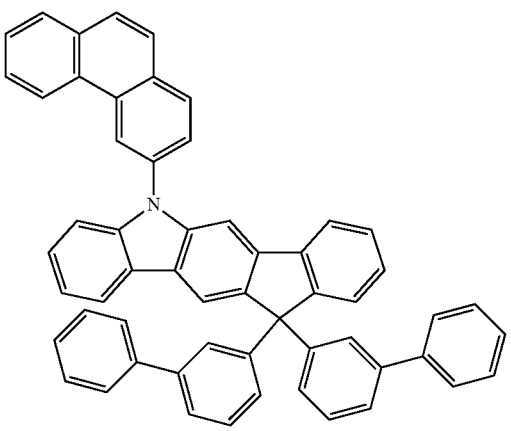
S-97
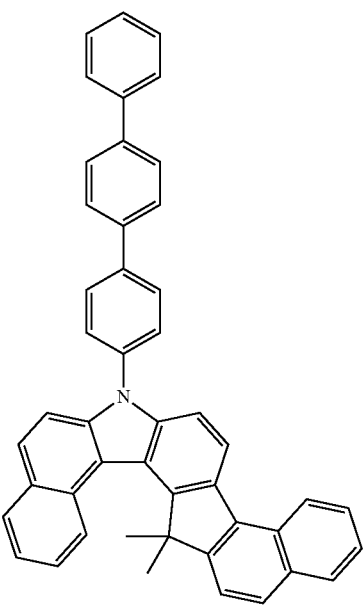

-continued
S-98
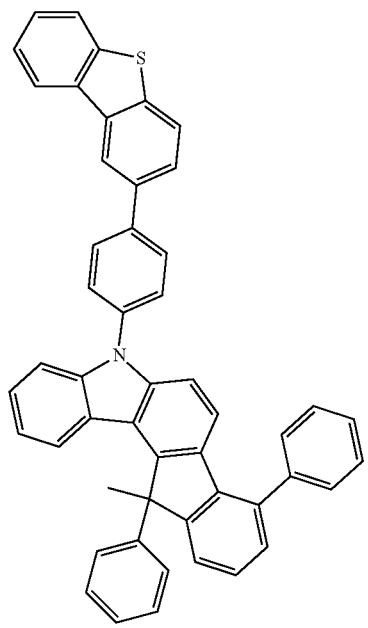
S-99
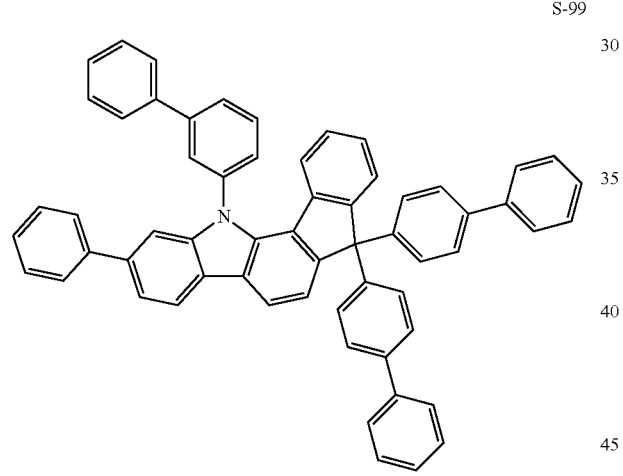
S-100
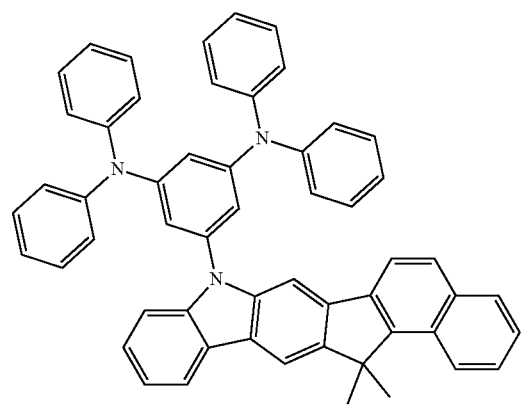
-continued
S-101
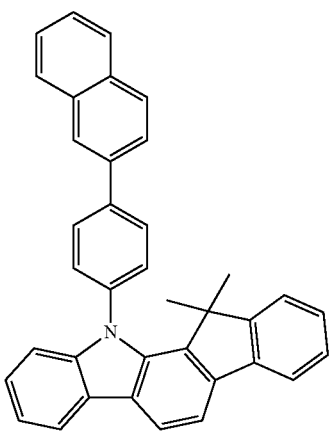
S-102
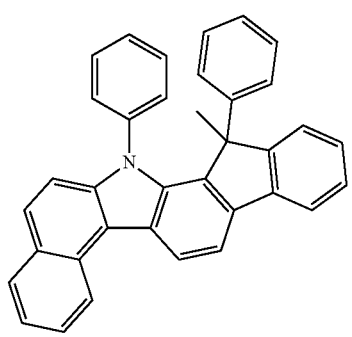
S-103
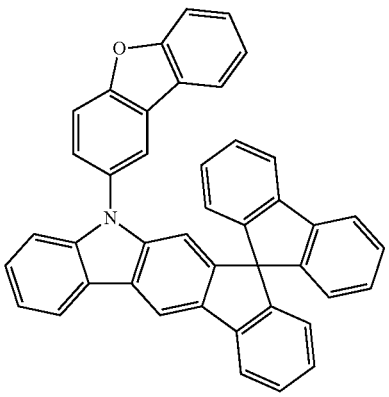
S-104
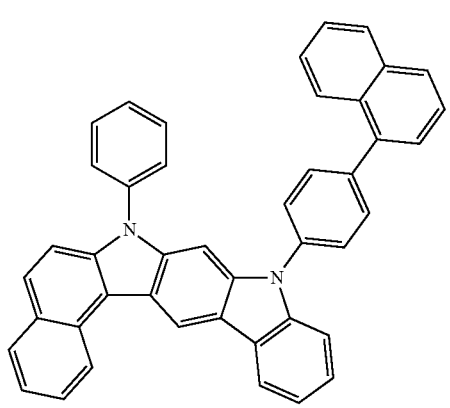

S-105

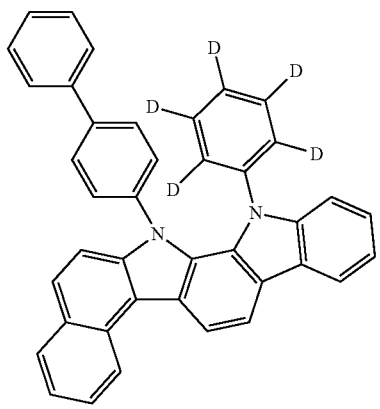

S-106

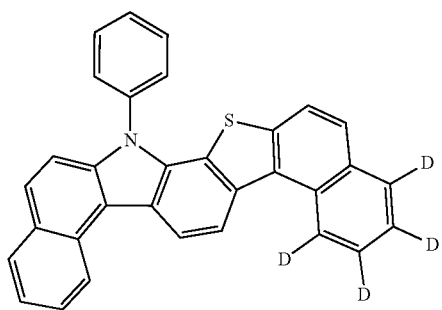

S-107

S-108

The present invention may further include a light efficiency enhancing layer formed on at least one surface of the first electrode and the second electrode opposite to the organic material layer.

Also, the organic material layer may include 2 or more stacks including a hole transport layer, an emitting layer, and an electron transport layer sequentially formed on the anode, and the organic material layer may further include a charge generation layer formed between the 2 or more stacks.

In another aspect, the present invention provides an electronic device comprising a display device including the organic electronic element; and a control unit for driving the display device; here, the organic electronic element is at least one of an OLED, an organic solar cell, an organic photo conductor, an organic transistor and an element for monochromic or white illumination.

Hereinafter, Synthesis Examples of the compound represented by Formula according to the present invention and preparation examples of the organic electronic element according to the present invention will be described in detail by way of example, but are not limited to the following examples of the invention.

SYNTHESIS EXAMPLE

The compound was synthesized as follows.

The compound (final products) represented by Formula 1 according to the present invention is represented by <Reaction Scheme 1>, but is not limited thereto.

<Reaction Scheme 1>

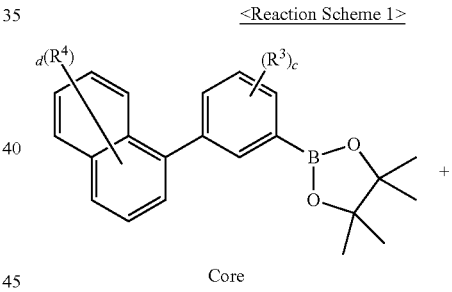

Core

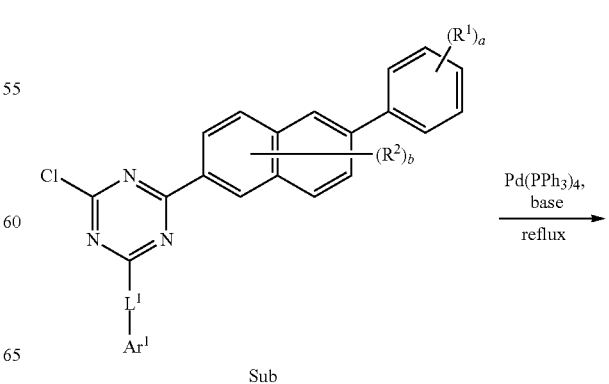

Sub

-continued

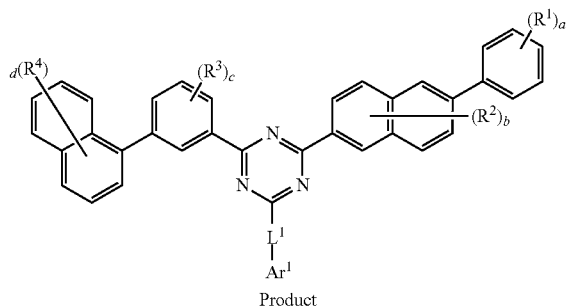

Product

I. Synthesis of Core

Core of <Reaction Scheme 1> may be synthesized by the reaction route of <Reaction Scheme 2>, but is not limited thereto.

<Reaction Scheme 2>

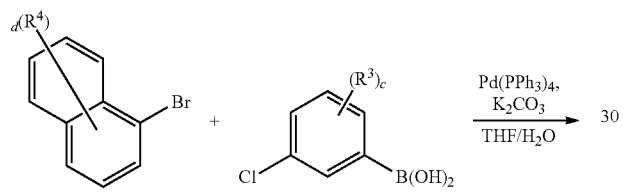

1. Synthesis Example of Core 5

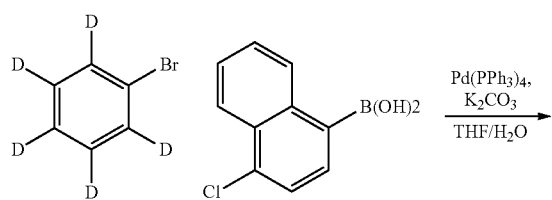

-continued

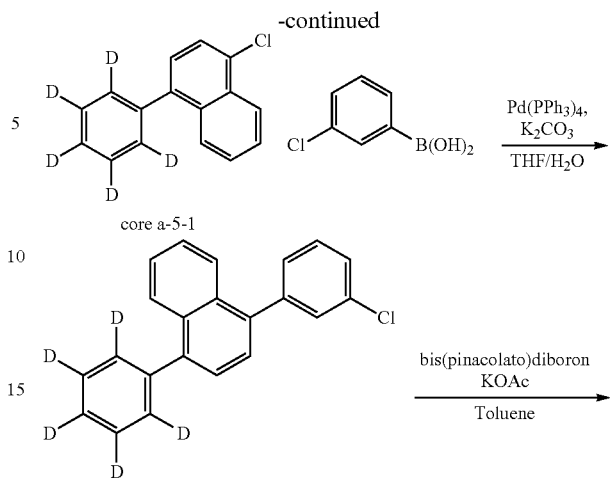

core a-5

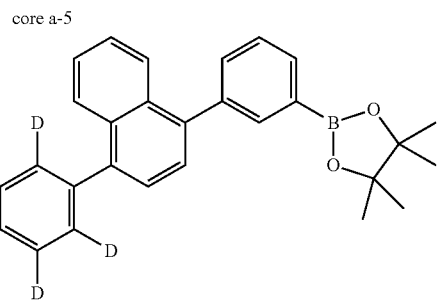

core 5

(1) Synthesis of Core a-5-1

1-bromobenzene-2,3,4,5,6-d5 (50 g, 1 eqiv.), (4-chloronaphthalen-1-yl)boronic acid (63.7 g, 1 eqiv.), Pd(PPh₃)₄ (10.7 g, 0.03 eqiv.), K₂CO₃ (128 g, 2 eqiv.), THE (1030 mL, 0.3 M), water were added to a round bottom flask and stirred at 80° C. When the reaction was completed, the resulting compound was extracted with CH₂Cl₂ and water, the organic layer was dried over MgSO₄, concentrated, and the resulting compound was recrystallized by silicagel column to obtain 45.1 g of Core a-5-1 (yield: 60%).

(2) Synthesis of Core a-5 core a-5-1 (45 g, 1 eqiv.), (3-chlorophenyl)boronic acid (43.4 g, 1 eqiv.), Pd(PPh₃)₄ (9.6 g, 0.03 eqiv.), K₂CO₃ (115 g, 2 eqiv.), THE (925 mL, 0.3 M), water were added to a round bottom flask and stirred at 80° C. When the reaction was completed, the resulting compound was extracted with CH₂Cl₂ and water, the organic layer was dried over MgSO₄, concentrated, and the resulting compound was recrystallized by silicagel column to obtain 48 g of Core a-5 (yield: 55%).

(3) Synthesis of Core 5

Core a-5 (45 g, 1 eqiv.), bis(pinacolato)diboron (43 g, 1.2 eqiv.), Pd₂(dba)₃ (3.9 g, 0.03 eqiv.), X-phos (2.3 g, 0.06 equiv.), KOAc (41 g, 2 eqiv.) were dissolved in Toluene (470 mL, 0.3 M) in a round-bottom flask and stirred at 120° C. When the reaction was completed, the resulting compound was extracted with CH₂Cl₂ and water, the organic layer was dried over MgSO₄, concentrated, and the resulting compound was recrystallized by silicagel column to obtain 41 g of Core 5 (yield: 71%).

2. Synthesis Example of Core 6

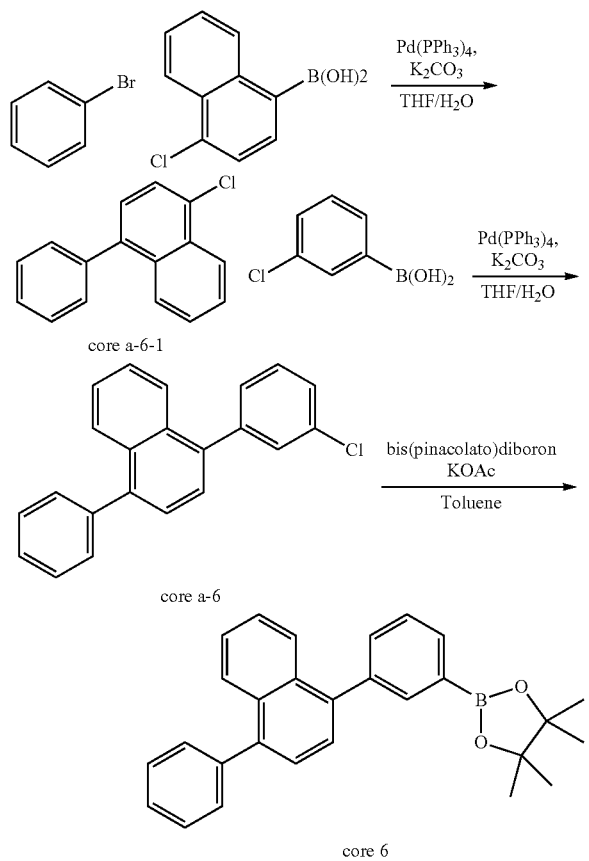

(1) Synthesis of Core a-6-1

1-bromobenzene (38 g, 1 eqiv.), (4-chloronaphthalen-1-yl)boronic acid (50 g, 1 eqiv.), Pd(PPh$_3$)$_4$ (8.4 g, 0.03 eqiv.), K$_2$CO$_3$ (100 g, 2 eqiv.), THF (807 mL, 0.3 M), water were added to a round bottom flask and stirred at 80° C. When the reaction was completed, the resulting compound was extracted with CH$_2$Cl$_2$ and water, the organic layer was dried over MgSO$_4$, concentrated, and the resulting compound was recrystallized by silicagel column to obtain 31 g of Core a-6-1 (yield: 53%).

(2) Synthesis of Core a-6

Core a-6-1 (30 g, 1 eqiv.), (3-chlorophenyl)boronic acid (20 g, 1 eqiv.), Pd(PPh$_3$)$_4$ (4.4 g, 0.03 eqiv.), K$_2$CO$_3$ (52 g, 2 eqiv.), THF (419 mL, 0.3 M), water were added to a round bottom flask and stirred at 80° C. When the reaction was completed, the resulting compound was extracted with CH$_2$Cl$_2$ and water, the organic layer was dried over MgSO$_4$, concentrated, and the resulting compound was recrystallized by silicagel column to obtain 26 g of Core a-6 (yield: 66%).

(3) Synthesis of Core 6

Core a-6 (25 g, 1 eqiv.), bis(pinacolato)diboron (24 g, 1.2 eqiv.), Pd$_2$(dba)$_3$ (2.2 g, 0.03 eqiv.), X-phos (2.3 g, 0.06 equiv.), KOAc (24 g, 2 eqiv.) were dissolved in Toluene (265 mL, 0.3 M) in a round-bottom flask and stirred at 120° C. When the reaction was completed, the resulting compound was extracted with CH$_2$Cl$_2$ and water, the organic layer was dried over MgSO$_4$, concentrated, and the resulting compound was recrystallized by silicagel column to obtain 25 g of Core 6 (yield: 80%).

3. Synthesis Example of Core 17

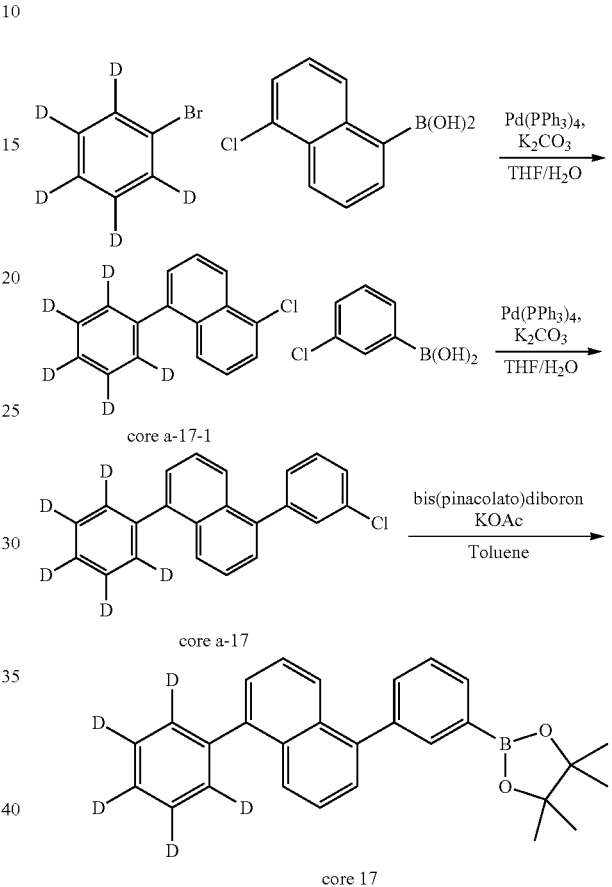

(1) Synthesis of Core a-17-1

1-bromobenzene-2,3,4,5,6-d5 (50 g, 1 eqiv.), (4-chloronaphthalen-1-yl)boronic acid (63.7 g, 1 eqiv.), Pd(PPh$_3$)$_4$ (10.7 g, 0.03 eqiv.), K$_2$CO$_3$ (128 g, 2 eqiv.), THF (1030 mL, 0.3 M), water were added to a round bottom flask and stirred at 80° C. When the reaction was completed, the resulting compound was extracted with CH$_2$Cl$_2$ and water, the organic layer was dried over MgSO$_4$, concentrated, and the resulting compound was recrystallized by silicagel column to obtain 56 g of Core a-17-1 (yield: 78%).

(2) Synthesis of Core a-17

Core a-17-1 (55 g, 1 eqiv.), (3-chlorophenyl)boronic acid (35 g, 1 eqiv.), Pd(PPh$_3$)$_4$ (7.8 g, 0.03 eqiv.), K$_2$CO$_3$ (94 g, 2 eqiv.), THF (750 mL, 0.3 M), water were added to a round bottom flask and stirred at 80° C. When the reaction was completed, the resulting compound was extracted with CH$_2$Cl$_2$ and water, the organic layer was dried over MgSO$_4$, concentrated, and the resulting compound was recrystallized by silicagel column to obtain 46 g of Core a-17 (yield: 64%).

(3) Synthesis of Core 17

Core a-17 (45 g, 1 eqiv.), bis(pinacolato)diboron (43 g, 1.2 eqiv.), $Pd_2(dba)_3$ (3.9 g, 0.03 eqiv.), X-phos (4.0 g, 0.06 equiv.), KOAc (41 g, 2 eqiv.) were dissolved in Toluene (470 mL, 0.3 M) in a round-bottom flask and stirred at 120° C. When the reaction was completed, the resulting compound was extracted with $CH_2Cl_2$ and water, the organic layer was dried over $MgSO_4$, concentrated, and the resulting compound was recrystallized by silicagel column to obtain 42 g of Core 17 (yield: 73%).

4. Synthesis Example of Core 20

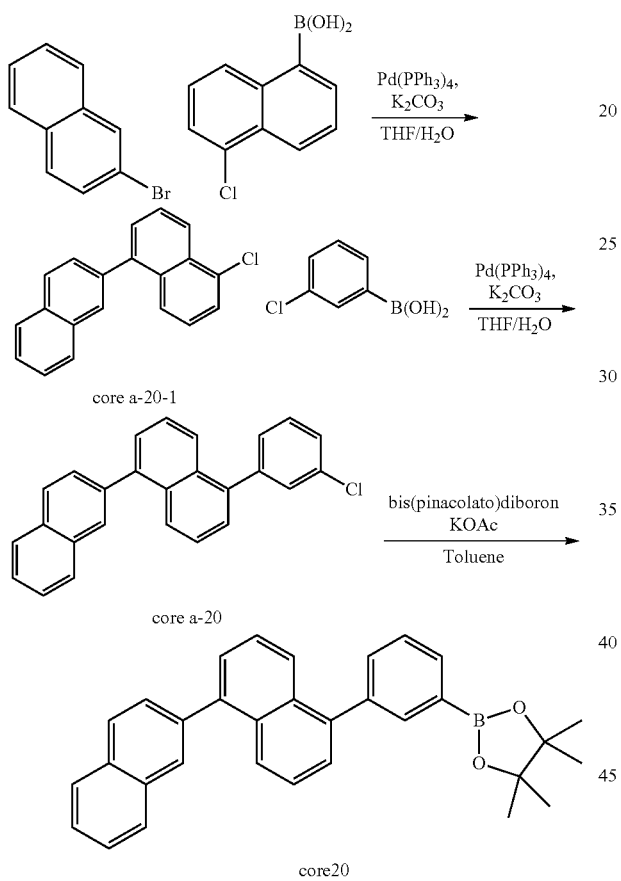

(1) Synthesis of Core a-20-1

2-bromonaphthalene (50 g, 1 eqiv.), (5-chloronaphthalen-1-yl)boronic acid (50 g, 1 eqiv.), $Pd(PPh_3)_4$ (8.4 g, 0.03 eqiv.), $K_2CO_3$ (100 g, 2 eqiv.), THF (800 mL, 0.3 M), water were added to a round bottom flask and stirred at 80° C. When the reaction was completed, the resulting compound was extracted with $CH_2Cl_2$ and water, the organic layer was dried over $MgSO_4$, concentrated, and the resulting compound was recrystallized by silicagel column to obtain 58 g of Core a-20-1 (yield: 83%).

(2) Synthesis of Core a-20

Core a-20-1 (39 g, 1 eqiv.), (3-chlorophenyl)boronic acid (21 g, 1 eqiv.), $Pd(PPh_3)_4$ (4.7 g, 0.03 eqiv.), $K_2CO_3$ (56 g, 2 eqiv.), THF (450 mL, 0.3 M), water were added to a round bottom flask and stirred at 80° C. When the reaction was completed, the resulting compound was extracted with $CH_2Cl_2$ and water, the organic layer was dried over $MgSO_4$, concentrated, and the resulting compound was recrystallized by silicagel column to obtain 32 g of Core a-20 (yield: 66%).

(3) Synthesis of Core 20

Core a-20 (32 g, 1 eqiv.), bis(pinacolato) diboron (27 g, 1.2 eqiv.), $Pd_2(dba)_3$ (2.4 g, 0.03 eqiv.), X-phos (2.5 g, 0.06 equiv.), KOAc (26 g, 2 eqiv.) were dissolved in Toluene (290 mL, 0.3 M) in a round-bottom flask and stirred at 120° C. When the reaction was completed, the resulting compound was extracted with $CH_2Cl_2$ and water, the organic layer was dried over $MgSO_4$, concentrated, and the resulting compound was recrystallized by silicagel column to obtain 25 g of Core 20 (yield: 63%).

5. Synthesis Example of Core 33

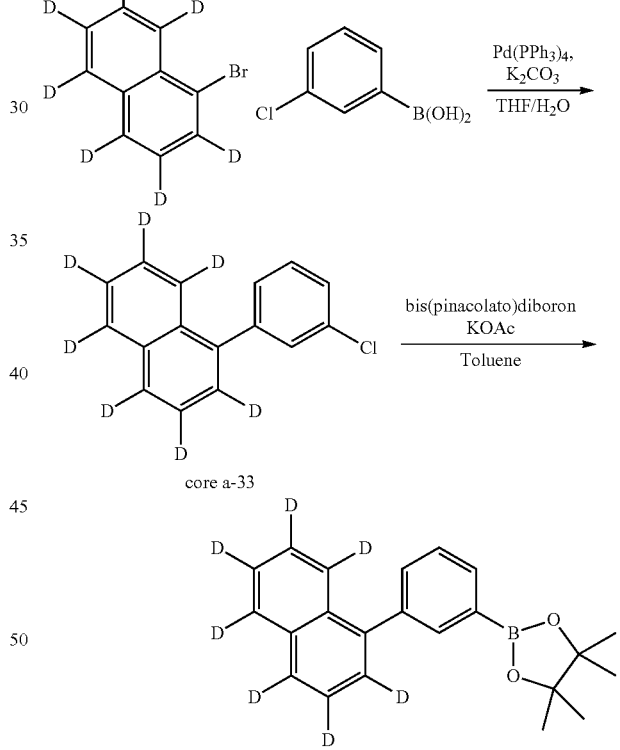

(1) Synthesis of Core a-33

1-bromonaphthalene-2,3,4,5,6,7,8-d7 (50 g, 1 eqiv.), (3-chlorophenyl) boronic acid (36.5 g, 1 eqiv.), $Pd(PPh_3)_4$ (8.1 g, 0.03 eqiv.), $K_2CO_3$ (97 g, 2 eqiv.), THF (778 mL, 0.3M), water were added to a round bottom flask and stirred at 80° C. When the reaction was completed, the resulting compound was extracted with $CH_2Cl_2$ and water, the organic layer was dried over $MgSO_4$, concentrated, and the resulting compound was recrystallized by silicagel column to obtain 38.5 g of Core a-33 (yield: 67%).

(2) Synthesis of Core 33

Core a-33 (30 g, 1 eqiv.), bis(pinacolato) diboron (37.2 g, 1.2 eqiv.), $Pd_2(dba)_3$ (3.4 g, 0.03 eqiv.), X-phos (4.0 g, 0.06 equiv.), KOAc (36 g, 2 eqiv.) were dissolved in Toluene (407 mL, 0.3 M) in a round-bottom flask and stirred at 120° C. When the reaction was completed, the resulting compound was extracted with $CH_2Cl_2$ and water, the organic layer was dried over $MgSO_4$, concentrated, and the resulting compound was recrystallized by silicagel column to obtain 32.9 g of Core 33 (yield: 80%).

6. Synthesis Example of Core 34

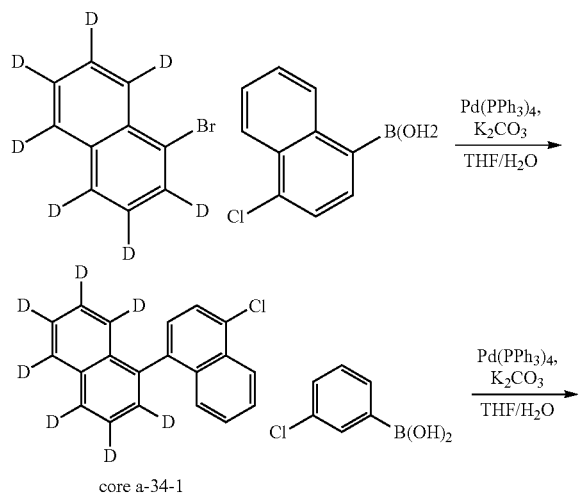

core a-34-1

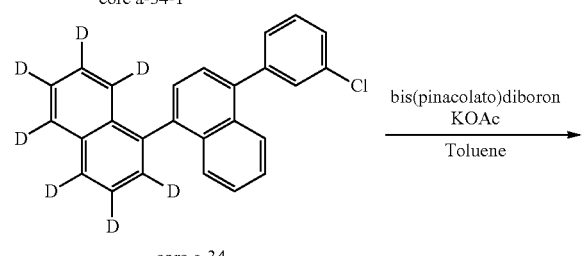

core a-34

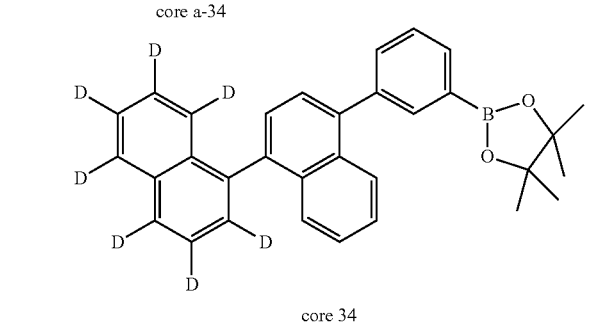

core 34

(1) Synthesis of Core a-34-1

1-bromonaphthalene-2,3,4,5,6,7,8-d7 (50 g, 1 eqiv.), (4-chloronaphthalen-1-yl)boronic acid (48 g, 1 eqiv.), $Pd(PPh_3)_4$ (8.1 g, 0.03 eqiv.), $K_2CO_3$ (97 g, 2 eqiv.), THF (780 mL, 0.3M), water were added to a round bottom flask and stirred at 80° C. When the reaction was completed, the resulting compound was extracted with $CH_2Cl_2$ and water, the organic layer was dried over $MgSO_4$, concentrated, and the resulting compound was recrystallized by silicagel column to obtain 49 g of Core a-34-1 (yield: 71%).

(2) Synthesis of Core a-34

Core a-34-1 (49 g, 1 eqiv.), (3-chlorophenyl)boronic acid (26 g, 1 eqiv.), $Pd(PPh_3)_4$ (5.7 g, 0.03 eqiv.), $K_2CO_3$ (69 g, 2 eqiv.), THF (550 mL, 0.3M), water were added to a round bottom flask and stirred at 80° C. When the reaction was completed, the resulting compound was extracted with $CH_2Cl_2$ and water, the organic layer was dried over $MgSO_4$, concentrated, and the resulting compound was recrystallized by silicagel column to obtain 47 g of Core a-34 (yield: 77%).

(3) Synthesis of Core 34

Core a-34 (45 g, 1 eqiv.), bis(pinacolato)diboron (37 g, 1.2 eqiv), $Pd_2(dba)_3$ (3.3 g, 0.03 eqiv.), X-Phos (3.5 g, 0.06 equiv.), KOAc (35 g, 2 eqiv.) were dissolved in Toluene (400 mL, 0.3 M) in a round-bottom flask and stirred at 120° C. When the reaction was completed, the resulting compound was extracted with $CH_2Cl_2$ and water, the organic layer was dried over $MgSO_4$, concentrated, and the resulting compound was recrystallized by silicagel column to obtain 38 g of Core 34 (yield: 68%).

7. Synthesis Example of Core 35

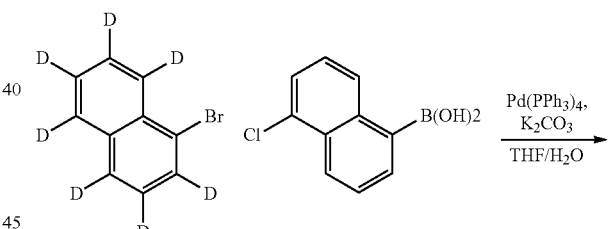

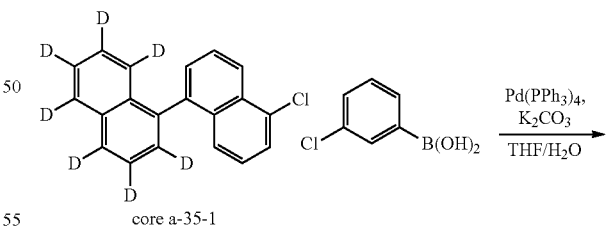

core a-35-1

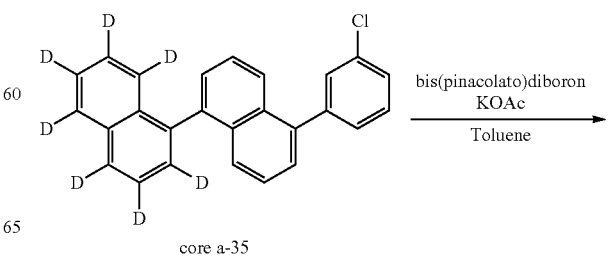

core a-35

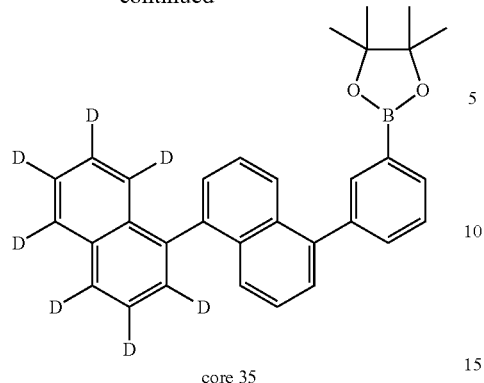

core 35

(1) Synthesis of Core a-35-1

1-bromonaphthalene-2,3,4,5,6,7,8-d7 (50 g, 1 eqiv.), (4-chloronaphthalen-1-yl)boronic acid (48.2 g, 1 eqiv.), Pd(PPh$_3$)$_4$ (8.1 g, 0.03 eqiv.), K$_2$CO$_3$ (97 g, 2 eqiv.), THF (780 mL, 0.3M), water were added to a round bottom flask and stirred at 80° C. When the reaction was completed, the resulting compound was extracted with CH$_2$Cl$_2$ and water, the organic layer was dried over MgSO$_4$, concentrated, and the resulting compound was recrystallized by silicagel column to obtain 54 g of Core a-35-1 (yield: 79%).

(2) Synthesis of Core a-35

Core a-35-1 (54 g, 1 eqiv.), (3-chlorophenyl)boronic acid (28.5 g, 1 eqiv.), Pd(PPh$_3$)$_4$ (6.3 g, 0.03 eqiv.), K$_2$CO$_3$ (76 g, 2 eqiv.), THF (600 mL, 0.3M), water were added to a round bottom flask and stirred at 80° C. When the reaction was completed, the resulting compound was extracted with CH$_2$Cl$_2$ and water, the organic layer was dried over MgSO$_4$, concentrated, and the resulting compound was recrystallized by silicagel column to obtain 46 g of Core a-35 (yield: 68%).

(3) Synthesis of Core 35

Core a-35 (45 g, 1 eqiv.), bis(pinacolato) diboron (37 g, 1.2 eqiv.), Pd$_2$(dba)$_3$ (3.3 g, 0.03 eqiv.), X-Phos (3.5 g, 0.06 equiv.), KOAc (36 g, 2 eqiv.) were dissolved in Toluene (400 mL, 0.3 M) in a round-bottom flask and stirred at 120° C. When the reaction was completed, the resulting compound was extracted with CH$_2$Cl$_2$ and water, the organic layer was dried over MgSO$_4$, concentrated, and the resulting compound was recrystallized by silicagel column to obtain 43 g of Core 35 (yield: 77%).

Meanwhile, the compound belonging to Core may be the following compounds, but is not limited thereto, and Table 1 shows the FD-MS (Field Desorption-Mass Spectrometry) values of the compounds belonging to Core.

core1

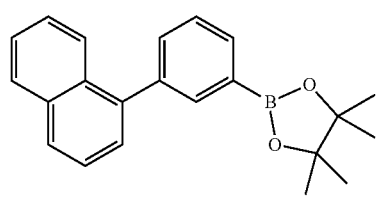

core2

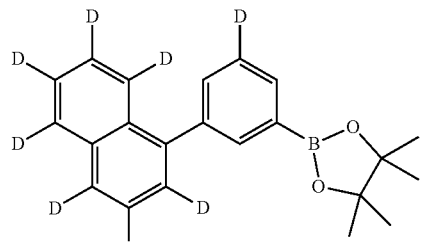

core3

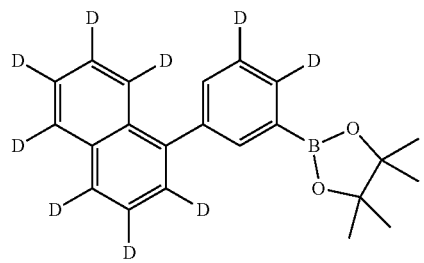

core4

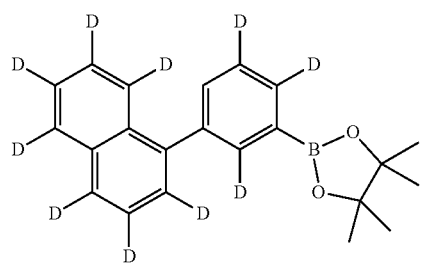

core5

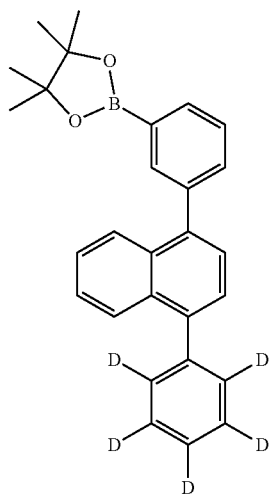

core6 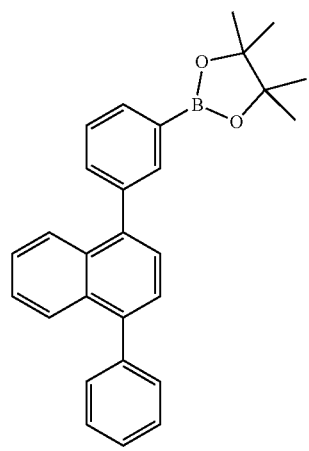
core7 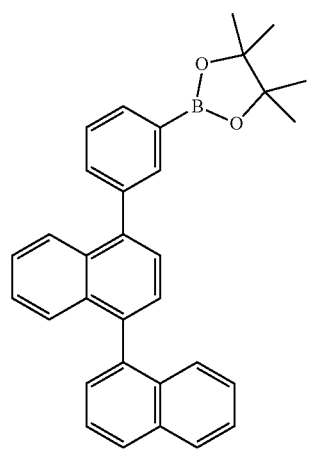
core8
core9 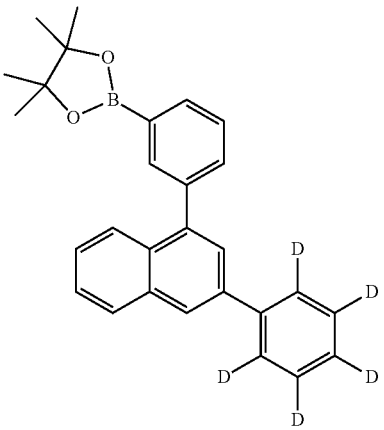
core10 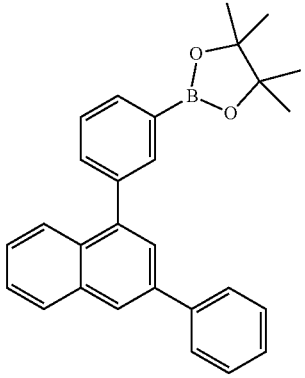
core11 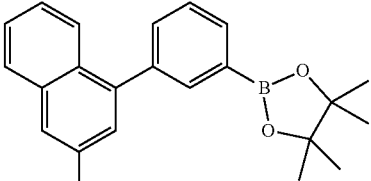
core12 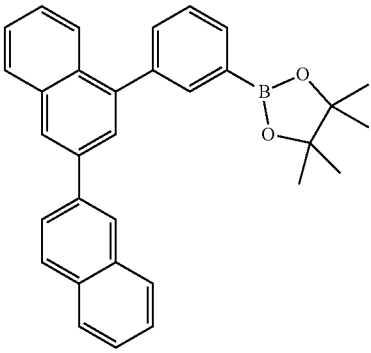

core13
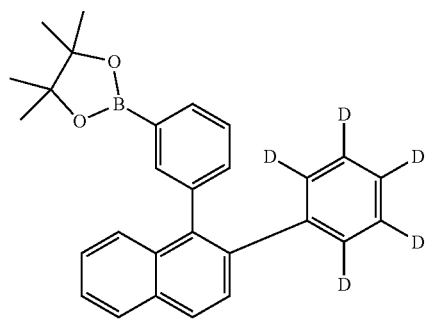
core14
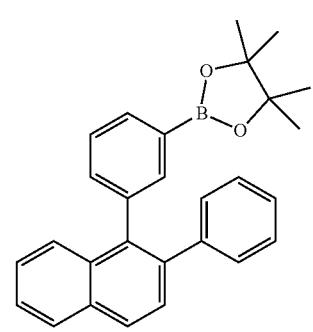
core15
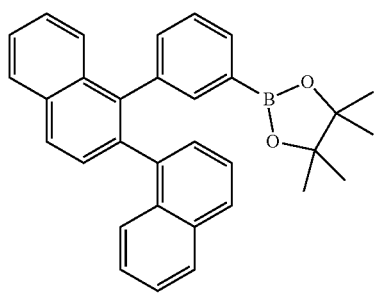
core16
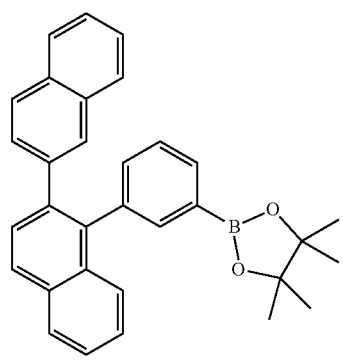
core17
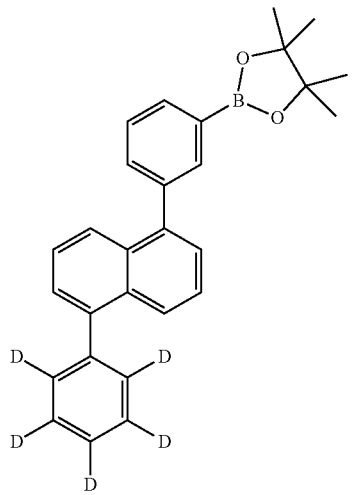
core18
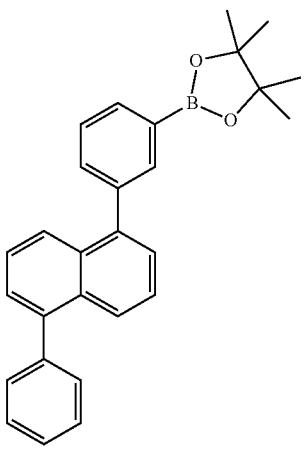
core19
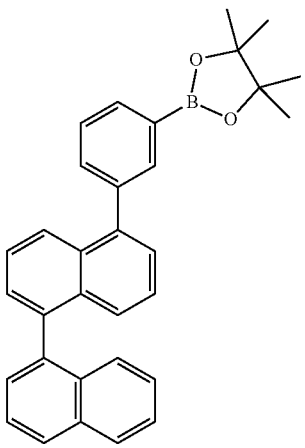

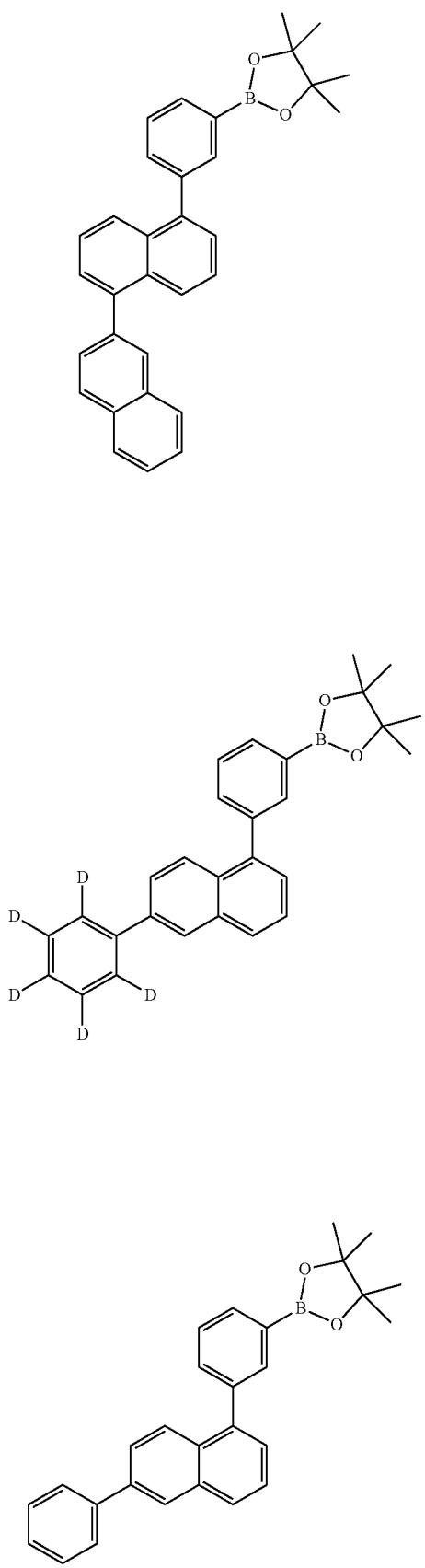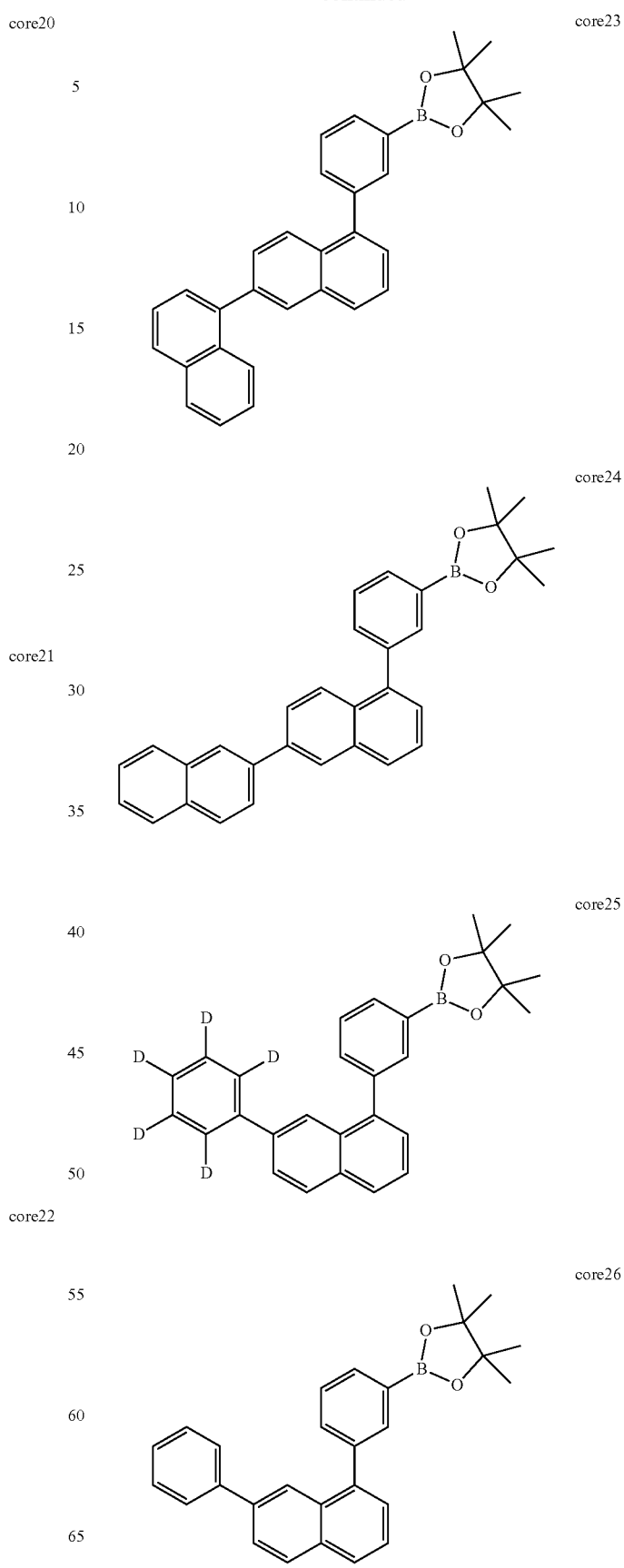

-continued
core27
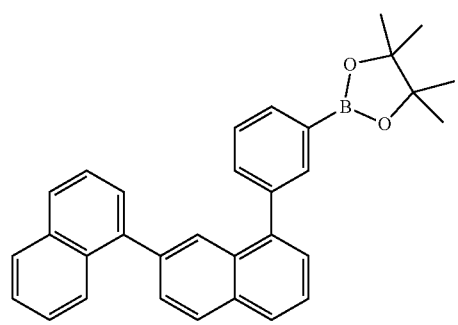
core28
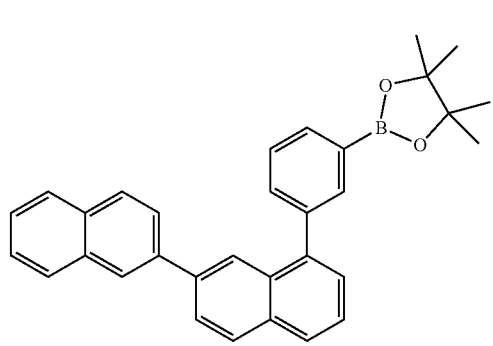
core29
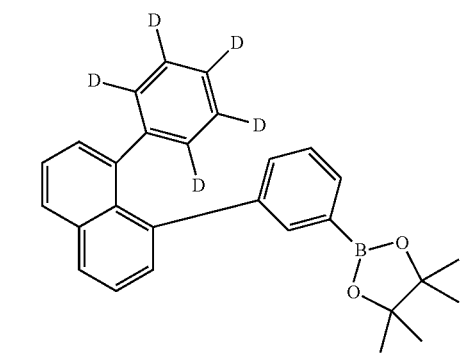
core30
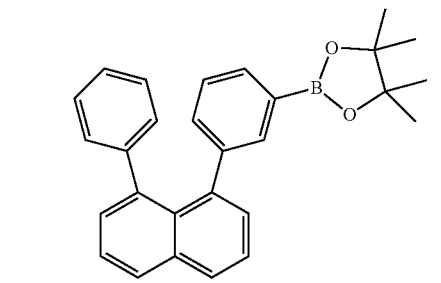
core31
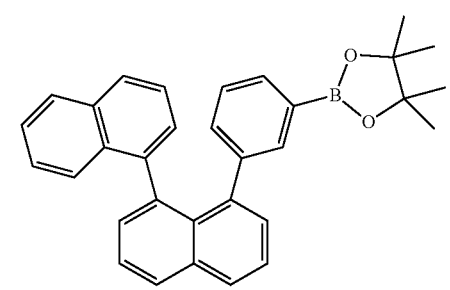
-continued
core32
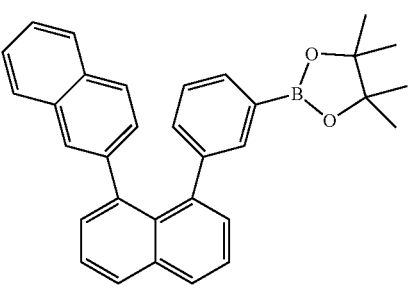
core33
core34
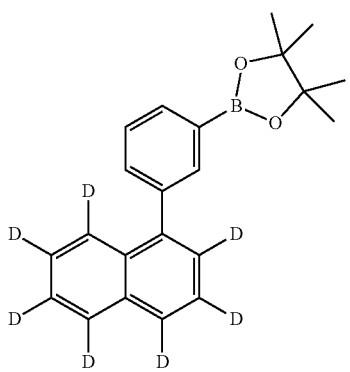

core35

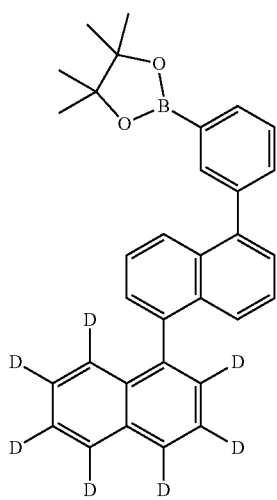

TABLE 1

| Cpd. | FD-MS |
|---|---|
| Core1 | m/z = 330.18($C_{22}H_{23}BO_2$ = 330.23) |
| Core2 | m/z = 338.23($C_{22}H_{15}D_8BO_2$ = 338.28) |
| Core3 | m/z = 339.24($C_{22}H_{14}D_9BO_2$ = 339.29) |
| Core4 | m/z = 340.24($C_{22}H_{13}D_{10}BO_2$ = 340.30) |
| Core5 | m/z = 411.24($C_{28}H_{22}D_5BO_2$ = 411.36) |
| Core6 | m/z = 406.21($C_{28}H_{27}BO_2$ = 406.33) |
| Core7 | m/z = 456.23($C_{32}H_{29}BO_2$ = 456.39) |
| Core8 | m/z = 456.23($C_{32}H_{29}BO_2$ = 456.39) |
| Core9 | m/z = 411.24($C_{28}H_{22}D_5BO_2$ = 411.36) |
| Core10 | m/z = 406.21($C_{28}H_{27}BO_2$ = 406.33) |
| Core11 | m/z = 456.23($C_{32}H_{29}BO_2$ = 456.39) |
| Core12 | m/z = 456.23($C_{32}H_{29}BO_2$ = 456.39) |
| Core13 | m/z = 411.24($C_{28}H_{22}D_5BO_2$ = 411.36) |
| Core14 | m/z = 406.21($C_{28}H_{27}BO_2$ = 406.33) |
| Core15 | m/z = 456.23($C_{32}H_{29}BO_2$ = 456.39) |
| Core16 | m/z = 456.23($C_{32}H_{29} BO_2$ = 456.39) |
| Core17 | m/z = 411.24($C_{28}H_{22}D_5BO_2$ = 411.36) |
| Core18 | m/z = 406.21($C_{28}H_{27}BO_2$ = 406.33) |
| Core19 | m/z = 456.23($C_{32}H_{29}BO_2$ = 456.39) |
| Core20 | m/z = 456.23($C_{32}H_{29} BO_2$ = 456.39) |
| Core21 | m/z = 411.24($C_{28}H_{22}D_5BO_2$ = 411.36) |
| Core22 | m/z = 406.21($C_{28}H_{27}BO_2$ = 406.33) |
| Core23 | m/z = 456.23($C_{32}H_{29}BO_2$ = 456.39) |
| Core24 | m/z = 456.23($C_{32}H_{29} BO_2$ = 456.39) |
| Core25 | m/z = 411.24($C_{28}H_{22}D_5BO_2$ = 411.36) |
| Core26 | m/z = 406.21($C_{28}H_{27}BO_2$ = 406.33) |
| Core27 | m/z = 456.23($C_{32}H_{29}BO_2$ = 456.39) |
| Core28 | m/z = 456.23($C_{32}H_{29} BO_2$ = 456.39) |
| Core29 | m/z = 411.24($C_{28}H_{22}D_5BO_2$ = 411.36) |
| Core30 | m/z = 406.21($C_{28}H_{27}BO_2$ = 406.33) |
| Core31 | m/z = 456.23($C_{32}H_{29}BO_2$ = 456.39) |
| Core32 | m/z = 456.23($C_{32}H_{29} BO_2$ = 456.39) |
| Core33 | m/z = 337.22($C_{22}H_{16}D_7BO_2$ = 337.28) |
| Core34 | m/z = 463.27($C_{32}H_{22}D_7BO_2$ = 463.43) |
| Core35 | m/z = 463.27($C_{32}H_{22}D_7BO_2$ = 463.43) |

II. Synthesis of Sub

Sub of <Reaction Scheme 1> may be synthesized by the reaction route of <Reaction Scheme 3>, but is not limited thereto.

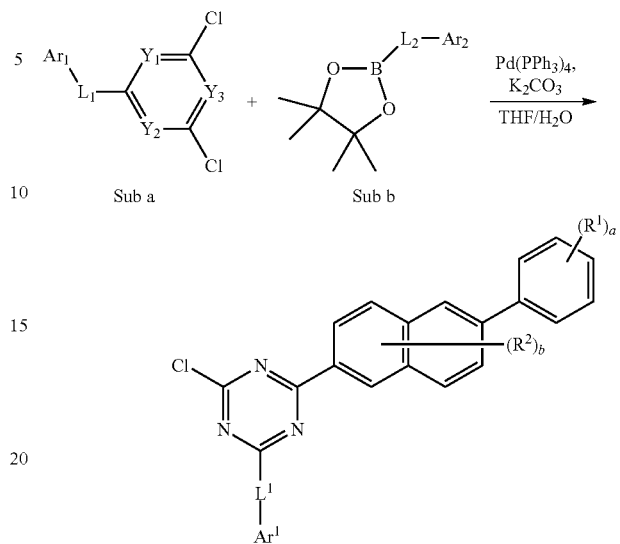

1. Synthesis Example of Sub 1

2,4-dichloro-6-phenyl-1,3,5-triazine (30 g, 2 equiv.), Sub 1-1 (22 g, 1 equiv.), Pd(PPh₃)₄ (2.3 g, 0.03 equiv.), K₂CO₃ (28 g, 2 equiv.), Toluene (220 mL, 0.3M) and water were added to a round-bottom flask and stirred at 50° C. When the reaction was completed, the resulting compound was extracted with CH₂Cl₂ and water, the organic layer was dried over MgSO₄, concentrated, and the resulting compound was recrystallized by silicagel column to obtain 12 g of Sub 1 (yield: 48%).

2. Synthesis Example of Sub 2

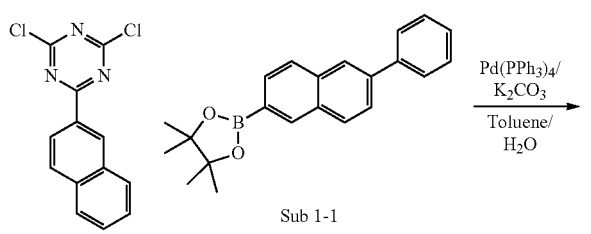

Sub 1-1

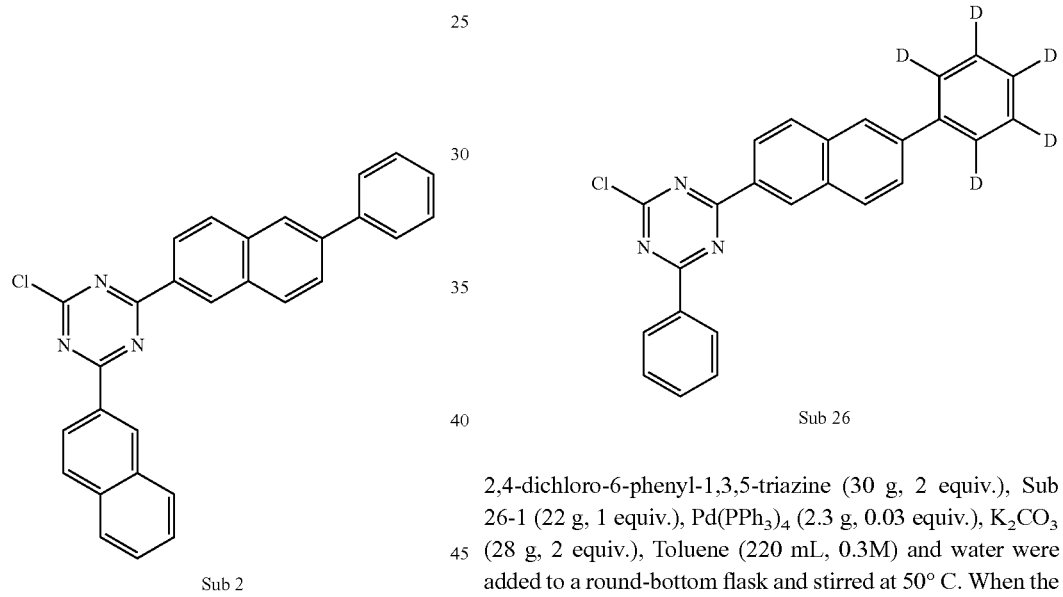

Sub 2

2,4-dichloro-6-phenyl-1,3,5-triazine (30 g, 2 equiv.), Sub1-1 (18 g, 1 equiv.), Pd(PPh₃)₄ (1.9 g, 0.03 equiv.), K₂CO₃ (23 g, 2 equiv.), Toluene (180 mL, 0.3M) and water were added to a round-bottom flask and stirred at 50° C. When the reaction was completed, the resulting compound was extracted with CH₂Cl₂ and water, the organic layer was dried over MgSO₄, concentrated, and the resulting compound was recrystallized by silicagel column to obtain 11 g of Sub 2 (yield: 45%).

3. Synthesis Example of Sub 26

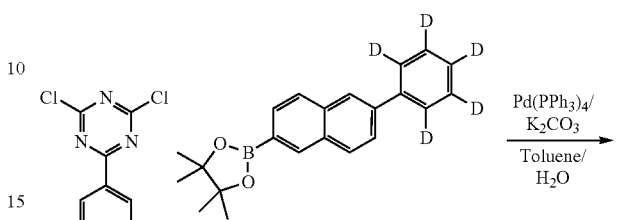

Sub 26-1

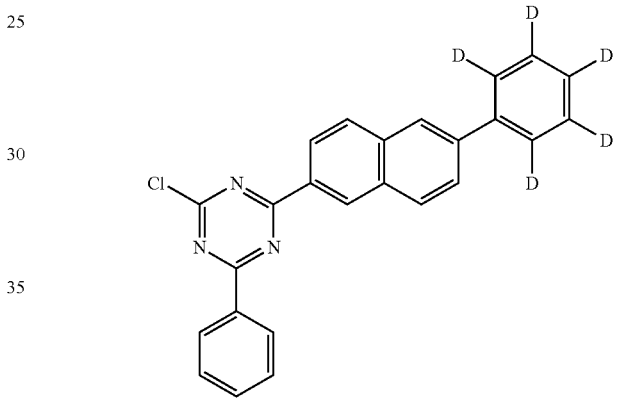

Sub 26

2,4-dichloro-6-phenyl-1,3,5-triazine (30 g, 2 equiv.), Sub 26-1 (22 g, 1 equiv.), Pd(PPh₃)₄ (2.3 g, 0.03 equiv.), K₂CO₃ (28 g, 2 equiv.), Toluene (220 mL, 0.3M) and water were added to a round-bottom flask and stirred at 50° C. When the reaction was completed, the resulting compound was extracted with CH₂Cl₂ and water, the organic layer was dried over MgSO₄, concentrated, and the resulting compound was recrystallized by silicagel column to obtain 11 g of Sub 26 (yield: 43%).

4. Synthesis Example of Sub 41

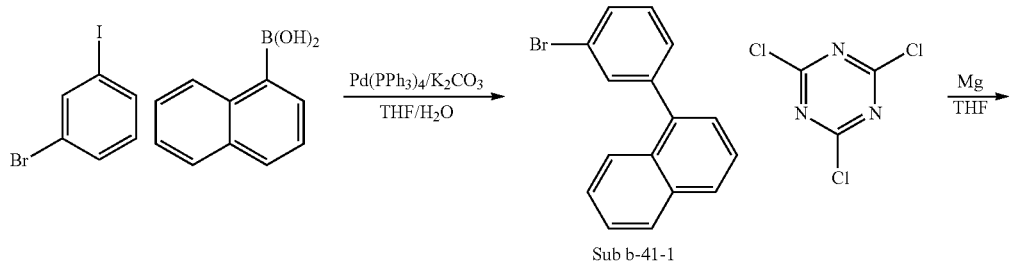

Sub b-41-1

149

-continued

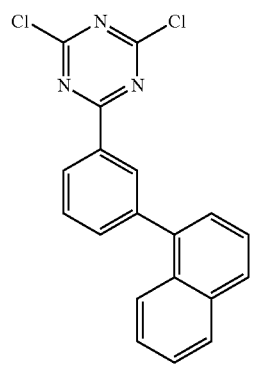
Sub b-41

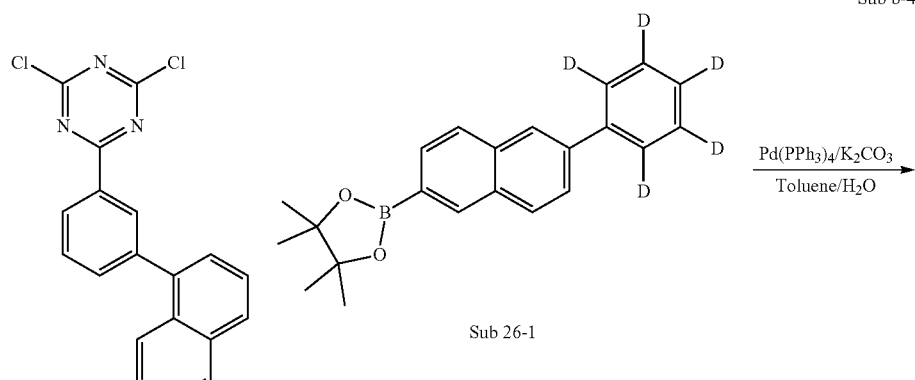

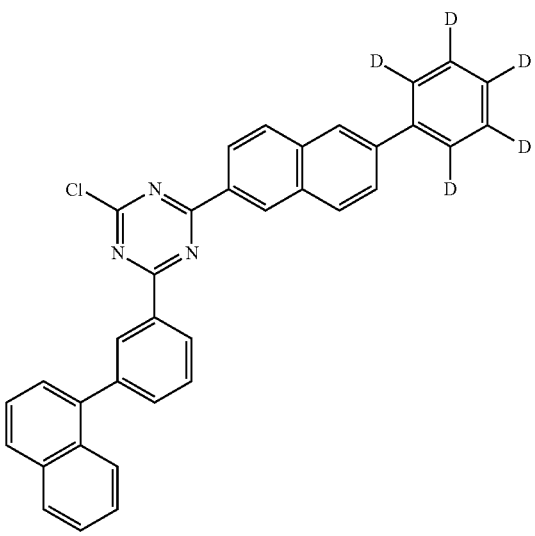
Sub 41

(1) Synthesis of Sub b-41-1

1-bromo-3-iodobenzene (25 g, 2 eqiv.), naphthalen-1-ylboronic acid (30 g, 1 eqiv.), Pd(PPh$_3$)$_4$ (3 g, 0.03 eqiv.), K$_2$CO$_3$ (36 g, 2 eqiv.), THE (300 mL, 0.3M) and water were added to a round-bottom flask and stirred at 80° C. When the reaction was completed, the resulting compound was extracted with CH$_2$Cl$_2$ and water, the organic layer was dried over MgSO$_4$, concentrated, and the resulting compound was recrystallized by silicagel column to obtain 18 g of Sub b-41-1 (yield: 75%).

(2) Synthesis of Sub b-41

Add Mg (5.3 g, 2 eqiv.) and THE (360 mL, 0.3M) to round-bottom flask 1 filled with nitrogen and stir at 50° C., then slowly add sub b-41-1 (20 g, 1 eqiv.) dropwise. After 6 hours, stop stirring and take the solution using a syringe. 2,4,6-trichloro-1,3,5-triazine (40 g, 2 eqiv.) was dissolved in THE in round bottom flask 2, and Grignard reagent was slowly added dropwise, followed by stirring for 12 hours. When the reaction was completed, the resulting compound was extracted with CH$_2$Cl$_2$ and water, the organic layer was dried over MgSO₄, concentrated, and the resulting compound was recrystallized by silicagel column to obtain 15 g of Sub b-41 (yield: 40%).

(3) Synthesis of Sub 41

2,4-dichloro-6-phenyl-1,3,5-triazine (30 g, 2 equiv.), Sub 26-1 (14 g, 1 equiv.), Pd(PPh₃)₄ (1.5 g, 0.03 equiv.), K₂CO₃ (18 g, 2 equiv.), Toluene (140 mL, 0.3M) and water were added to a round-bottom flask and stirred at 50° C. When the reaction was completed, the resulting compound was extracted with CH₂Cl₂ and water, the organic layer was dried over MgSO₄, concentrated, and the resulting compound was recrystallized by silicagel column to obtain 9 g of Sub 41 (yield: 40%).

Otherwise, the compound belonging to Sub may be the following compounds, but is not limited thereto, and Table 2 shows the FD-MS values of the compounds belonging to Sub.

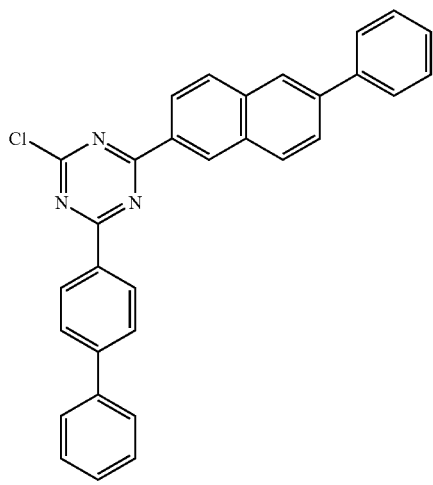
sub4

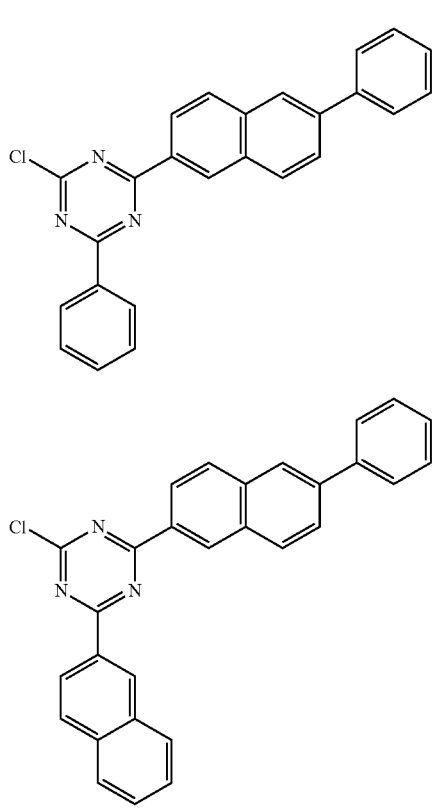
sub1 sub2 sub3

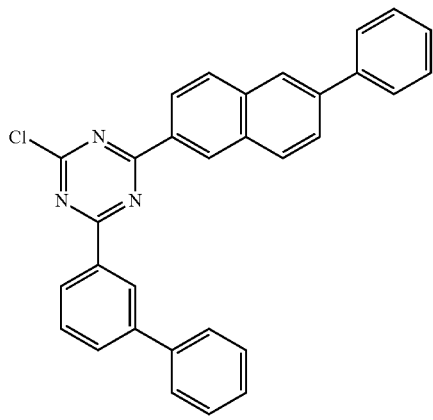
sub5

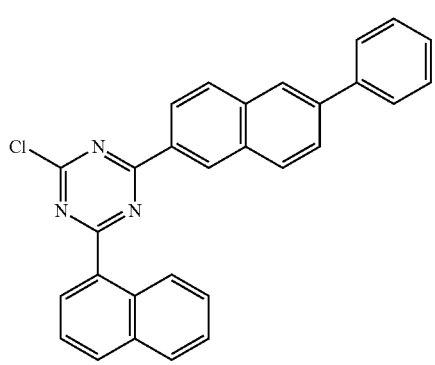

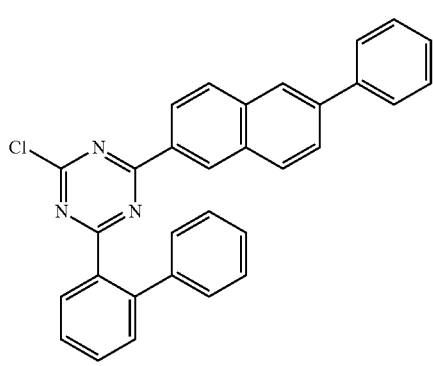
sub6 sub7
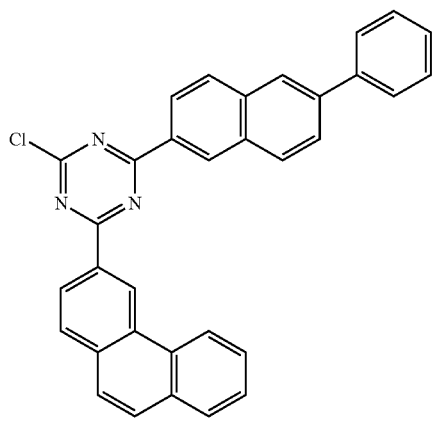
sub8
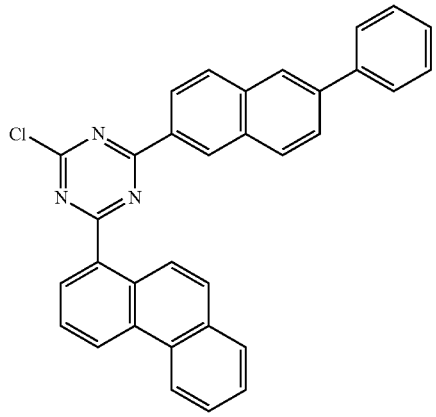
sub9
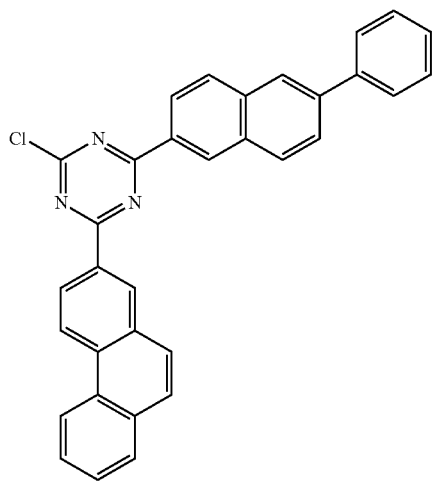
sub10
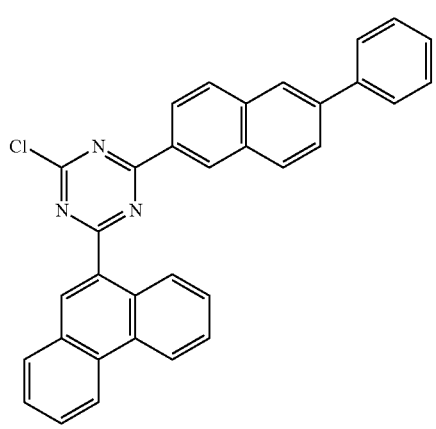
sub11
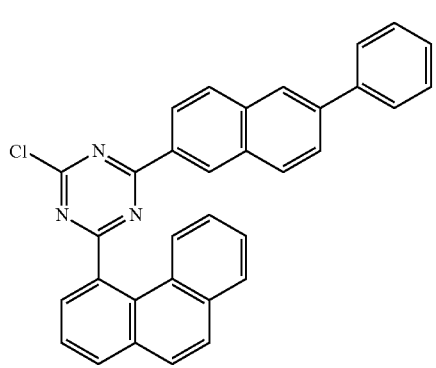
sub12
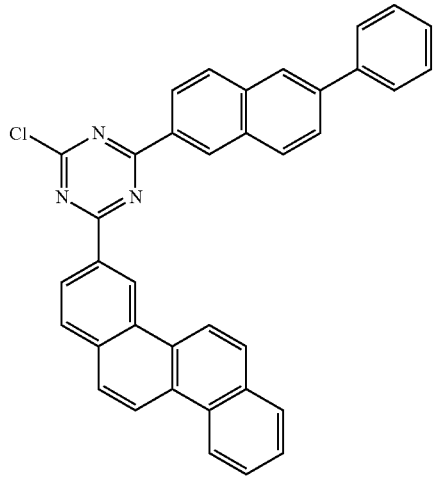

-continued
sub13
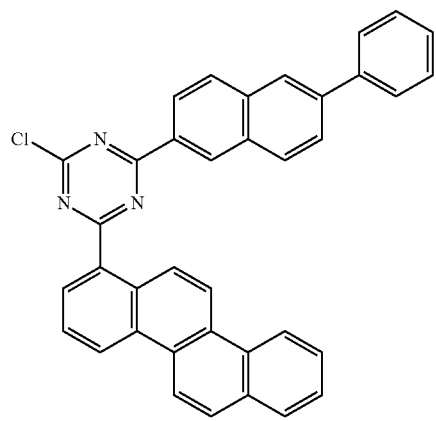
sub16
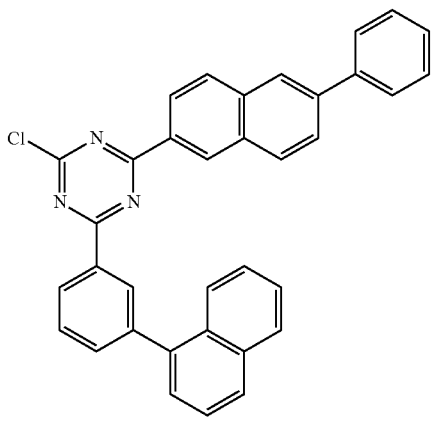
sub14
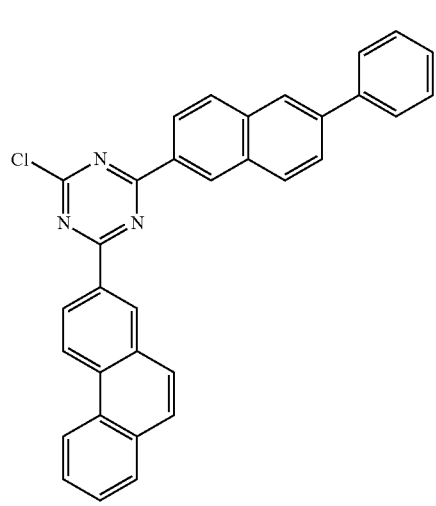
sub17
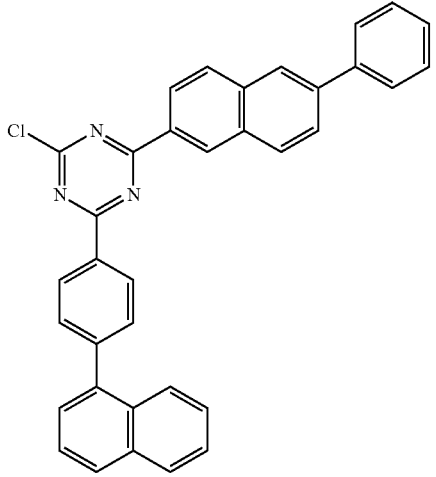
sub15
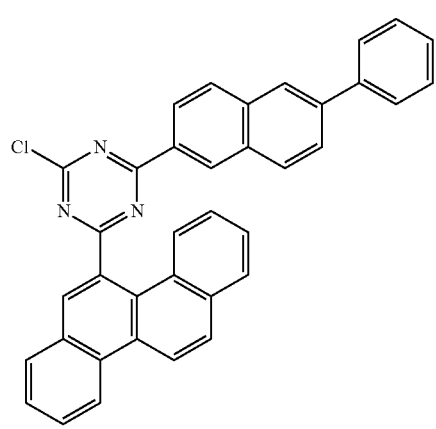
sub18
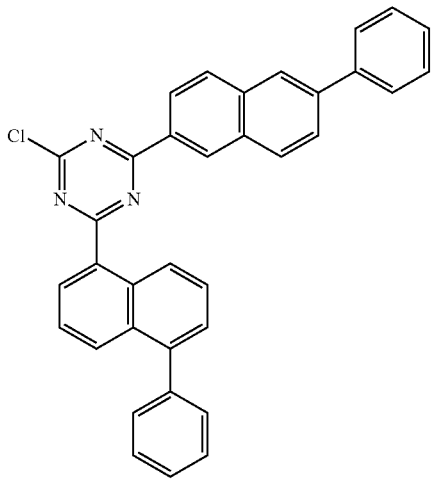

sub19
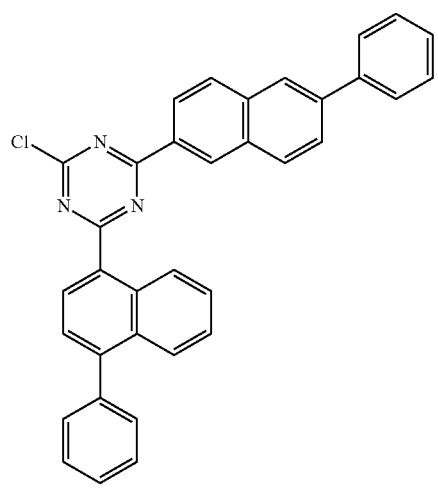
sub20
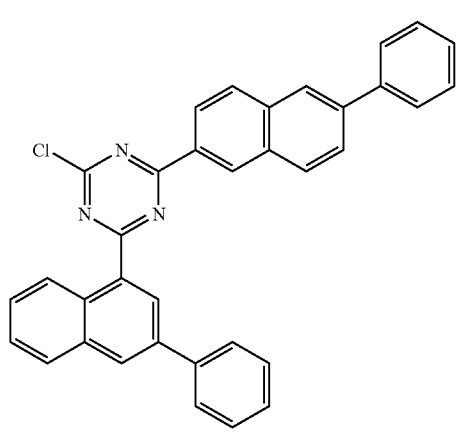
sub21
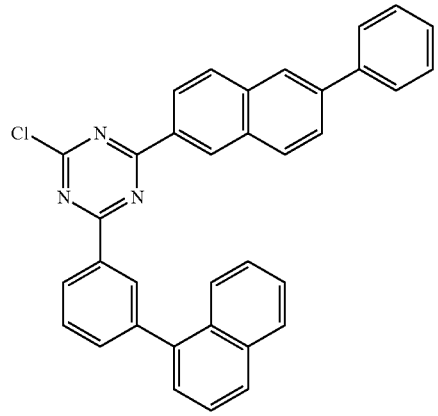
sub22
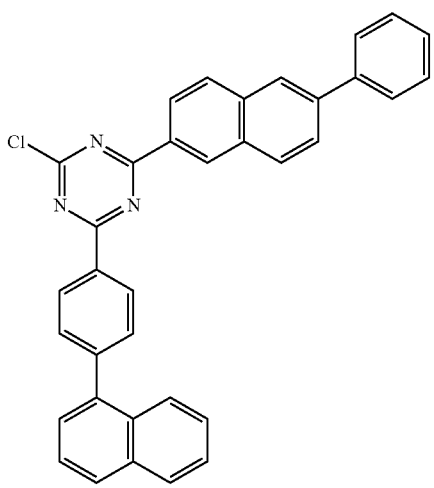
sub23
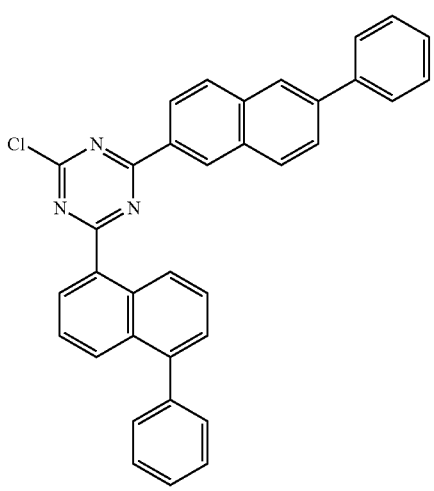
sub24
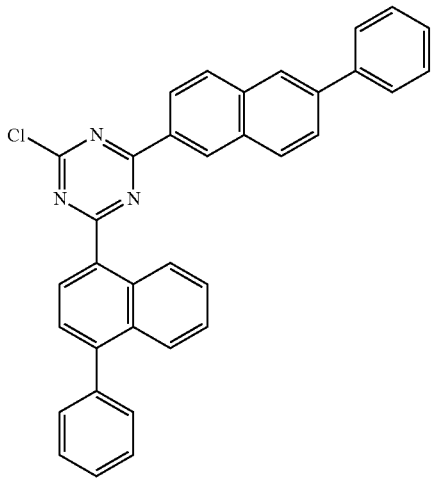

sub25
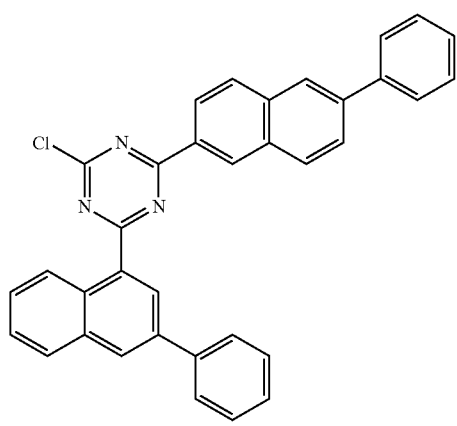
sub26
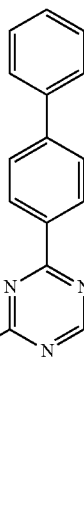
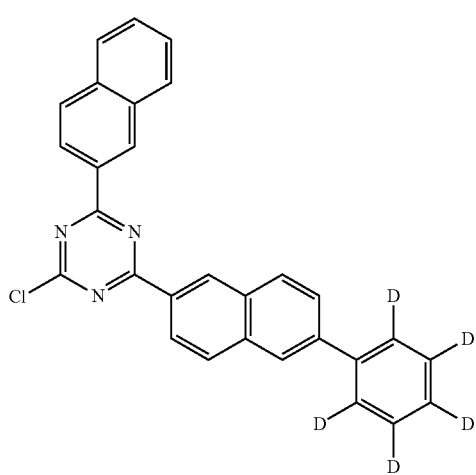
sub27
sub28
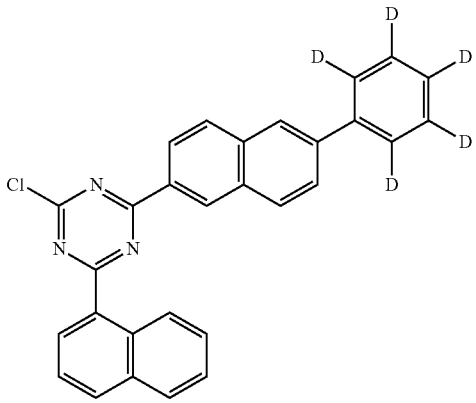
sub29
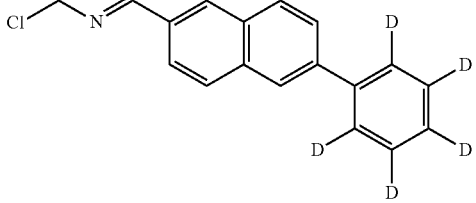
sub30
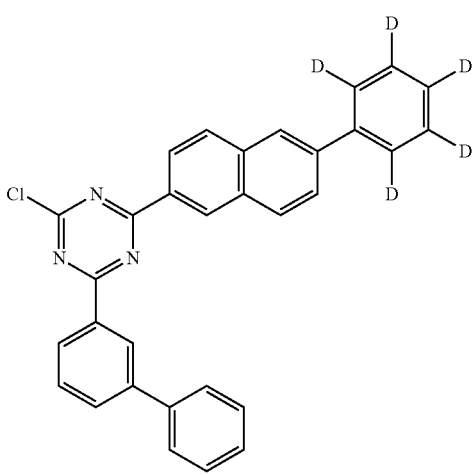

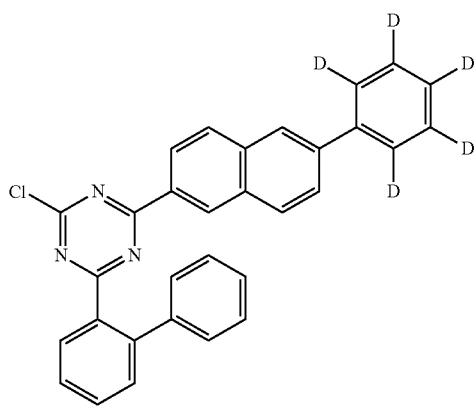
sub31
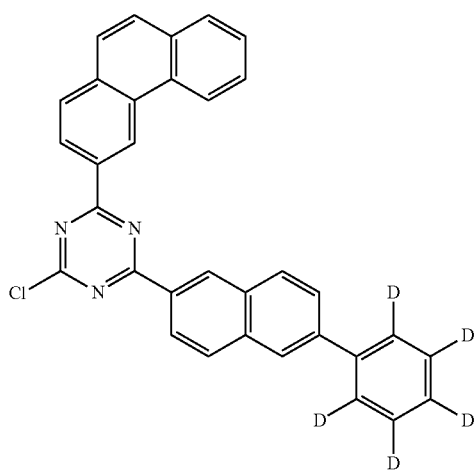
sub32
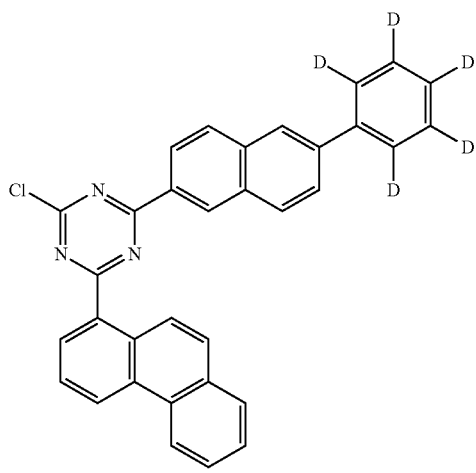
sub33
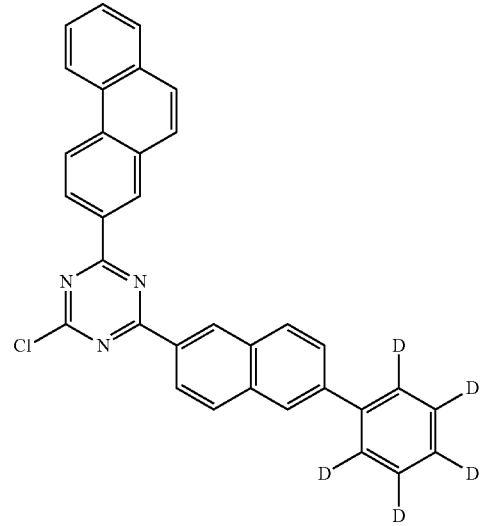
sub34
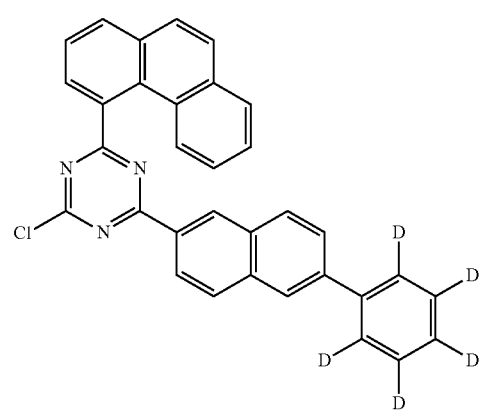
sub35
sub36 sub37
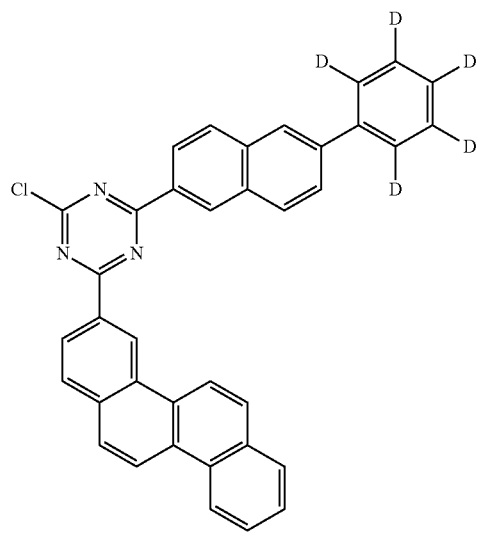
sub38
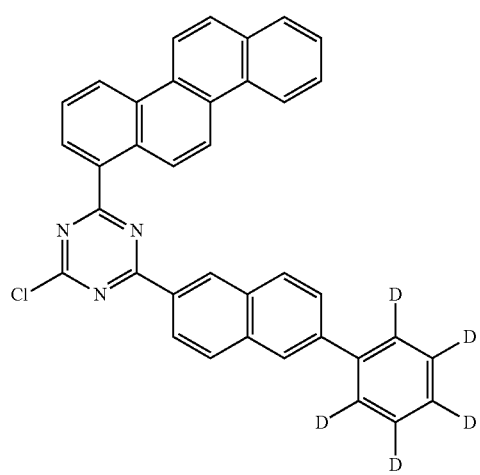
sub39
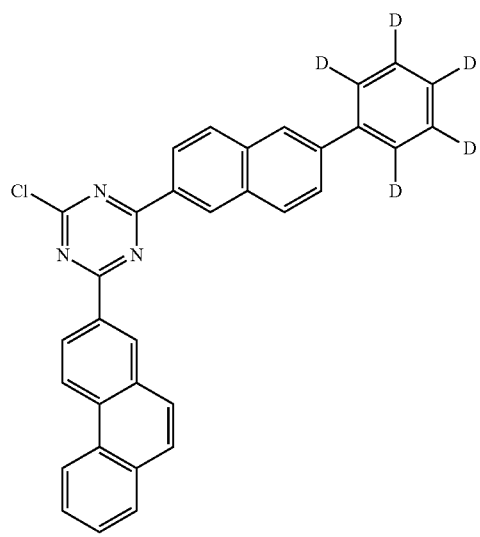
sub40
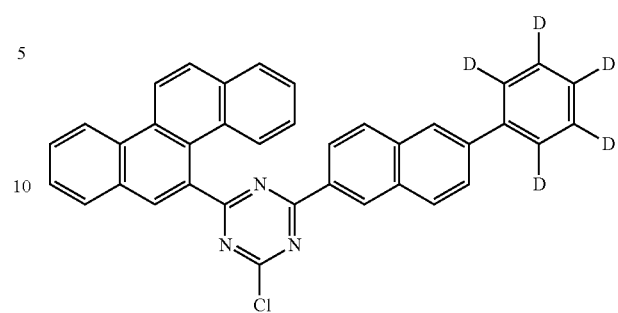
sub41
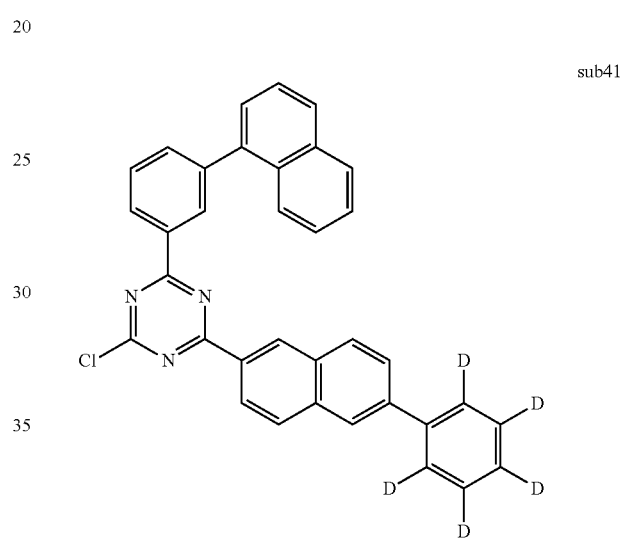
sub42
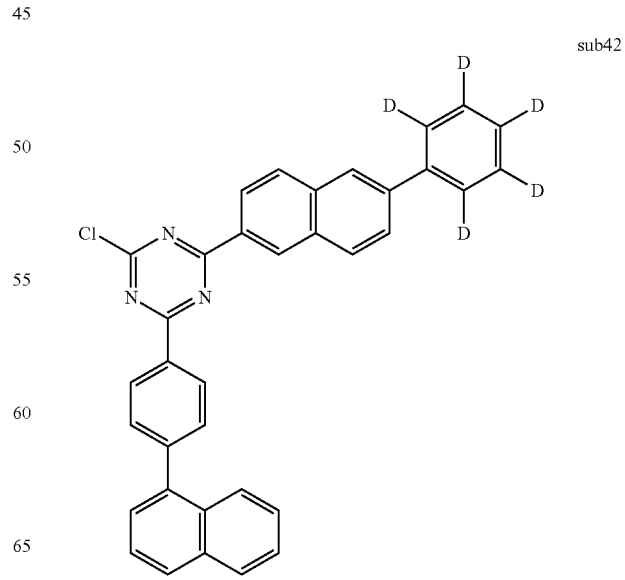

-continued sub43

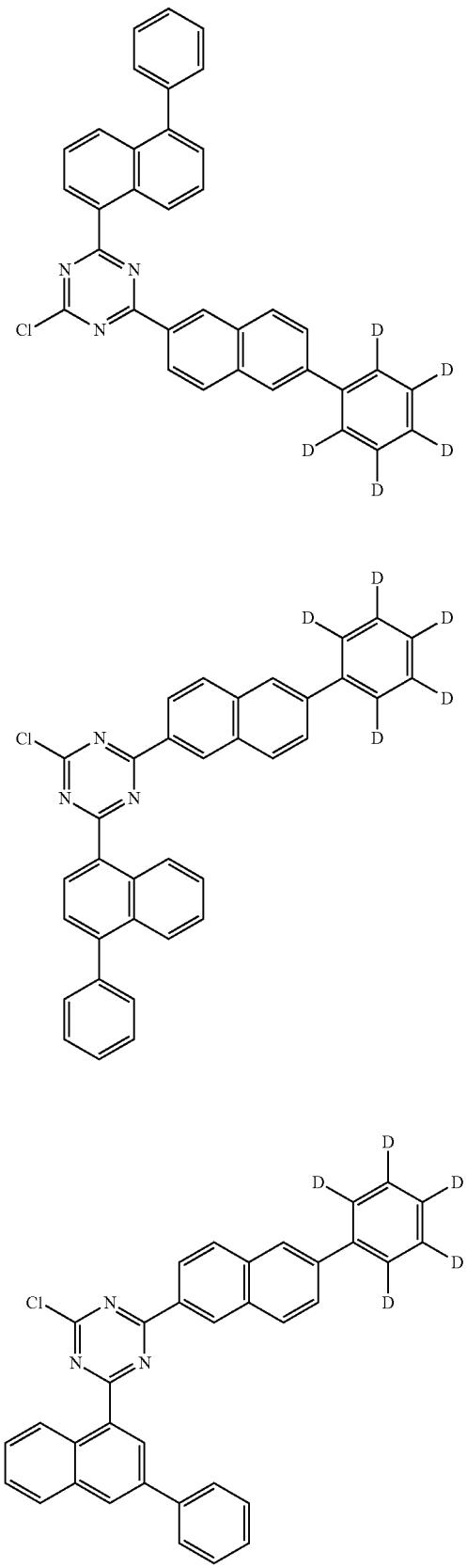

sub44 sub45

TABLE 2

| Cpd. | FD-MS |
|---|---|
| sub1 | m/z = 393.10($C_{25}H_{16}ClN_3$ = 393.87) |
| sub2 | m/z = 443.12($C_{29}H_{18}ClN_3$ = 443.93) |
| sub3 | m/z = 443.12($C_{29}H_{18}ClN_3$ = 443.93) |
| sub4 | m/z = 469.13($C_{31}H_{20}ClN_3$ = 469.97) |
| sub5 | m/z = 469.13($C_{31}H_{20}ClN_3$ = 469.97) |
| sub6 | m/z = 469.13($C_{31}H_{20}ClN_3$ = 469.97) |
| sub7 | m/z = 493.13($C_{33}H_{20}ClN_3$ = 493.99) |
| sub8 | m/z = 493.13($C_{33}H_{20}ClN_3$ = 493.99) |
| sub9 | m/z = 493.13($C_{33}H_{20}ClN_3$ = 493.99) |
| sub10 | m/z = 493.13($C_{33}H_{20}ClN_3$ = 493.99) |
| sub11 | m/z = 493.13($C_{33}H_{20}ClN_3$ = 493.99) |
| sub12 | m/z = 543.15($C_{37}H_{22}ClN_3$ = 544.05) |
| sub13 | m/z = 493.13($C_{33}H_{20}ClN_3$ = 493.99) |
| sub14 | m/z = 493.13($C_{33}H_{20}ClN_3$ = 493.99) |
| sub15 | m/z = 543.15($C_{37}H_{22}ClN_3$ = 544.05) |
| sub16 | m/z = 519.15($C_{35}H_{22}ClN_3$ = 520.03) |
| sub17 | m/z = 519.15($C_{35}H_{22}ClN_3$ = 520.03) |
| sub18 | m/z = 519.15($C_{35}H_{22}ClN_3$ = 520.03) |
| sub19 | m/z = 543.15($C_{37}H_{22}ClN_3$ = 544.05) |
| sub20 | m/z = 519.15($C_{35}H_{22}ClN_3$ = 520.03) |
| sub21 | m/z = 519.15(C35H22ClN3 = 520.03) |
| sub22 | m/z = 519.15($C_{35}H_{22}ClN_3$ = 520.03) |
| sub23 | m/z = 519.15($C_{35}H_{22}ClN_3$ = 520.03) |
| sub24 | m/z = 519.15($C_{35}H_{22}ClN_3$ = 520.03) |
| sub25 | m/z = 519.15($C_{35}H_{22}ClN_3$ = 520.03) |
| sub26 | m/z = 398.13($C_{25}H_{11}D_5ClN_3$ = 398.90) |
| sub27 | m/z = 448.15($C_{29}H_{13}D_5ClN_3$ = 448.96) |
| sub28 | m/z = 448.15($C_{29}H_{13}D_5ClN_3$ = 448.96) |
| sub29 | m/z = 474.17($C_{31}H_{15}D_5ClN_3$ = 475.00) |
| sub30 | m/z = 474.17($C_{31}H_{15}D_5ClN_3$ = 475.00) |
| sub31 | m/z = 474.17($C_{31}H_{15}D_5ClN_3$ = 475.00) |
| sub32 | m/z = 498.17($C_{33}H_{15}D_5ClN_3$ = 499.02) |
| sub33 | m/z = 498.17($C_{33}H_{15}D_5ClN_3$ = 499.02) |
| sub34 | m/z = 498.17($C_{33}H_{15}D_5ClN_3$ = 499.02) |
| sub35 | m/z = 498.17($C_{33}H_{15}D_5ClN_3$ = 499.02) |
| sub36 | m/z = 498.17($C_{33}H_{15}D_5ClN_3$ = 499.02) |
| sub37 | m/z = 548.18($C_{37}H_{17}D_5ClN_3$ = 549.08) |
| sub38 | m/z = 548.18($C_{37}H_{17}D_5ClN_3$ = 549.08) |
| sub39 | m/z = 498.17($C_{33}H_{15}D_5ClN_3$ = 499.02) |
| sub40 | m/z = 548.18($C_{37}H_{17}D_5ClN_3$ = 549.08) |
| sub41 | m/z = 524.18($C_{35}H_{17}D_5ClN_3$ = 525.06) |
| sub42 | m/z = 524.18($C_{35}H_{17}D_5ClN_3$ = 525.06) |
| sub43 | m/z = 524.18($C_{35}H_{17}D_5ClN_3$ = 525.06) |
| sub44 | m/z = 524.18($C_{35}H_{17}D_5ClN_3$ = 525.06) |
| sub45 | m/z = 524.18($C_{35}H_{17}D_5ClN_3$ = 525.06) |

III. Synthesis of Final Product

1. Synthesis Example of P-1

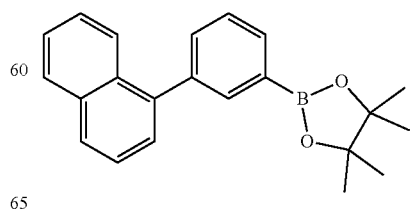

core 1

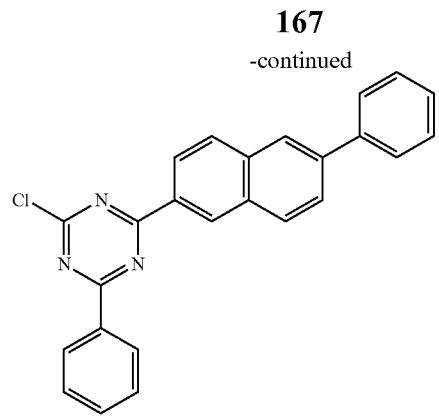

sub 1

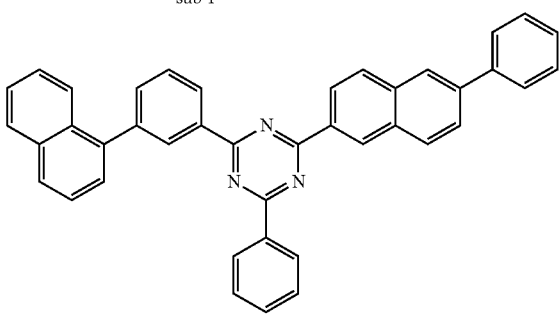

P-1

Core 1 (8.4 g, 1 equiv.), sub 1 (10 g, 1 equiv.), Pd(PPh$_3$)$_4$ (0.9 g, 0.03 equiv.), K$_2$CO$_3$ (10.5 g, 2 equiv.), Toluene (44 mL), Ethanol (5 mL) and water were added to a round-bottom flask and stirred at 120° C. When the reaction was completed, the resulting compound was extracted with CH$_2$Cl$_2$ and water, the organic layer was dried over MgSO$_4$, concentrated, and the resulting compound was recrystallized by silicagel column to obtain 11 g of P-1 (yield: 77%).

2. Synthesis Example of P-22

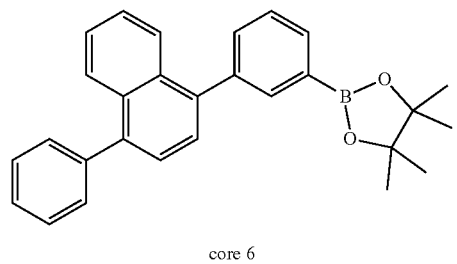

core 6

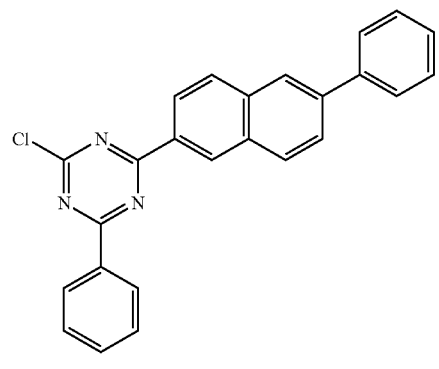

sub 1

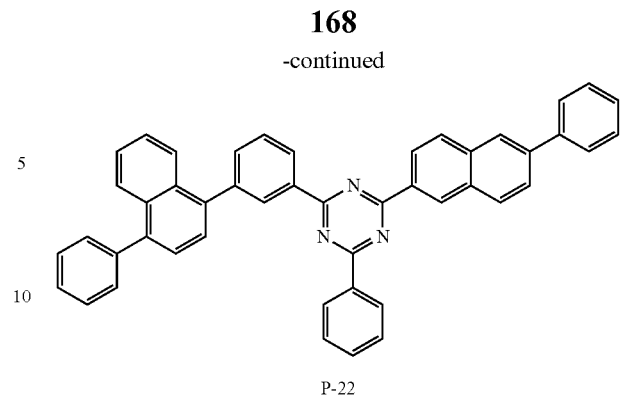

P-22

Core 6 (10.3 g, 1 equiv.), sub 1 (10 g, 1 equiv.), Pd(PPh$_3$)$_4$ (0.9 g, 0.03 equiv.), K$_2$CO$_3$ (10.5 g, 2 equiv.), Toluene (85 mL), Ethanol (9 mL) and water were added to a round-bottom flask and stirred at 120° C. When the reaction was completed, the resulting compound was extracted with CH$_2$Cl$_2$ and water, the organic layer was dried over MgSO$_4$, concentrated, and the resulting compound was recrystallized by silicagel column to obtain 134 g of P-22 (yield: 83%).

3. Synthesis Example of P-43

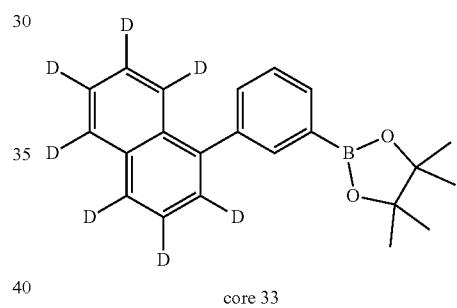

core 33

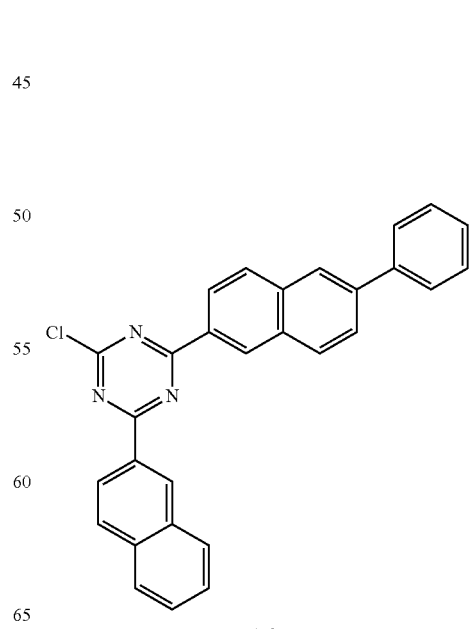

sub 2

169

-continued

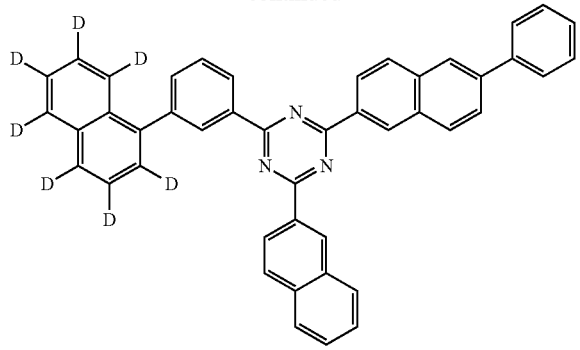

P-43

Core 33 (6.9 g, 1 equiv.), sub 2 (10 g, 1 equiv.), Pd(PPh₃)₄ (0.7 g, 0.03 equiv.), K₂CO₃ (8.5 g, 2 equiv.), Toluene (68 mL), Ethanol (7 mL) and water were added to a round-bottom flask and stirred at 120° C. When the reaction was completed, the resulting compound was extracted with CH₂Cl₂ and water, the organic layer was dried over MgSO₄, concentrated, and the resulting compound was recrystallized by silicagel column to obtain 8.5 g of P-43 (yield: 67%).

4. Synthesis Example of P-63

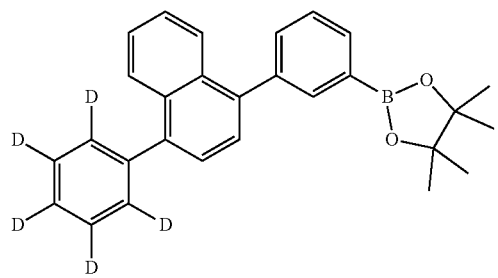

core 5

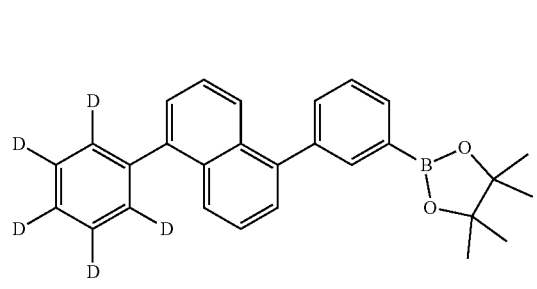

core 17

170

-continued

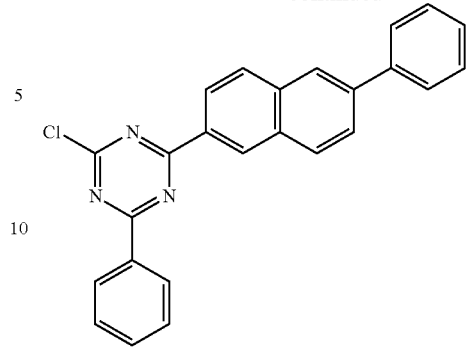

sub 1

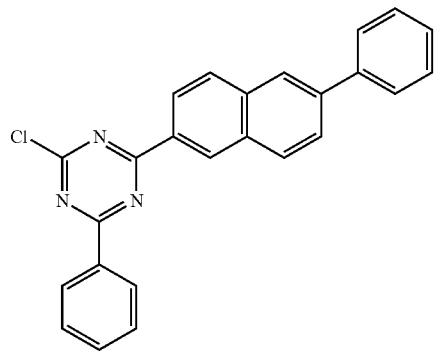

P-63

Core 5 (9.5 g, 1 equiv.), sub 1 (10 g, 1 equiv.), Pd(PPh₃)₄ (0.8 g, 0.03 equiv.), K₂CO₃ (9.6 g, 2 equiv.), Toluene (77 mL), Ethanol (8 mL) and water were added to a round-bottom flask and stirred at 120° C. When the reaction was completed, the resulting compound was extracted with CH₂Cl₂ and water, the organic layer was dried over MgSO₄, concentrated, and the resulting compound was recrystallized by silicagel column to obtain 10.4 g of P-63 (yield: 70%).

5. Synthesis Example of P-66

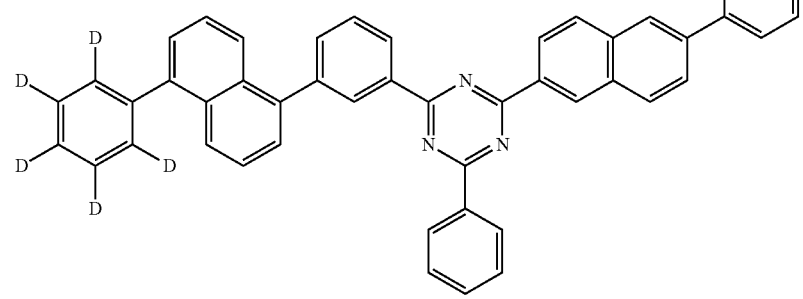

P-66

Core 17 (9.5 g, 1 equiv.), sub 1 (10 g, 1 equiv.), Pd(PPh₃)₄ (0.8 g, 0.03 equiv.), K₂CO₃ (9.6 g, 2 equiv.), Toluene (77 mL), Ethanol (8 mL) and water were added to a round-bottom flask and stirred at 120° C. When the reaction was completed, the resulting compound was extracted with CH₂Cl₂ and water, the organic layer was dried over MgSO₄, concentrated, and the resulting compound was recrystallized by silicagel column to obtain 9.8 g of P-66 (yield: 66%).

6. Synthesis Example of P-72

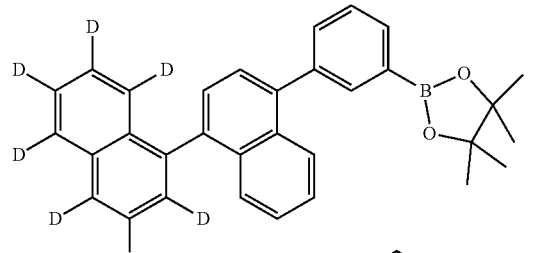

core 34

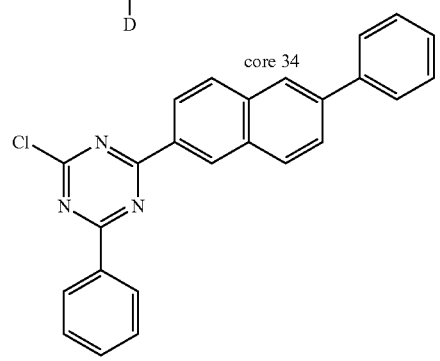

sub 1

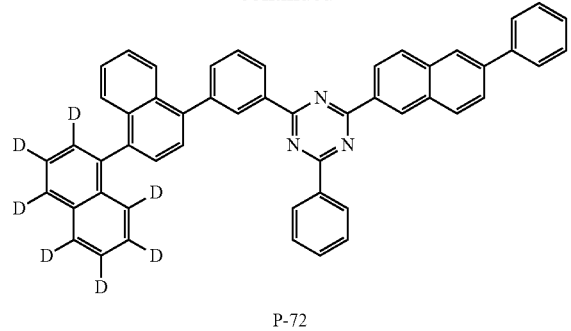

P-72

Core 34 (11.8 g, 1 equiv.), sub 1 (10 g, 1 equiv.), Pd(PPh₃)₄ (0.9 g, 0.03 equiv.), K₂CO₃ (10.5 g, 2 equiv.), Toluene (85 mL), Ethanol (8 mL) and water were added to a round-bottom flask and stirred at 120° C. When the reaction was completed, the resulting compound was extracted with CH₂Cl₂ and water, the organic layer was dried over MgSO₄, concentrated, and the resulting compound was recrystallized by silicagel column to obtain 12.9 g of P-72 (yield: 73%).

7. Synthesis Example of P-83

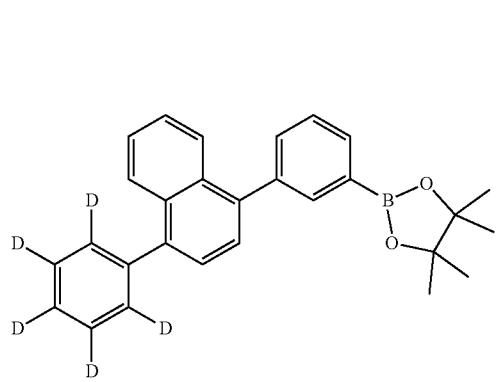

core 5

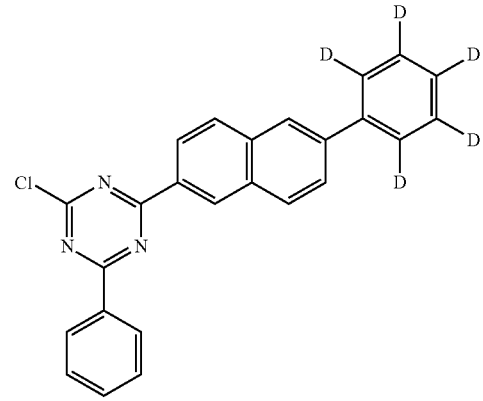

sub 26

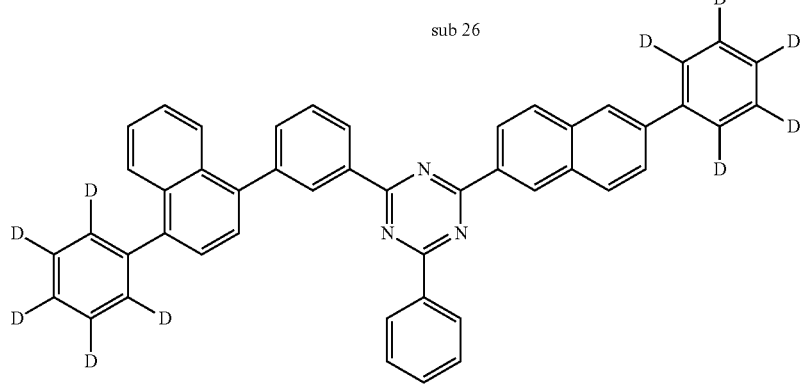

P-83

Core 5 (10.3 g, 1 equiv.), sub 26 (10 g, 1 equiv.), Pd(PPh₃)₄ (0.9 g, 0.03 equiv.), K₂CO₃ (10.4 g, 2 equiv.), Toluene (84 mL), Ethanol (8 mL) and water were added to a round-bottom flask and stirred at 120° C. When the reaction was completed, the resulting compound was extracted with CH₂Cl₂ and water, the organic layer was dried over MgSO₄, concentrated, and the resulting compound was recrystallized by silicagel column to obtain 8.9 g of P-83 (yield: 55%).

8. Synthesis Example of P-92

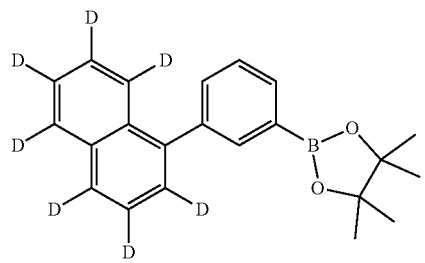
core 33

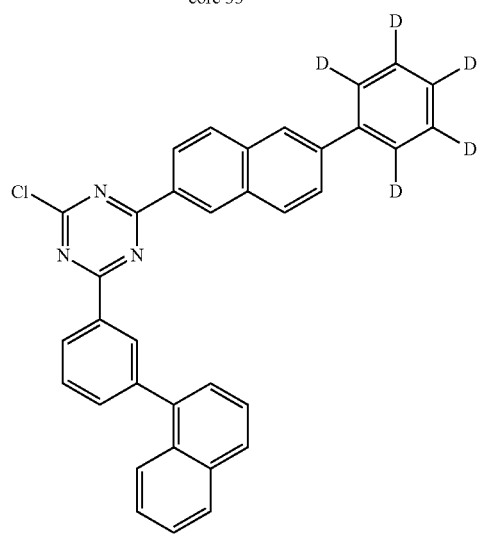
sub 41

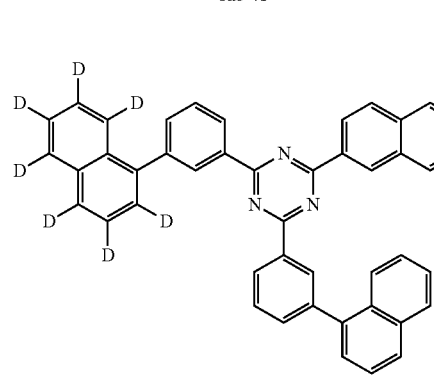
P-92

Core 33 (6.4 g, 1 equiv.), sub 41 (10 g, 1 equiv.), Pd(PPh₃)₄ (0.7 g, 0.03 equiv.), K₂CO₃ (7.9 g, 2 equiv.), Toluene (64 mL), Ethanol (6 mL) and water were added to a round-bottom flask and stirred at 120° C. When the reaction was completed, the resulting compound was extracted with CH₂Cl₂ and water, the organic layer was dried over MgSO₄, concentrated, and the resulting compound was recrystallized by silicagel column to obtain 9.8 g of P-92 (yield: 74%).

9. Synthesis Example of P-98

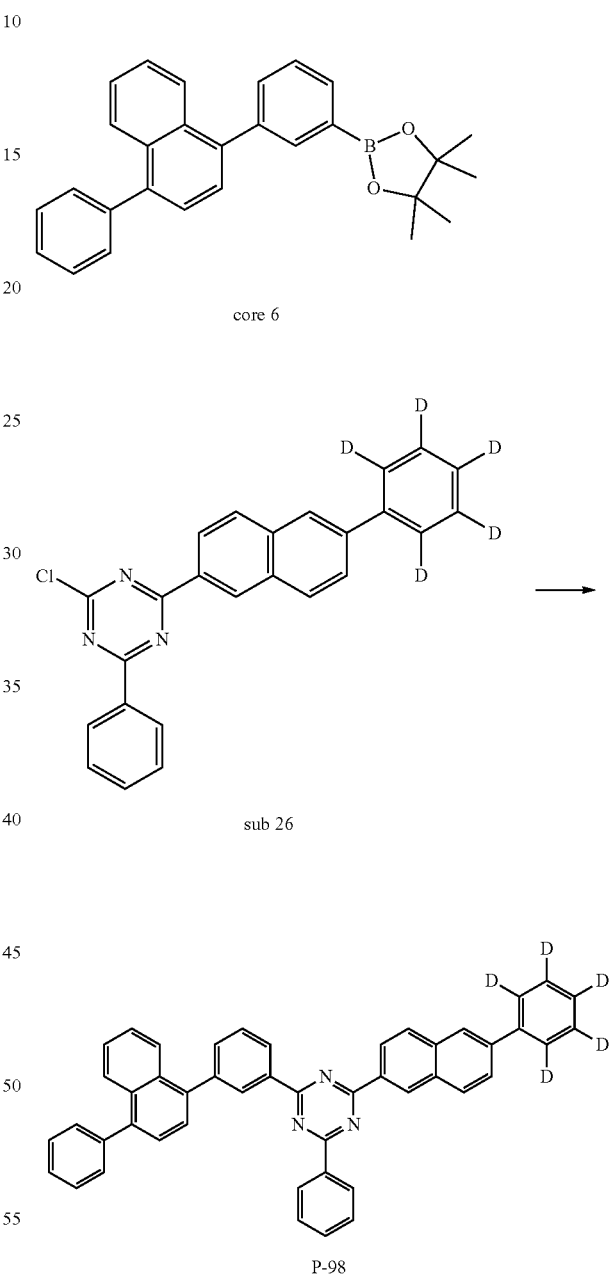

Core 6 (8.5 g, 1 equiv.), sub 26 (10 g, 1 equiv.), Pd(PPh₃)₄ (0.9 g, 0.03 equiv.), K₂CO₃ (10.4 g, 2 equiv.), Toluene (84 mL), Ethanol (8 mL) and water were added to a round-bottom flask and stirred at 120° C. When the reaction was completed, the resulting compound was extracted with CH₂Cl₂ and water, the organic layer was dried over MgSO₄, concentrated, and the resulting compound was recrystallized by silicagel column to obtain 9.8 g of P-98 (yield: 61%).

10. Synthesis Example of P-102

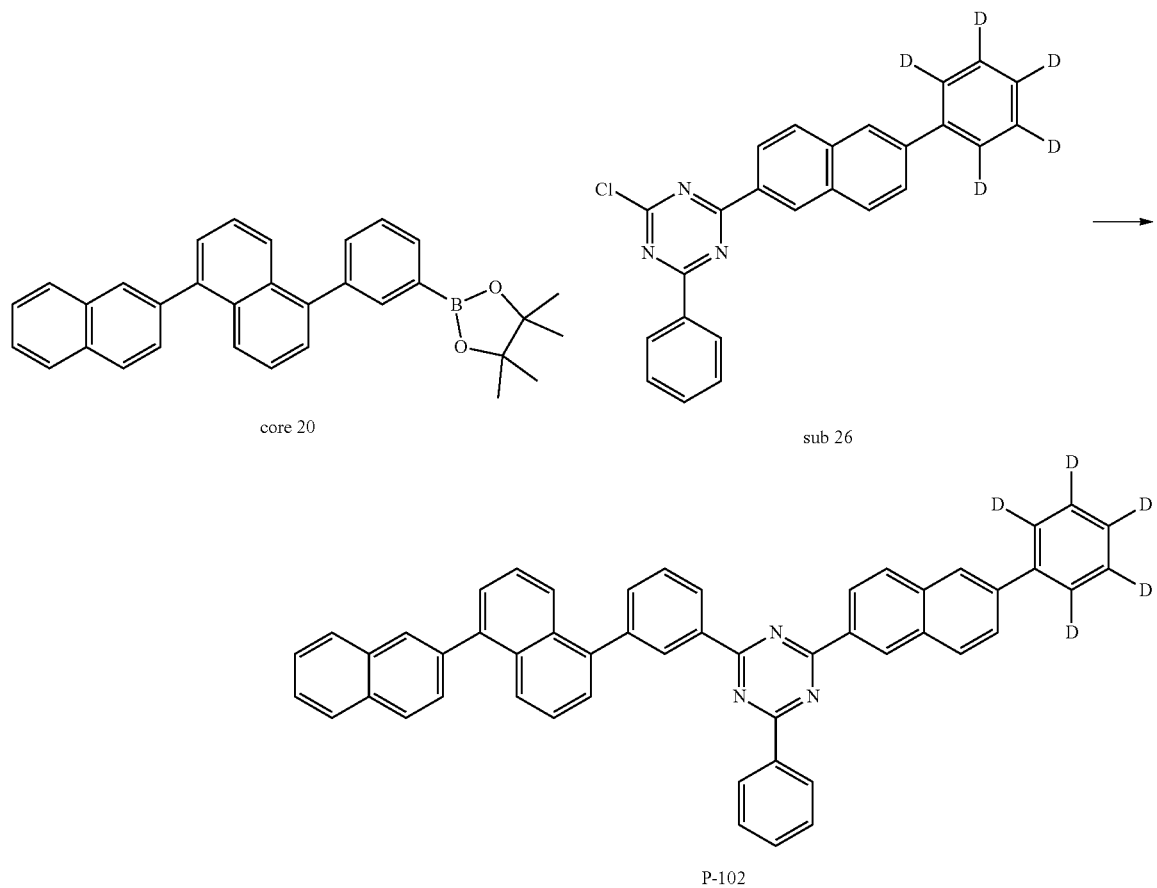

Core 20 (11.4 g, 1 equiv.), sub 26 (10 g, 1 equiv.), Pd(PPh$_3$)$_4$ (0.9 g, 0.03 equiv.), K$_2$CO$_3$ (10.4 g, 2 equiv.), Toluene (84 mL), Ethanol (8 mL) and water were added to a round-bottom flask and stirred at 120° C. When the reaction was completed, the resulting compound was extracted with CH$_2$Cl$_2$ and water, the organic layer was dried over MgSO$_4$, concentrated, and the resulting compound was recrystallized by silicagel column to obtain 9.2 g of P-102 (yield: 53%).

Besides, the FD-MS values of the compounds P-1 to P-104 of the present invention prepared according to the above synthesis examples are shown in Table 3.

TABLE 3

| Cpd. | FD-MS |
| --- | --- |
| P-1 | m/z = 561.22(C$_{41}$H$_{27}$N$_3$ = 561.69) |
| P-2 | m/z = 611.24(C$_{45}$H$_{29}$N$_3$ = 611.75) |
| P-3 | m/z = 611.24(C$_{45}$H$_{29}$N$_3$ = 611.75) |
| P-4 | m/z = 637.25(C$_{47}$H$_{31}$N$_3$ = 637.79) |
| P-5 | m/z = 637.25(C$_{47}$H$_{31}$N$_3$ = 637.79) |
| P-6 | m/z = 637.25(C$_{47}$H$_{31}$N$_3$ = 637.79) |
| P-7 | m/z = 661.25(C$_{49}$H$_{31}$N$_3$ = 661.81) |
| P-8 | m/z = 661.25(C$_{49}$H$_{31}$N$_3$ = 661.81) |
| P-9 | m/z = 711.27(C$_{53}$H$_{33}$N$_3$ = 711.87) |
| P-10 | m/z = 687.27(C$_{51}$H$_{33}$N$_3$ = 687.85) |
| P-11 | m/z = 687.27(C$_{51}$H$_{33}$N$_3$ = 687.85) |
| P-12 | m/z = 687.27(C$_{51}$H$_{33}$N$_3$ = 687.85) |
| P-13 | m/z = 687.27(C$_{51}$H$_{33}$N$_3$ = 687.85) |
| P-14 | m/z = 687.27(C$_{51}$H$_{33}$N$_3$ = 687.85) |

TABLE 3-continued

| Cpd. | FD-MS |
| --- | --- |
| P-15 | m/z = 687.27(C$_{51}$H$_{33}$N$_3$ = 687.85) |
| P-16 | m/z = 737.28(C$_{55}$H$_{35}$N$_3$ = 737.91) |
| P-17 | m/z = 737.28(C$_{55}$H$_{35}$N$_3$ = 737.91) |
| P-18 | m/z = 737.28(C$_{55}$H$_{35}$N$_3$ = 737.91) |
| P-19 | m/z = 763.30(C$_{57}$H$_{37}$N$_3$ = 763.94) |
| P-20 | m/z = 763.30(C$_{57}$H$_{37}$N$_3$ = 763.94) |
| P-21 | m/z = 763.30(C$_{57}$H$_{37}$N$_3$ = 763.94) |
| P-22 | m/z = 637.25(C$_{47}$H$_{31}$N$_3$ = 637.79) |
| P-23 | m/z = 637.25(C$_{47}$H$_{31}$N$_3$ = 637.79) |
| P-24 | m/z = 637.25(C$_{47}$H$_{31}$N$_3$ = 637.79) |
| P-25 | m/z = 637.25(C$_{47}$H$_{31}$N$_3$ = 637.79) |
| P-26 | m/z = 637.25(C$_{47}$H$_{31}$N$_3$ = 637.79) |
| P-27 | m/z = 637.25(C$_{47}$H$_{31}$N$_3$ = 637.79) |
| P-28 | m/z = 687.27(C$_{51}$H$_{33}$N$_3$ = 687.85) |
| P-29 | m/z = 687.27(C$_{51}$H$_{33}$N$_3$ = 687.85) |
| P-30 | m/z = 687.27(C$_{51}$H$_{33}$N$_3$ = 687.85) |
| P-31 | m/z = 687.27(C$_{51}$H$_{33}$N$_3$ = 687.85) |
| P-32 | m/z = 687.27(C$_{51}$H$_{33}$N$_3$ = 687.85) |
| P-33 | m/z = 687.27(C$_{51}$H$_{33}$N$_3$ = 687.85) |
| P-34 | m/z = 687.27(C$_{51}$H$_{33}$N$_3$ = 687.85) |
| P-35 | m/z = 687.27(C$_{51}$H$_{33}$N$_3$ = 687.85) |
| P-36 | m/z = 687.27(C$_{51}$H$_{33}$N$_3$ = 687.85) |
| P-37 | m/z = 687.27(C$_{51}$H$_{33}$N$_3$ = 687.85) |
| P-38 | m/z = 687.27(C$_{51}$H$_{33}$N$_3$ = 687.85) |
| P-39 | m/z = 687.27(C$_{51}$H$_{33}$N$_3$ = 687.85) |
| P-40 | m/z = 687.27(C$_{51}$H$_{33}$N$_3$ = 687.85) |
| P-41 | m/z = 687.27(C$_{51}$H$_{33}$N$_3$ = 687.85) |
| P-42 | m/z = 568.26(C$_{41}$H$_{20}$D$_7$N$_3$ = 568.73) |
| P-43 | m/z = 618.28(C$_{45}$H$_{22}$D$_7$N$_3$ = 618.79) |
| P-44 | m/z = 618.28(C$_{45}$H$_{22}$D$_7$N$_3$ = 618.79) |

TABLE 3-continued

| Cpd. | FD-MS |
|---|---|
| P-45 | m/z = 644.30($C_{47}H_{24}D_7N_3$ = 644.83) |
| P-46 | m/z = 644.30($C_{47}H_{24}D_7N_3$ = 644.83) |
| P-47 | m/z = 644.30($C_{47}H_{24}D_7N_3$ = 644.83) |
| P-48 | m/z = 668.30($C_{49}H_{24}D_7N_3$ = 668.85) |
| P-49 | m/z = 668.30($C_{49}H_{24}D_7N_3$ = 668.85) |
| P-50 | m/z = 718.31($C_{53}H_{26}D_7N_3$ = 718.91) |
| P-51 | m/z = 694.31($C_{51}H_{26}D_7N_3$ = 694.89) |
| P-52 | m/z = 694.31($C_{51}H_{26}D_7N_3$ = 694.89) |
| P-53 | m/z = 694.31($C_{51}H_{26}D_7N_3$ = 694.89) |
| P-54 | m/z = 694.31($C_{51}H_{26}D_7N_3$ = 694.89) |
| P-55 | m/z = 694.31($C_{51}H_{26}D_7N_3$ = 694.89) |
| P-56 | m/z = 694.31($C_{51}H_{26}D_7N_3$ = 694.89) |
| P-57 | m/z = 770.34($C_{57}H_{30}D_7N$ = = 770.99) |
| P-58 | m/z = 744.33($C_{55}H_{28}D_7N_3$ = 744.95) |
| P-59 | m/z = 744.33($C_{55}H_{28}D_7N_3$ = 744.95) |
| P-60 | m/z = 770.34($C_{57}H_{30}D_7N_3$ = 770.99) |
| P-61 | m/z = 642.28($C_{47}H_{26}D_5N_3$ = 642.82) |
| P-62 | m/z = 770.34($C_{57}H_{30}D_7N_3$ = 770.99) |
| P-63 | m/z = 642.28($C_{47}H_{26}D_5N_3$ = 642.82) |
| P-64 | m/z = 642.28($C_{47}H_{26}D_5N_3$ = 642.82) |
| P-65 | m/z = 642.28($C_{47}H_{26}D_5N_3$ = 642.82) |
| P-66 | m/z = 642.28($C_{47}H_{26}D_5N_3$ = 642.82) |
| P-67 | m/z = 642.28($C_{47}H_{26}D_5N_3$ = 642.82) |
| P-68 | m/z = 642.28($C_{47}H_{26}D_5N_3$ = 642.82) |
| P-69 | m/z = 694.31($C_{51}H_{26}D_7N_3$ = 694.89) |
| P-70 | m/z = 694.31($C_{51}H_{26}D_7N_3$ = 694.89) |
| P-71 | m/z = 694.31($C_{51}H_{26}D_7N_3$ = 694.89) |
| P-72 | m/z = 694.31($C_{51}H_{26}D_7N_3$ = 694.89) |
| P-73 | m/z = 694.31($C_{51}H_{26}D_7N_3$ = 694.89) |
| P-74 | m/z = 694.31($C_{51}H_{26}D_7N_3$ = 694.89) |
| P-75 | m/z = 694.31($C_{51}H_{26}D_7N_3$ = 694.89) |
| P-76 | m/z = 694.31($C_{51}H_{26}D_7N_3$ = 694.89) |
| P-77 | m/z = 694.31($C_{51}H_{26}D_7N_3$ = 694.89) |
| P-78 | m/z = 694.31($C_{51}H_{26}D_7N_3$ = 694.89) |
| P-79 | m/z = 694.31($C_{51}H_{26}D_7N_3$ = 694.89) |
| P-80 | m/z = 694.31($C_{51}H_{26}D_7N_3$ = 694.89) |
| P-81 | m/z = 694.31($C_{51}H_{26}D_7N_3$ = 694.89) |
| P-82 | m/z = 694.31($C_{51}H_{26}D_7N_3$ = 694.89) |
| P-83 | m/z = 647.31($C_{47}H_{21}D_{10}N_3$ = 647.85) |
| P-84 | m/z = 647.31($C_{47}H_{21}D_{10}N_3$ = 647.85) |
| P-85 | m/z = 647.31($C_{47}H_{21}D_{10}N_3$ = 647.85) |
| P-86 | m/z = 699.34($C_{51}H_{21}D_{12}N_3$ = 699.92) |
| P-87 | m/z = 573.30($C_{41}H_{15}D_{12}N_3$ = 573.76) |
| P-88 | m/z = 623.31($C_{45}H_{17}D_{12}N_3$ = 623.82) |
| P-89 | m/z = 623.31($C_{45}H_{17}D_{12}N_3$ = 623.82) |
| P-90 | m/z = 649.33($C_{47}H_{19}D_{12}N_3$ = 649.86) |
| P-91 | m/z = 699.34($C_{51}H_{21}D_{12}N_3$ = 699.92) |
| P-92 | m/z = 699.34($C_{51}H_{21}D_{12}N_3$ = 699.92) |
| P-93 | m/z = 699.34($C_{51}H_{21}D_{12}N_3$ = 699.92) |
| P-94 | m/z = 699.34($C_{51}H_{21}D_{12}N_3$ = 699.92) |
| P-95 | m/z = 699.34($C_{51}H_{21}D_{12}N_3$ = 699.92) |
| P-96 | m/z = 699.34($C_{51}H_{21}D_{12}N_3$ = 699.92) |
| P-97 | m/z = 699.34($C_{51}H_{21}D_{12}N_3$ = 699.92) |
| P-98 | m/z = 642.28($C_{47}H_{26}D_5N_3$ = 642.82) |
| P-99 | m/z = 642.28($C_{47}H_{26}D_5N_3$ = 642.82) |
| P-100 | m/z = 642.28($C_{47}H_{26}D_5N_3$ = 642.82) |
| P-101 | m/z = 692.30($C_{51}H_{28}D_5N_3$ = 692.88) |
| P-102 | m/z = 692.30($C_{51}H_{28}D_5N_3$ = 692.88) |
| P-103 | m/z = 692.30($C_{51}H_{28}D_5N_3$ = 692.88) |
| P-104 | m/z = 692.30($C_{51}H_{28}D_5N_3$ = 692.88) |

Synthesis Example 2

1. Synthesis Example of N-12

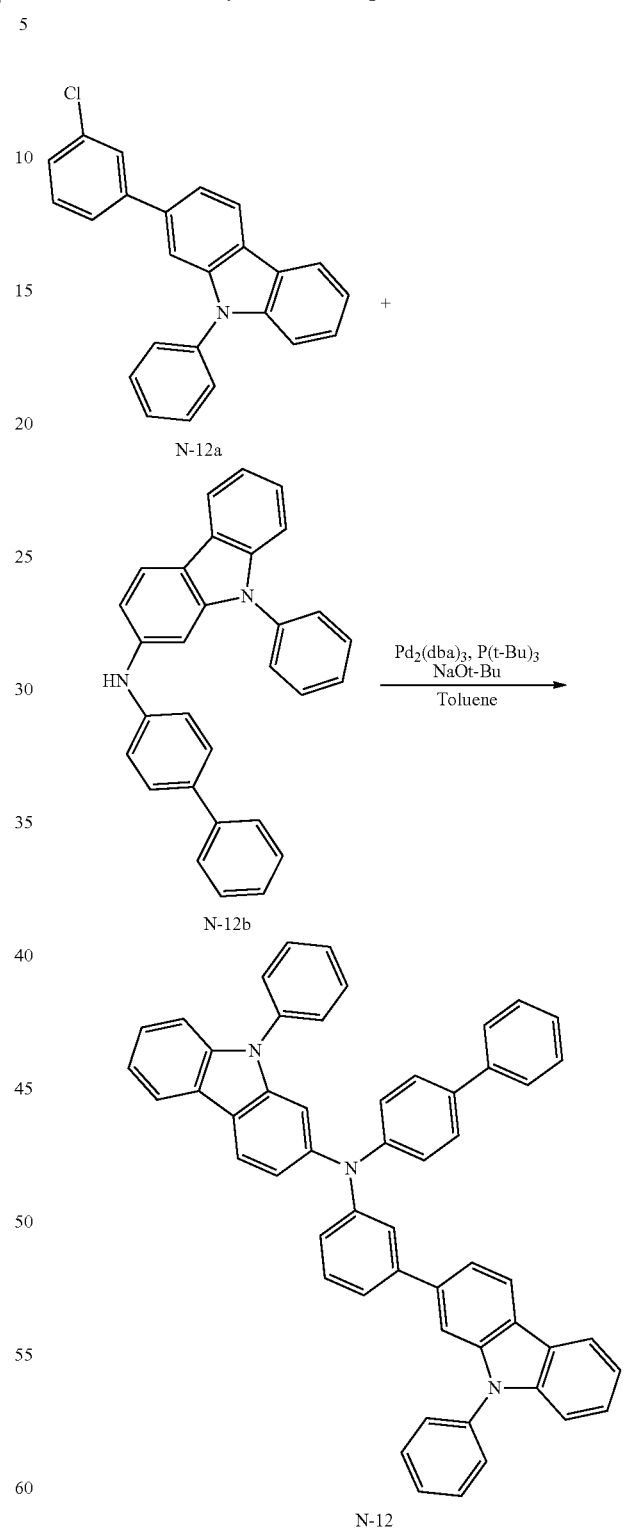

N-12a (30 g, 0.08 mol), N-12b (34.8 g, 0.08 mol), $Pd_2(dba)_3$ (2.3 g, 0.003 mol), NaOt-Bu (24.5 g, 0.25 mol), P(t-Bu)$_3$ (2.1 g, 0.005 mol), Toluene (170 mL) were added and reacted at 135° C. for 6 hours. When the reaction was completed, 53 g (85.8%) of the product N-12 was obtained by using the separation method for P-1.

2. Synthesis Example of N-19

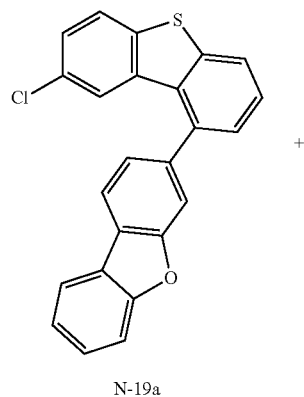

N-19a

+

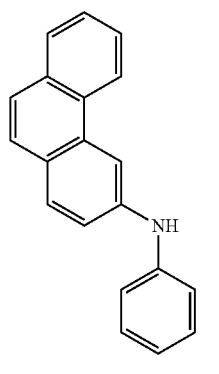

N-19b

Pd₂(dba)₃, P(t-Bu)₃
NaOt-Bu
—————————→
Toluene

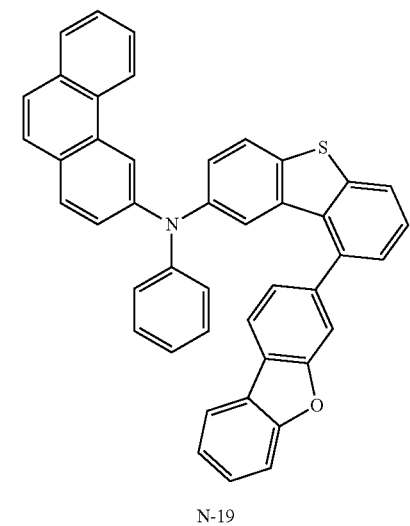

N-19

N-19a (50 g, 0.13 mol), N-19b (35 g, 0.13 mol), Pd₂(dba)₃ (3.6 g, 0.004 mol), NaOt-Bu (37.6 g, 0.40 mol), P(t-Bu)₃ (3.2 g, 0.008 mol), Toluene (260 mL) were added and reacted at 135° C. for 6 hours. When the reaction was completed, 67 g (83.4%) of the product N-19 was obtained by using the separation method for P-1.

3. Synthesis Example of S-32

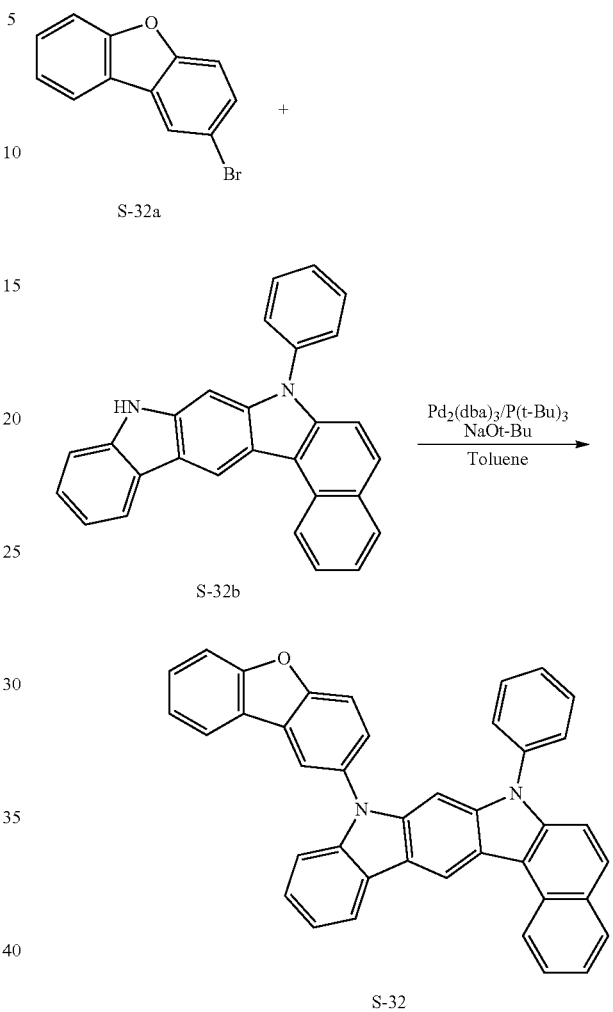

S-32a (10 g, 0.04 mol), S-32b (15.6 g, 0.04 mol), Pd₂(dba)₃ (1.1 g, 0.001 mol), NaOt-Bu (11.7 g, 0.12 mol), P(t-Bu)₃ (1.0 g, 0.002 mol), Toluene (80 mL) were added and reacted at 135° C. for 6 hours. When the reaction was completed, 18 g (80.8%) of the product S-32 was obtained by using the separation method for P-1.

4. Synthesis Example of S-74

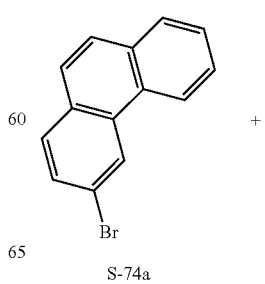

S-74a

+

-continued

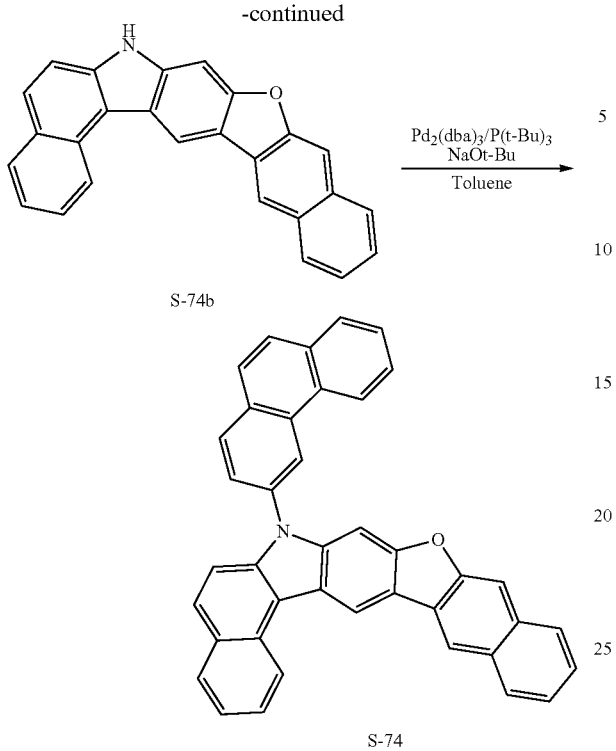

S-74a (15 g, 0.06 mol), S-74b (20.9 g, 0.06 mol), Pd₂(dba)₃ (1.6 g, 0.002 mol), NaOt-Bu (16.9 g, 0.18 mol), P(t-Bu)₃ (1.4 g, 0.004 mol), Toluene (120 mL) were added and reacted at 135° C. for 6 hours. When the reaction was completed, 27 g (86.4%) of the product S-74 was obtained by using the separation method for P-1.

5. Synthesis Example of S-104

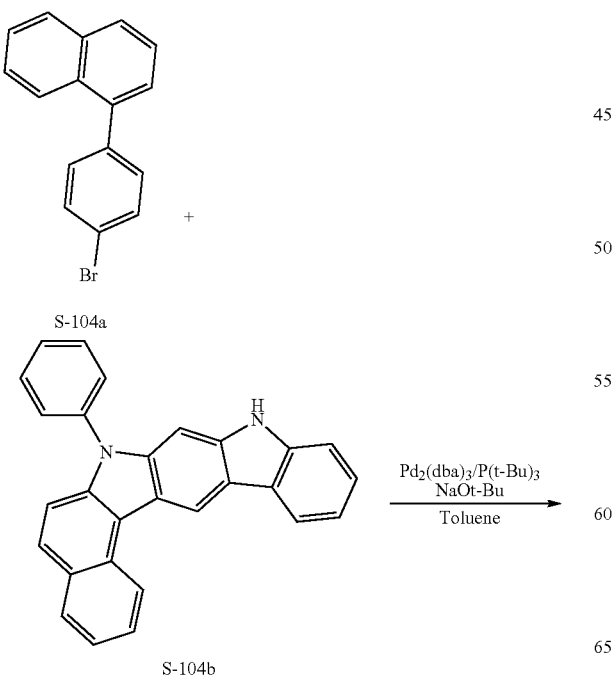

-continued

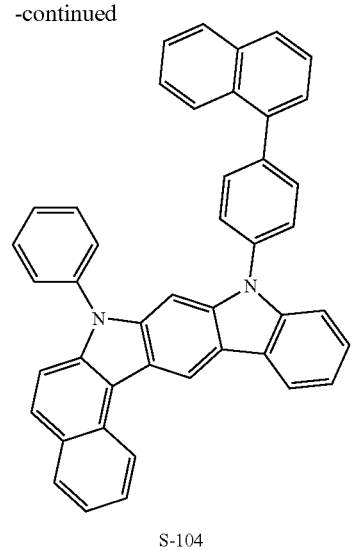

S-104a (30 g, 0.13 mol), S-104b (48.2.9 g, 0.13 mol), Pd₂(dba)₃ (3.5 g, 0.004 mol), NaOt-Bu (36.4 g, 0.38 mol), P(t-Bu)₃ (3.1 g, 0.008 mol), Toluene (250 mL) were added and reacted at 135° C. for 6 hours. When the reaction was completed, 60 g (81.5%) of the product S-104 was obtained by using the separation method for P-1.

Meanwhile, FD-MS values of compounds N-1 to N-96 and S-1 to S-108 of the present invention prepared according to the above synthesis examples are shown in Tables 4 and 5.

TABLE 4

| Cpd. | FD-MS |
| --- | --- |
| N-1 | m/z = 487.19($C_{36}H_{25}NO$ = 487.6) |
| N-2 | m/z = 553.19($C_{40}H_{27}NS$ = 553.72) |
| N-3 | m/z = 563.26($C_{43}H_{33}N$ = 563.74) |
| N-4 | m/z = 602.27($C_{45}H_{34}N_2$ = 602.78) |
| N-5 | m/z = 517.15($C_{36}H_{23}NOS$ = 517.65) |
| N-6 | m/z = 603.2($C_{44}H_{29}NS$ = 603.78) |
| N-7 | m/z = 735.29($C_{57}H_{37}N$ = 735.93) |
| N-8 | m/z = 562.24($C_{42}H_{30}N_2$ = 562.72) |
| N-9 | m/z = 565.17($C_{40}H_{23}NO_3$ = 565.63) |
| N-10 | m/z = 581.14($C_{40}H_{23}NO_2S$ = 581.69) |
| N-11 | m/z = 823.24($C_{59}H_{37}NS_2$ = 824.07) |
| N-12 | m/z = 727.3($C_{54}H_{37}N_3$ = 727.91) |
| N-13 | m/z = 627.22($C_{46}H_{29}NO_2$ = 627.74) |
| N-14 | m/z = 633.16($C_{44}H_{27}NS_2$ = 633.83) |
| N-15 | m/z = 675.29($C_{52}H_{37}N$ = 675.88) |
| N-16 | m/z = 678.3($C_{51}H_{38}N_2$ = 678.88) |
| N-17 | m/z = 669.21($C_{48}H_{31}NOS$ = 669.84) |
| N-18 | m/z = 785.22($C_{56}H_{35}NS_2$ = 786.02) |
| N-19 | m/z = 617.18($C_{44}H_{27}NOS$ = 617.77) |
| N-20 | m/z = 601.2($C_{44}H_{27}NO_2$ = 601.71) |
| N-21 | m/z = 779.32($C_{59}H_{41}NO$ = 779.98) |
| N-22 | m/z = 583.23($C_{42}H_{33}NS$ = 583.79) |
| N-23 | m/z = 679.32($C_{52}H_{41}N$ = 679.91) |
| N-24 | m/z = 726.27($C_{54}H_{34}N_2O$ = 726.88) |
| N-25 | m/z = 593.18($C_{42}H_{27}NOS$ = 593.74) |
| N-26 | m/z = 774.22($C_{54}H_{34}N_2S_2$ = 775) |
| N-27 | m/z = 557.24($C_{40}H_{31}NO_2$ = 557.69) |
| N-28 | m/z = 652.25($C_{48}H_{32}N_2O$ = 652.8) |
| N-29 | m/z = 619.29($C_{46}H_{37}NO$ = 619.81) |
| N-30 | m/z = 603.2($C_{44}H_{29}NS$ = 603.78) |
| N-31 | m/z = 813.3($C_{62}H_{39}NO$ = 814) |
| N-32 | m/z = 784.29($C_{57}H_{40}N_2S$ = 785.02) |
| N-33 | m/z = 577.2($C_{42}H_{27}NO_2$ = 577.68) |
| N-34 | m/z = 607.14($C_{42}H_{25}NS_2$ = 607.79) |
| N-35 | m/z = 801.34($C_{62}H_{43}N$ = 802.03) |
| N-36 | m/z = 575.24($C_{42}H_{29}N_3$ = 575.72) |

TABLE 4-continued

| Cpd. | FD-MS |
|---|---|
| N-37 | m/z = 577.2($C_{42}H_{27}NO_2$ = 577.68) |
| N-38 | m/z = 607.14($C_{42}H_{25}NS_2$ = 607.79) |
| N-39 | m/z = 801.34($C_{62}H_{43}N$ = 802.03) |
| N-40 | m/z = 575.24($C_{42}H_{29}N_3$ = 575.72) |
| N-41 | m/z = 601.2($C_{44}H_{27}NO_2$ = 601.71) |
| N-42 | m/z = 471.11($C_{31}H_{21}NS_2$ = 471.64) |
| N-43 | m/z = 675.29($C_{52}H_{37}N$ = 675.88) |
| N-44 | m/z = 727.3($C_{54}H_{37}N_3$ = 727.91) |
| N-45 | m/z = 603.2($C_{44}H_{29}NS$ = 603.78) |
| N-46 | m/z = 561.16($C_{38}H_{27}NS_2$ = 561.76) |
| N-47 | m/z = 799.32($C_{62}H_{41}N$ = 800.02) |
| N-48 | m/z = 702.27($C_{52}H_{34}N_2O$ = 702.86) |
| N-49 | m/z = 729.27($C_{54}H_{35}NO_2$ = 729.88) |
| N-50 | m/z = 785.22($C_{56}H_{35}NS_2$ = 786.02) |
| N-51 | m/z = 812.32($C_{62}H_{40}N_2$ = 813.02) |
| N-52 | m/z = 681.22($C_{48}H_{31}N_3S$ = 681.86) |
| N-53 | m/z = 615.18($C_{44}H_{25}NO_3$ = 615.69) |
| N-54 | m/z = 763.15($C_{52}H_{29}NS_3$ = 763.99) |
| N-55 | m/z = 593.31($C_{45}H_{39}N$ = 593.81) |
| N-56 | m/z = 840.33($C_{62}H_{40}N_4$ = 841.03) |
| N-57 | m/z = 657.18($C_{46}H_{27}NO_2S$ = 657.79) |
| N-58 | m/z = 824.23($C_{58}H_{36}N_2S_2$ = 825.06) |
| N-59 | m/z = 1195.42($C_{91}H_{57}NS$ = 1196.52) |
| N-60 | m/z = 656.19($C_{46}H_{28}N_2OS$ = 656.8) |
| N-61 | m/z = 607.16($C_{42}H_{25}NO_2S$ = 607.73) |
| N-62 | m/z = 773.2($C_{54}H_{31}NO_3S$ = 773.91) |
| N-63 | m/z = 1013.4($C_{79}H_{51}N$ = 1014.28) |
| N-64 | m/z = 758.24($C_{54}H_{34}N_2OS$ = 758.94) |
| N-65 | m/z = 623.14($C_{42}H_{25}NOS_2$ = 623.79) |
| N-66 | m/z = 763.16($C_{52}H_{29}NO_2S_2$ = 763.93) |
| N-67 | m/z = 799.2($C_{56}H_{33}NOS_2$ = 800.01) |
| N-68 | m/z = 743.23($C_{54}H_{33}NOS$ = 743.92) |
| N-69 | m/z = 872.25($C_{62}H_{36}N_2O_2S$ = 873.04) |
| N-70 | m/z = 772.22($C_{54}H_{32}N_2O_2S$ = 772.92) |
| N-71 | m/z = 830.28($C_{61}H_{38}N_2S$ = 831.05) |
| N-72 | m/z = 808.25($C_{58}H_{33}FN_2O_2$ = 808.91) |
| N-73 | m/z = 929.21($C_{64}H_{35}NO_3S_2$ = 930.11) |
| N-74 | m/z = 963.27($C_{68}H_{41}N_3S_2$ = 964.22) |
| N-75 | m/z = 809.24($C_{58}H_{35}NO_2S$ = 809.98) |
| N-76 | m/z = 893.29($C_{66}H_{39}NO_3$ = 894.04) |
| N-77 | m/z = 794.28($C_{58}H_{38}N_2S$ = 795.02) |
| N-78 | m/z = 900.26($C_{64}H_{40}N_2S_2$ = 901.16) |
| N-79 | m/z = 758.28($C_{55}H_{38}N_2S$ = 758.98) |
| N-80 | m/z = 1082.37($C_{81}H_{50}N_2S$ = 1083.37) |
| N-81 | m/z = 573.25($C_{44}H_{31}N$ = 573.74) |
| N-82 | m/z = 649.28($C_{50}H_{35}N$ = 649.84) |
| N-83 | m/z = 699.29($C_{54}H_{37}N$ = 699.9) |
| N-84 | m/z = 699.29($C_{54}H_{37}N$ = 699.9) |
| N-85 | m/z = 673.28($C_{52}H_{35}N$ = 673.86) |
| N-86 | m/z = 649.28($C_{50}H_{35}N$ = 649.84) |
| N-87 | m/z = 625.28($C_{48}H_{35}N$ = 625.82) |
| N-88 | m/z = 673.28($C_{52}H_{35}N$ = 673.86) |
| N-89 | m/z = 773.31($C_{60}H_{39}N$ = 773.98) |
| N-90 | m/z = 749.31($C_{58}H_{39}N$ = 749.96) |
| N-91 | m/z = 699.29($C_{54}H_{37}N$ = 699.9) |
| N-92 | m/z = 599.26($C_{46}H_{33}N$ = 599.78) |
| N-93 | m/z = 639.26($C_{48}H_{33}NO$ = 639.8) |
| N-94 | m/z = 765.25($C_{57}H_{35}NS$ = 765.97) |
| N-95 | m/z = 677.31($C_{52}H_{39}N$ = 677.89) |
| N-96 | m/z = 727.3($C_{54}H_{37}N_3$ = 727.91) |

TABLE 5

| Cpd. | FD-MS |
|---|---|
| S-1 | m/z = 408.16($C_{30}H_{20}N_2$ = 408.5) |
| S-2 | m/z = 534.21($C_{40}H_{26}N_2$ = 534.66) |
| S-3 | m/z = 560.23($C_{42}H_{28}N_2$ = 560.7) |
| S-4 | m/z = 584.23($C_{44}H_{28}N_2$ = 584.72) |
| S-5 | m/z = 560.23($C_{42}H_{28}N_2$ = 560.7) |
| S-6 | m/z = 634.24($C_{48}H_{30}N_2$ = 634.78) |
| S-7 | m/z = 610.24($C_{46}H_{30}N_2$ = 610.76) |
| S-8 | m/z = 498.17($C_{36}H_{22}N_2O$ = 498.59) |
| S-9 | m/z = 574.2($C_{42}H_{26}N_2O$ = 574.68) |
| S-10 | m/z = 660.26($C_{50}H_{32}N_2$ = 660.82) |
| S-11 | m/z = 686.27($C_{52}H_{34}N_2$ = 686.86) |
| S-12 | m/z = 620.14($C_{42}H_{24}N_2S_2$ = 620.79) |
| S-13 | m/z = 640.2($C_{46}H_{28}N_2S$ = 640.8) |
| S-14 | m/z = 560.23($C_{42}H_{28}N_2$ = 560.7) |
| S-15 | m/z = 558.21($C_{42}H_{26}N_2$ = 558.68) |
| S-16 | m/z = 548.19($C_{40}H_{24}N_2S$ = 548.65) |
| S-17 | m/z = 573.22($C_{42}H_{27}N_3$ = 573.7) |
| S-18 | m/z = 564.17($C_{40}H_{24}N_2S$ = 564.71) |
| S-19 | m/z = 574.2($C_{42}H_{26}N_2O$ = 574.68) |
| S-20 | m/z = 564.17($C_{40}H_{24}N_2S$ = 564.71) |
| S-21 | m/z = 564.17($C_{40}H_{24}N_2S$ = 564.71) |
| S-22 | m/z = 813.31($C_{61}H_{39}N_3$ = 814) |
| S-23 | m/z = 696.26($C_{53}H_{32}N_2$ = 696.85) |
| S-24 | m/z = 691.23($C_{49}H_{29}N_3O_2$ = 691.79) |
| S-25 | m/z = 710.27($C_{54}H_{34}N_2$ = 710.88) |
| S-26 | m/z = 610.24($C_{46}H_{30}N_2$ = 610.76) |
| S-27 | m/z = 670.15($C_{46}H_{26}N_2S_2$ = 670.85) |
| S-28 | m/z = 640.29($C_{48}H_{36}N_2$ = 640.83) |
| S-29 | m/z = 598.2($C_{44}H_{26}N_2O$ = 598.71) |
| S-30 | m/z = 623.24($C_{46}H_{29}N_3$ = 623.76) |
| S-31 | m/z = 458.18($C_{34}H_{22}N_2$ = 458.56) |
| S-32 | m/z = 548.19($C_{40}H_{24}N_2O$ = 548.65) |
| S-33 | m/z = 508.19($C_{38}H_{24}N_2$ = 508.62) |
| S-34 | m/z = 508.19($C_{38}H_{24}N_2$ = 508.62) |
| S-35 | m/z = 623.24($C_{46}H_{29}N_3$ = 623.76) |
| S-36 | m/z = 564.17($C_{40}H_{24}N_2S$ = 564.71) |
| S-37 | m/z = 627.2($C_{46}H_{29}NS$ = 627.81) |
| S-38 | m/z = 505.1($C_{34}H_{19}NS_2$ = 505.65) |
| S-39 | m/z = 514.15($C_{36}H_{22}N_2S$ = 514.65) |
| S-40 | m/z = 575.17($C_{42}H_{25}NS$ = 575.73) |
| S-41 | m/z = 642.21($C_{46}H_{30}N_2S$ = 642.82) |
| S-42 | m/z = 575.17($C_{42}H_{25}NS$ = 575.73) |
| S-43 | m/z = 606.18($C_{42}H_{26}N_2OS$ = 606.74) |
| S-44 | m/z = 575.17($C_{42}H_{25}NS$ = 575.73) |
| S-45 | m/z = 551.17($C_{40}H_{25}NS$ = 551.71) |
| S-46 | m/z = 607.14($C_{42}H_{25}NS_2$ = 607.79) |
| S-47 | m/z = 525.16($C_{38}H_{23}NS$ = 525.67) |
| S-48 | m/z = 642.21($C_{46}H_{30}N_2S$ = 642.82) |
| S-49 | m/z = 548.19($C_{40}H_{24}N_2O$ = 548.65) |
| S-50 | m/z = 473.14($C_{34}H_{19}NO_2$ = 473.53) |
| S-51 | m/z = 566.15($C_{39}H_{22}N_2OS$ = 566.68) |
| S-52 | m/z = 459.16($C_{34}H_{21}NO$ = 459.55) |
| S-53 | m/z = 473.14($C_{34}H_{19}NO_2$ = 473.53) |
| S-54 | m/z = 523.16($C_{38}H_{21}NO_2$ = 523.59) |
| S-55 | m/z = 539.13($C_{38}H_{21}NOS$ = 539.65) |
| S-56 | m/z = 548.19($C_{40}H_{24}N_2O$ = 548.65) |
| S-57 | m/z = 489.12($C_{34}H_{19}NOS$ = 489.59) |
| S-58 | m/z = 545.09($C_{36}H_{19}NOS_2$ = 545.67) |
| S-59 | m/z = 549.17($C_{40}H_{23}NO_2$ = 549.63) |
| S-60 | m/z = 565.15($C_{40}H_{23}NOS$ = 565.69) |
| S-61 | m/z = 523.16($C_{38}H_{21}NO_2$ = 523.59) |
| S-62 | m/z = 598.2($C_{44}H_{26}N_2O$ = 598.71) |
| S-63 | m/z = 539.13($C_{38}H_{21}NOS$ = 539.65) |
| S-64 | m/z = 589.15($C_{42}H_{23}NOS$ = 589.71) |
| S-65 | m/z = 498.17($C_{36}H_{22}N_2O$ = 498.59) |
| S-66 | m/z = 509.18($C_{38}H_{23}NO$ = 509.61) |
| S-67 | m/z = 548.19($C_{40}H_{24}N_2O$ = 548.65) |
| S-68 | m/z = 549.17($C_{40}H_{23}NO_2$ = 549.63) |
| S-69 | m/z = 449.12($C_{32}H_{19}NS$ = 449.57) |
| S-70 | m/z = 439.1($C_{30}H_{17}NOS$ = 439.53) |
| S-71 | m/z = 647.22($C_{49}H_{29}NO$ = 647.78) |
| S-72 | m/z = 717.28($C_{52}H_{35}N_3O$ = 717.87) |
| S-73 | m/z = 459.16($C_{34}H_{21}NO$ = 459.55) |
| S-74 | m/z = 533.18($C_{40}H_{23}NO$ = 533.63) |
| S-75 | m/z = 525.16($C_{38}H_{23}NS$ = 525.67) |
| S-76 | m/z = 564.17($C_{40}H_{24}N_2S$ = 564.71) |
| S-77 | m/z = 575.19($C_{42}H_{25}NO_2$ = 575.67) |
| S-78 | m/z = 663.22($C_{49}H_{29}NO_2$ = 663.78) |
| S-79 | m/z = 647.22($C_{49}H_{29}NO$ = 647.78) |
| S-80 | m/z = 496.16($C_{36}H_{20}N_2O$ = 496.57) |
| S-81 | m/z = 565.15($C_{40}H_{23}NOS$ = 565.69) |
| S-82 | m/z = 505.1($C_{34}H_{19}NS_2$ = 505.65) |
| S-83 | m/z = 765.25($C_{56}H_{35}NOSi$ = 765.99) |
| S-84 | m/z = 615.17($C_{44}H_{25}NOS$ = 615.75) |
| S-85 | m/z = 603.17($C_{43}H_{25}NOS$ = 603.74) |
| S-86 | m/z = 772.29($C_{59}H_{36}N_2$ = 772.95) |
| S-87 | m/z = 802.33($C_{61}H_{42}N_2$ = 803.02) |
| S-88 | m/z = 607.23($C_{47}H_{29}N$ = 607.76) |

TABLE 5-continued

| Cpd. | FD-MS |
|---|---|
| S-89 | m/z = 524.23($C_{39}H_{28}N_2$ = 524.67) |
| S-90 | m/z = 665.22($C_{49}H_{31}NS$ = 665.85) |
| S-91 | m/z = 633.25($C_{49}H_{31}N$ = 633.79) |
| S-92 | m/z = 775.29($C_{59}H_{37}NO$ = 775.95) |
| S-93 | m/z = 535.23($C_{41}H_{29}N$ = 535.69) |
| S-94 | m/z = 623.22($C_{47}H_{29}NO$ = 623.76) |
| S-95 | m/z = 687.2($C_{51}H_{29}NS$ = 687.86) |
| S-96 | m/z = 735.29($C_{57}H_{37}N$ = 735.93) |
| S-97 | m/z = 611.26($C_{47}H_{33}N$ = 611.79) |
| S-98 | m/z = 679.23($C_{50}H_{33}NS$ = 679.88) |
| S-99 | m/z = 787.32($C_{61}H_{41}N$ = 788.01) |
| S-100 | m/z = 743.33($C_{55}H_{41}N_3$ = 743.95) |
| S-101 | m/z = 485.21($C_{37}H_{27}N$ = 485.63) |
| S-102 | m/z = 471.2($C_{36}H_{25}N$ = 471.6) |
| S-103 | m/z = 571.19($C_{43}H_{25}NO$ = 571.68) |
| S-104 | m/z = 584.23($C_{44}H_{28}N_2$ = 584.72) |
| S-105 | m/z = 539.24($C_{40}H_{21}D_5N_2$ = 539.69) |
| S-106 | m/z = 453.15($C_{32}H_{15}NS$ = 471.6) |
| S-107 | m/z = 563.26($C_{43}H_{26}D_4NO$ = 563.74) |
| S-108 | m/z = 589.26($C_{44}H_{23}D_5N_2$ = 584.72) |

Element Data

[Example 1] Red Organic Light Emitting Device (Phosphorescent Host)

An organic electroluminescent device was manufactured according to a conventional method by using the compound obtained through synthesis as a light emitting host material of the emitting layer. First, N1-(naphthalen-2-yl)-N4, N4-bis (4-(naphthalen-2-yl(phenyl)amino)phenyl)-N1-phenylbenzene-1,4-diamine (hereinafter, 2-TNANA) film was vacuum-deposited on the ITO layer (anode) formed on a glass substrate to form a hole injection layer having a thickness of 60 nm, and then on the hole injection layer, 4,4-bis[N-(1-naphthyl)-N-phenylamino]biphenyl (hereinafter, -NPB) as a hole transport compound was vacuum-deposited to a thickness of 60 nm to form a hole transport layer. Tris(4-(9H-carbazol-9-yl)phenyl)amine (hereinafter, TCTA) was vacuum-deposited to a thickness of 10 nm as an emitting auxiliary layer material on the hole transport layer to form a emitting auxiliary layer. After forming the emitting auxiliary layer, on the emitting auxiliary layer, the compound P-1 of the present invention represented by Formula 1 and the compound N-12 of the present invention represented by Formula (2) were used in a weight ratio (5:5) as a host, and an emitting layer was deposited to a thickness of 30 nm by doping (piq)$_2$r(acac) as a dopant material at a weight ratio of 95:5. Then, as a hole blocking layer, (1,1'-bisphenyl)-4-oleato)bis(2-methyl-8-quinolineoleato)aluminum (hereinafter, BAlq) was vacuum-deposited to a thickness of 10 nm, and as an electron transport layer, bis(10-hydroxybenzo[h]quinolinato)beryllium (hereinafter, BeBq$_2$) was deposited to a thickness of 45 nm. Thereafter, LiF, which is an alkali metal halide, was deposited as an electron injection layer to a thickness of 0.2 nm, and then Al was deposited to a thickness of 150 nm and used as a cathode, thereby manufacturing an organic electroluminescent device.

[Example 2] to [Example 32]

An organic electroluminescent device was manufactured in the same manner as in Example 1 by using the compounds of the present invention shown in Table 6 instead of the compounds P-1 and N-12 of the present invention as the host material of the emitting layer of Example 1.

[Comparative Example 1] to [Comparative Example 2]

An organic electroluminescent device was manufactured in the same manner as in Example 1, except that Comparative Compound A or Comparative Compound B was used instead of Compound P-1 of the present invention as a host material for the emitting layer.

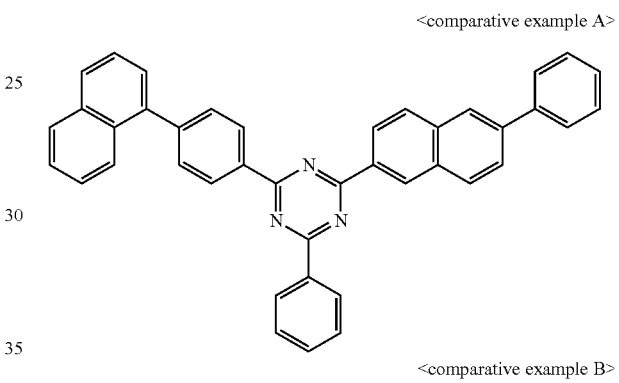

<comparative example A>

<comparative example B>

The electroluminescence (EL) characteristics were measured with a PR-650 of a photo research company by applying a forward bias DC voltage to the organic electric devices manufactured in Examples and Comparative Examples prepared in this way, as a result of the measurement, the T95 lifespan was measured using a lifespan measuring device manufactured by McScience at a standard luminance of 2500 cd/m$^2$. Table 6 shows the results of device fabrication and evaluation.

TABLE 6

| | First compound | Second compound | Voltage (V) | Current Density (mA/cm$^2$) | Efficiency (cd/A) | T(95) |
|---|---|---|---|---|---|---|
| Comp. Example 1 | Comp. Compound A | Compound (N-12) | 4.9 | 8.8 | 28.5 | 114.5 |
| Comp. Example 2 | Comp. Compound B | Compound (N-12) | 5.2 | 11.0 | 22.6 | 102.1 |
| Example 1 | Compound (P-1) | Compound (N-12) | 4.8 | 8.1 | 30.8 | 123.8 |
| Example 2 | Compound (P-5) | Compound (N-12) | 4.8 | 8.1 | 31.0 | 125.0 |
| Example 3 | Compound (P-22) | Compound (N-12) | 4.7 | 7.9 | 31.6 | 123.3 |
| Example 4 | Compound (P-25) | Compound (N-12) | 4.7 | 8.3 | 30.1 | 129.1 |
| Example 5 | Compound (P-42) | Compound (N-12) | 4.7 | 7.9 | 31.7 | 129.4 |
| Example 6 | Compound (P-63) | Compound (N-12) | 4.7 | 7.7 | 32.5 | 127.4 |
| Example 7 | Compound (P-72) | Compound (N-12) | 4.7 | 7.6 | 32.8 | 125.5 |
| Example 8 | Compound (P-98) | Compound (N-12) | 4.7 | 7.8 | 32.1 | 125.1 |
| Example 9 | Compound (P-1) | Compound (N-17) | 4.6 | 7.7 | 32.4 | 131.0 |
| Example 10 | Compound (P-1) | Compound (N-82) | 4.7 | 8.0 | 31.1 | 129.4 |
| Example 11 | Compound (P-1) | Compound (S-32) | 4.7 | 7.8 | 32.1 | 136.9 |
| Example 12 | Compound (P-1) | Compound (S-108) | 4.6 | 7.5 | 33.4 | 139.9 |
| Example 13 | Compound (P-22) | Compound (N-17) | 4.5 | 7.5 | 33.2 | 129.8 |
| Example 14 | Compound (P-22) | Compound (N-82) | 4.6 | 7.8 | 31.9 | 127.4 |
| Example 15 | Compound (P-22) | Compound (S-32) | 4.6 | 7.6 | 32.8 | 134.7 |
| Example 16 | Compound (P-22) | Compound (S-108) | 4.5 | 7.3 | 34.1 | 138.7 |
| Example 17 | Compound (P-25) | Compound (N-17) | 4.5 | 7.9 | 31.6 | 136.7 |
| Example 18 | Compound (P-25) | Compound (N-82) | 4.6 | 8.3 | 30.3 | 134.3 |
| Example 19 | Compound (P-25) | Compound (S-32) | 4.6 | 8.0 | 31.2 | 141.7 |
| Example 20 | Compound (P-25) | Compound (S-108) | 4.5 | 7.7 | 32.5 | 146.2 |
| Example 21 | Compound (P-42) | Compound (N-17) | 4.5 | 7.5 | 33.4 | 136.7 |
| Example 22 | Compound (P-42) | Compound (N-82) | 4.6 | 7.8 | 32.0 | 134.3 |
| Example 23 | Compound (P-42) | Compound (S-32) | 4.7 | 7.6 | 32.9 | 141.6 |
| Example 24 | Compound (P-42) | Compound (S-108) | 4.6 | 7.3 | 34.2 | 145.7 |
| Example 25 | Compound (P-63) | Compound (N-17) | 4.4 | 7.3 | 34.2 | 135.3 |
| Example 26 | Compound (P-63) | Compound (N-82) | 4.5 | 7.6 | 32.8 | 133.2 |
| example27 | compound (P-63) | compound (S-32) | 4.6 | 7.4 | 33.8 | 140.5 |
| example28 | compound (P-63) | compound (S-108) | 4.5 | 7.1 | 35.1 | 144.4 |
| example29 | compound (P-98) | compound (N-17) | 4.5 | 7.4 | 33.9 | 133.2 |
| example30 | compound (P-98) | compound (N-82) | 4.5 | 7.7 | 32.5 | 130.6 |
| example31 | compound (P-98) | compound (S-32) | 4.6 | 7.5 | 33.5 | 138.0 |
| example32 | compound (P-98) | compound (S-108) | 4.5 | 7.2 | 34.7 | 141.9 |

Referring to Table 6, when the compound of the present invention is used as the emitting layer material, it can be seen that the driving voltage is lowered and the efficiency and lifespan are improved compared to the case of using the comparative compound A or the comparative compound B.

As can be seen above, when a host of the emitting layer is formed by mixing a plurality of compounds, the characteristics are different depending on the type of the first compound and the second compound, and when the same compound is applied to the second compound, the characteristic difference is remarkably displayed depending on the type of the first compound. Similarly, it shows a difference in driving voltage, efficiency, and lifespan according to the type of the second compound.

Comparing Comparative Compound A and the compound of the present invention, Comparative Compound A and the compound of the present invention have similar structures, but the substituent of Comparative Compound A has a -p-phenyl-naphthyl structure, and the substituent of the compound of the present invention is -m-phenyl-naphthyl structure. Also, as can be seen in Table 6, when the compound of the present invention is applied to the element, it can be confirmed that the overall performance of the element is improved.

Table 7 shows data measured using the DFT Method (B3LYP/6-31 g(D)) of the comparative compound A and the compound P-1 of the present invention by the Gaussian program.

TABLE 7

| | G.HOMO | G.LUMO | G.BG | G.S1 | G.T1 |
|---|---|---|---|---|---|
| Comparative compound A | −5.7084 | −1.9862 | 3.7222 | 3.3427 | 2.403 |
| P-1 | −5.673 | −1.9682 | 3.7048 | 3.3016 | 2.3999 |

As can be seen in Table 7, compared with Comparative Compound A, in compound P-1 of the present invention, T1 is similar, but the energy bandgap is decreased, and in particular, it can be confirmed that S1 is lowered. Due to this, the wavelength of the energy emitted from the host increases, and the energy is better transferred to the red dopant. In other words, the low S1 of the compound P-1 of the present invention facilitates the transfer of Foster energy to the dopant, so it seems to affect the overall performance improvement of the element.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:
1. A compound represented by Formula 1:

<Formula 1>

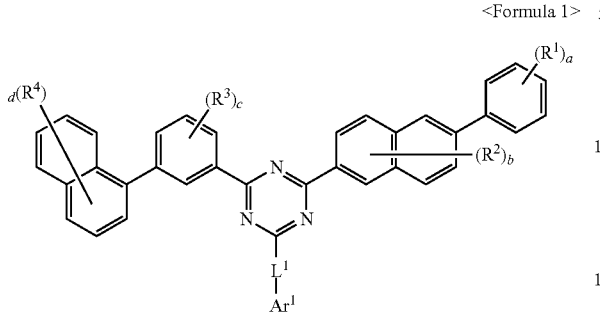

wherein:
$R^1$, $R^2$ and $R^3$ are each independently selected from the group consisting of hydrogen; deuterium; halogen; and a $C_1$~$C_{60}$ alkyl group,
$R^4$ is hydrogen; deuterium; a $C_6$~$C_{60}$ aryl group; or $C_6$~$C_{60}$ aryl group substituted with deuterium,
$L^1$ is a single bond; or $C_6$~$C_{60}$ arylene group,
$Ar^1$ is a $C_6$~$C_{60}$ aryl group,
a is an integer of 0 to 5, b is an integer of 0 to 6, c is an integer of 0 to 4, d is an integer of 0 to 7,
wherein the alkyl group, aryl group or arylene group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by combination thereof.

2. The compound of claim 1, wherein Formula 1 is represented by Formula 1-3 or Formula 1-4:

<Formula 1-3>

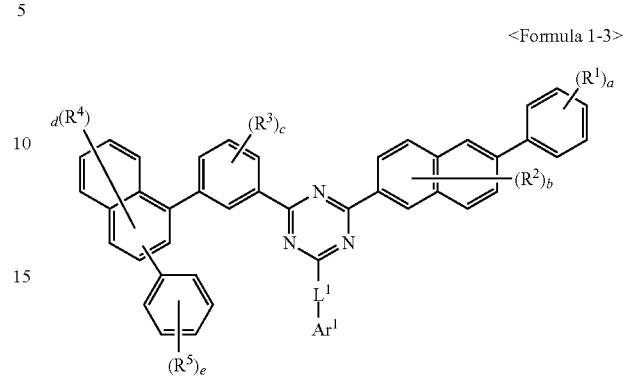

<Formula 1-4>

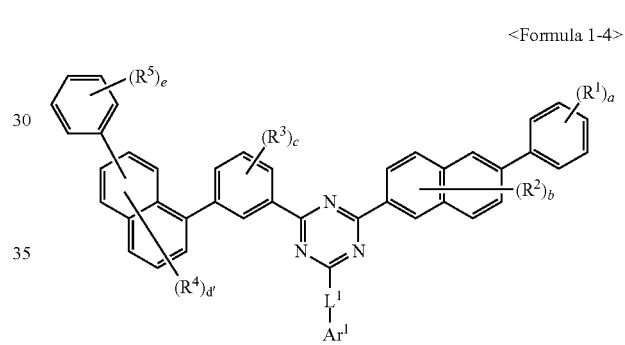

wherein:
$R^1$, $R^2$, $R^3$, $R^4$, a, b, c, $L^1$ and $Ar^1$ are the same as defined in claim 1,
d' is an integer from 0 to 6, e is an integer from 0 to 5, and
$R^5$ is hydrogen; or deuterium.

3. The compound of claim 1, wherein Formula 1 is represented by any one of Formulas 1-3-1 to 1-3-3:

<Formula 1-3-1>

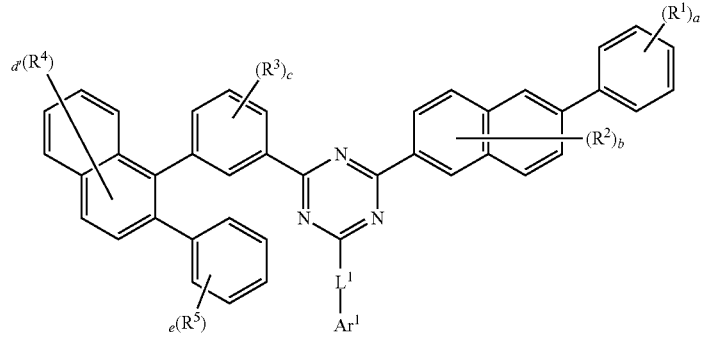

<Formula 1-3-2>
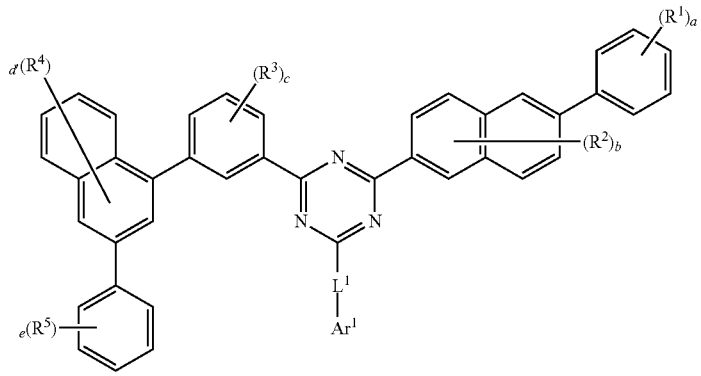
<Formula 1-3-3>
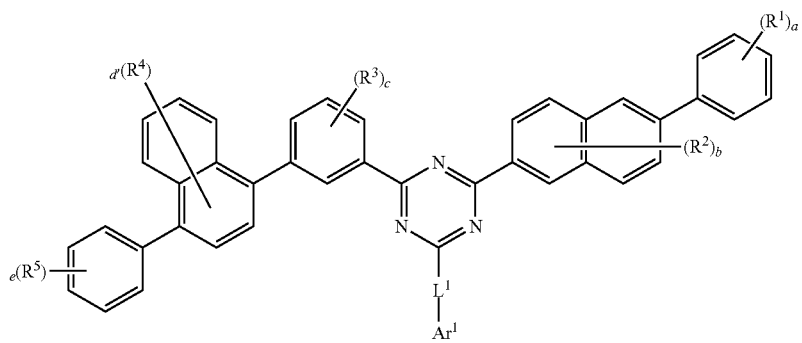
wherein:
R¹, R², R³, R⁴, a, b, c, L¹ and Ar¹ are the same as defined in claim 1,
d' is an integer of 0 to 6, e is an integer of 0 to 5, and
R⁵ is hydrogen; or deuterium.
4. The compound of claim 1, wherein Formula 1 is represented by any one of Formulas 1-4-1 to 1-4-4:
<Formula 1-4-1>
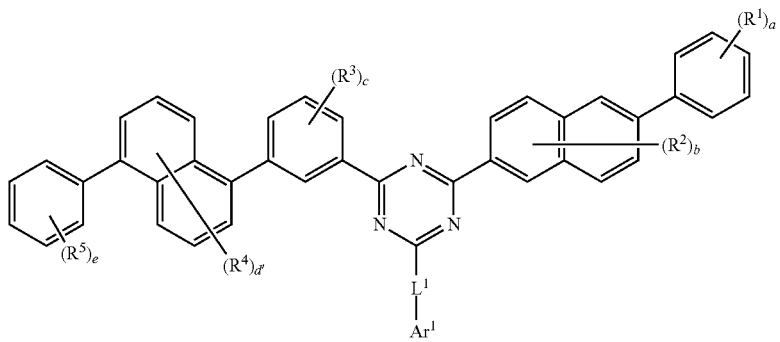

<Formula 1-4-2>

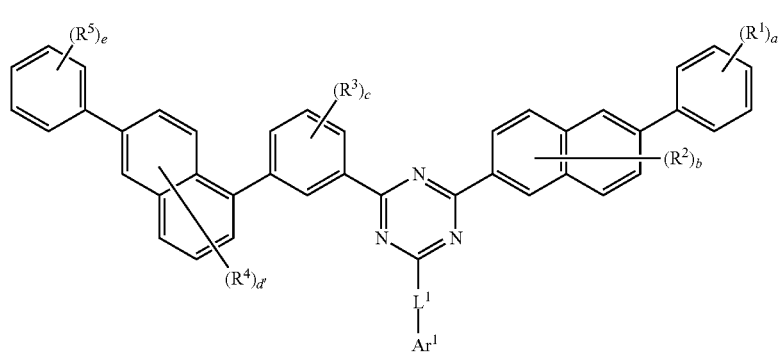

<Formula 1-4-3>

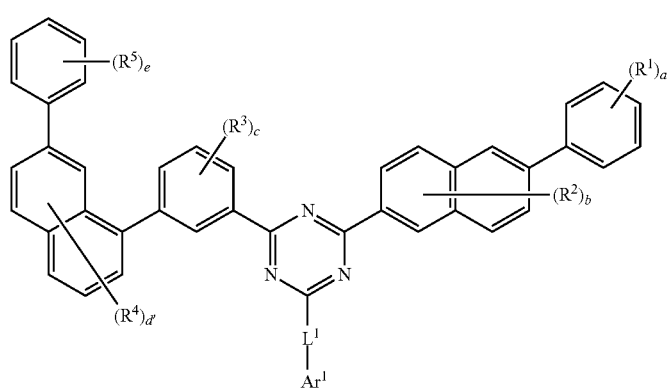

<Formula 1-4-4>

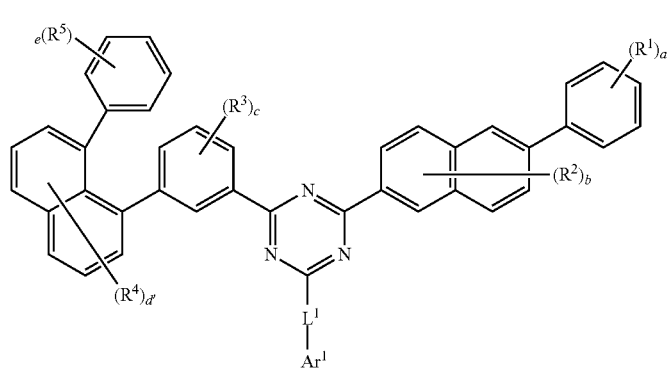

wherein:

$R^1$, $R^2$, $R^3$, $R^4$, a, b, c, $L^1$ and $Ar^1$ are the same as defined in claim 1, d' is an integer of 0 to 6, e is an integer of 0 to 5, and $R^5$ is hydrogen; or deuterium.

5. The compound of claim 1, wherein, $L^1$ of Formula 1 is represented by Formula L1 or Formula L2:

<Formula L1>

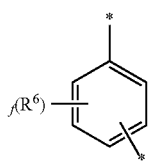

<Formula L2>

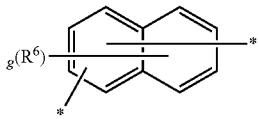

wherein:

$R^6$ is hydrogen; or deuterium, f is an integer of 0 to 4, g is an integer of 0 to 6, and

* indicates the bonding position.

6. The compound of claim 1, wherein, $Ar^1$ of Formula 1 is represented by any one of Formulas Ar1 to Ar3:

<Formula Ar1>
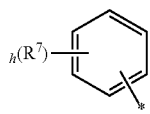
<Formula Ar2>
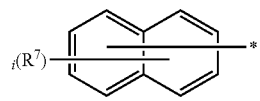
<Formula Ar3>
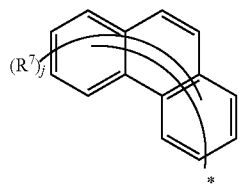
wherein:
R$^7$ is hydrogen; or deuterium,
h is an integer of 0 to 5, i is an integer of 0 to 7, j is an integer of 0 to 9, and
* means the bonding position.
7. The compound of claim 1, wherein, Formula 1 is represented by any one of Compounds P-1 to P-104:
P-1
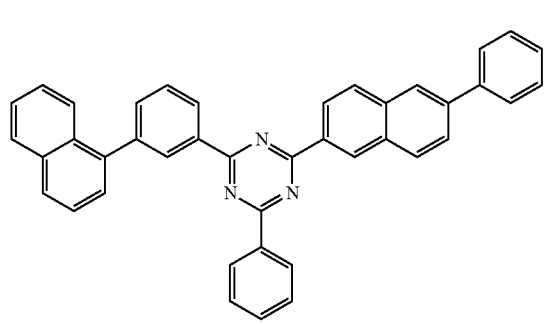
P-2
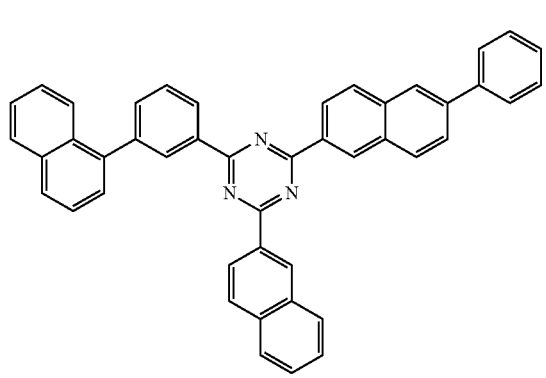
P-3
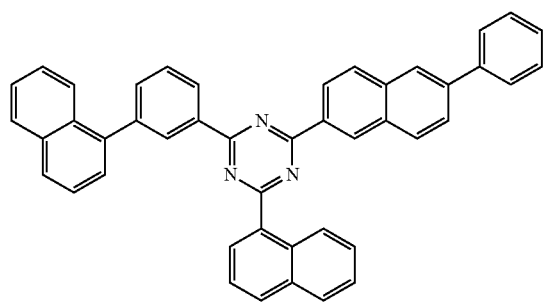
P-4
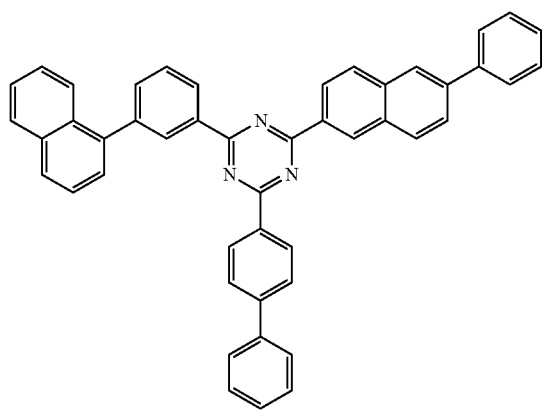
P-5
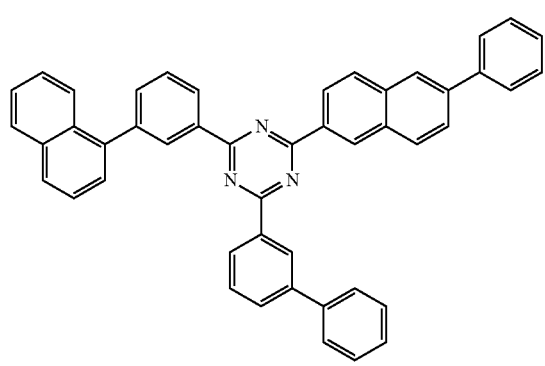
P-6
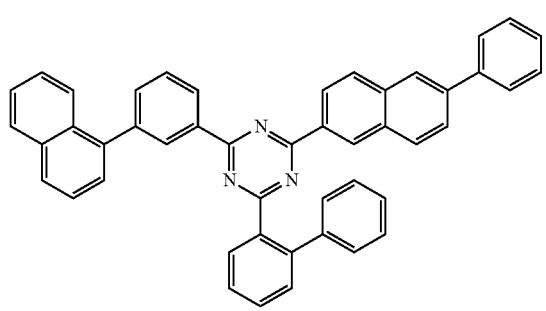

-continued
P-7
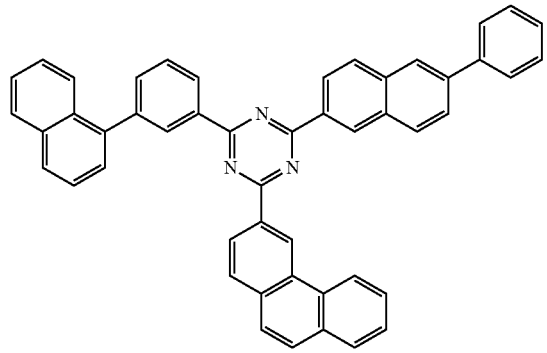
P-8
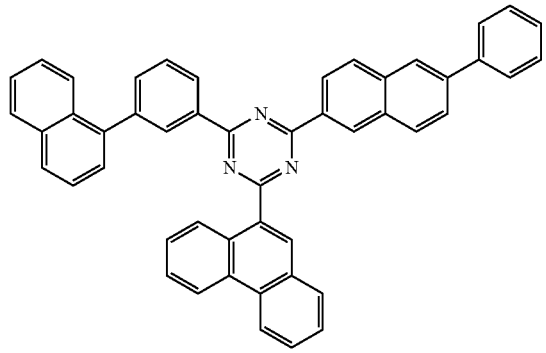
P-9
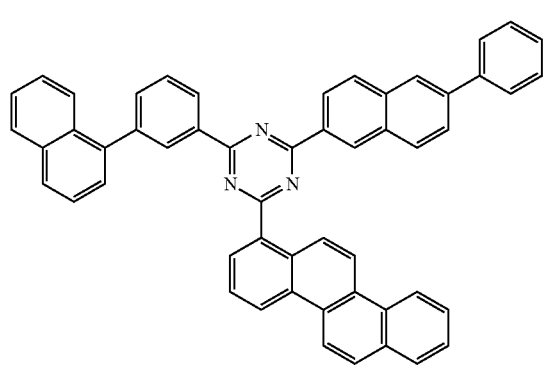
P-10
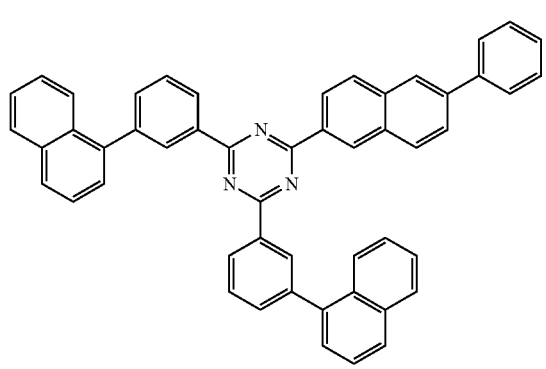
P-11
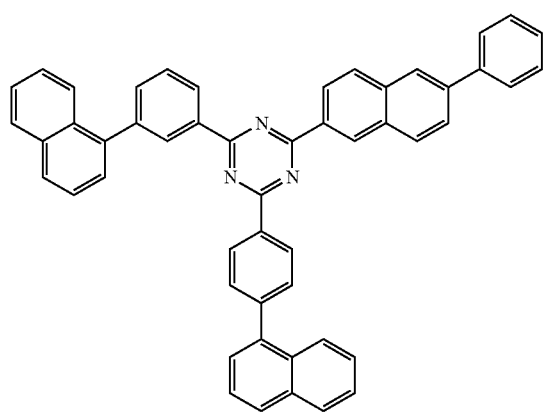
P-12
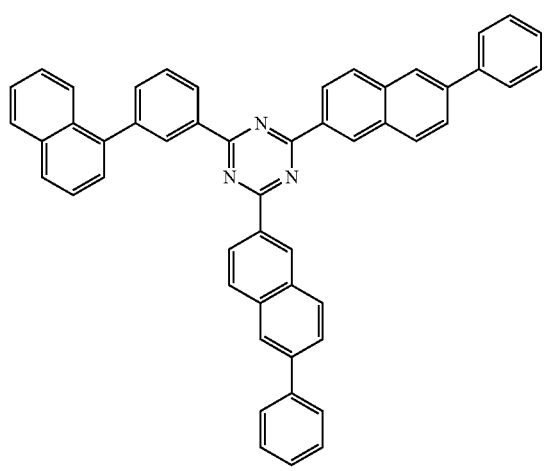
P-13
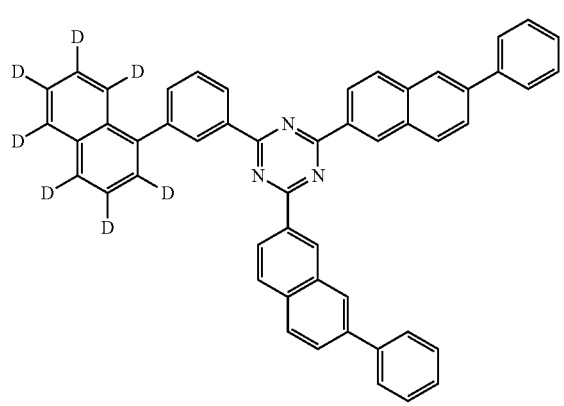
P-14
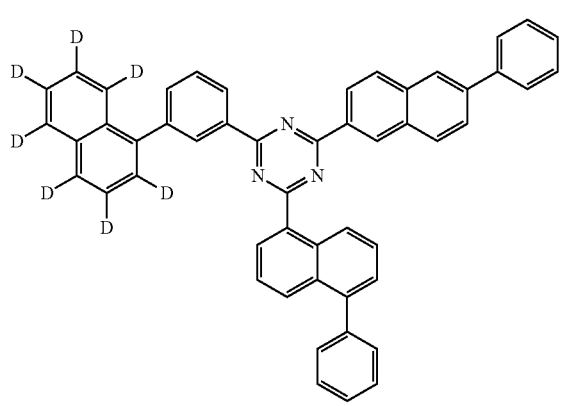

-continued
P-15
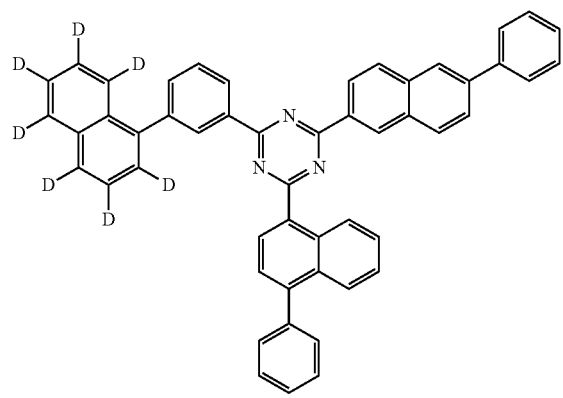
P-16
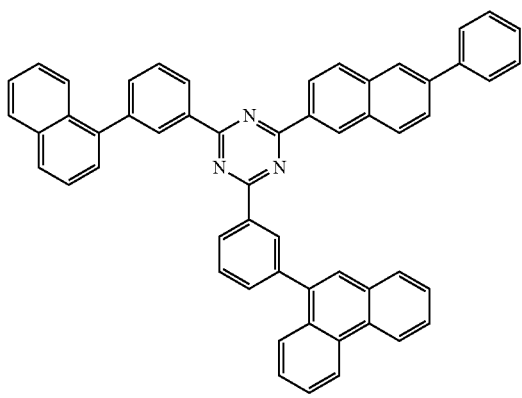
P-17
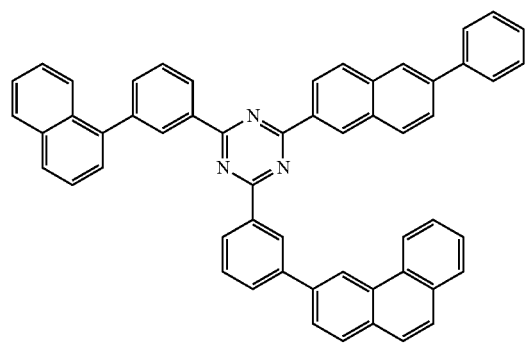
P-18
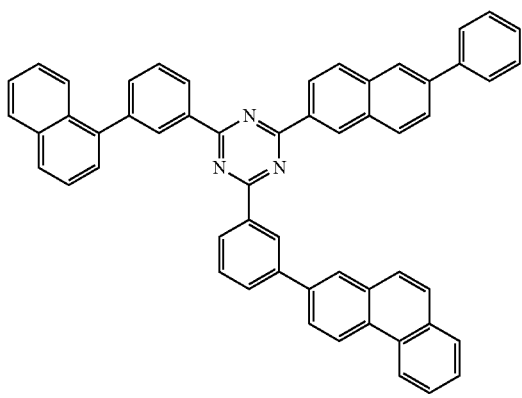
P-19
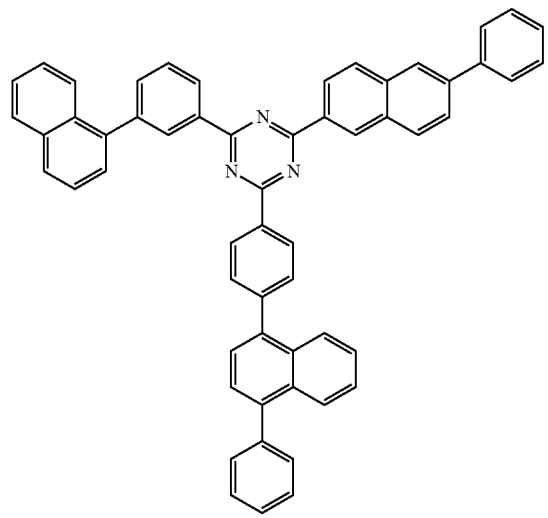
P-20
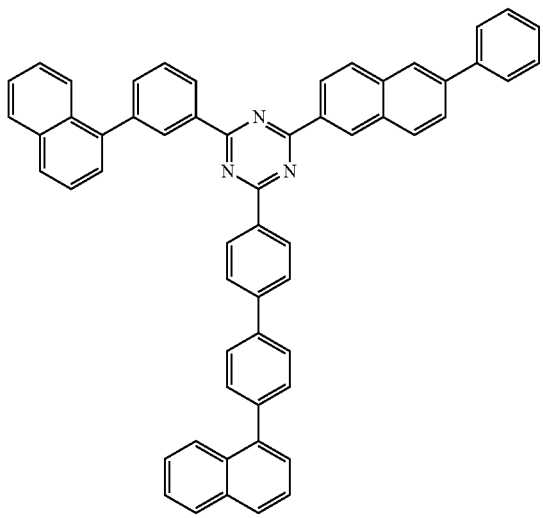

-continued
P-21
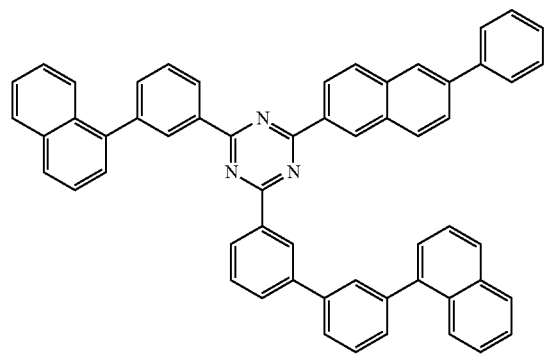
P-22
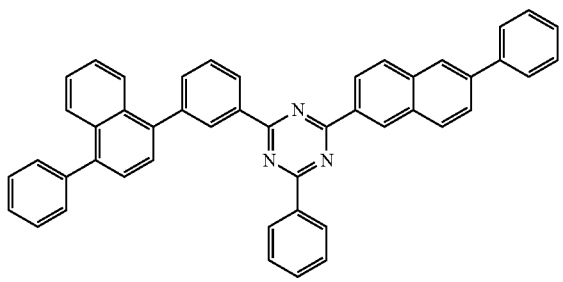
P-23
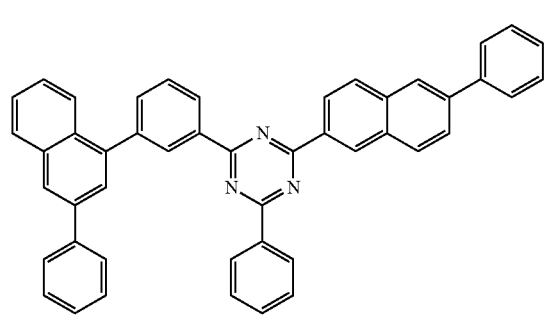
P-24
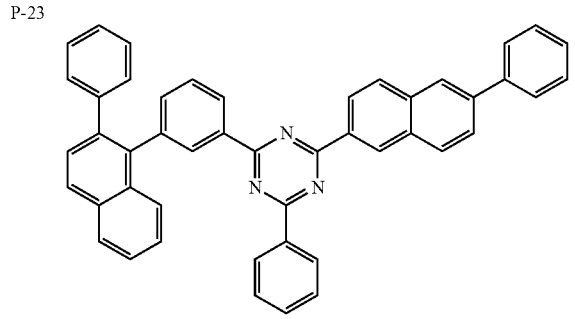
P-25
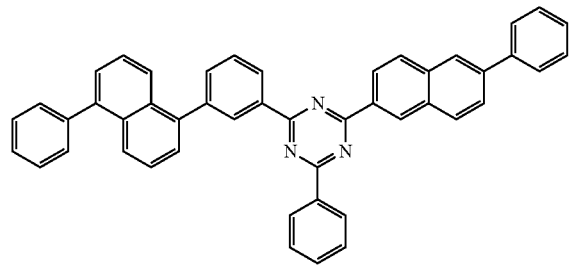
P-26
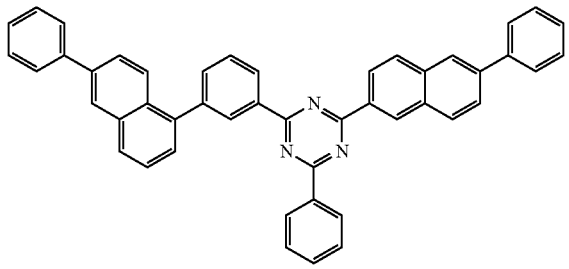
P-27
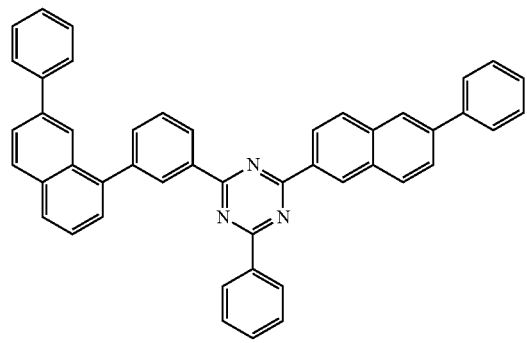
P-28
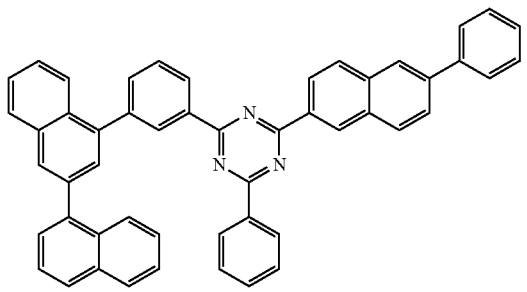

-continued
P-29
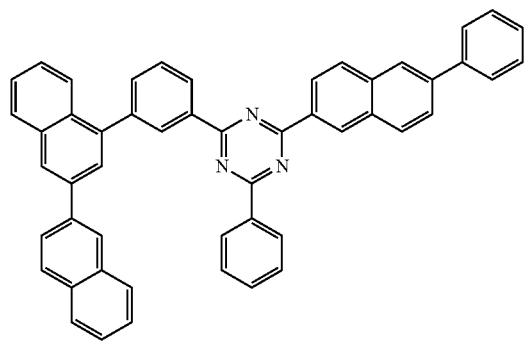
P-30
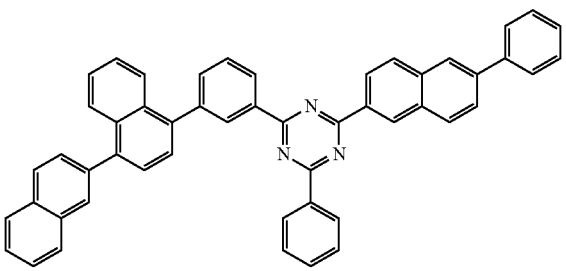
P-31
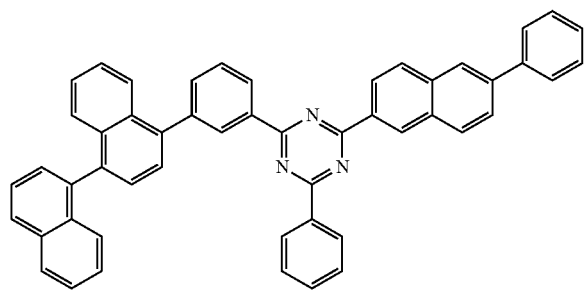
P-32
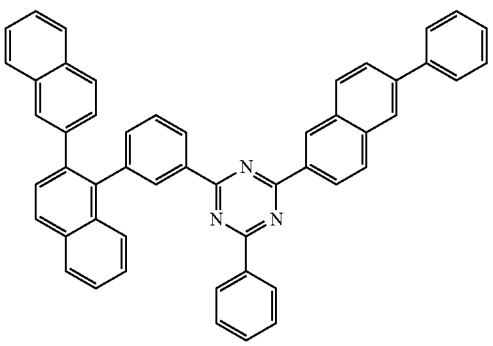
P-33
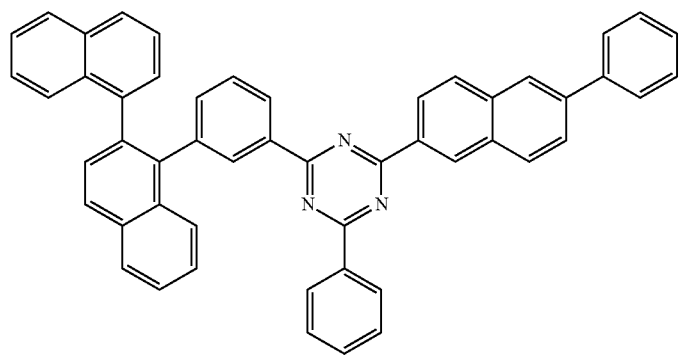
P-34
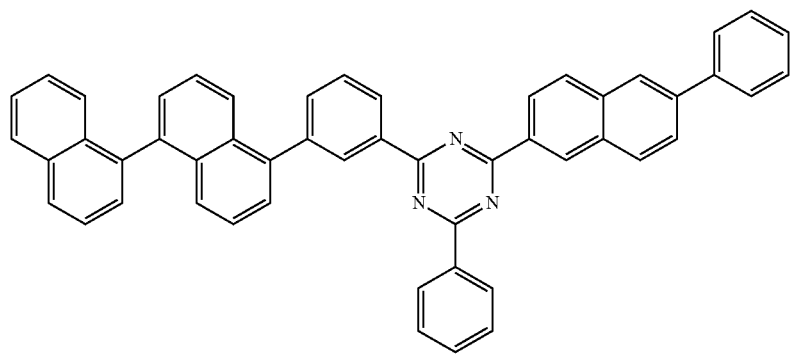

P-35
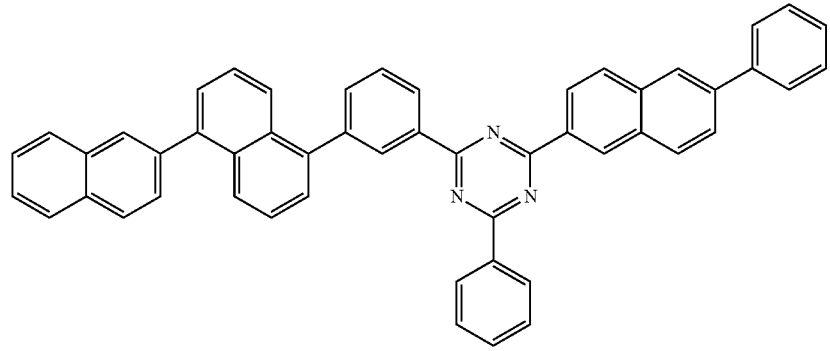
P-36
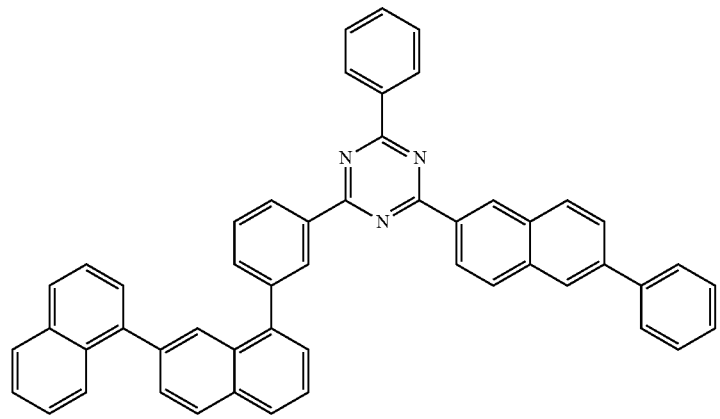
P-37
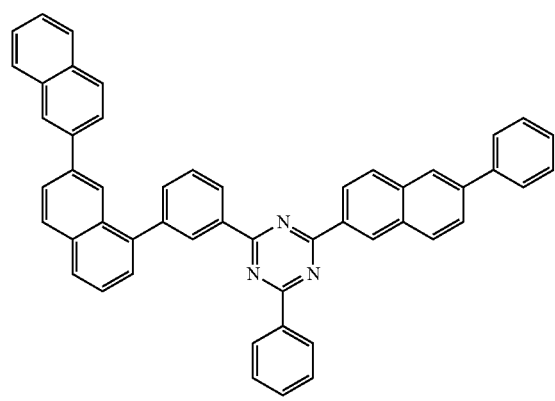
P-38
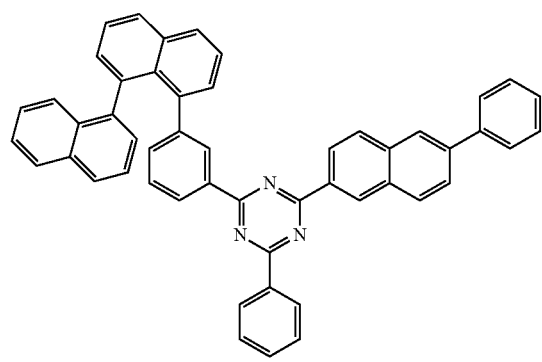
P-39
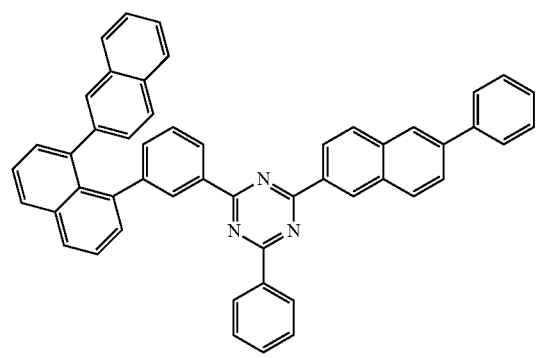
P-40
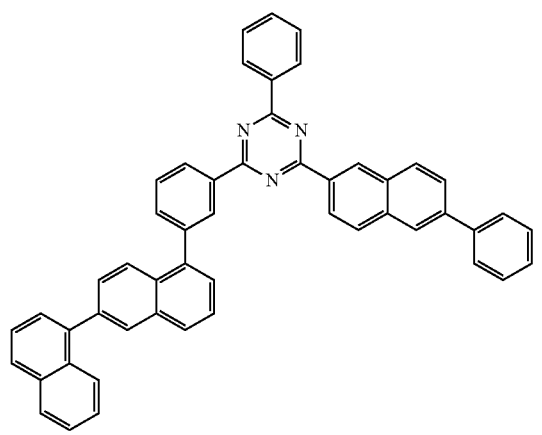

-continued
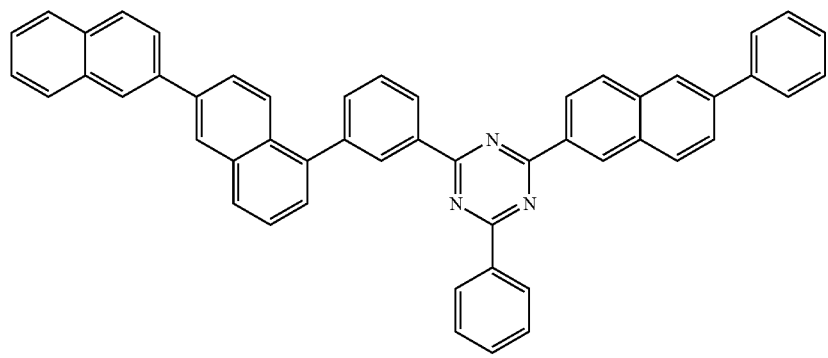
P-41
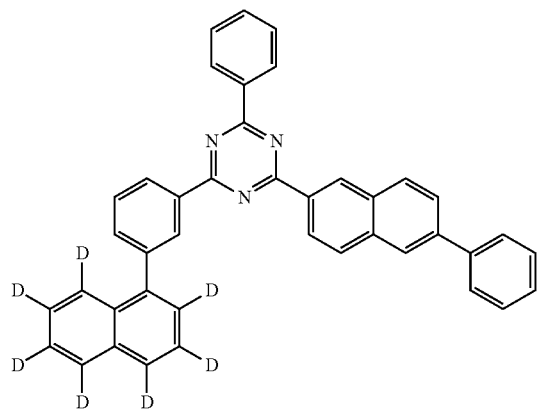
P-42
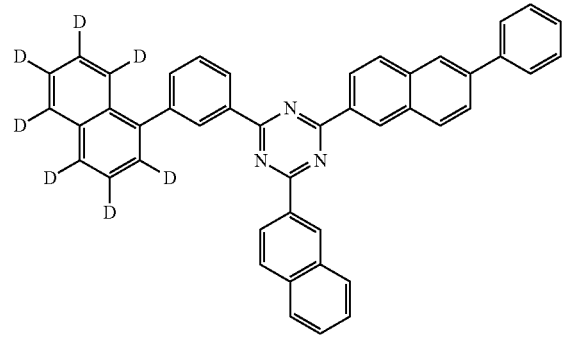
P-43
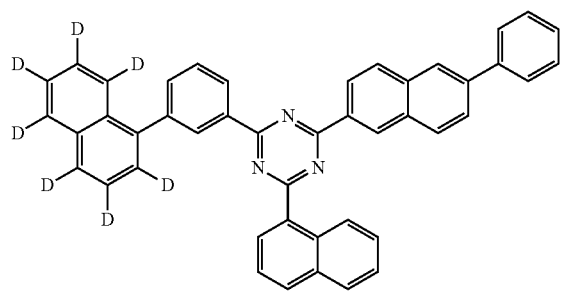
P-44
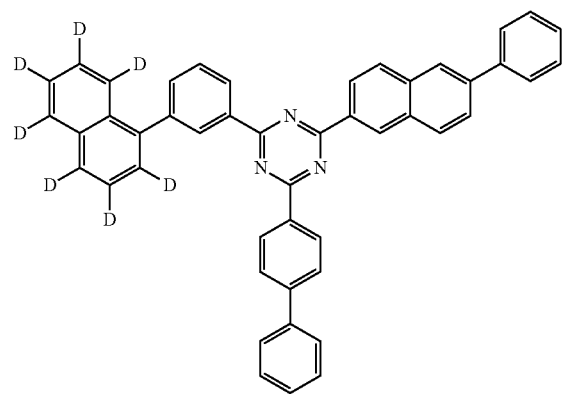
P-45
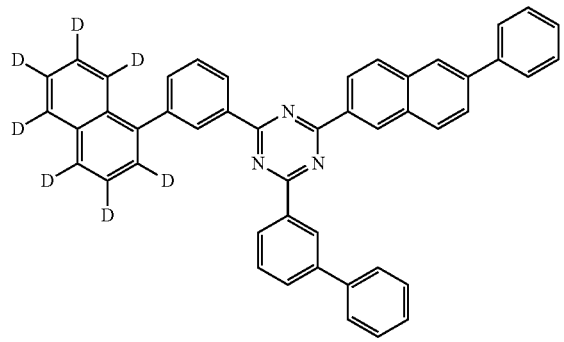
P-46
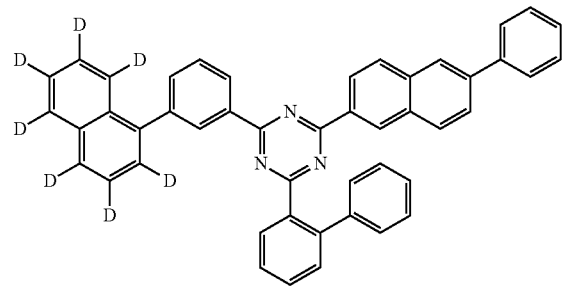
P-47

-continued
P-48
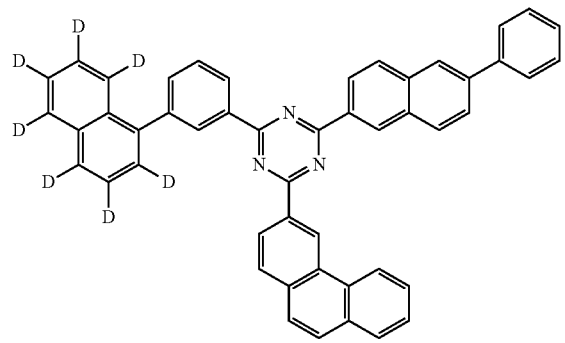
P-49
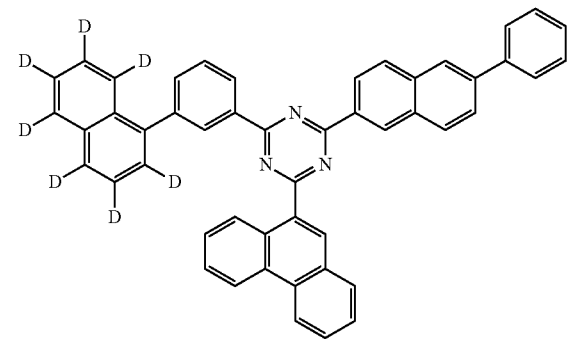
P-50
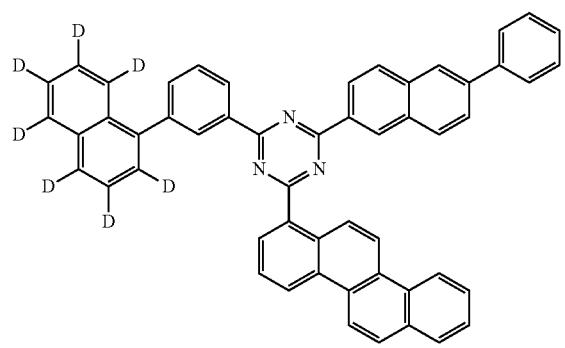
P-51
P-52
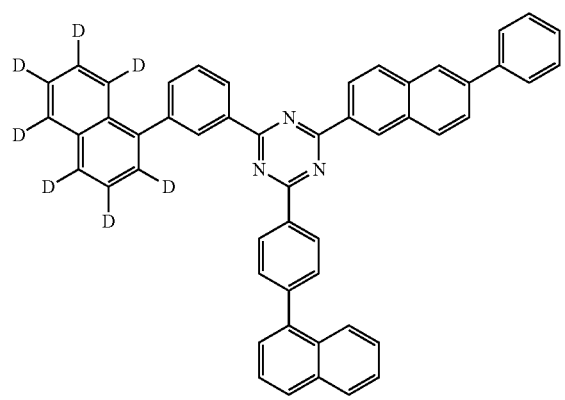
P-53
P-54
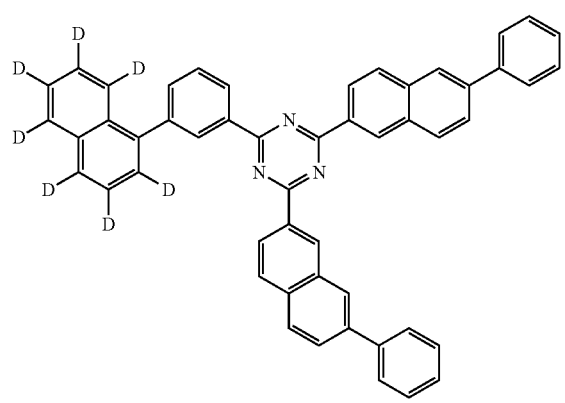
P-55
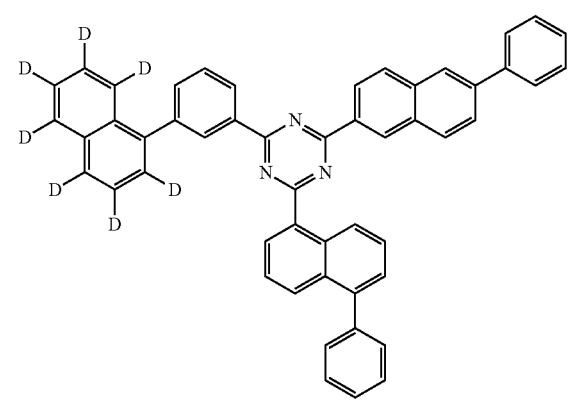

-continued
P-56
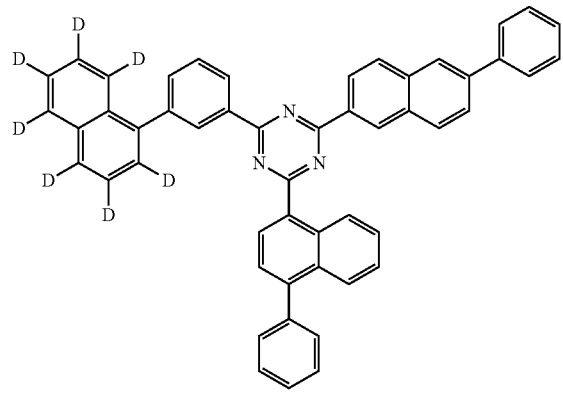
P-57
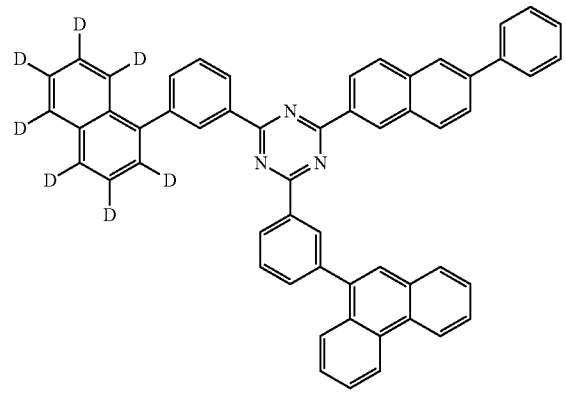
P-58
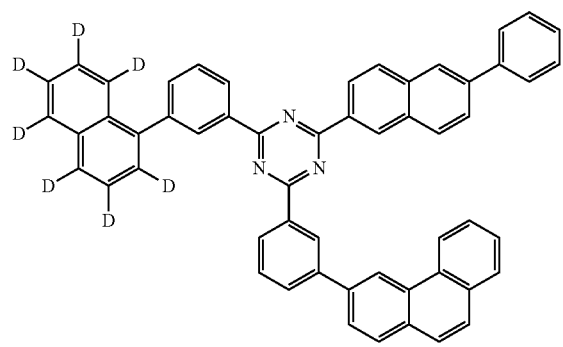
P-59
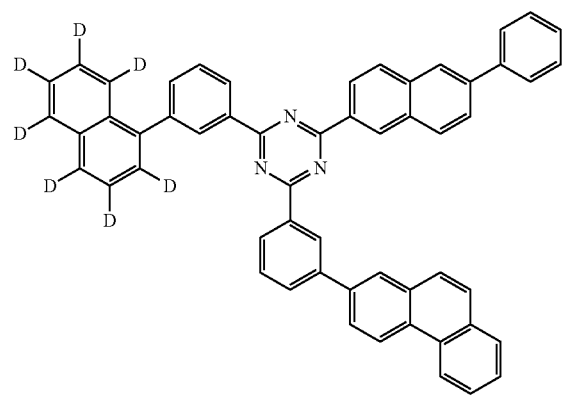
P-60
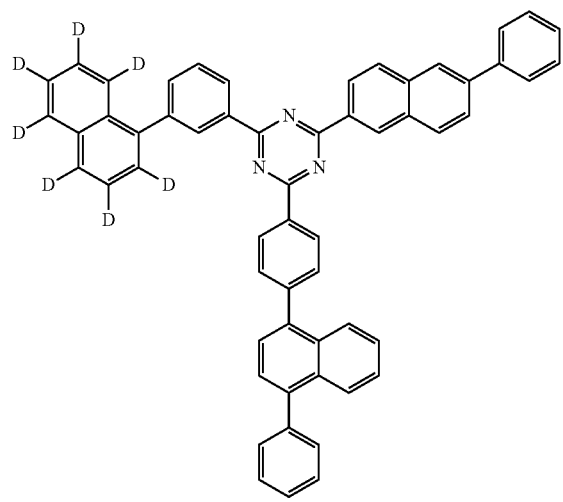
P-61
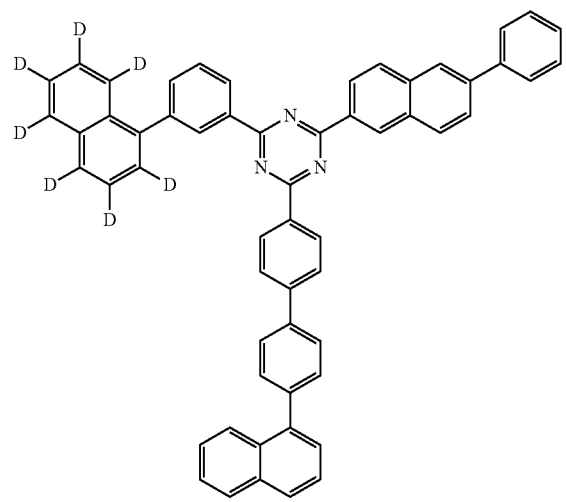

-continued
P-62
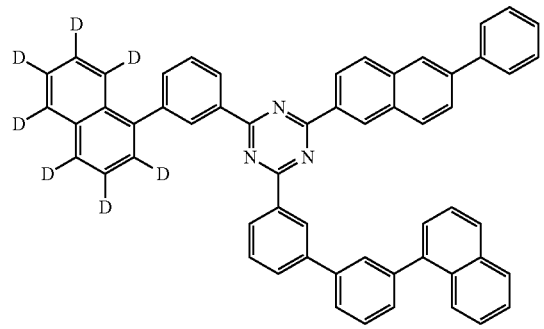
P-63
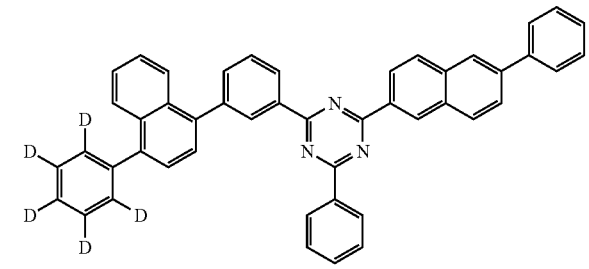
P-64
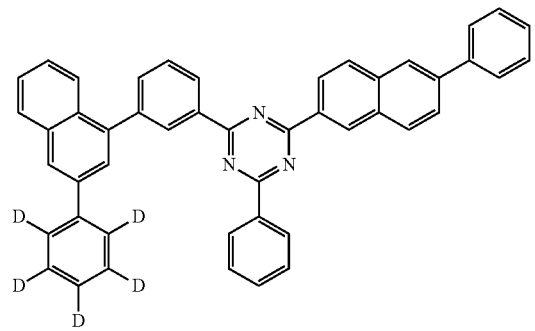
P-65
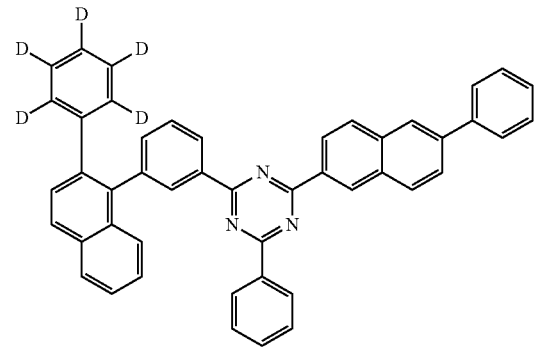
P-66
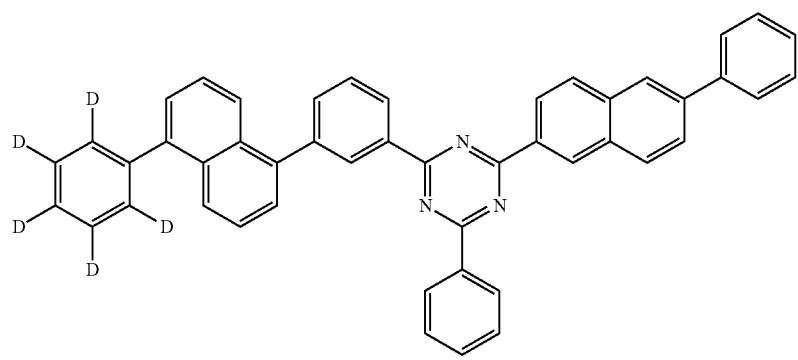
P-67
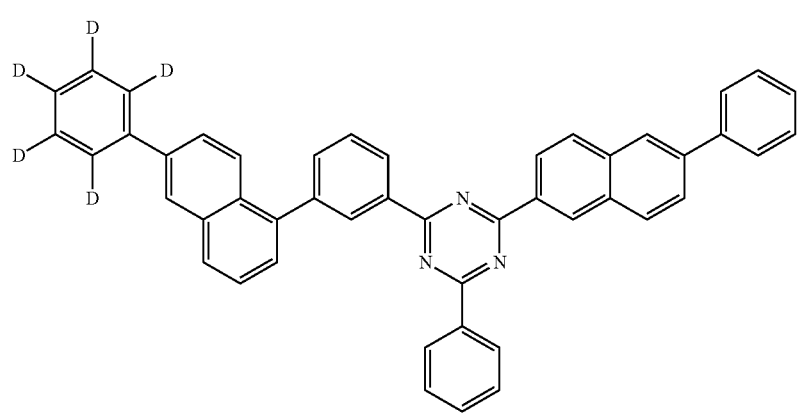

-continued
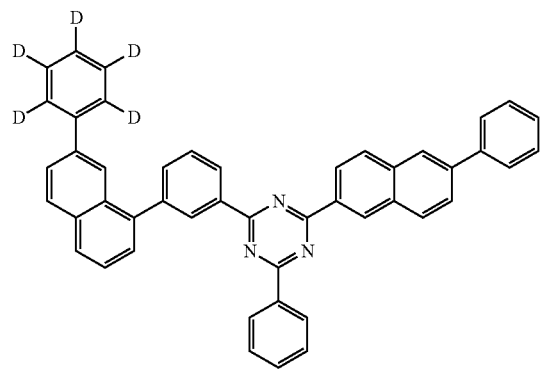
P-68
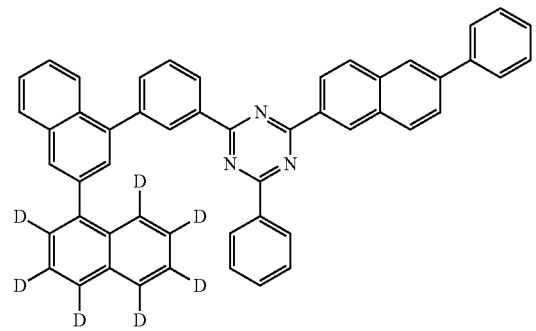
P-69
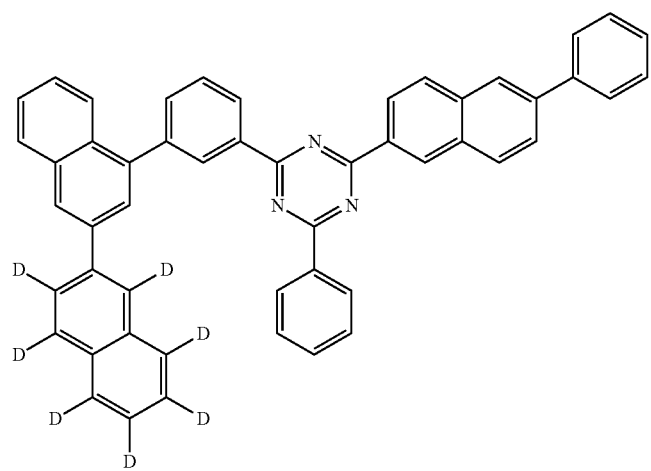
P-70
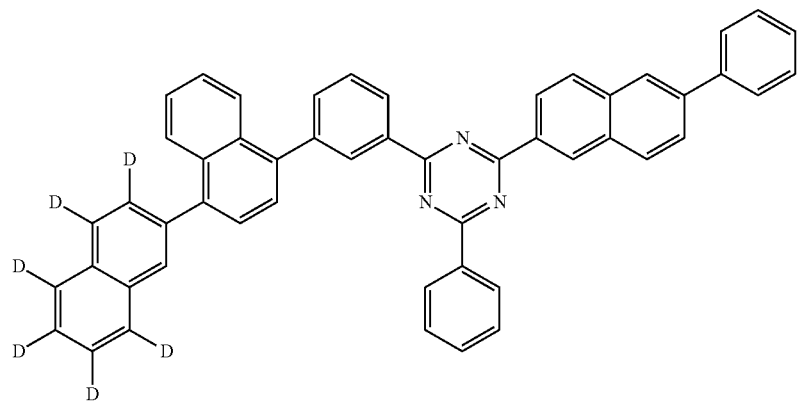
P-71

-continued
P-72
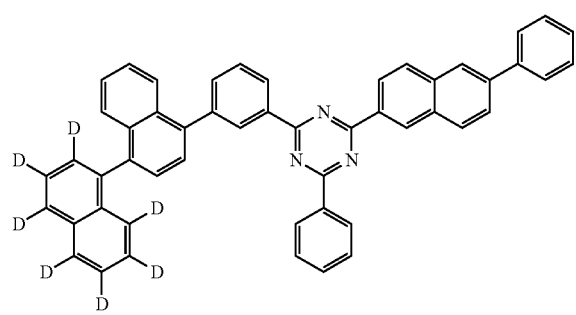
P-73
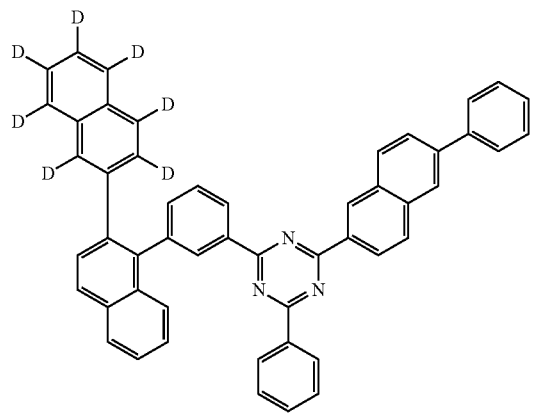
P-74
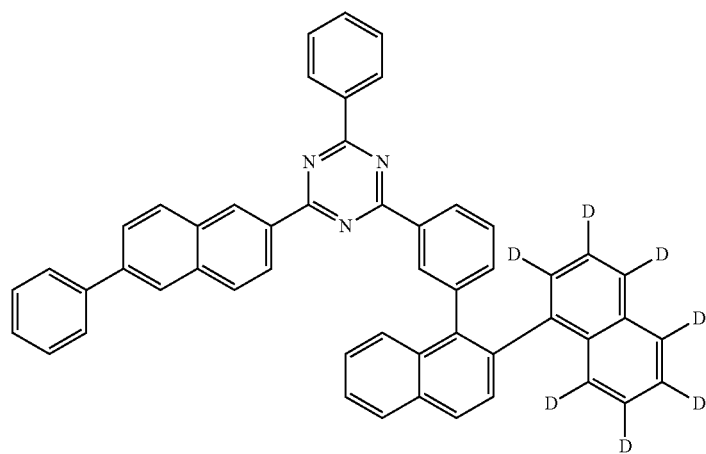
P-75
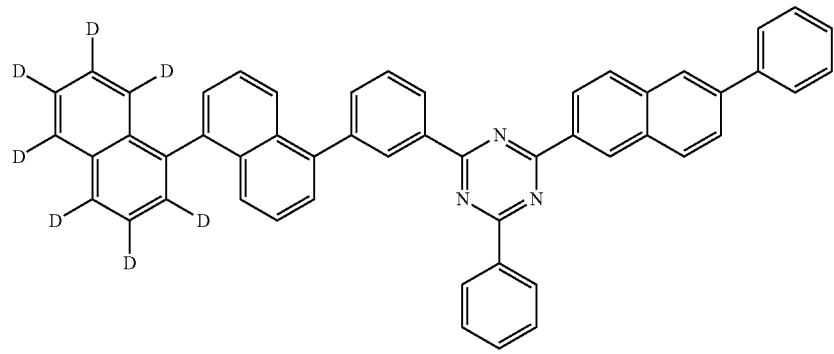

-continued
P-76
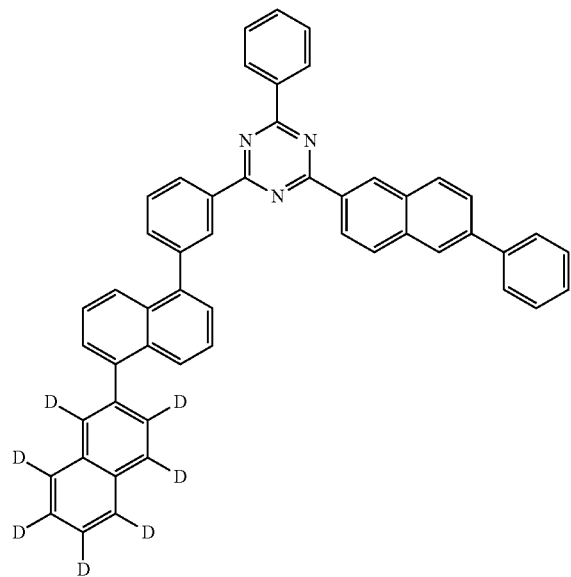
P-77
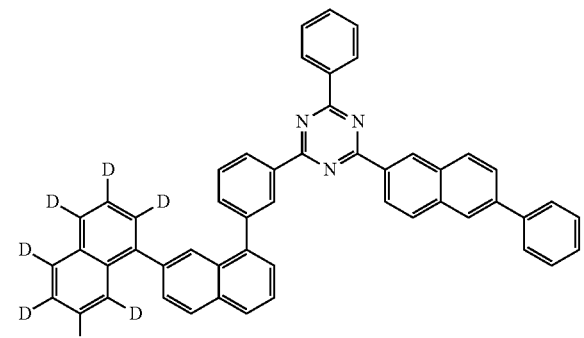
P-78
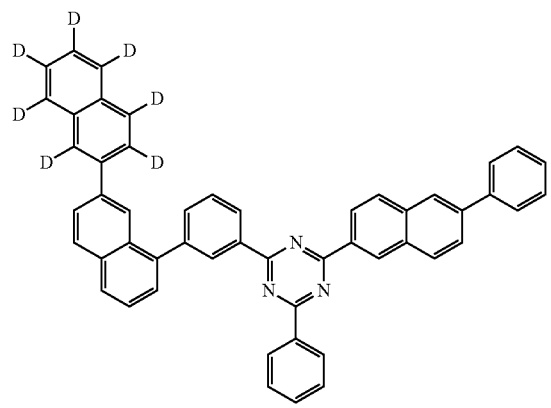
P-79
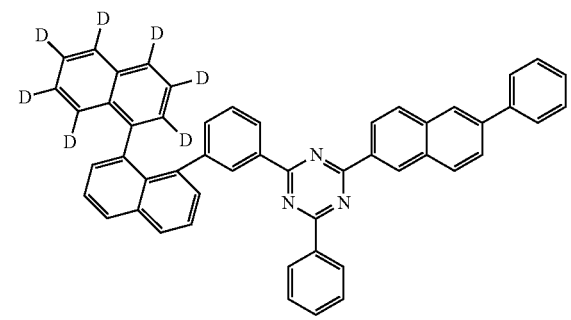
P-80
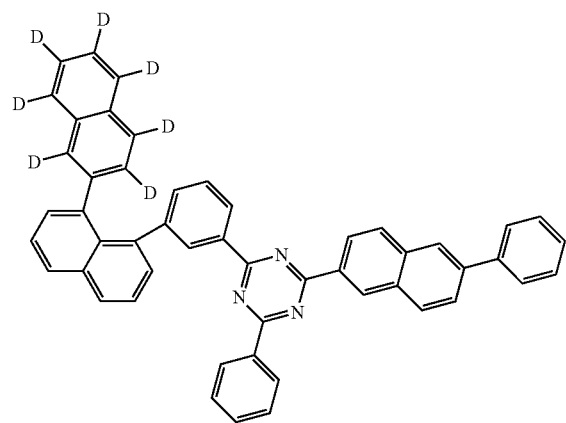
P-81
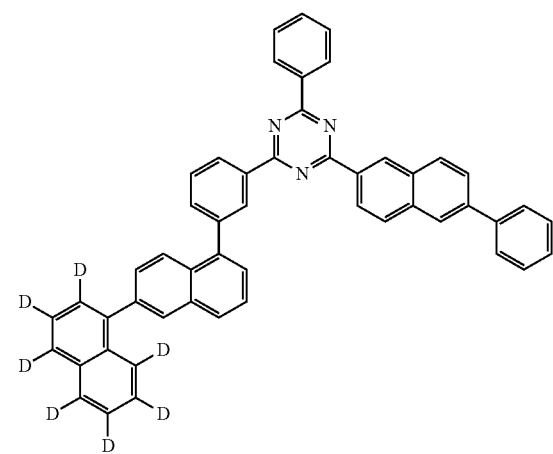

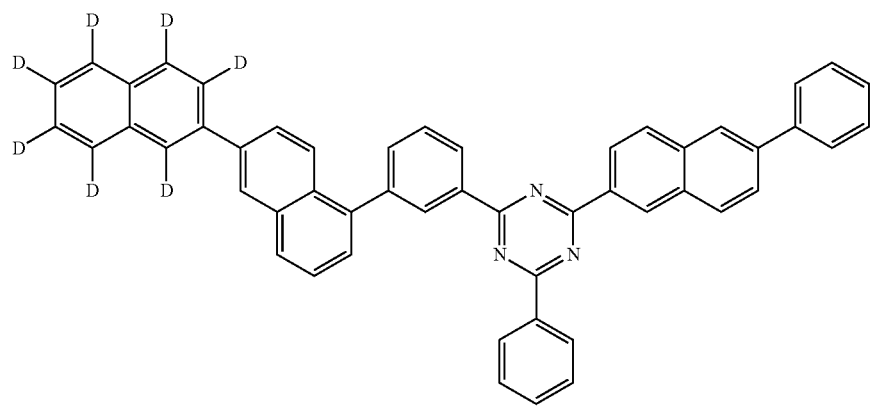
P-82
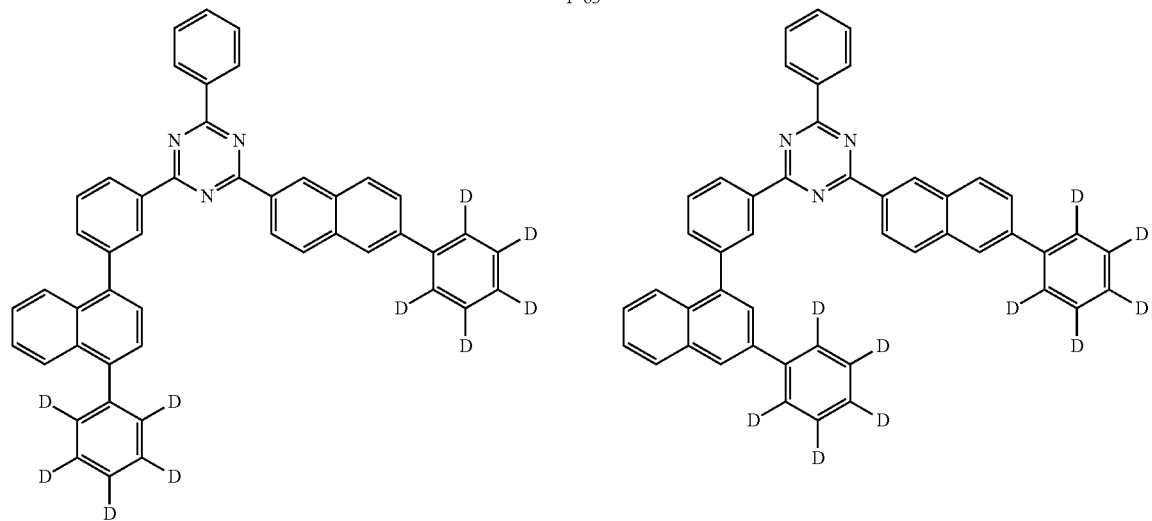
P-83
P-84
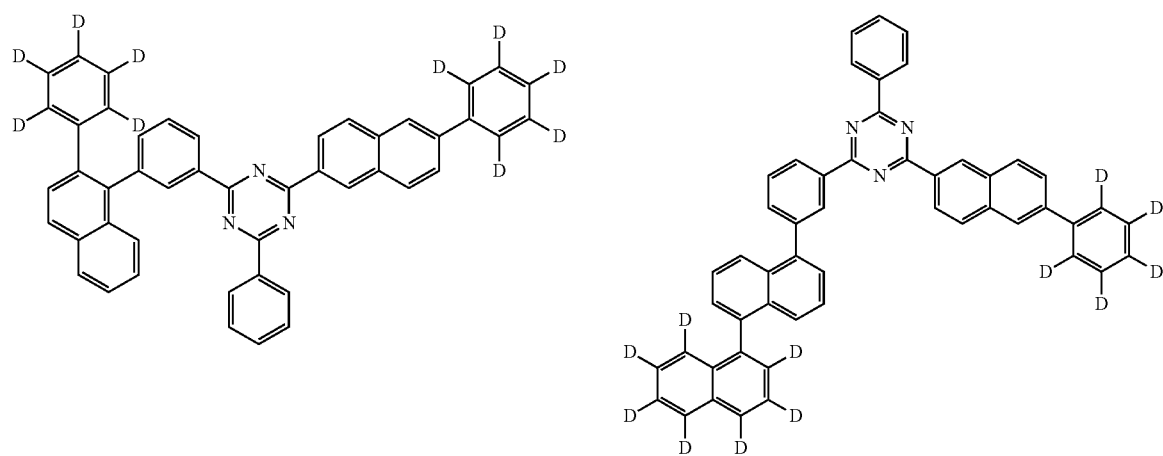
P-85
P-86

-continued
P-87
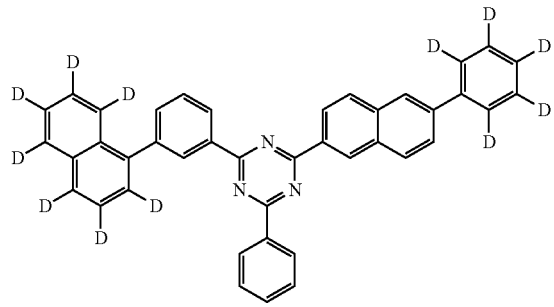
P-88
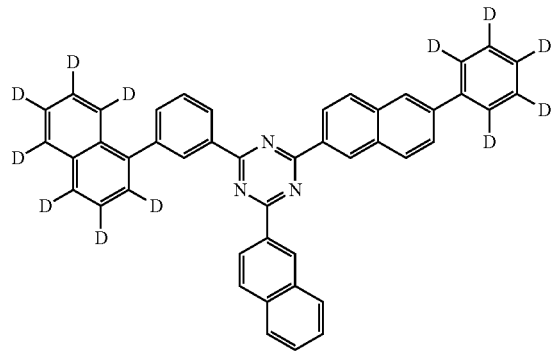
P-89
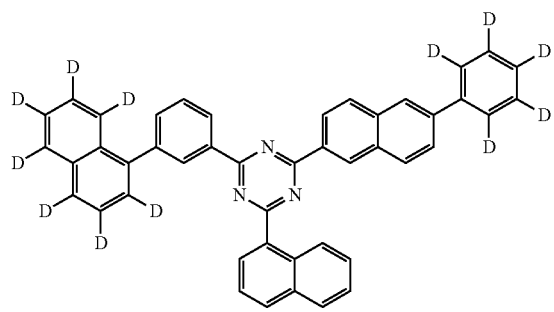
P-90
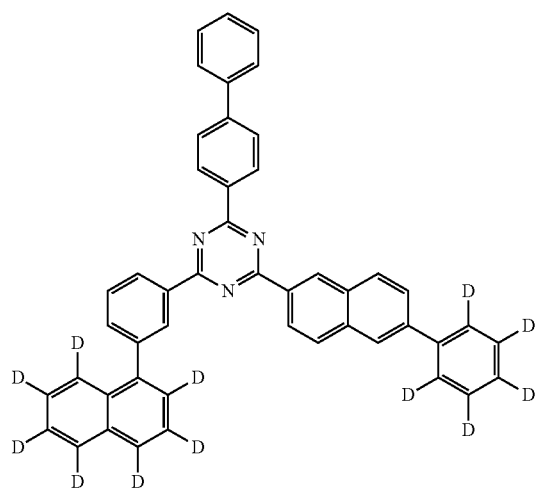
P-91
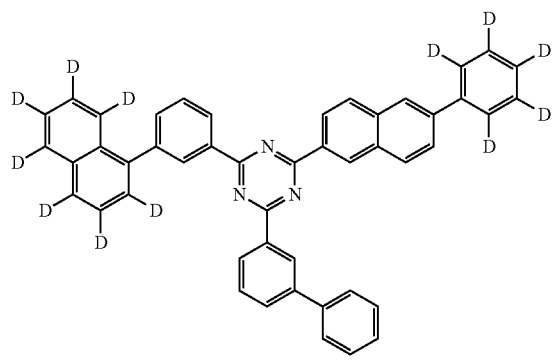
P-92
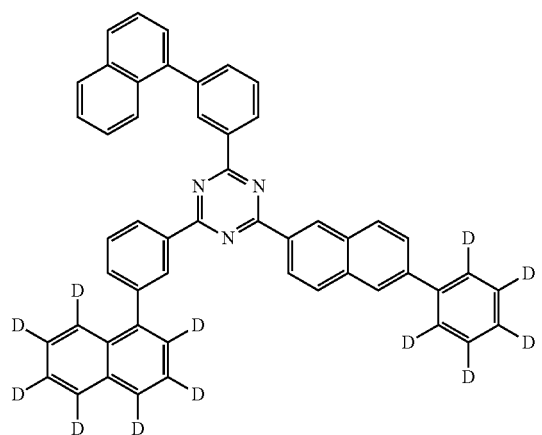

-continued
P-93
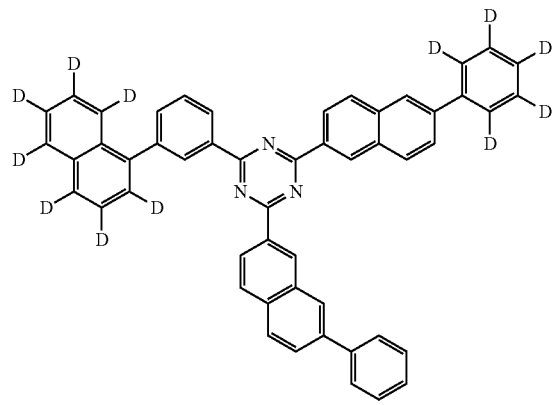
P-94
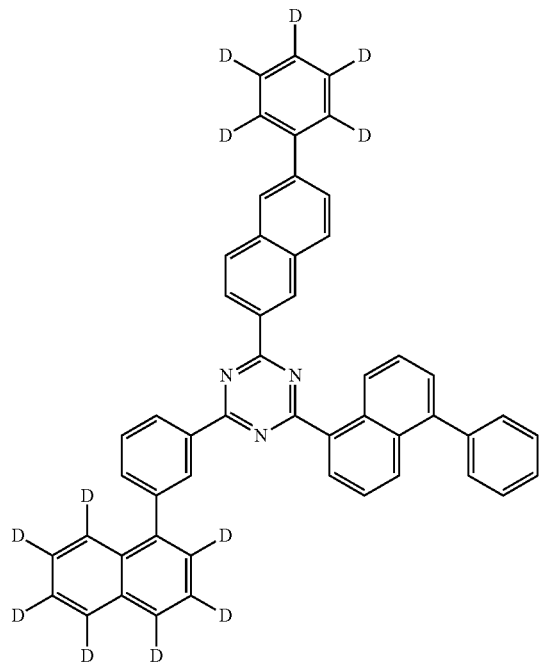
P-95
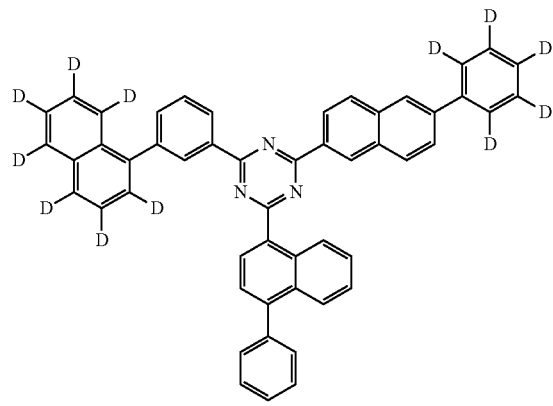
P-96
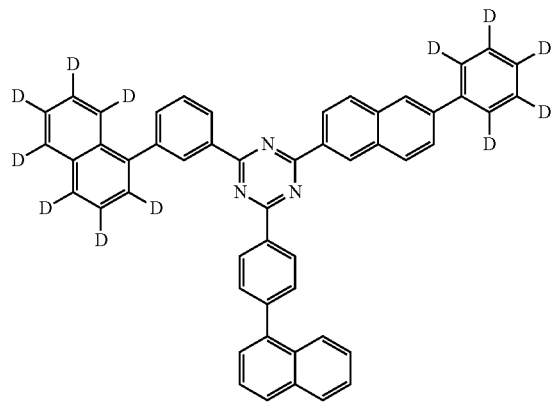
P-97
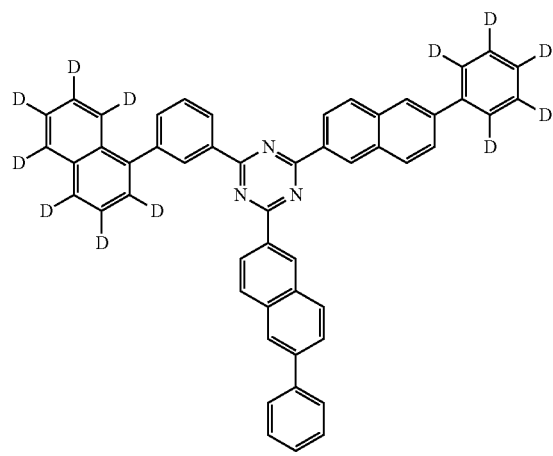
P-98
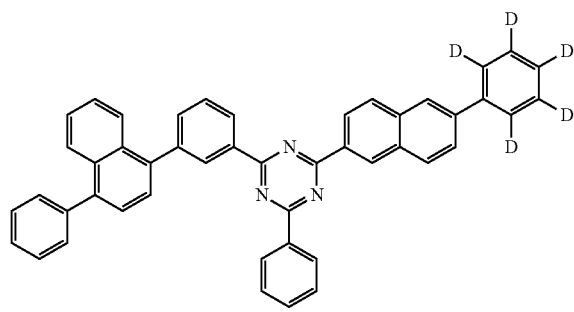

P-99
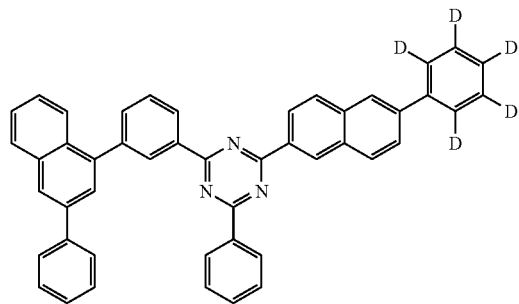
P-100
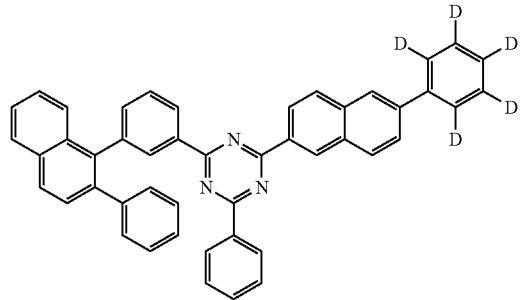
P-101
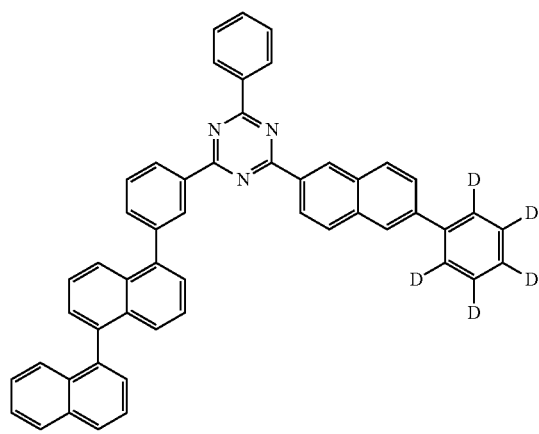
P-102
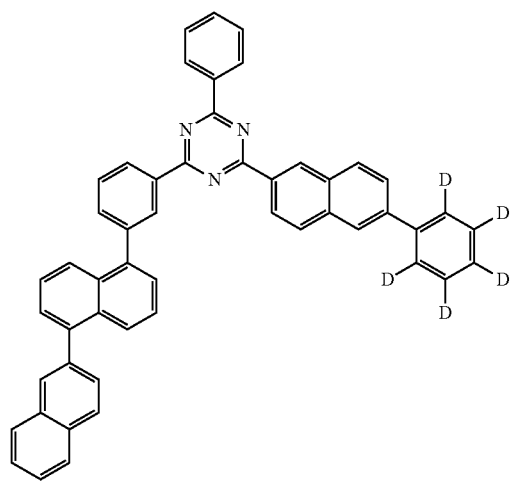
P-103
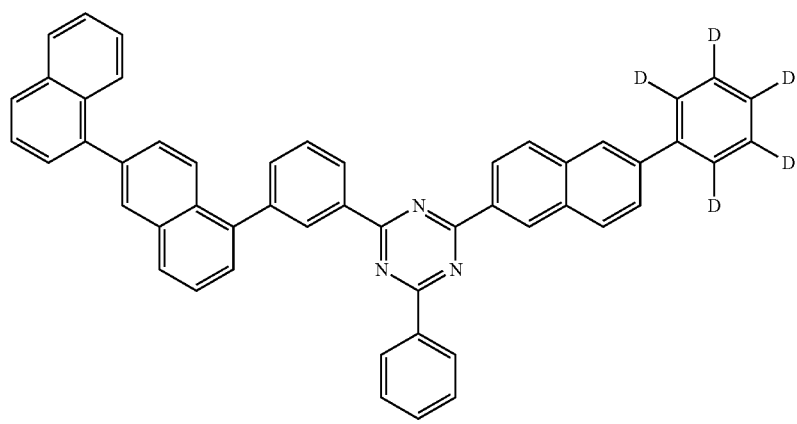

P-104

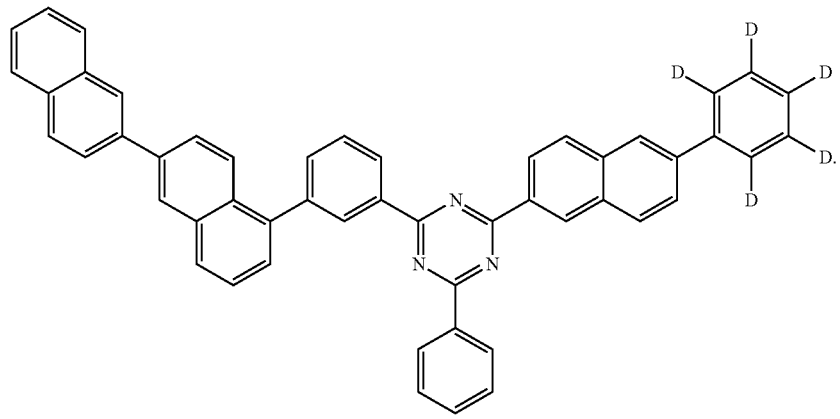

8. An organic electronic element comprising a first electrode, a second electrode, and an organic material layer formed between the first electrode and the second electrode, wherein the organic material layer includes an emitting layer, wherein the emitting layer is a phosphorescent emitting layer and comprises a first host compound represented by Formula 1 of claim 1 and a second host compound represented by Formula 2 or Formula 3:

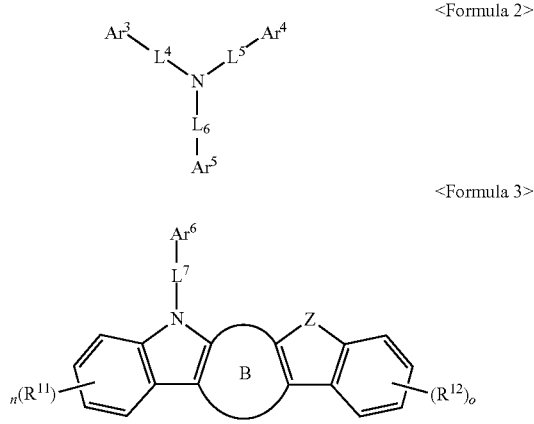

<Formula 2>

<Formula 3> wherein:

$L^4$, $L^5$, $L^6$ and $L^7$ are each independently selected from the group consisting of a single bond; a $C_6$-$C_{60}$ arylene group; fluorenylene group; a fused ring group of a $C_3$-$C_{60}$ aliphatic ring and a $C_6$-$C_{60}$ aromatic ring; and a $C_2$-$C_{60}$ heterocyclic group, $Ar^3$, $Ar^4$ and $Ar^5$ are each independently selected from the group consisting of a $C_6$-$C_{60}$ aryl group; fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring, $Ar^6$ is selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-N($R^b$)($R^c$), wherein L' is selected from the group consisting of a single bond; a $C_6$-$C_{60}$ arylene group; a $C_2$-$C_{60}$ heterocyclic group including at least one heteroatom of O, N, S, Si or P, and wherein $R^b$ and $R^c$ are each independently selected from the group consisting of a $C_6$-$C_{60}$ aryl group; fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P; $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group;

Z is O, S, CR'R" or NRa,

B is a $C_6$-$C_{20}$ aryl group,

R' and R" are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group, and R' and R" may be bonded to each other to form a ring, $R^{11}$ and $R^{12}$ are each independently selected from the group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group, and a plurality of adjacent $R^{11}$ or a plurality of $R^{12}$ may be bonded to each other to form a ring, n and o are each independently an integer of 0 to 4, Ra is a $C_6$-$C_{60}$ aryl group; or a $C_2$-$C_{60}$ heterocyclic group including at least one heteroatom of O, N, S, Si and P, wherein the aryl group, arylene group, heterocyclic group, fluorenyl group, fluorenylene group, fused ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.
9. The organic electronic element of claim 8, wherein the compound represented by Formula 2 is any one of Compounds N-1 to N-96:
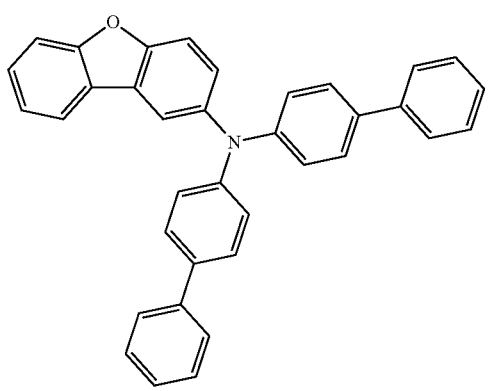
N-1
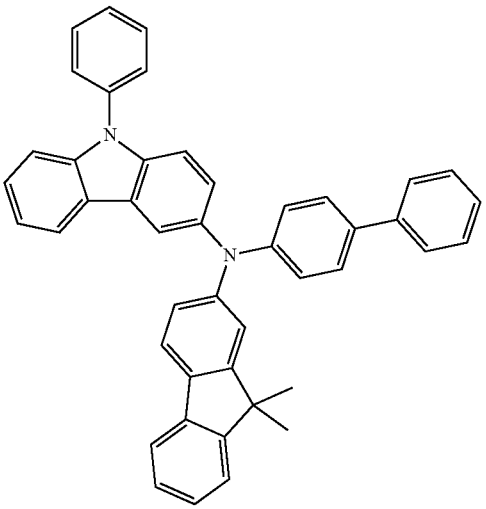
N-4
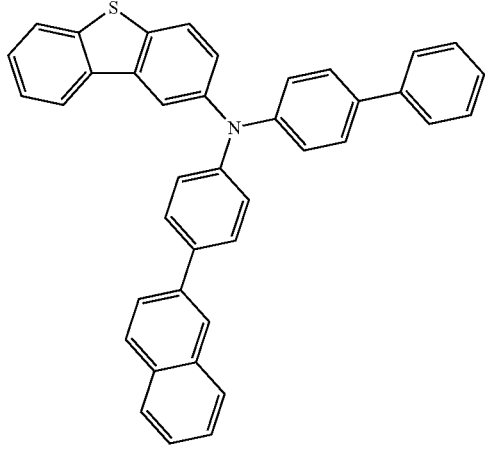
N-2
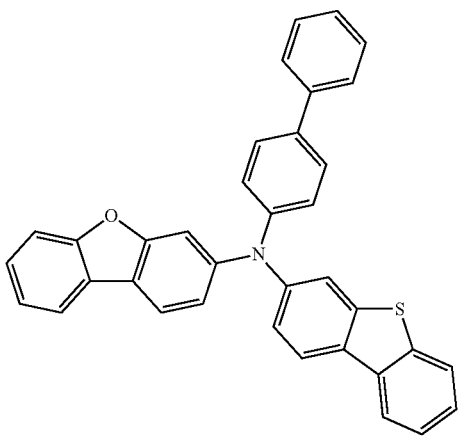
N-5
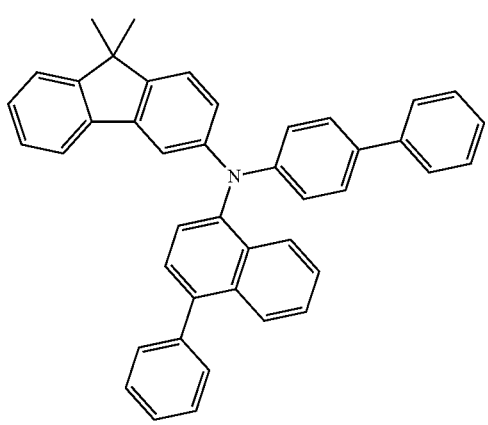
N-3
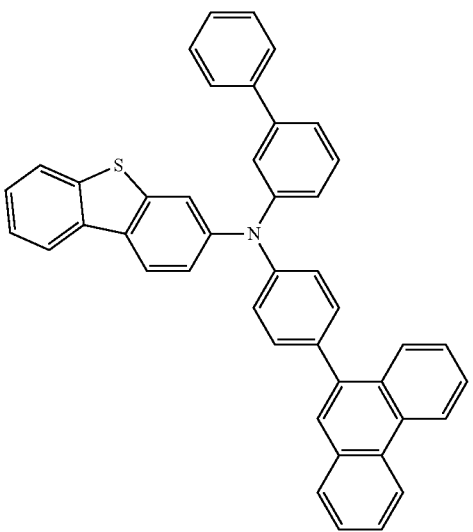
N-6

N-7
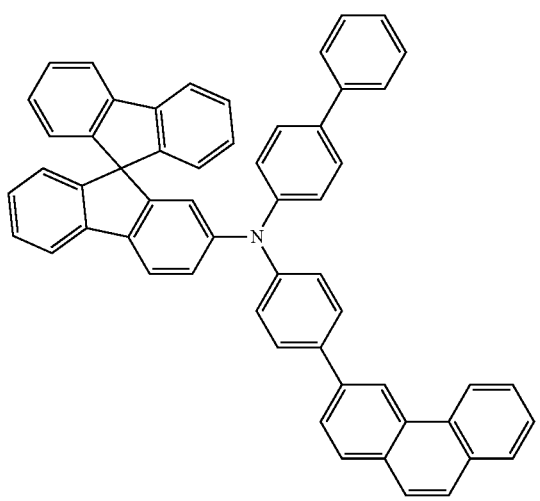
N-8
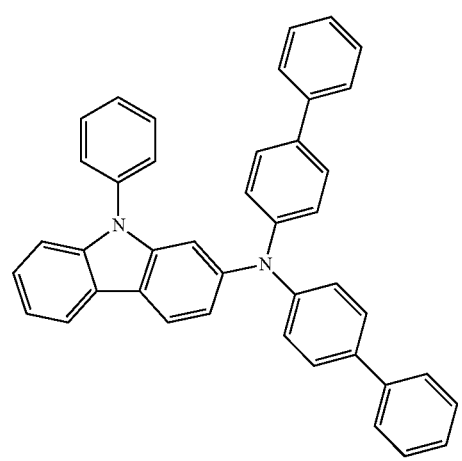
N-9
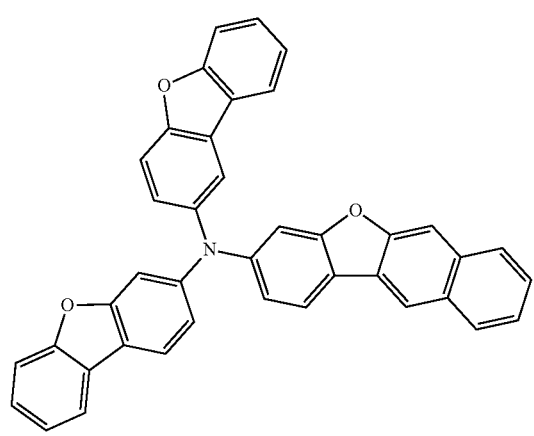
N-10
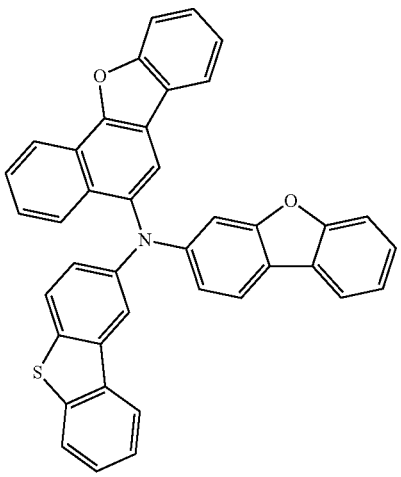
N-11
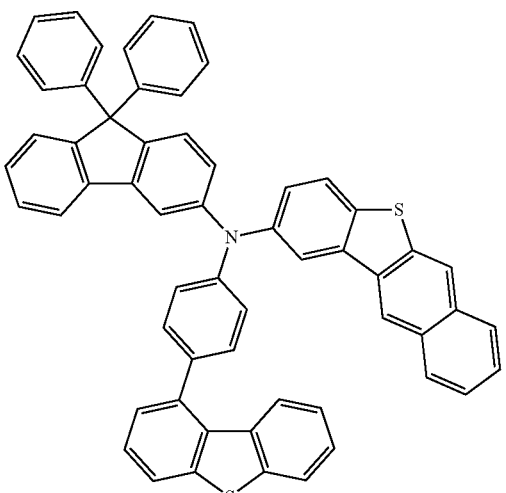
N-12
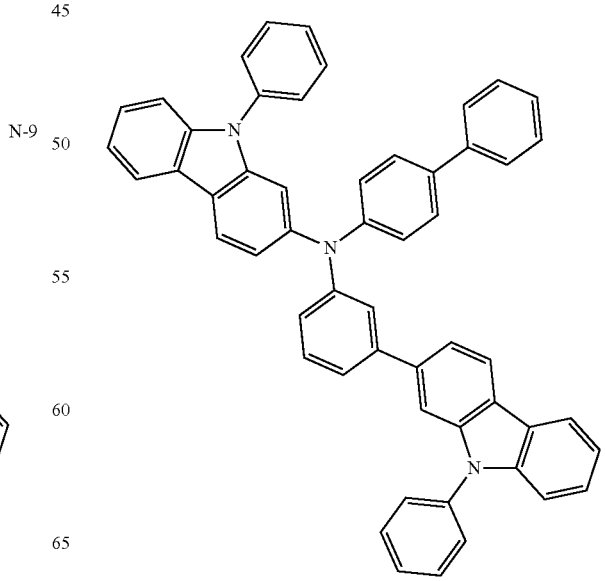

-continued
N-13
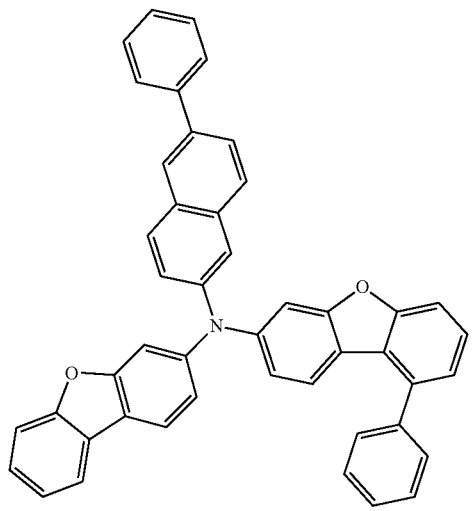
N-16
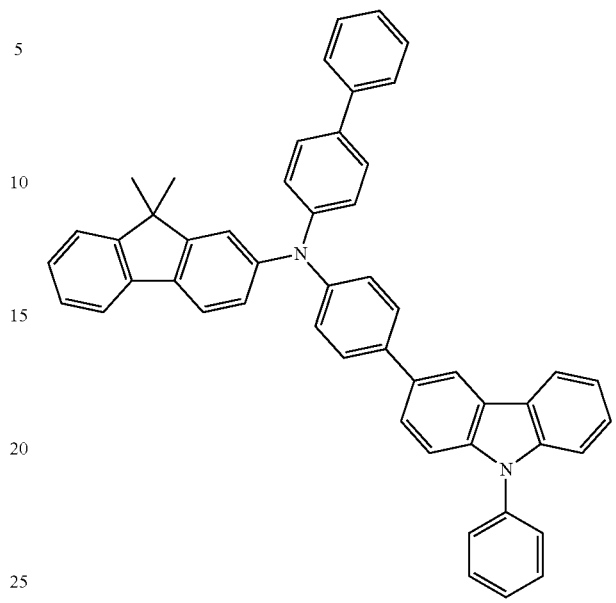
N-14
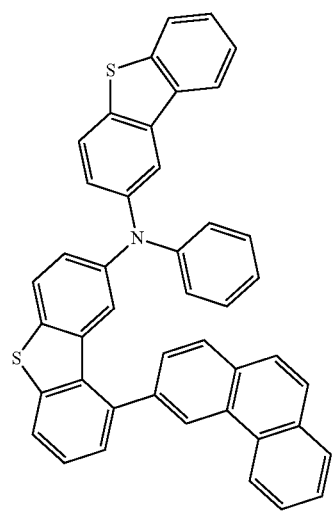
N-17
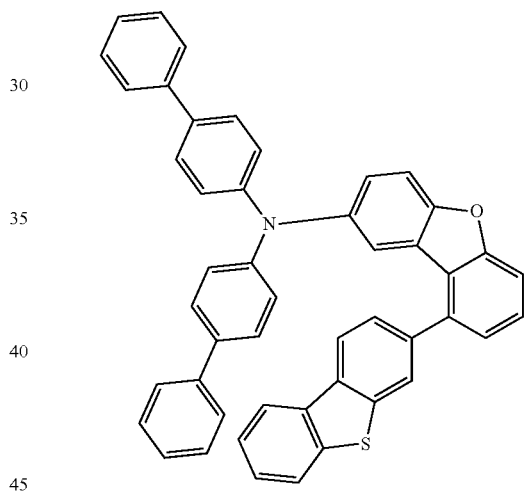
N-15
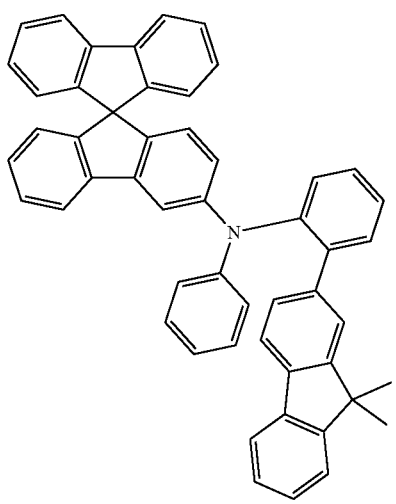
N-18
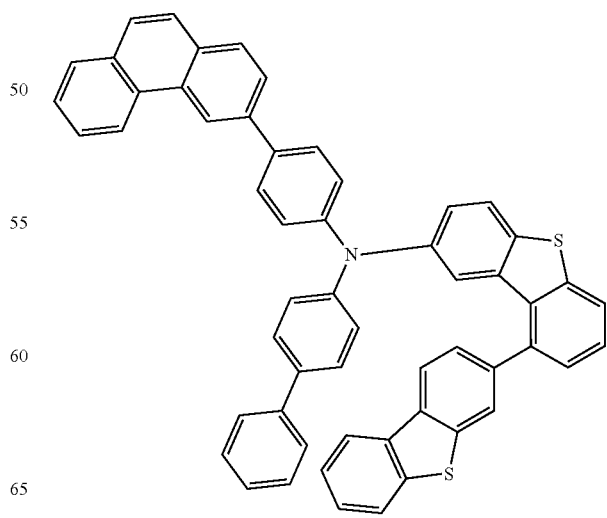

N-19
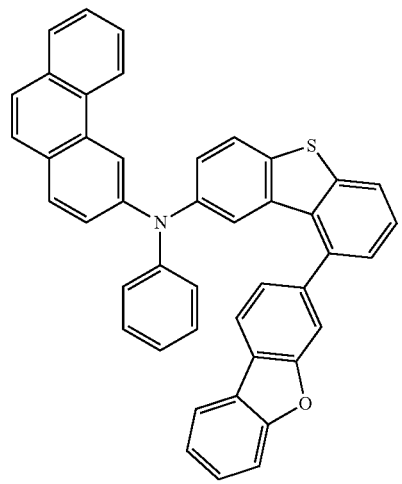
N-20
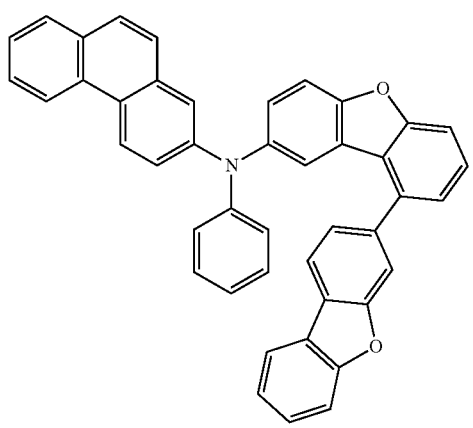
N-21
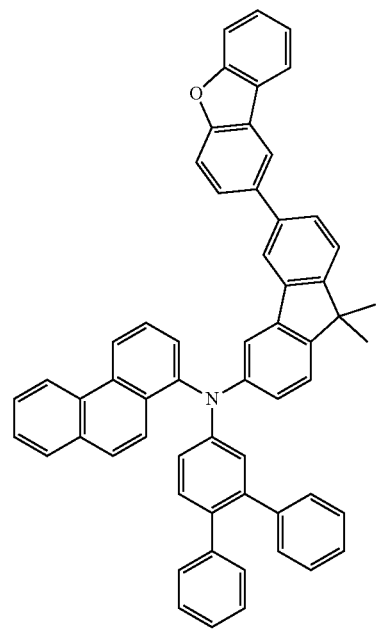
N-22
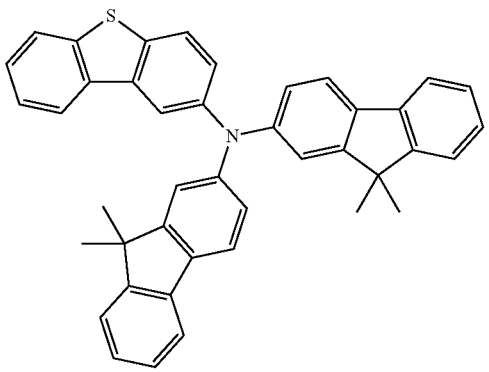
N-23
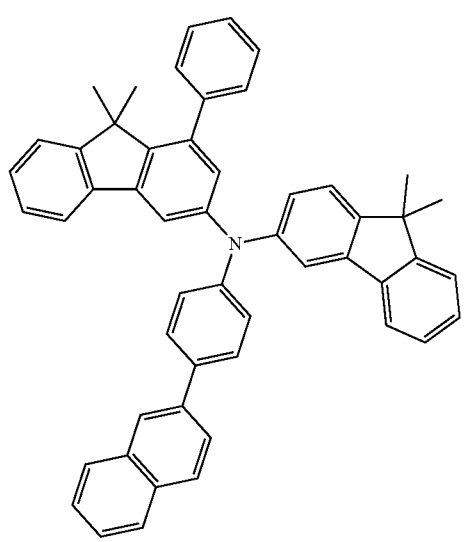
N-24
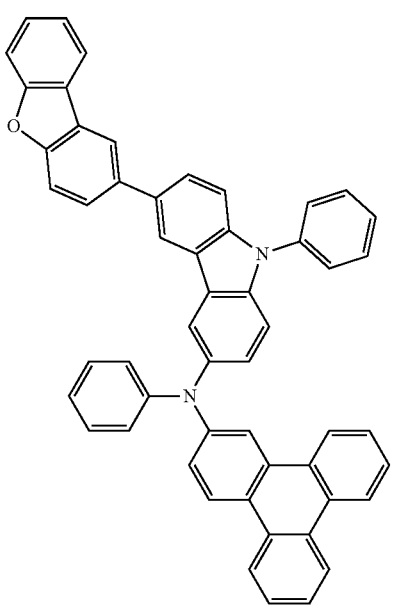

N-25
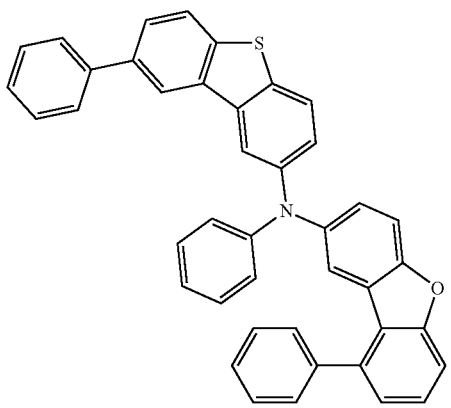
N-26
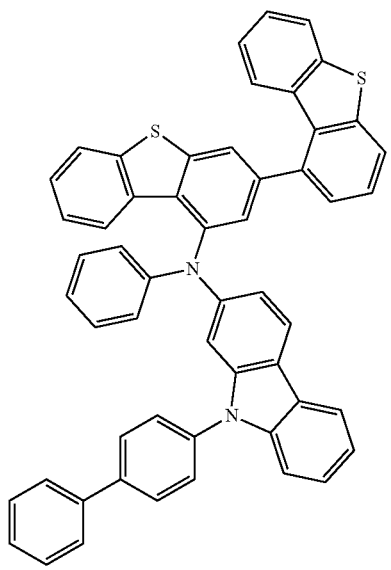
N-27
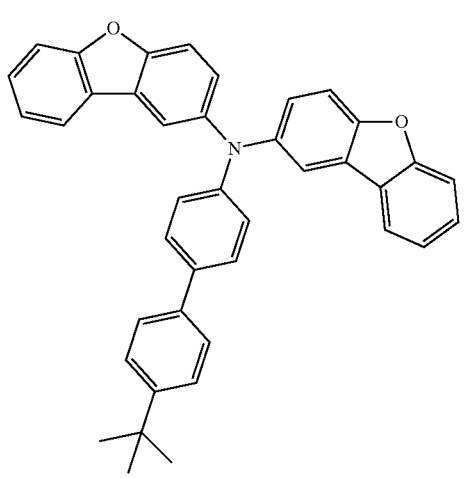
N-28
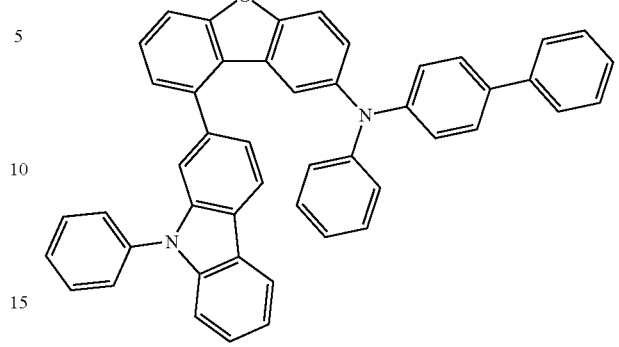
N-29
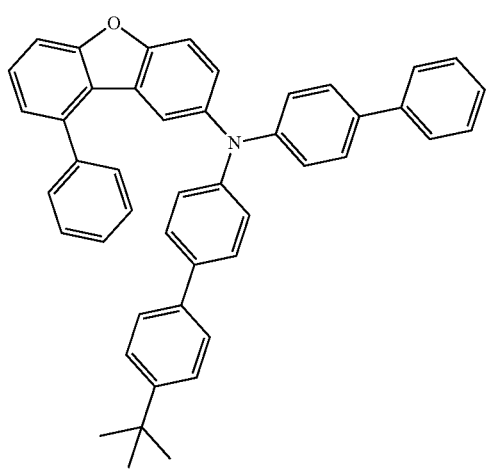
N-30
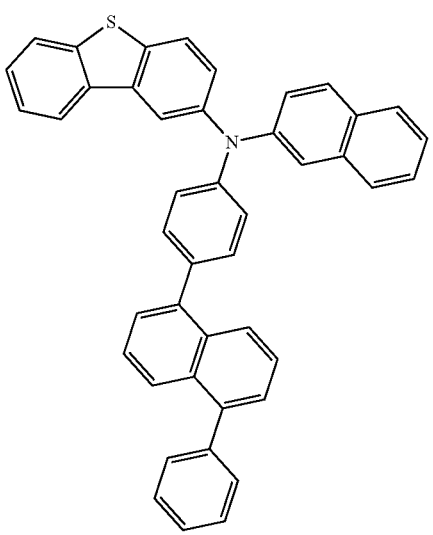

N-31
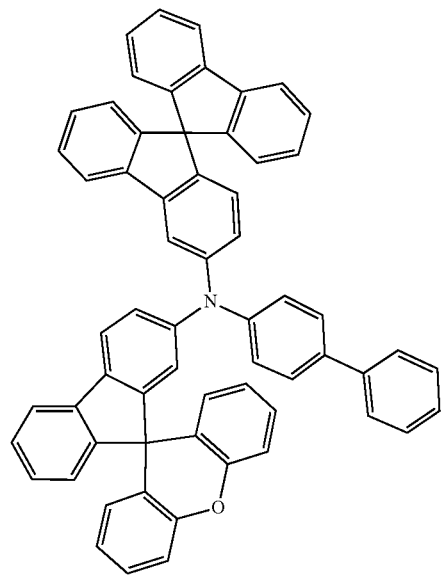
N-34
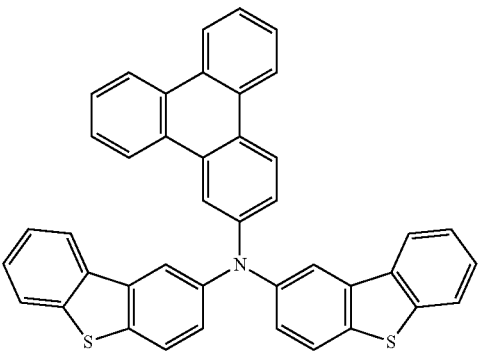
N-35
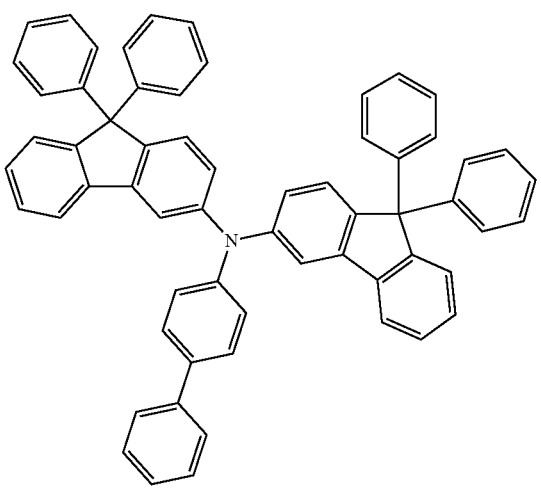
N-32
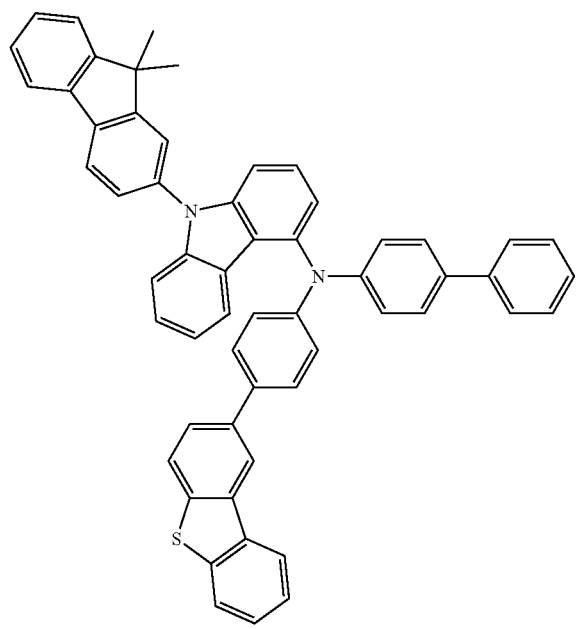
N-36
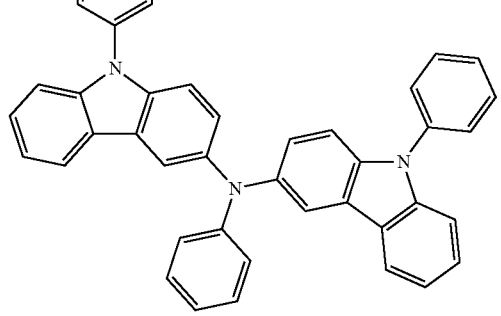
N-33
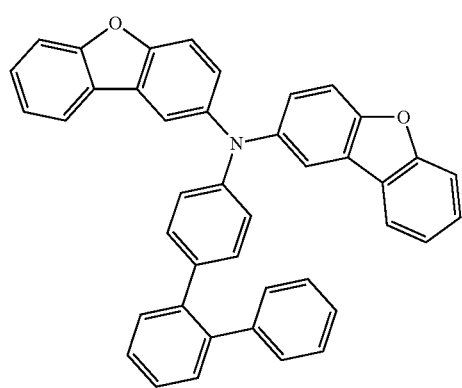
N-37
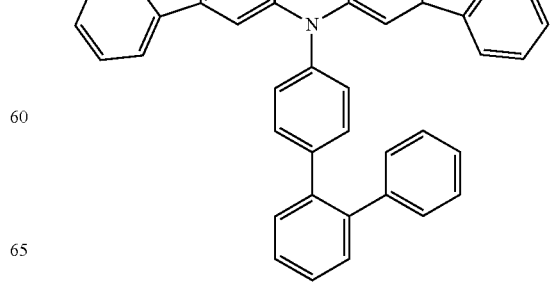

-continued
N-38
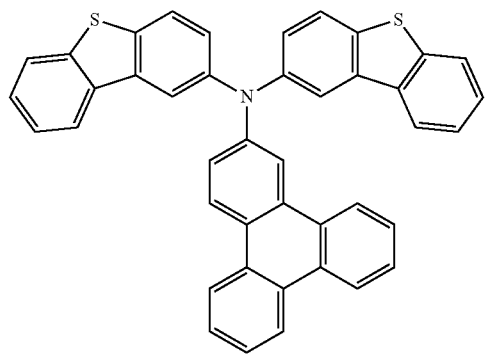
N-39
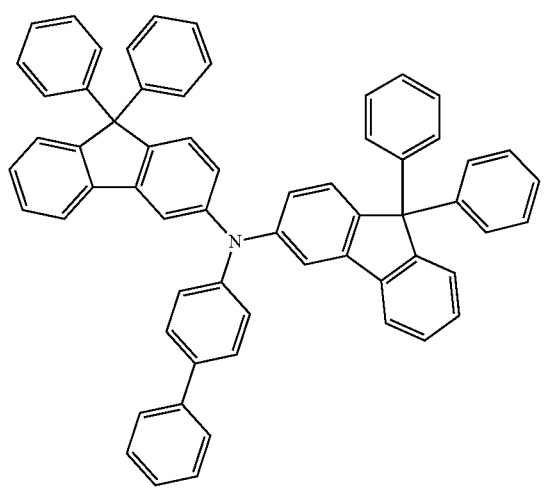
N-40
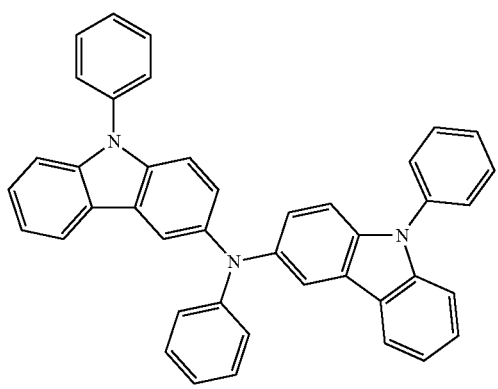
N-41
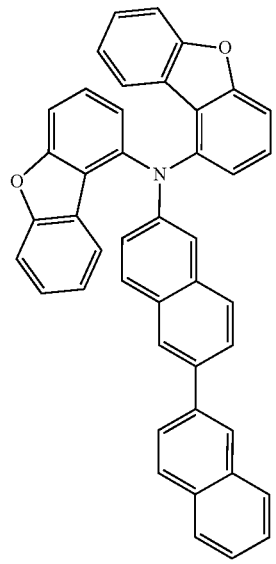
N-42
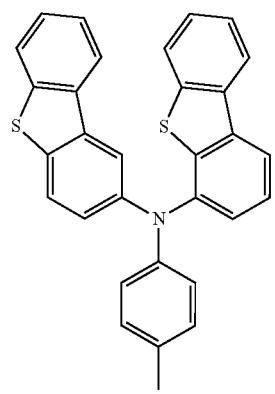
N-43
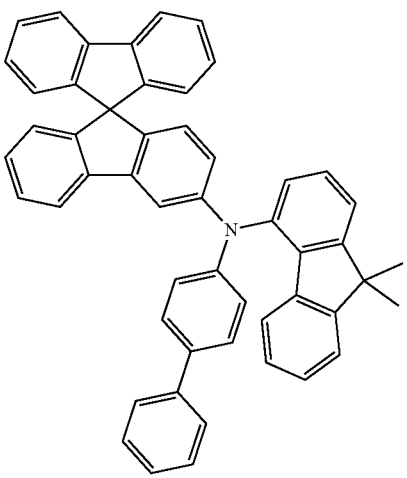

N-44
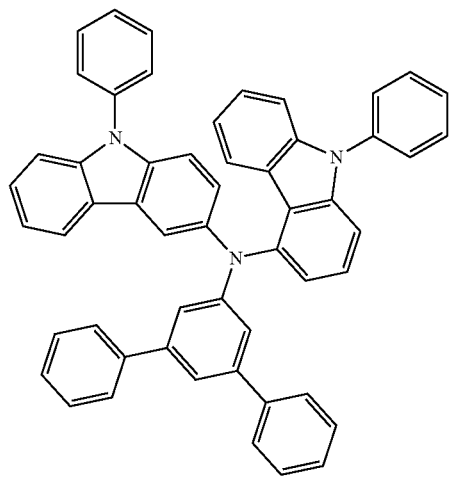
N-45
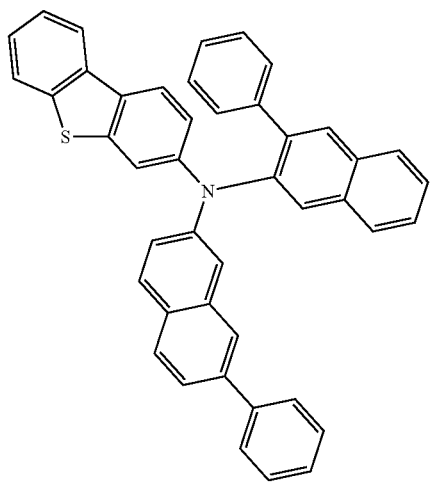
N-46
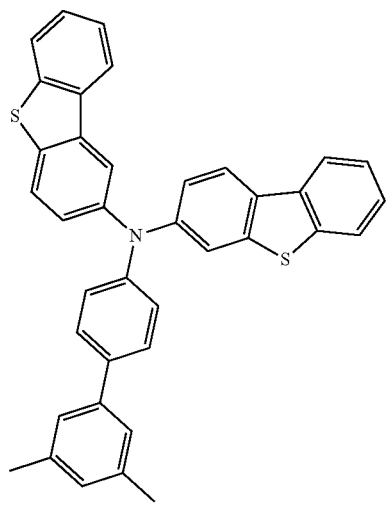
N-47
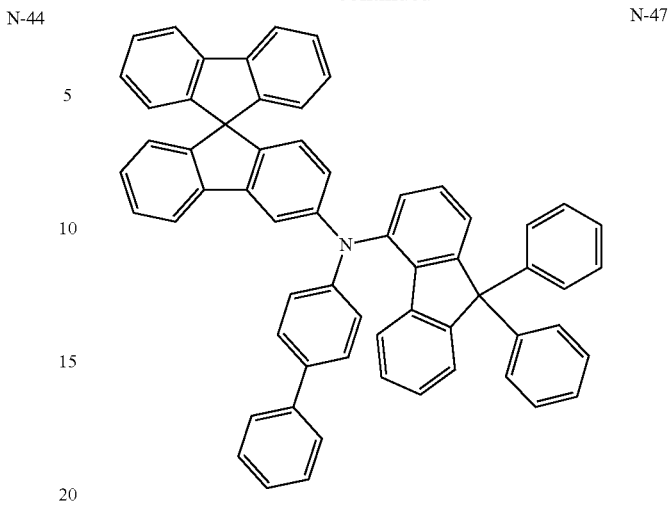
N-48
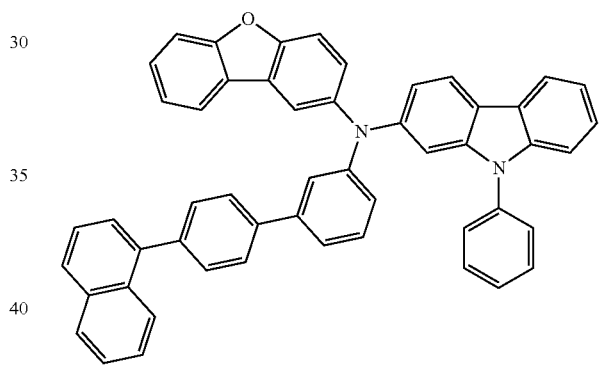
N-49
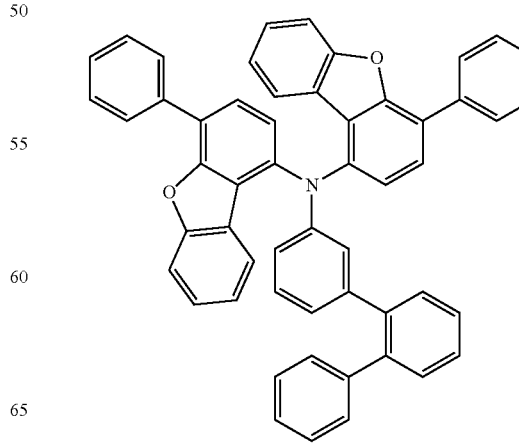

N-50
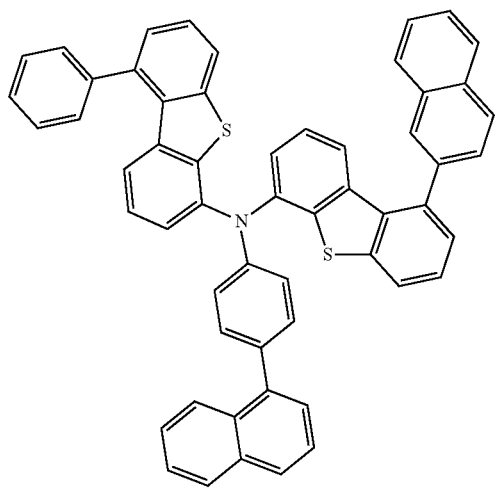
N-51
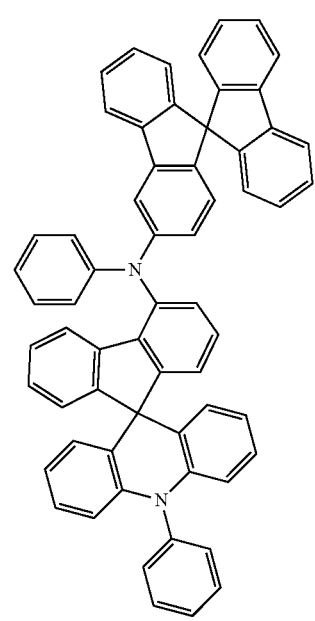
N-52
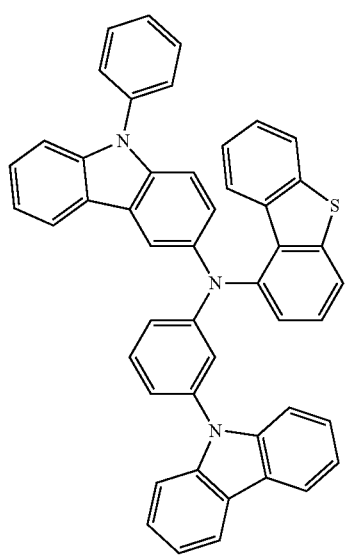
N-53
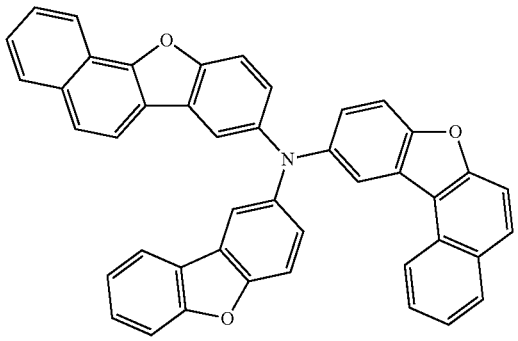
N-54
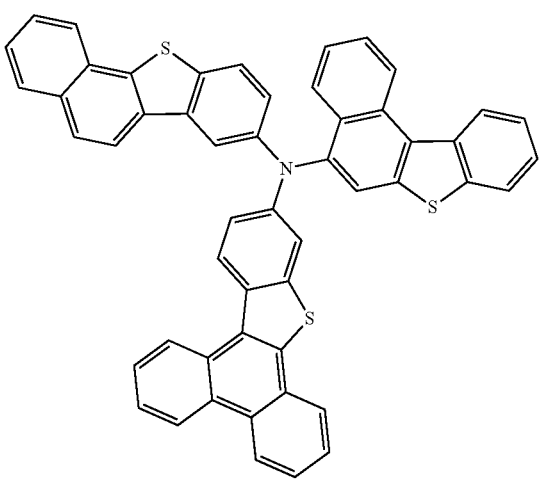
N-55
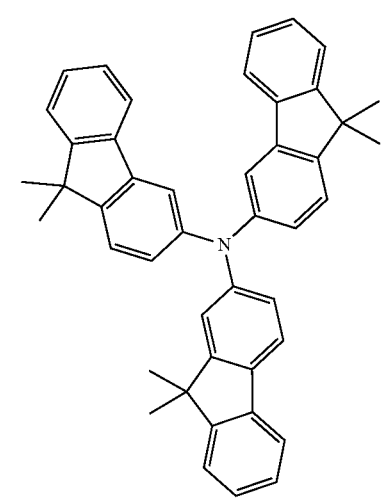

-continued
N-56
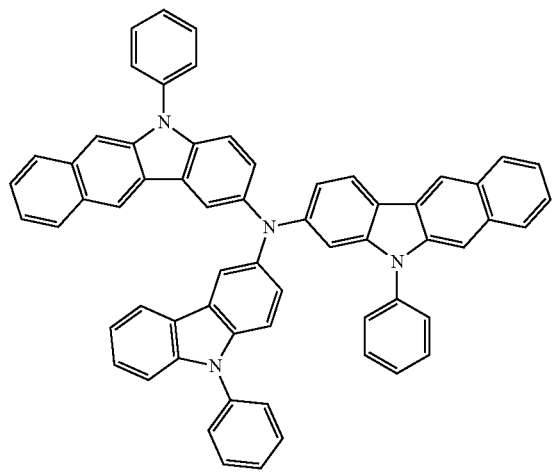
N-57
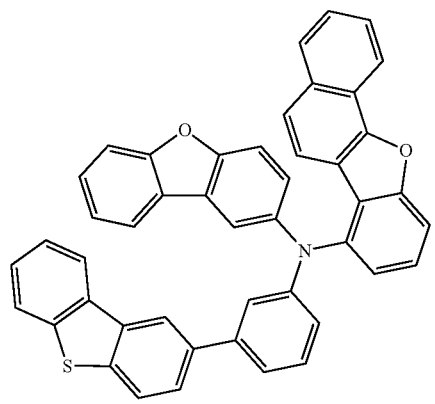
N-58
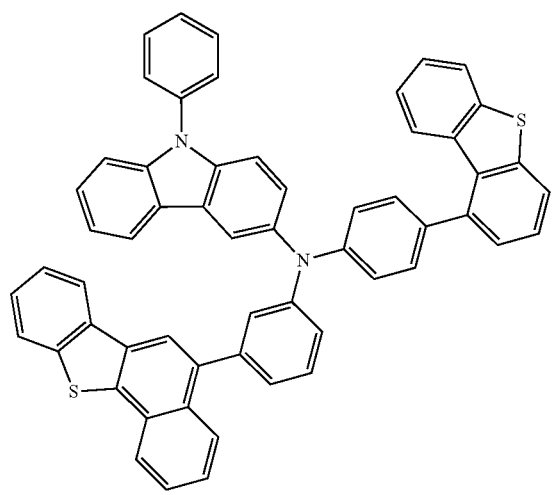
-continued
N-59
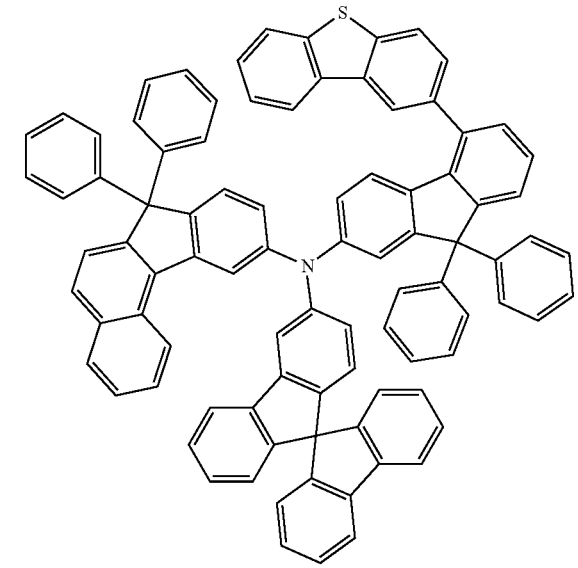
N-60
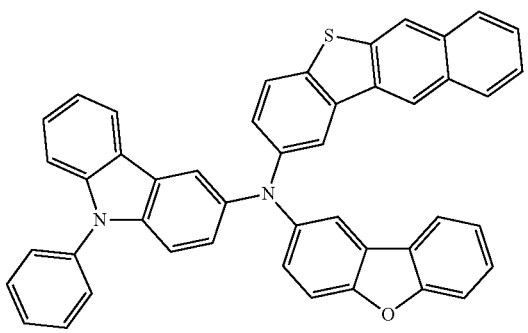
N-61
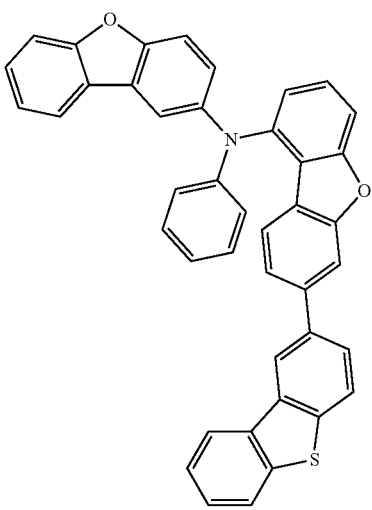

N-62
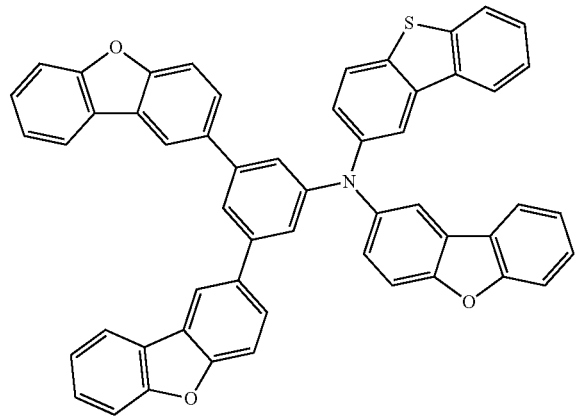
N-63
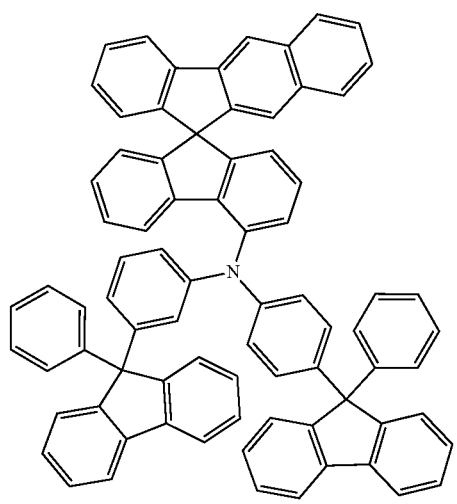
N-64
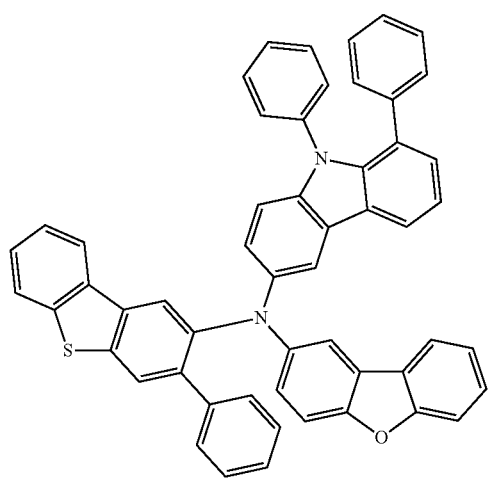
N-65
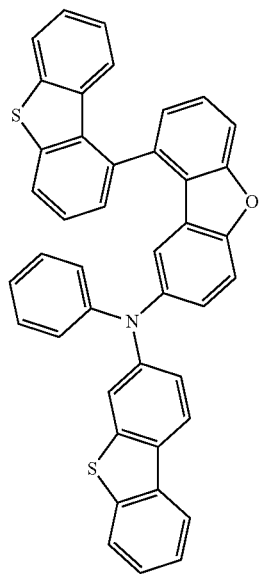
N-66
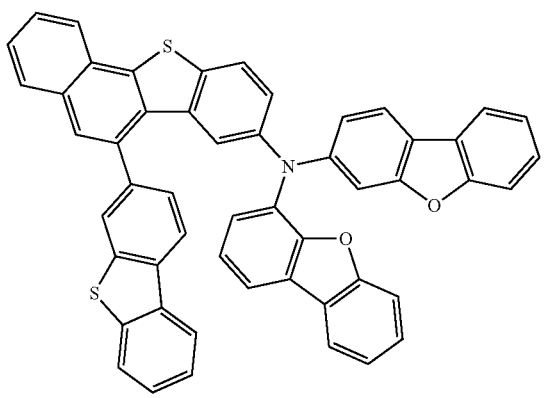
N-67
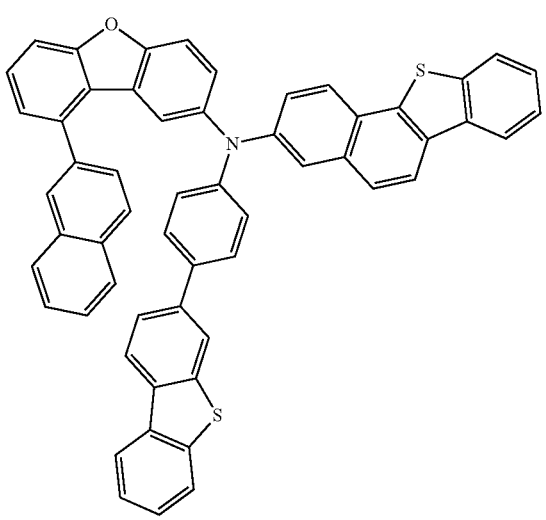

N-68
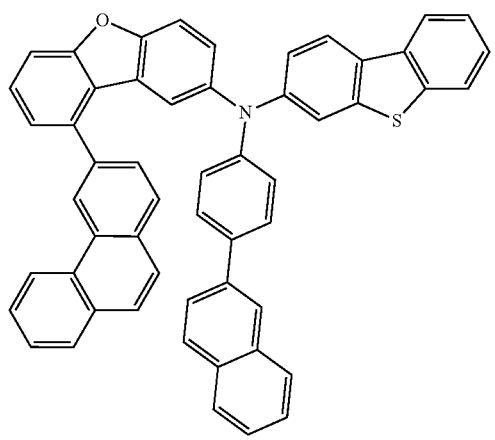
N-69
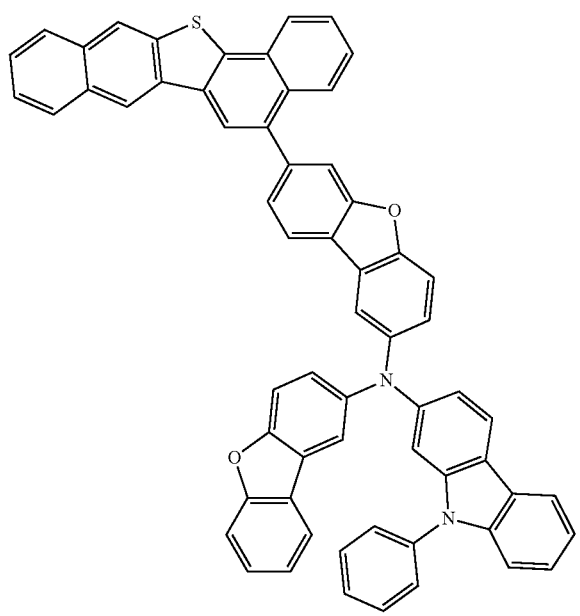
N-70
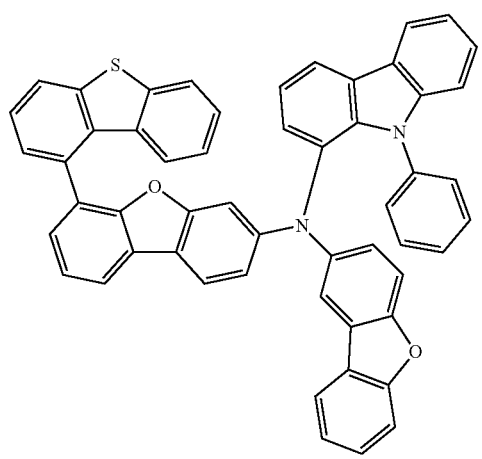
N-71
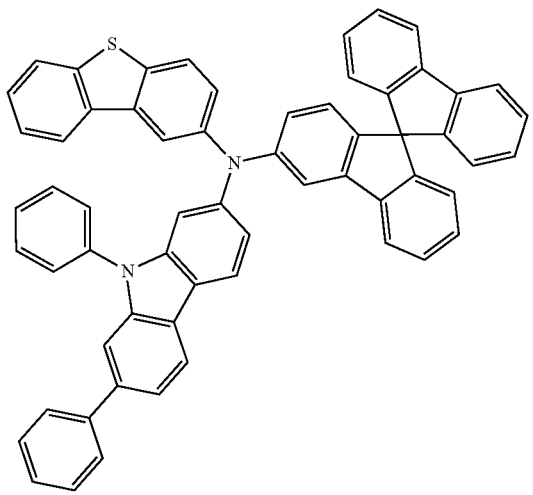
N-72
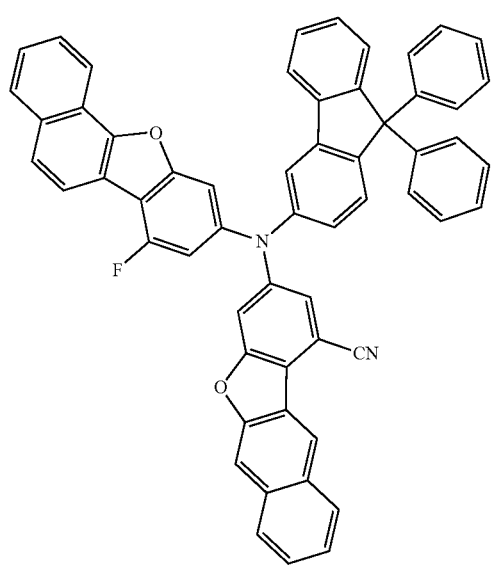
N-73
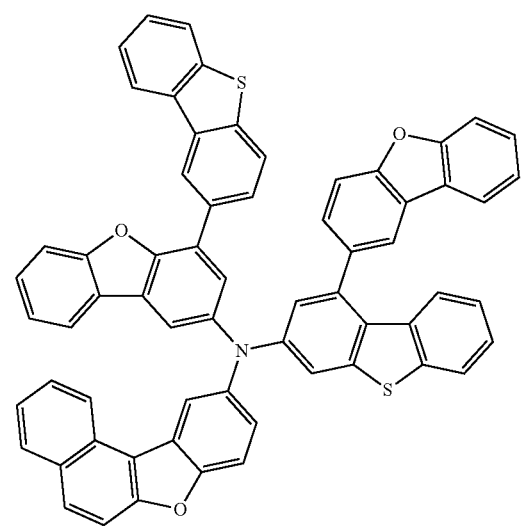

N-74
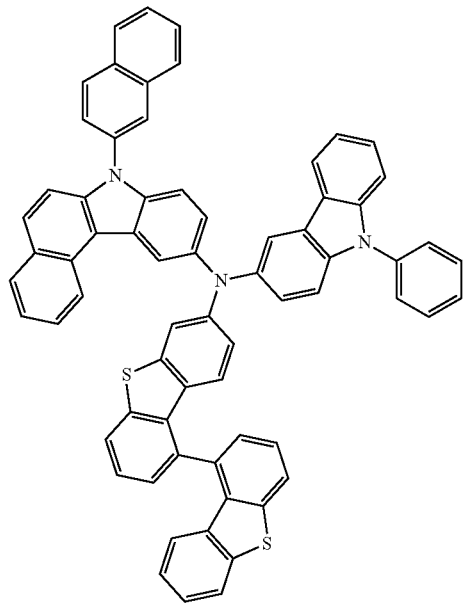
N-76
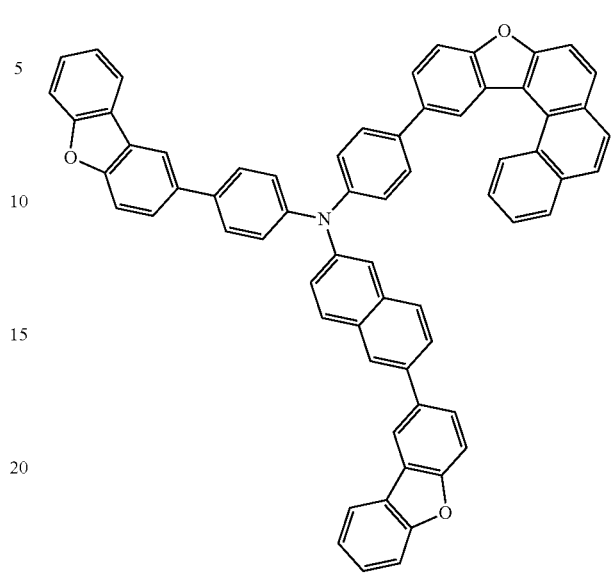
N-75
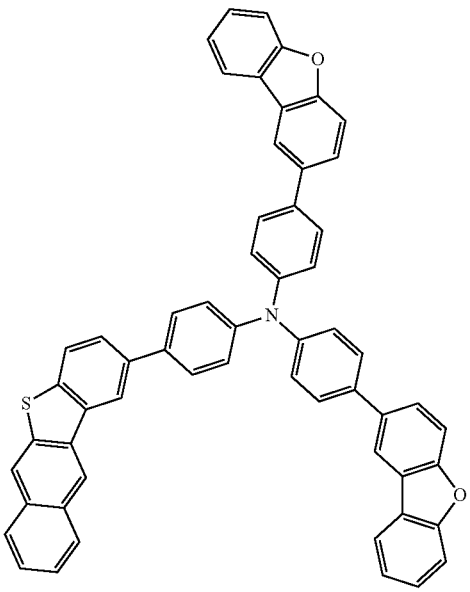
N-77
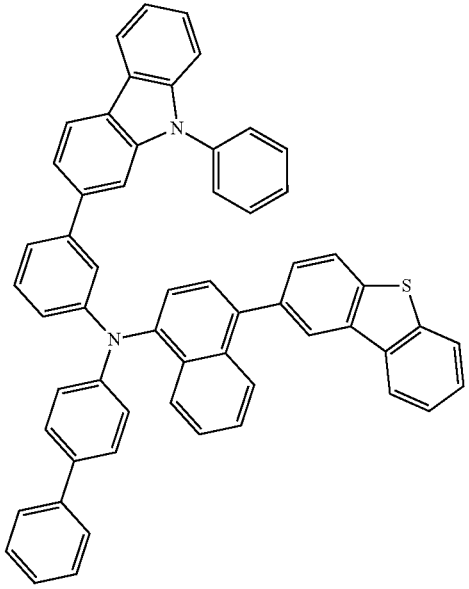

N-78
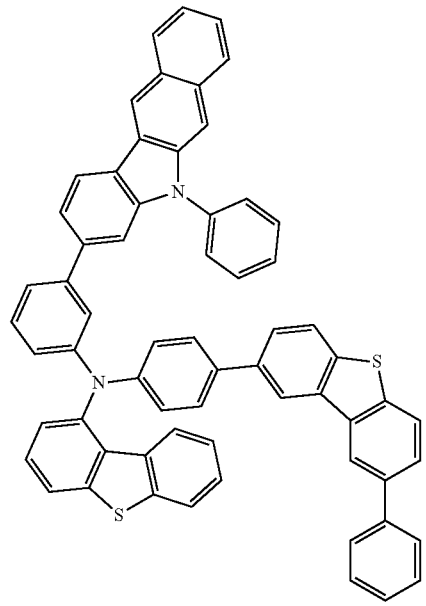
N-79
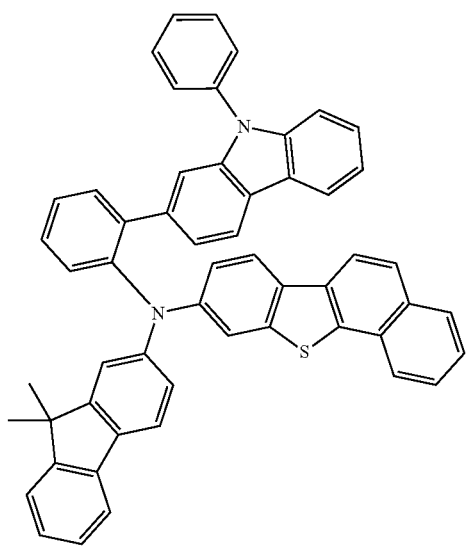
N-80
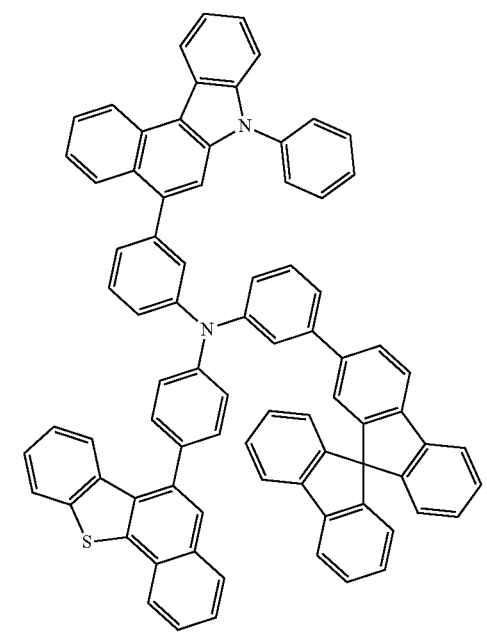
N-81
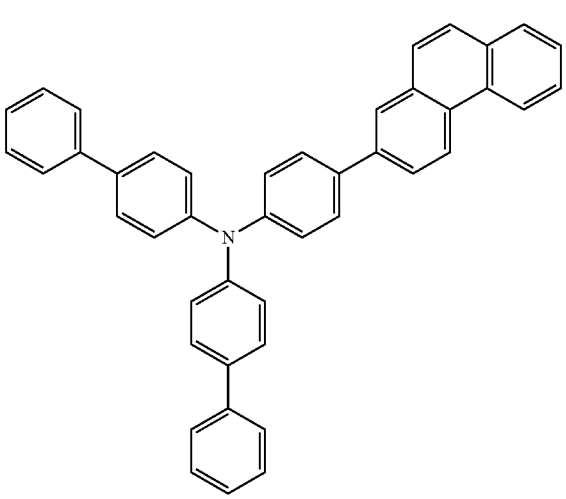

N-82
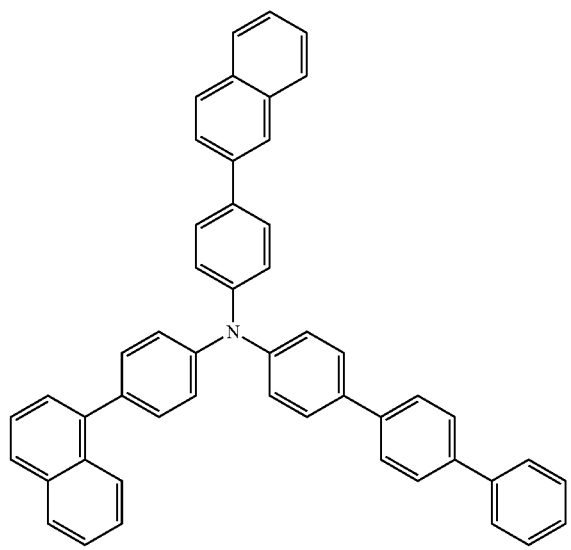
N-84
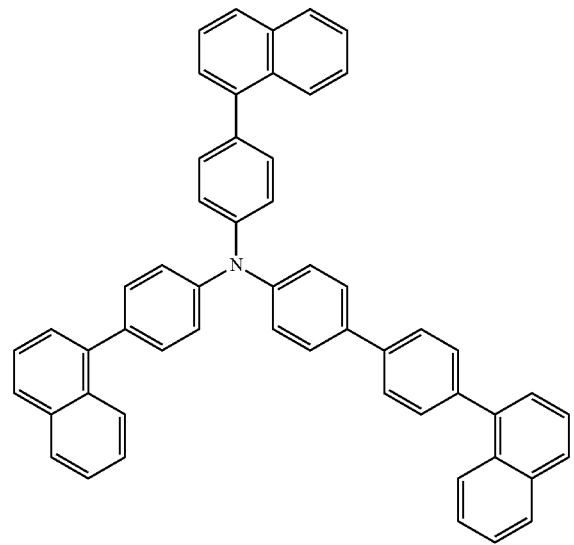
N-83
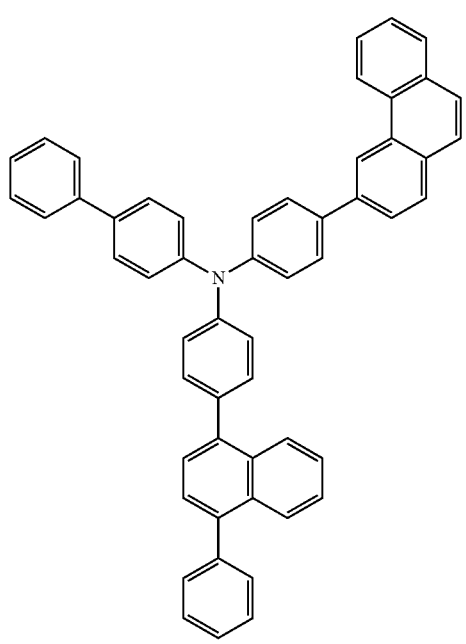
N-85
N-86
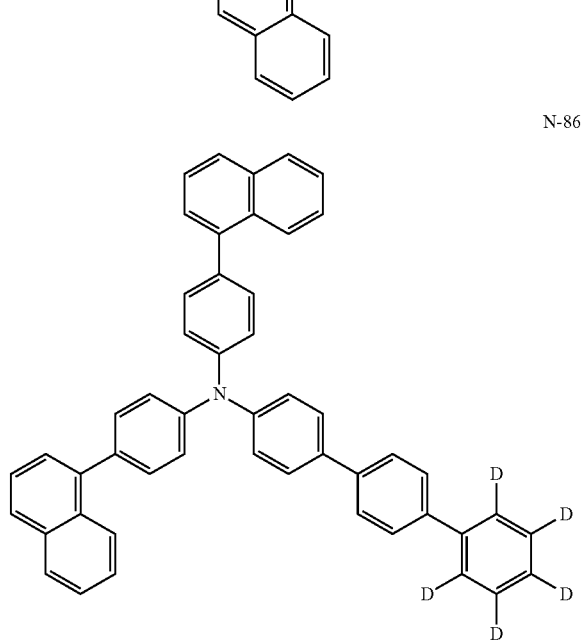

N-87
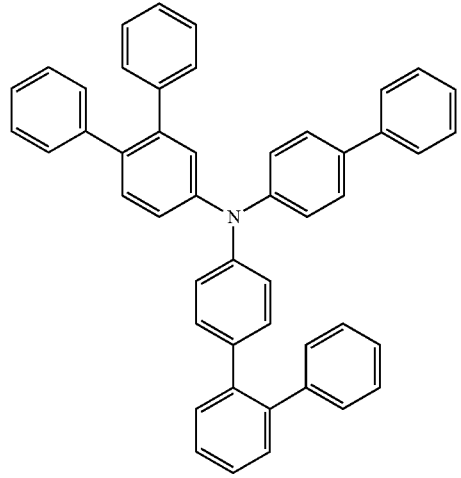
N-88
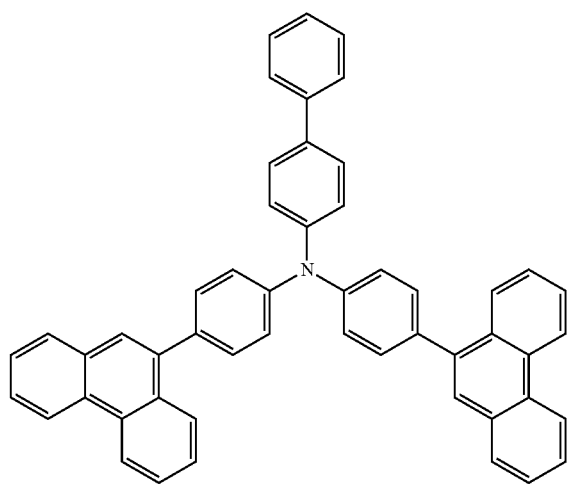
N-89
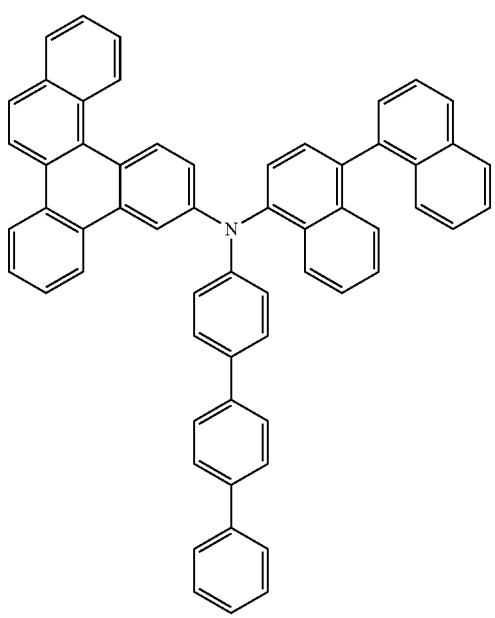
N-90
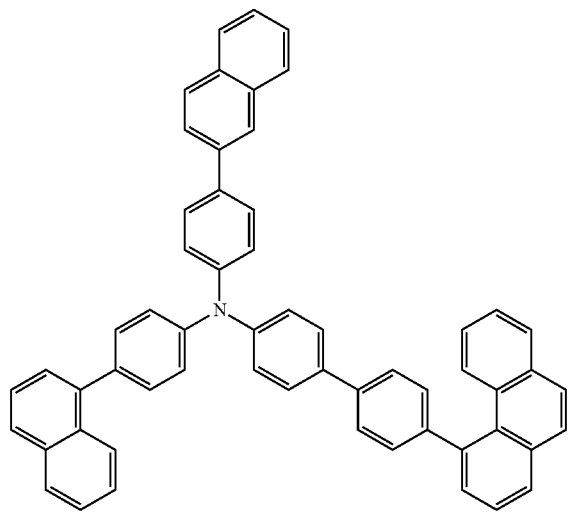
N-91
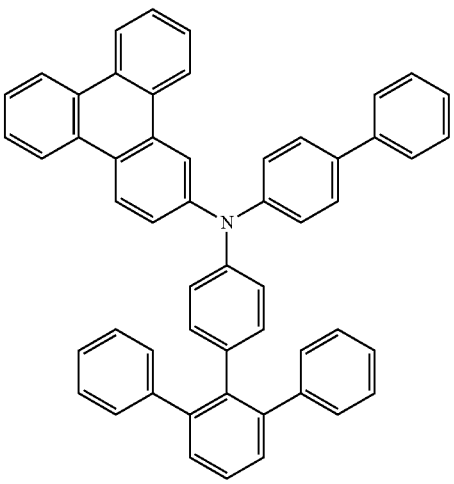
N-92
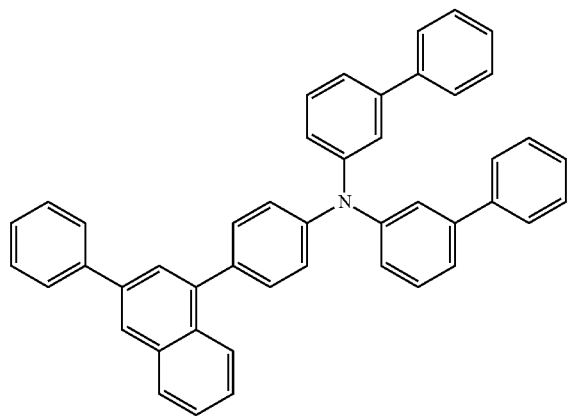

N-93
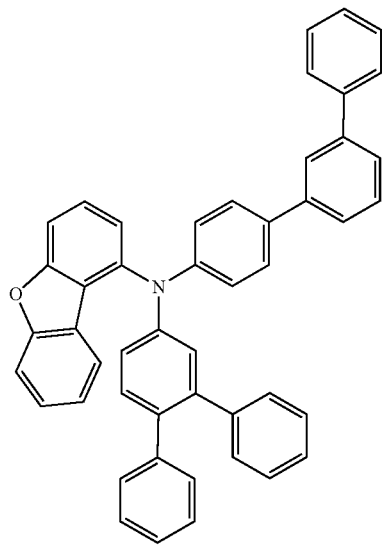
N-96
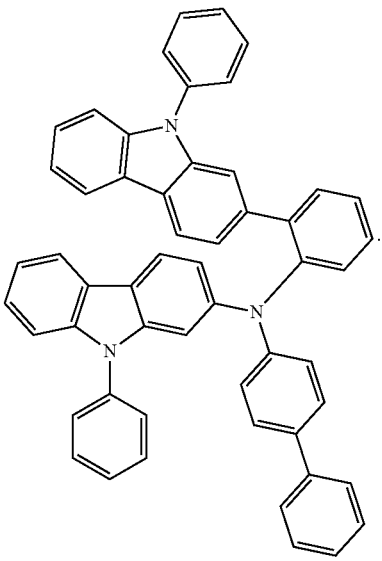
N-94
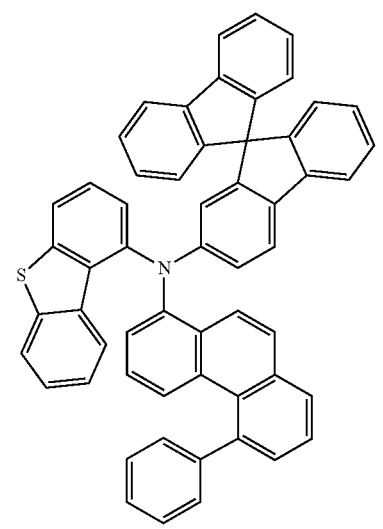
10. The organic electronic element of claim 8, wherein the compound represented by Formula 3 is any one of Compounds S-1 to S-108:
S-1
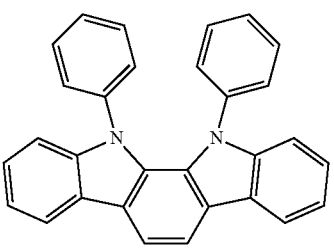
N-95
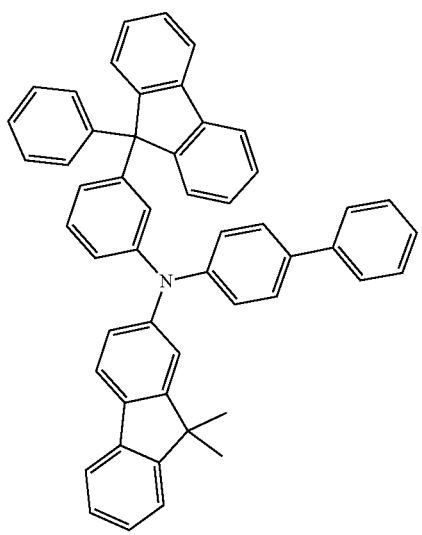
S-2
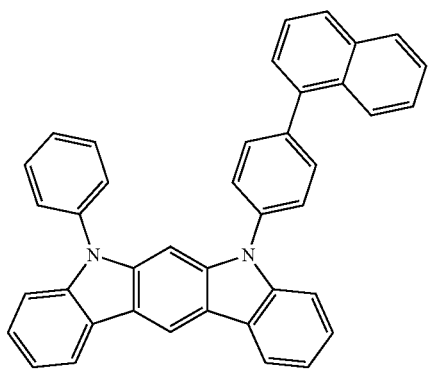

S-3
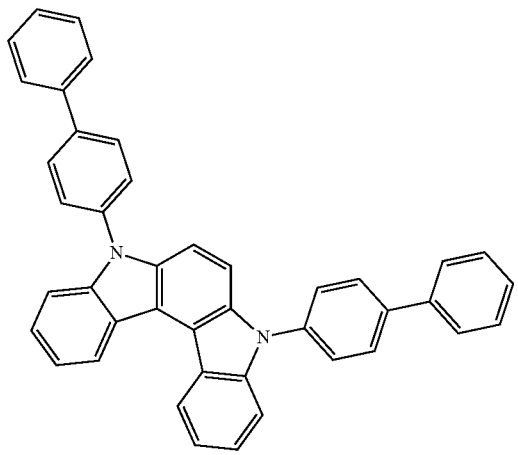
S-4
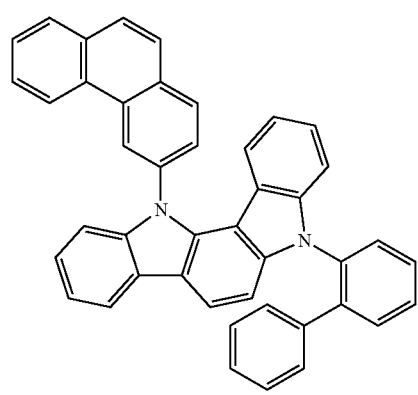
S-5
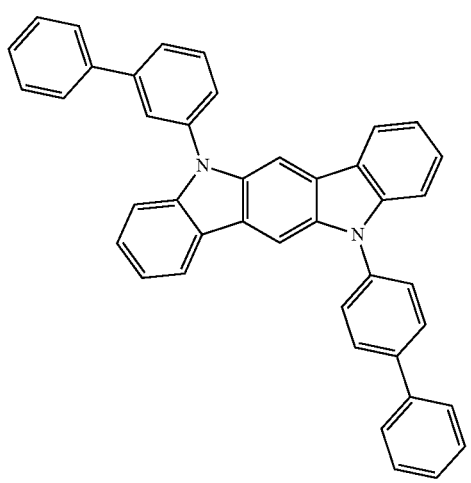
S-6
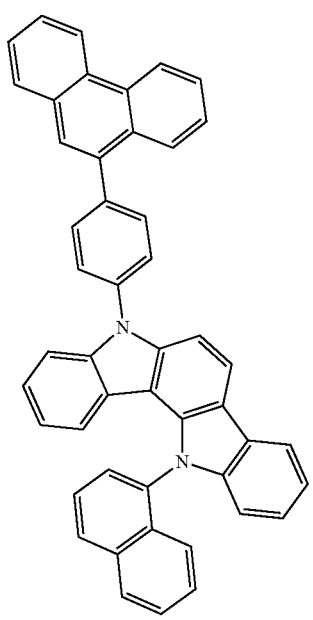
S-7
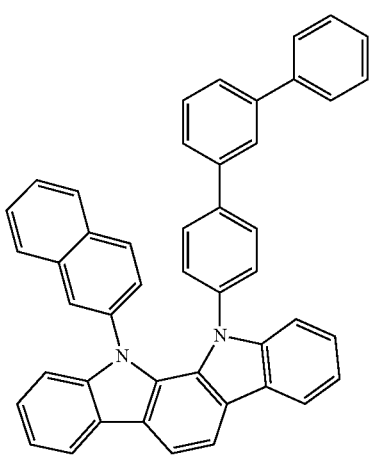
S-8
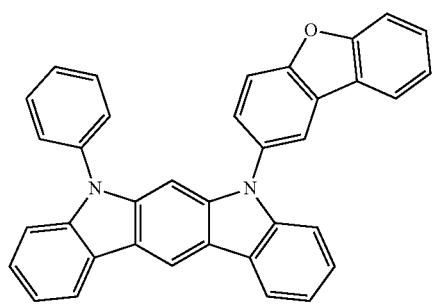

-continued
S-9
S-10
S-11
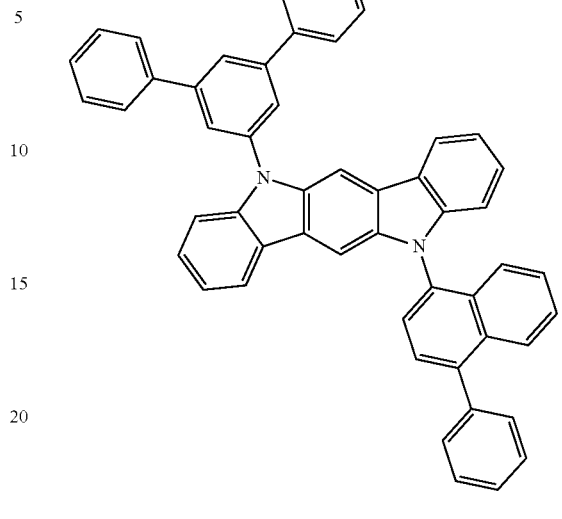
S-12
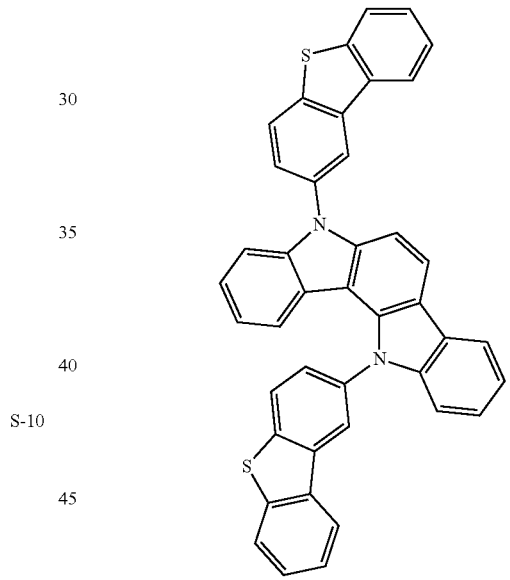
S-13
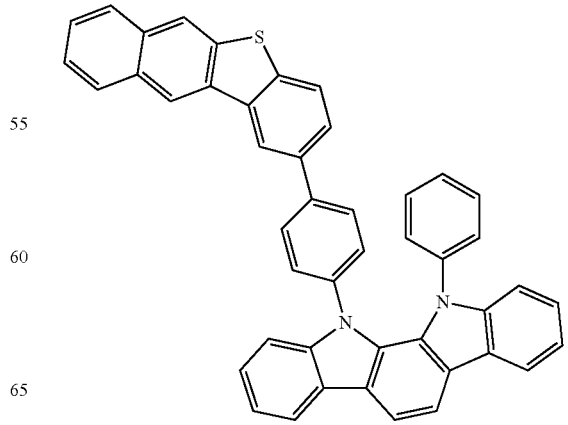

S-14
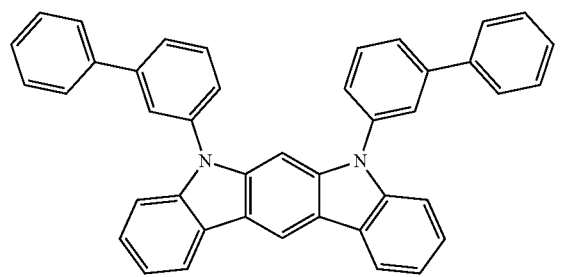
S-15
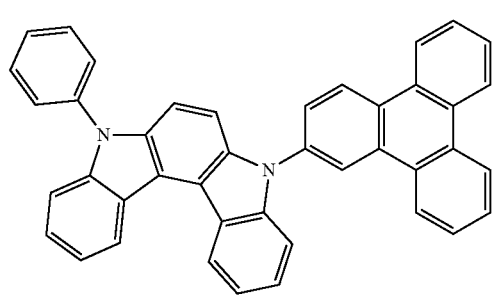
S-16
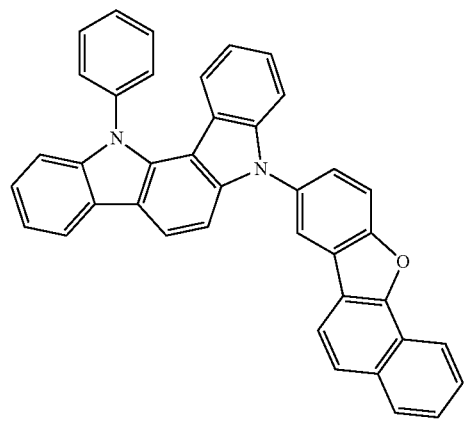
S-17
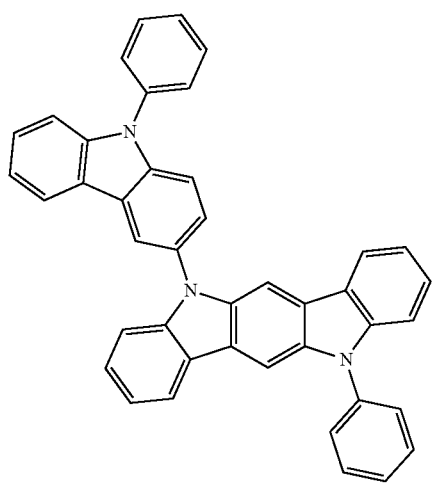
S-18
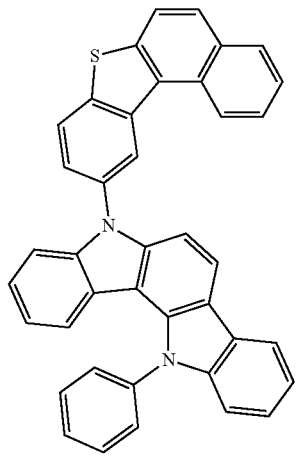
S-19
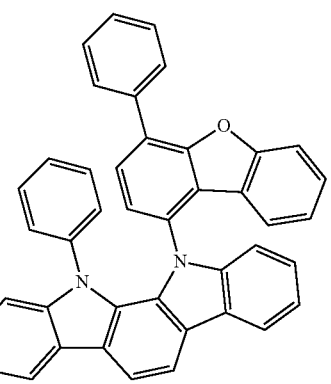
S-20
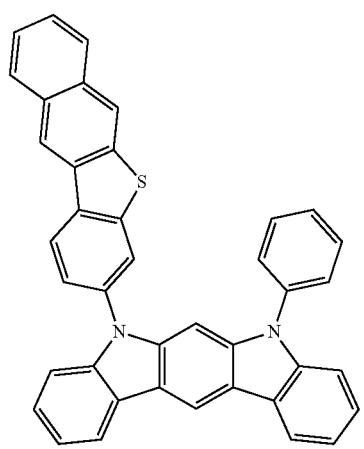

-continued
S-21
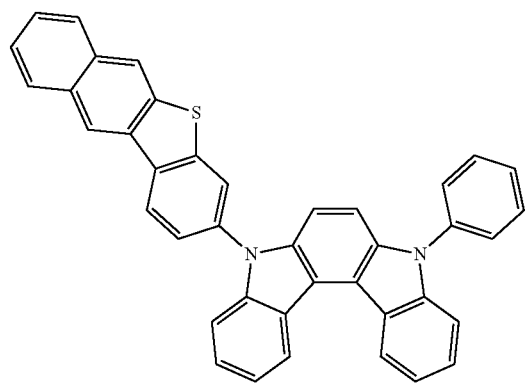
S-22
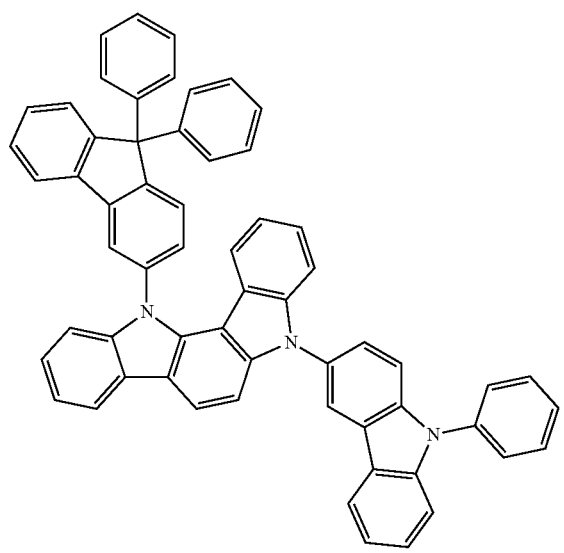
S-23
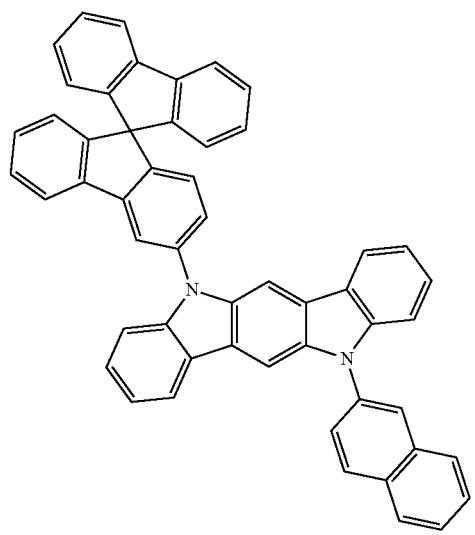
S-24
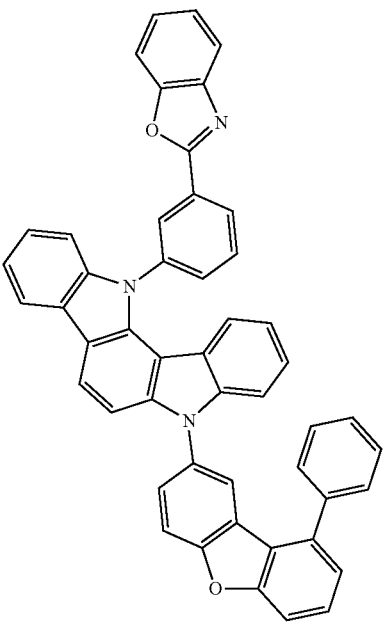
S-25
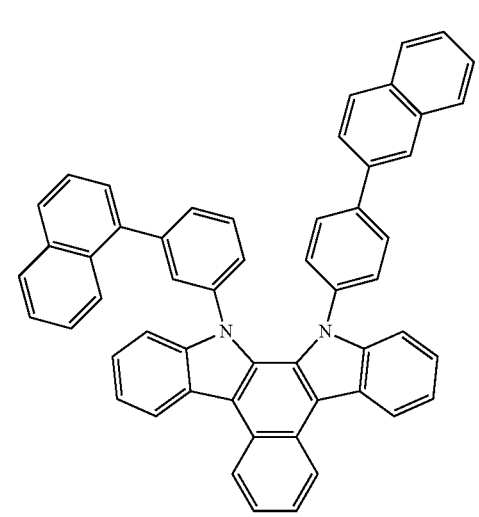
S-26
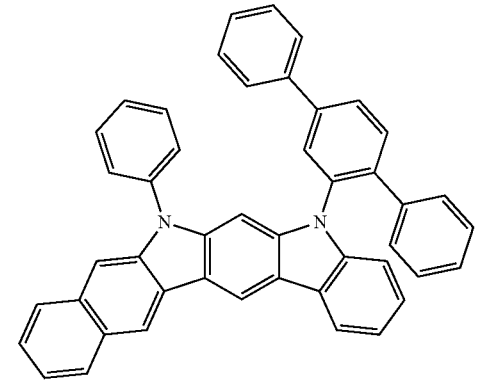

S-27
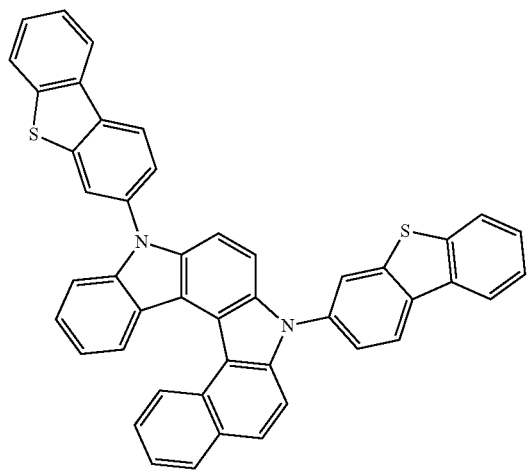
S-28
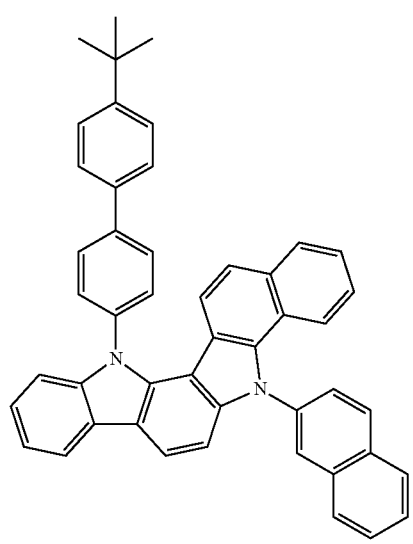
S-29
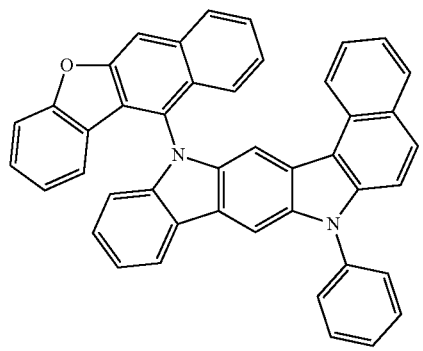
S-30
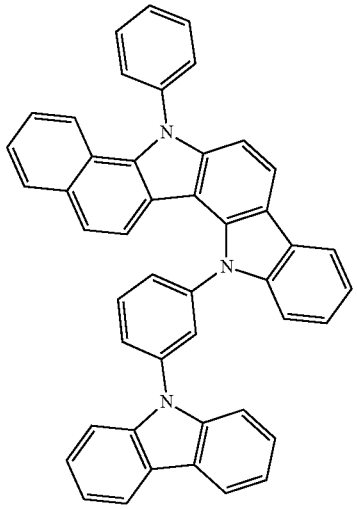
S-31
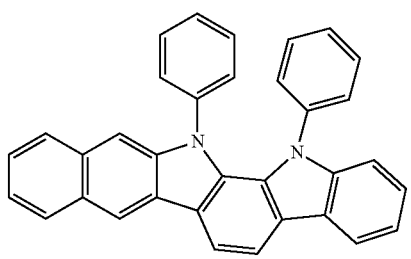
S-32
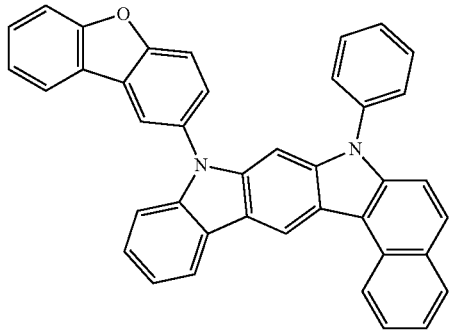
S-33
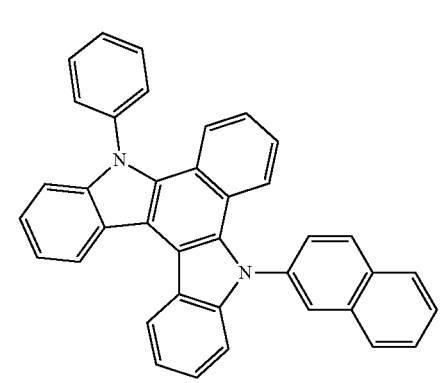

-continued
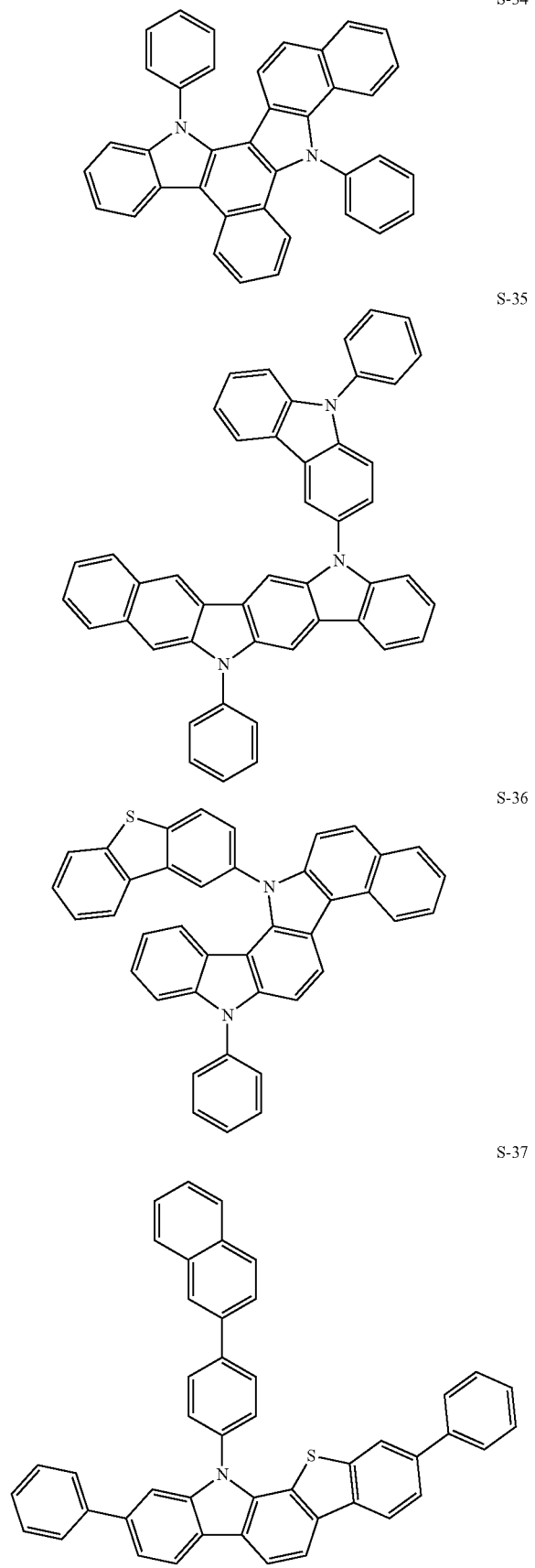
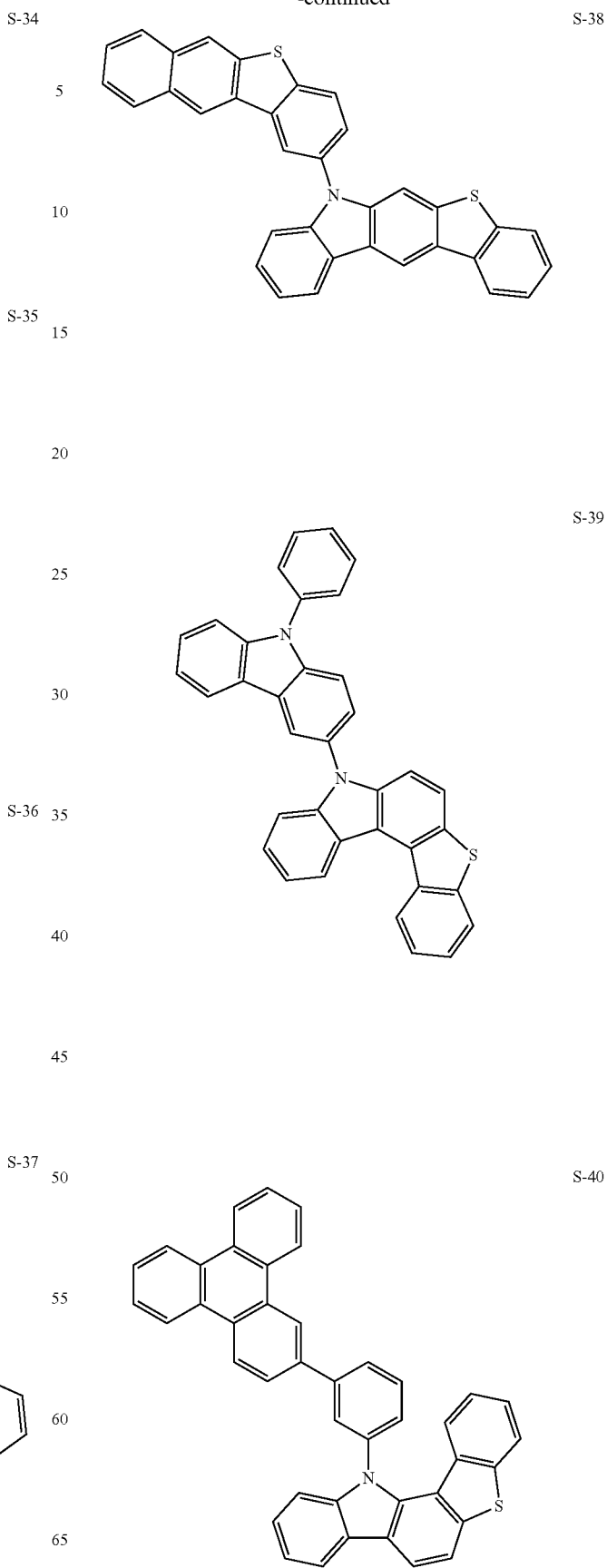

-continued
S-41
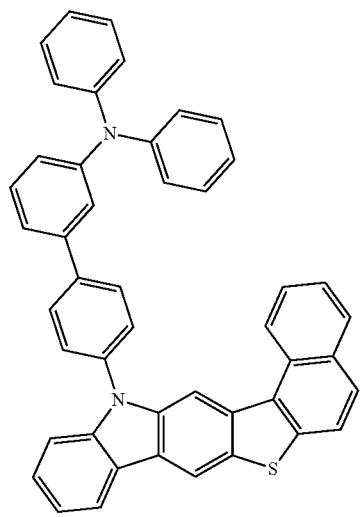
S-42
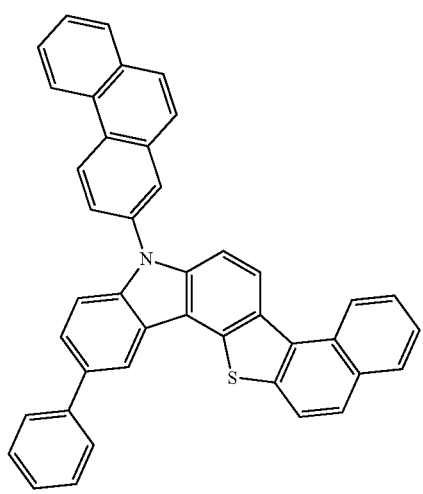
S-43
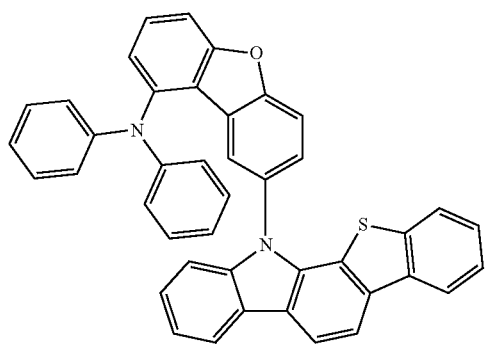
-continued
S-44
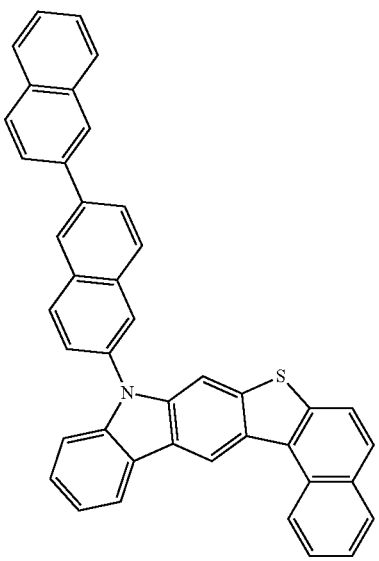
S-45
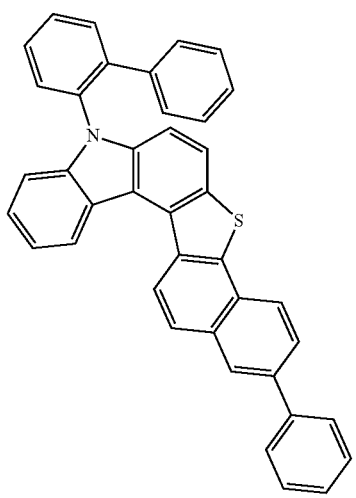
S-46
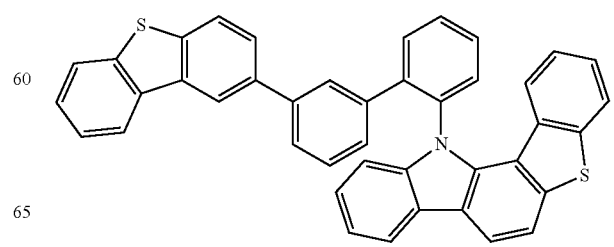

-continued
S-47
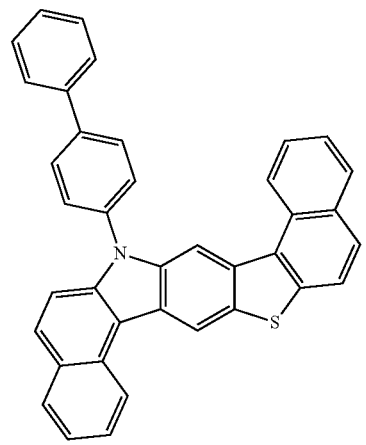
S-48
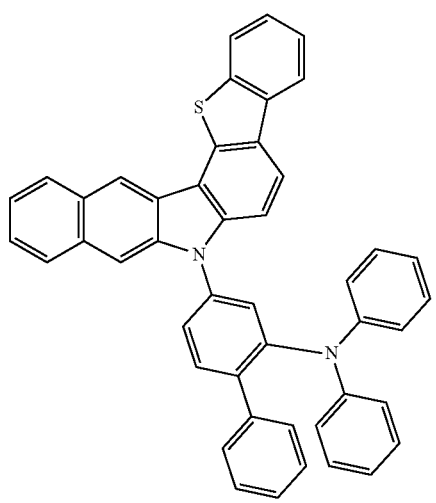
S-49
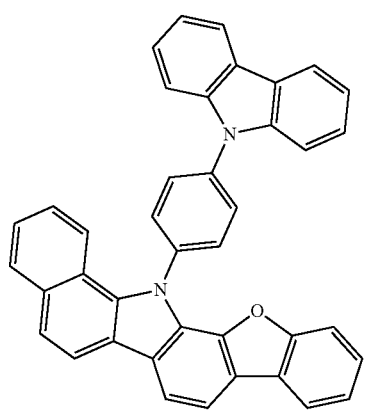
-continued
S-50
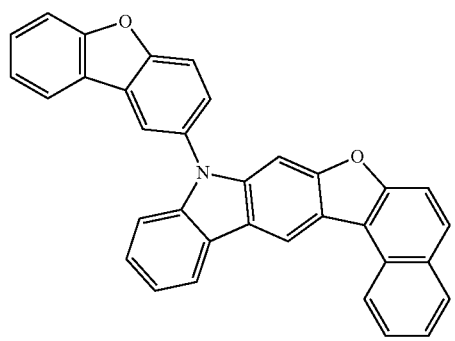
S-51
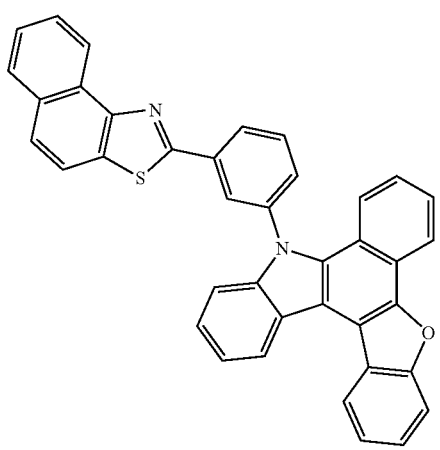
S-52
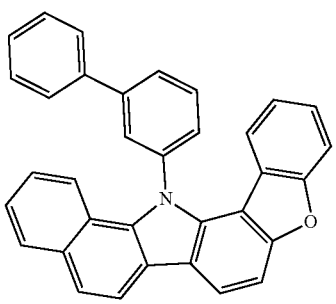
S-53
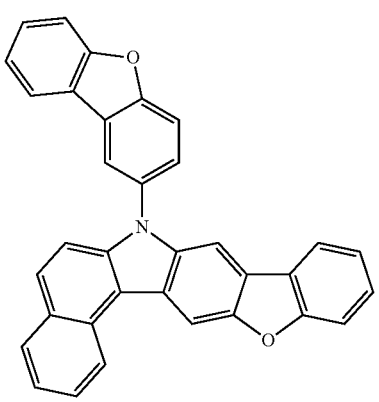

S-54
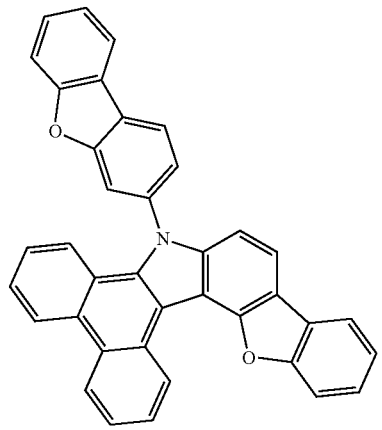
S-55
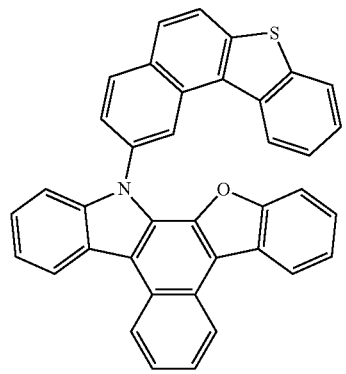
S-56
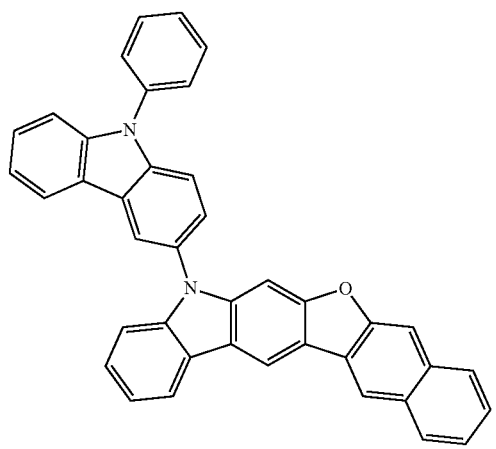
S-57
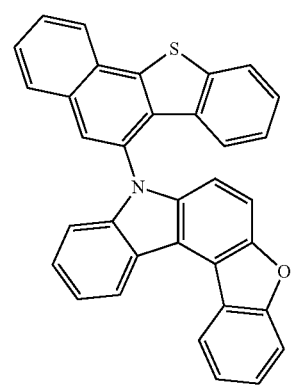
S-58
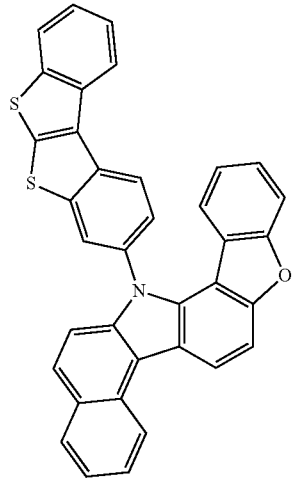
S-59
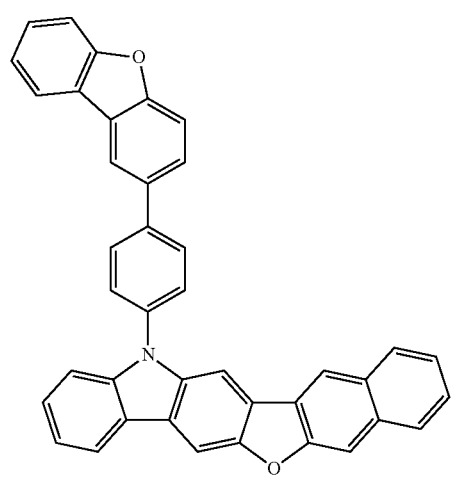
S-60
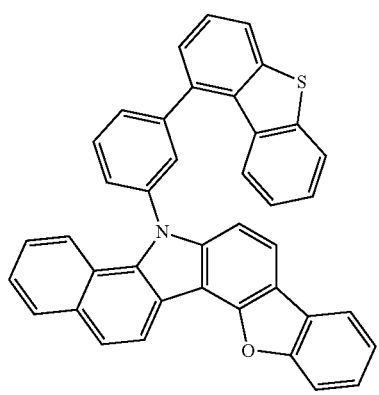

S-61
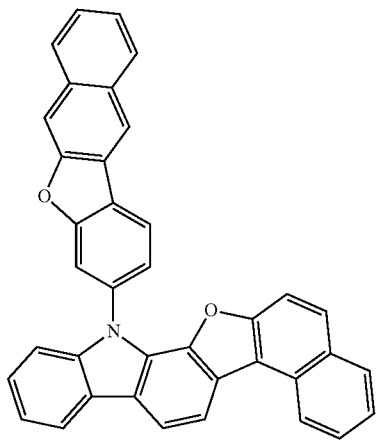
S-64
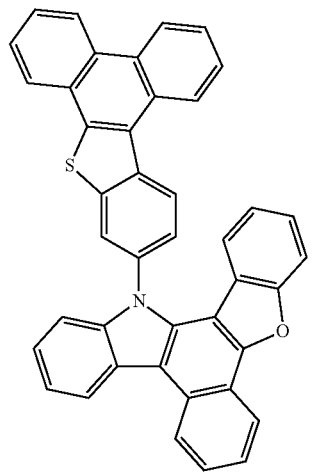
S-62
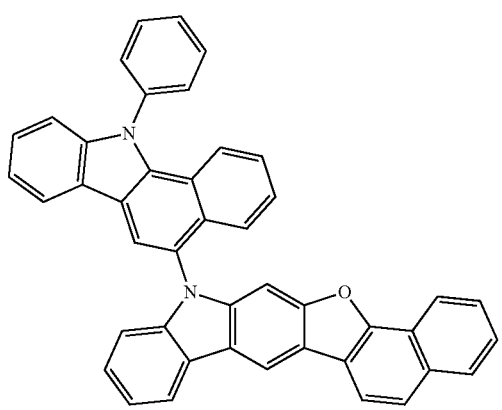
S-65
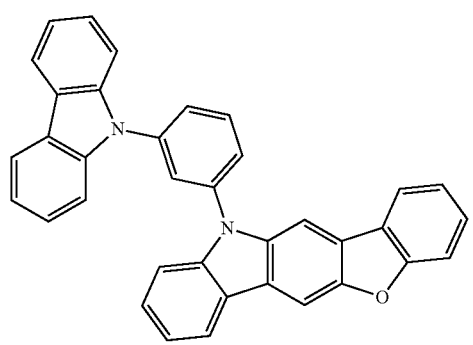
S-66
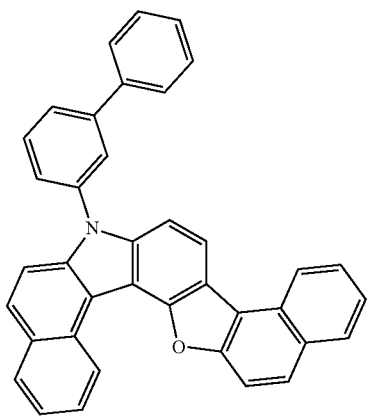
S-63
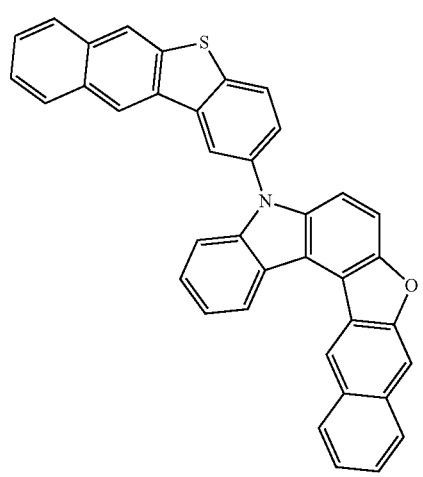
S-67
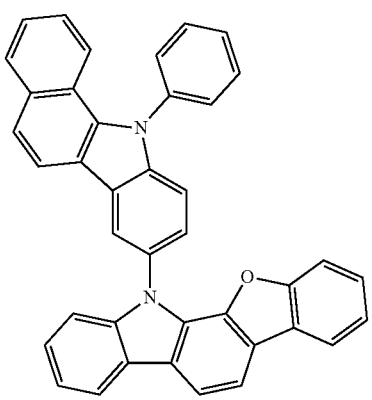

S-68
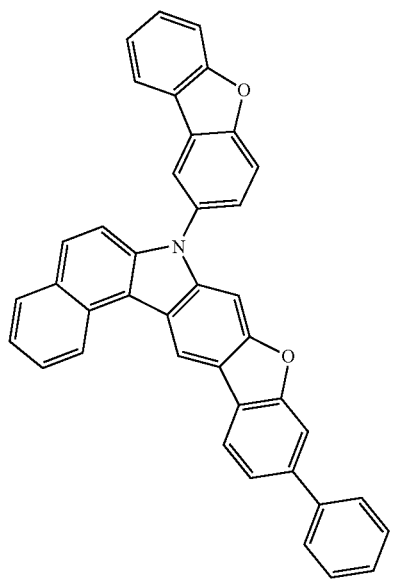
S-69
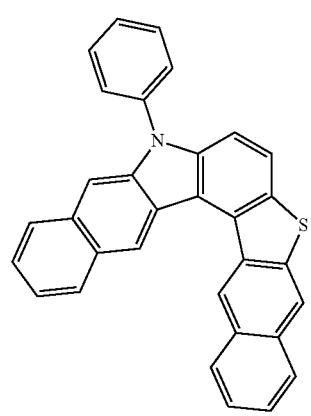
S-70
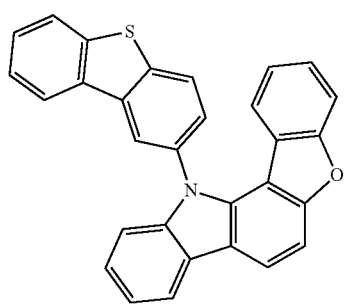
S-71
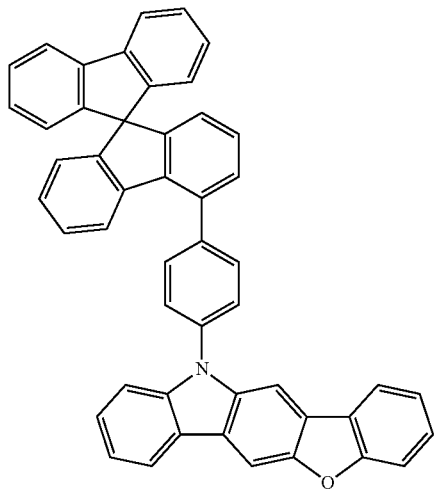
S-72
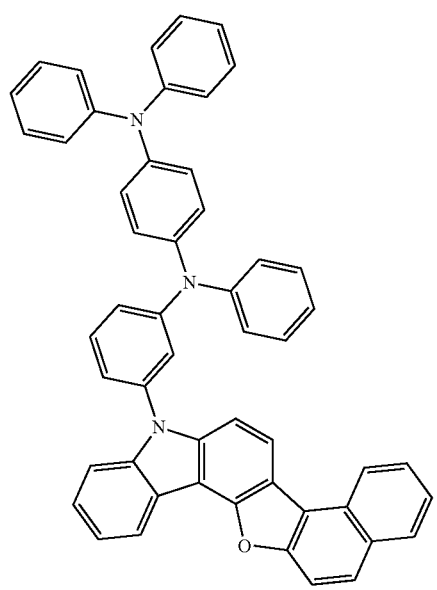
S-73
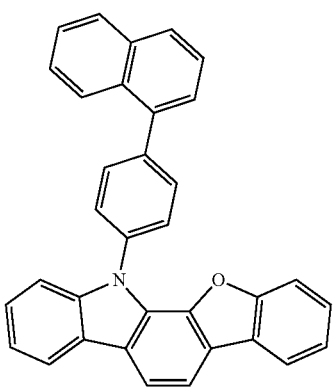

S-74
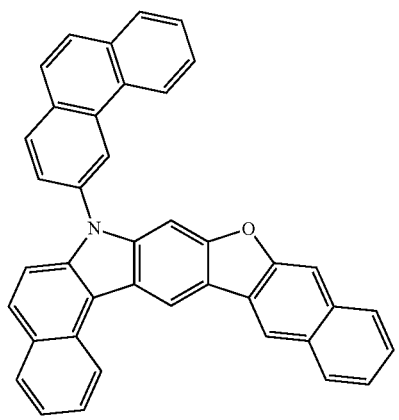
S-75
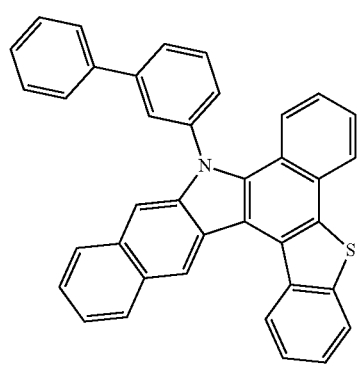
S-76
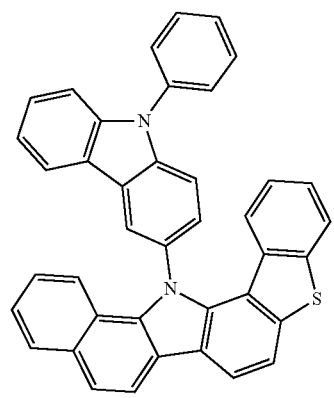
S-77
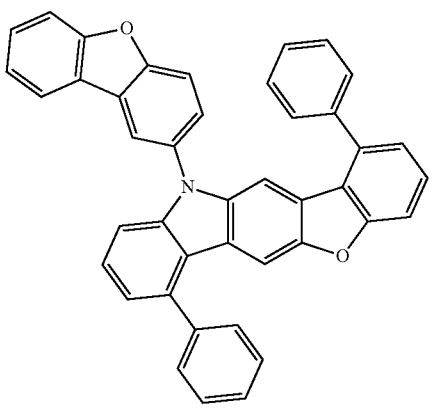
S-78
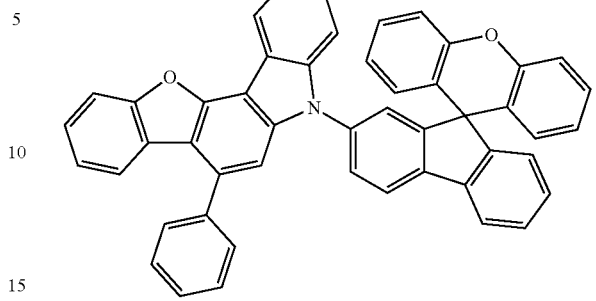
S-79
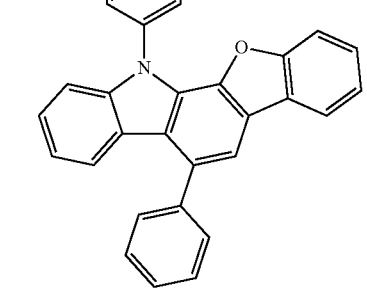
S-80
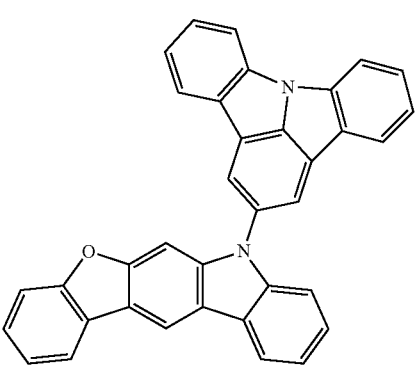
S-81
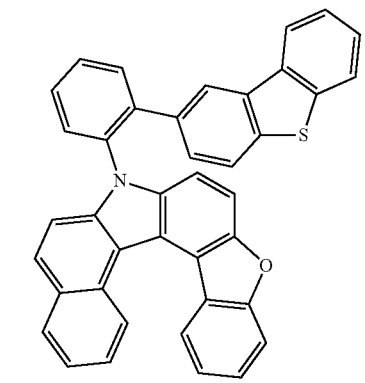

S-82
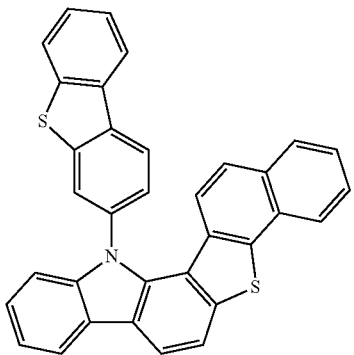
S-83
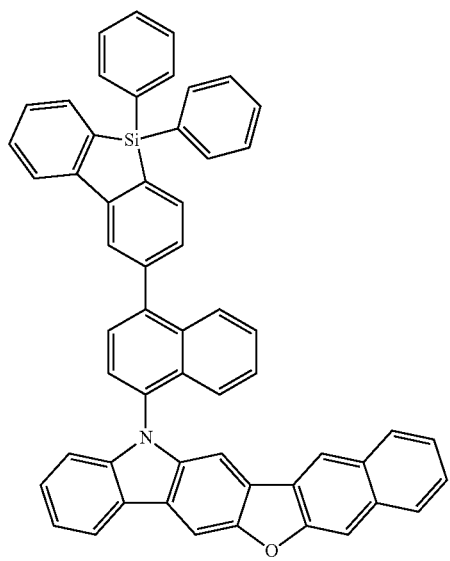
S-84
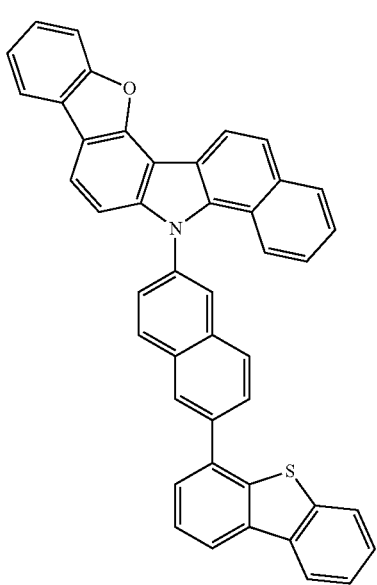
S-85
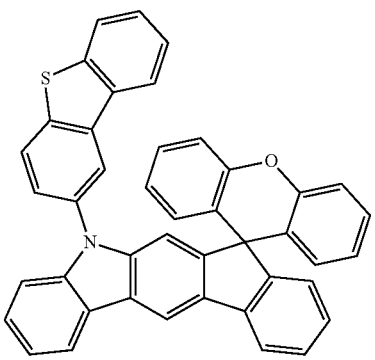
S-86
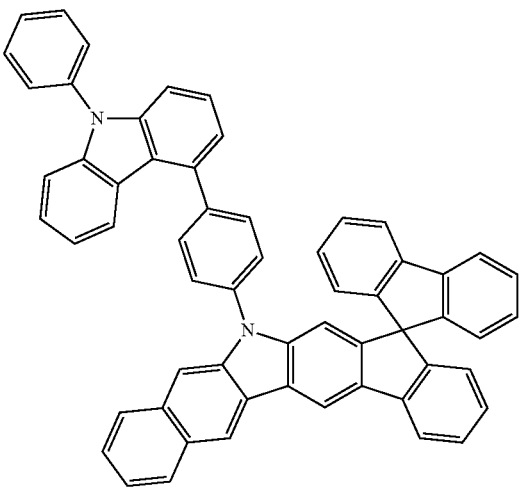
S-87
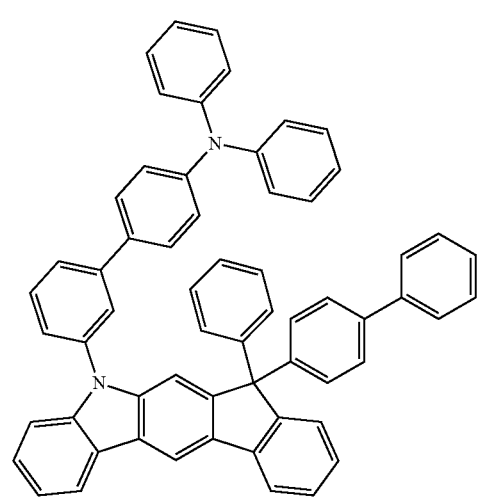

-continued
S-88
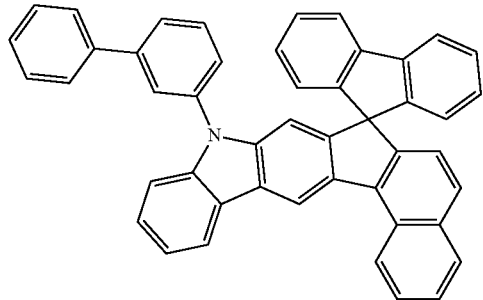
S-89
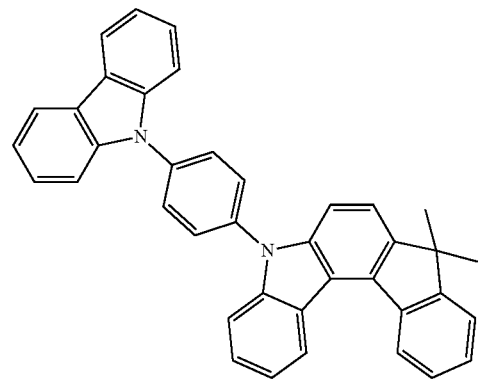
S-90
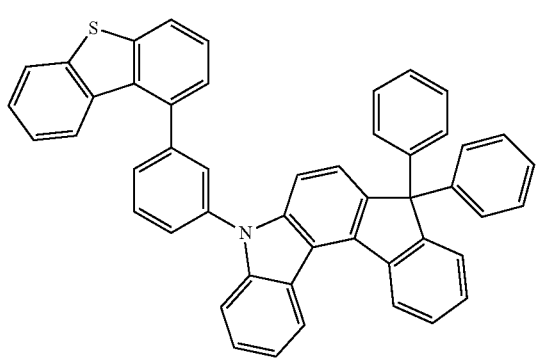
S-91
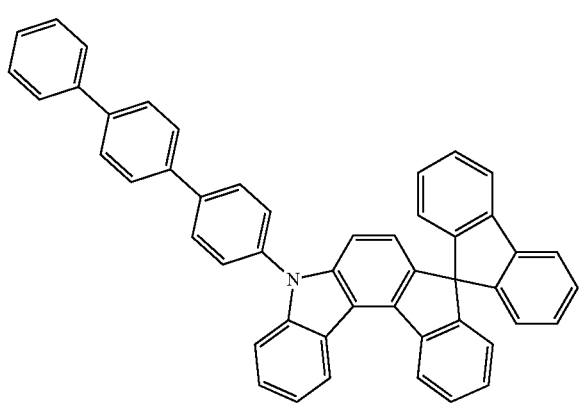
-continued
S-92
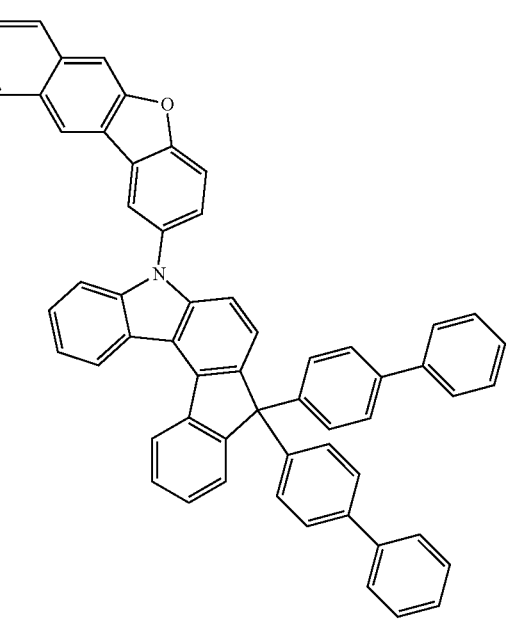
S-93
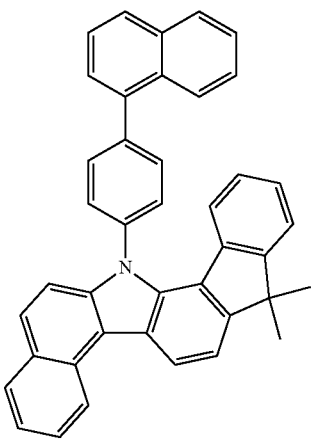
S-94
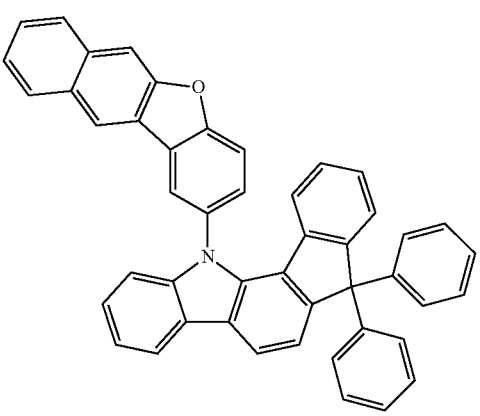

-continued
S-95
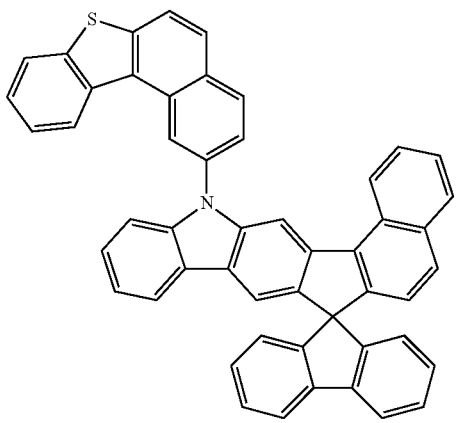
S-96
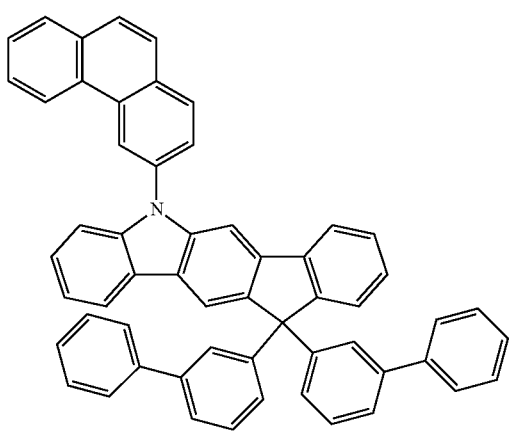
S-97
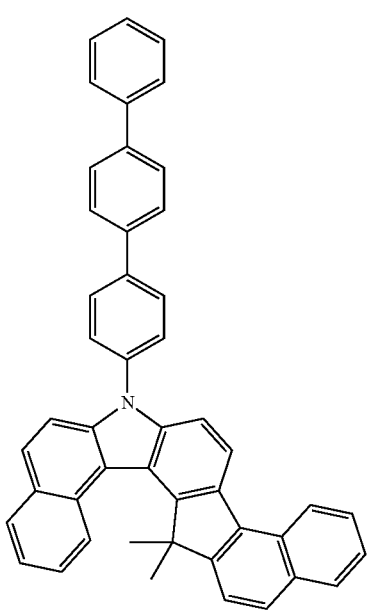
-continued
S-98
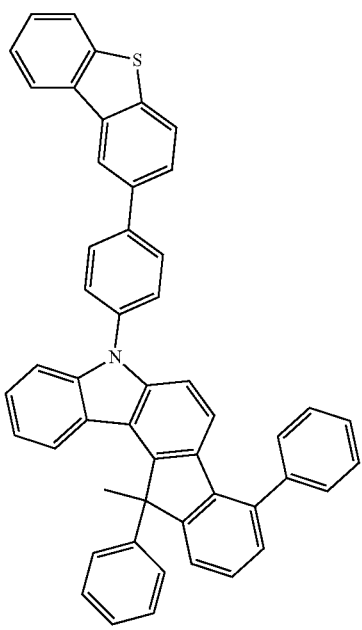
S-99
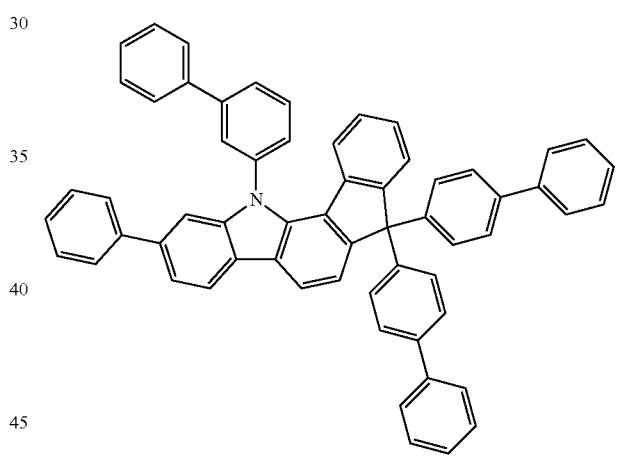
S-100
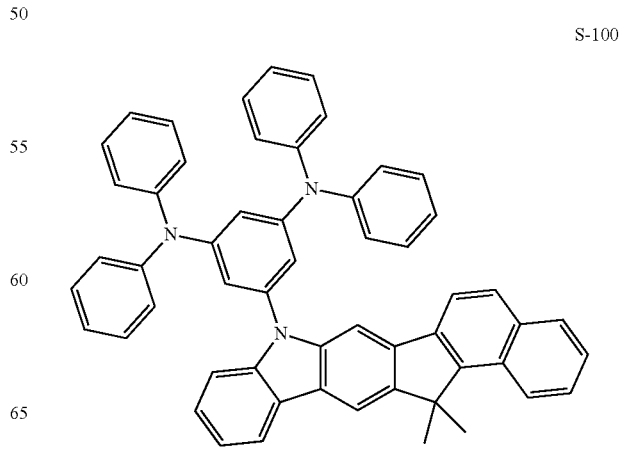

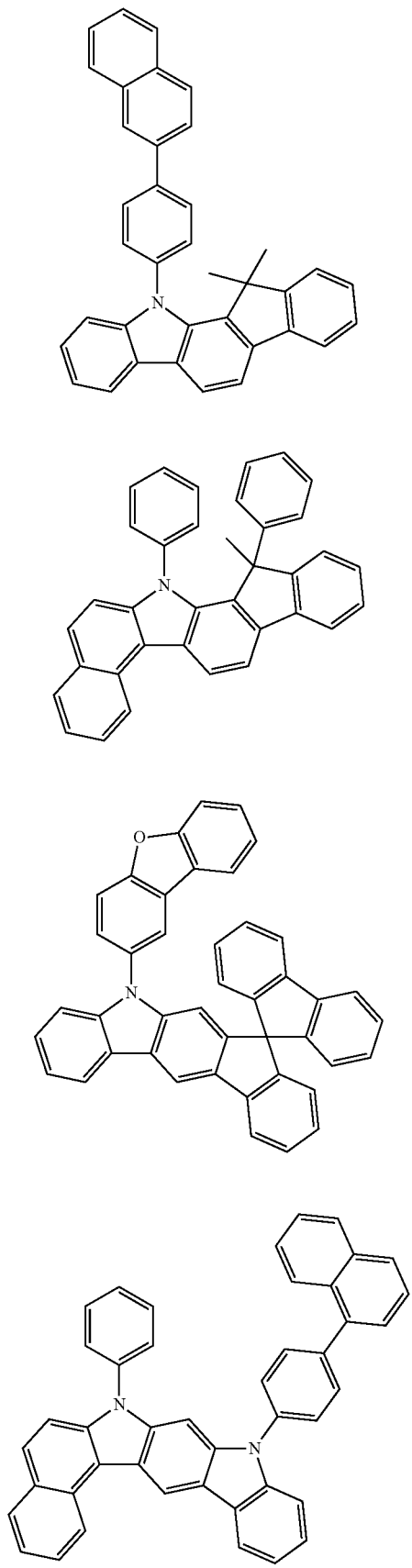
S-101
S-102
S-103
S-104
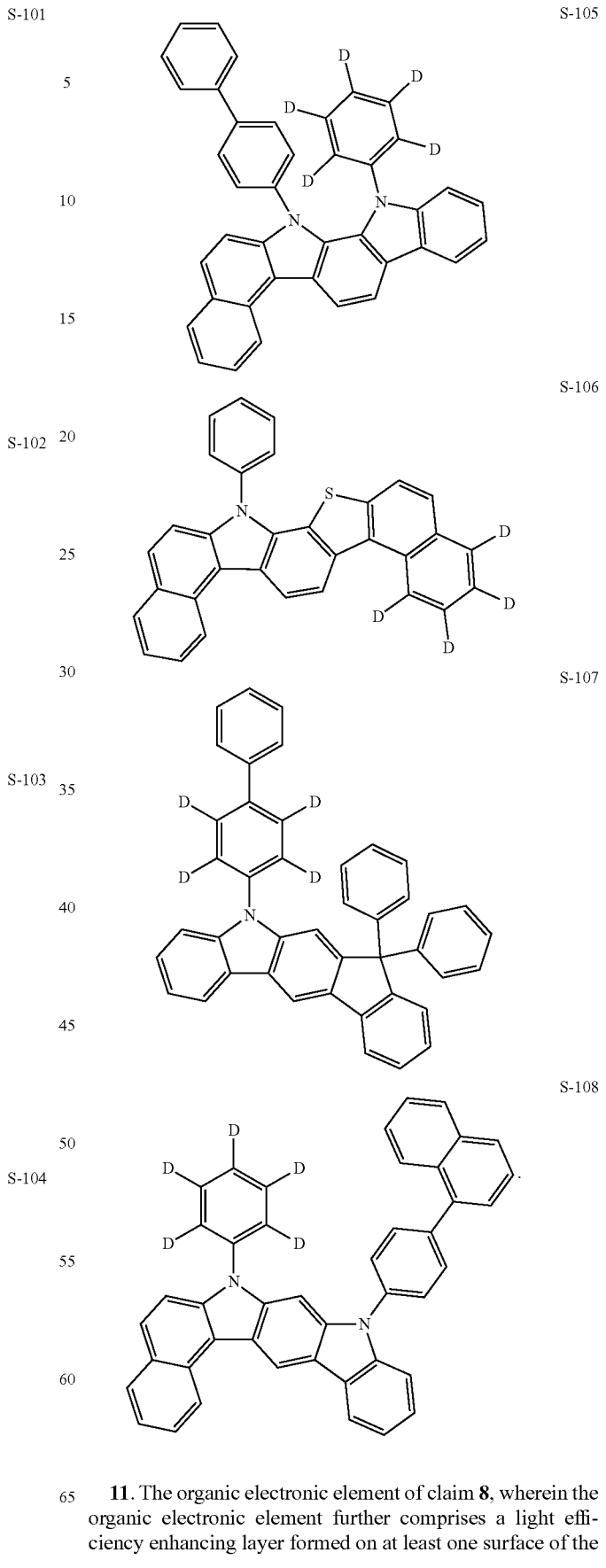
S-105
S-106
S-107
S-108
11. The organic electronic element of claim 8, wherein the organic electronic element further comprises a light efficiency enhancing layer formed on at least one surface of the first electrode and the second electrode, the surface being opposite to the organic material layer.

12. The organic electronic element of claim 8, wherein the organic material layer comprises 2 or more stacks, each including a hole transport layer, an emitting layer, and an electron transport layer sequentially formed on the first electrode.

13. The organic electronic element of claim 12, wherein the organic material layer further comprises a charge generation layer formed between the 2 or more stacks.

14. An electronic device comprising a display device comprising the organic electronic element of claim 8; and a control unit for driving the display device.

15. The electronic device according to claim 14, wherein the organic electronic element is at least one of an OLED, an organic solar cell, an organic photo conductor (OPC), organic transistor (organic TFT) and an element for monochromic or white illumination.

* * * * *

UNITED STATES PATENT AND TRADEMARK OFFICE
CERTIFICATE OF CORRECTION

PATENT NO. : 11,690,292 B2
APPLICATION NO. : 18/058957
DATED : June 27, 2023
INVENTOR(S) : Song et al.

Page 1 of 1

It is certified that error appears in the above-identified patent and that said Letters Patent is hereby corrected as shown below:

In the Claims

Column 190, Claim 2, <Formula 1-3>:

Please delete " 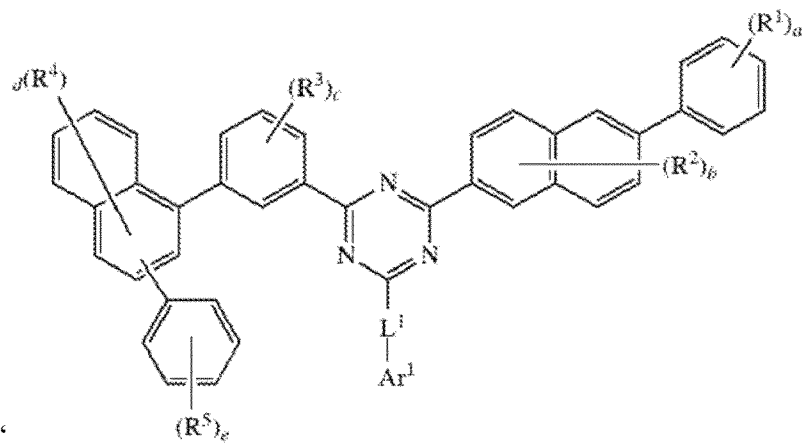 "

And replace with -- 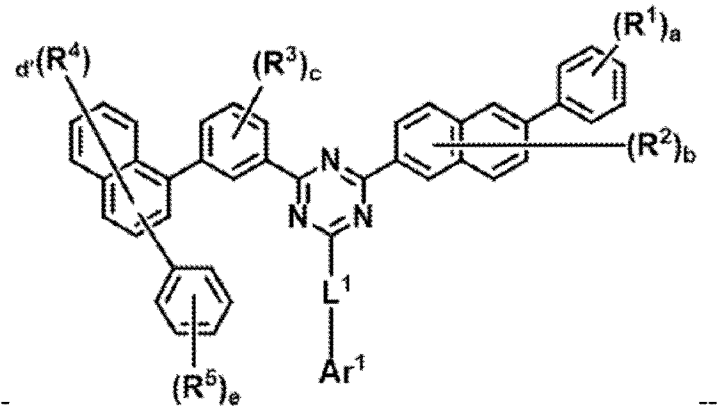 --

Signed and Sealed this
Twelfth Day of September, 2023

Katherine Kelly Vidal
*Director of the United States Patent and Trademark Office*